United States Patent
Pinto

(10) Patent No.: US 7,135,469 B2
(45) Date of Patent: Nov. 14, 2006

(54) LINEAR CHAIN SUBSTITUTED MONOCYCLIC AND BICYCLIC DERIVATIVES AS FACTOR XA INHIBITORS

(75) Inventor: Donald J. Pinto, Kennett Square, PA (US)

(73) Assignee: Bristol Myers Squibb, Co., Princeton, NJ (US)

( * ) Notice: Subject to any disclaimer, the term of this patent is extended or adjusted under 35 U.S.C. 154(b) by 139 days.

(21) Appl. No.: 10/801,519

(22) Filed: Mar. 16, 2004

(65) Prior Publication Data

US 2004/0214808 A1 Oct. 28, 2004

Related U.S. Application Data

(60) Provisional application No. 60/455,708, filed on Mar. 18, 2003.

(51) Int. Cl.
*A61K 31/5377* (2006.01)
*A61K 31/497* (2006.01)
*A61K 31/437* (2006.01)
*C07D 413/02* (2006.01)
*C07D 471/02* (2006.01)

(52) U.S. Cl. ............... 514/234.2; 514/253.04; 514/303; 544/117; 544/362; 546/120

(58) Field of Classification Search ............... None
See application file for complete search history.

(56) References Cited

U.S. PATENT DOCUMENTS 6,060,491 A * 5/2000 Pruitt et al. .................. 514/355

FOREIGN PATENT DOCUMENTS

WO  WO 95/01980  *  1/1995
WO  WO 02/057236     7/2002

OTHER PUBLICATIONS

Duplantier, STN International (2006) HCAPLUS Database, Columbus, OH, Accession No. 1995:480325.*
Bauer, K.A., "Fondaparinux: a new synthetic and selective inhibitor of Factor Xa", Best Practice & Research Clinical Haematology, vol. 17, No. 1, pp. 89-104, 2004.
Gresele et al., "Novel approaches to the treatment of thrombosis", TRENDS in Pharmacological Sciences, vol. 23, No. 1, pp. 25-32, Jan. 2002.
Linkins et al., "New Anticoagulants", Seminars in Thrombosis and Hemostasis, vol. 29, No. 6, pp. 619-631, 2003.
Rauch et al., "Thrombus Formation on Atherosclerotic Plaques: Pathogenesis and Clinical Consequences", Annals of Internal Medicine, vol. 134, No. 3., pp. 224-238, Feb. 6, 2001.
Ruef et al., "New antithrombotic drugs on the horizon", Expert Opin. Investig. Drugs, vol. 12, No. 5, pp. 781-797, 2003.
Weitz et al., "Thrombophilia and New Anticoagulant Drugs", Hematology, pp. 424-438, 2004.

* cited by examiner

*Primary Examiner*—Joseph K. McKane
*Assistant Examiner*—Andrew B. Freistein
(74) *Attorney, Agent, or Firm*—Jing G. Sun; David H. Vance

(57) ABSTRACT

The present application describes linear chain substituted monocyclic and bicyclic compounds and derivatives thereof of Formula I:

$$P_4\text{-}P\text{-}M\text{-}M_4 \qquad \text{I}$$

or pharmaceutically acceptable salt forms thereof, P-M are rings substituted by a linear group. Compounds of the present invention are useful as inhibitors of trypsin-like serine proteases, specifically factor Xa.

16 Claims, No Drawings

LINEAR CHAIN SUBSTITUTED MONOCYCLIC AND BICYCLIC DERIVATIVES AS FACTOR XA INHIBITORS

CROSS-REFERENCE TO RELATED APPLICATIONS

The present application claims the priority benefit of U.S. Provisional Application No. 60/455,708, filed Mar. 18, 2003, which is expressly incorporated fully herein by reference.

FIELD OF THE INVENTION

This invention relates generally to linear chain substituted monocyclic and bicyclic compounds and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

WO02/057236 describes factor Xa inhibitors of the following formula:

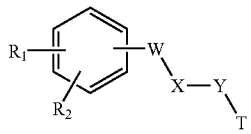

wherein $R_1$ is selected from a small number of nitrogen containing groups, W—X form a linear core with at least one O or N, Y can be a ring, and T can be a heterocycle. WO02/057236 does not suggest or exemplify compounds like those of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel linear chain substituted monocyclic and bicyclic compounds and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a mammal in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that linear chain substituted monocyclic and bicyclic compounds of Formula I:

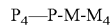

$$P_4\text{—}P\text{-}M\text{-}M_4 \qquad\qquad I$$

wherein P, $P_4$, M, and $M_4$ are defined below, or pharmaceutically acceptable salt or prodrug forms thereof, are effective factor Xa inhibitors.

DETAILED DESCRIPTION OF PREFERRED EMBODIMENTS

In a first embodiment, the present invention provides a novel compound of Formula I:

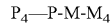

$$P_4\text{—}P\text{-}M\text{-}M_4 \qquad\qquad I$$

or a stereoisomer or pharmaceutically acceptable salt thereof, wherein;

M is a 3–10 membered carbocycle or a 4–10 membered heterocycle, consisting of: carbon atoms and 1–3 heteroatoms selected from O, $S(O)_p$, N, and $NZ^2$;

ring M is substituted with 0–3 $R^{1a}$ and 0–2 carbonyl groups, and there are 0–3 ring double bonds;

P is fused onto ring M and is a 5, 6, or 7 membered carbocycle or a 5, 6, or 7 membered heterocycle, consisting of: carbon atoms and 1–3 heteroatoms selected from O, $S(O)_p$, and N;

ring P is substituted with 0–3 $R^{1a}$ and 0–2 carbonyl groups, and there are 0–3 ring double bonds;

alternatively, ring P is absent and $P_4$ is directly attached to ring M, provided that when ring P is absent, $P_4$ and $M_4$ are attached to the 1,2, 1,3, or 1,4 positions of ring M;

one of $P_4$ and $M_4$ is -A-B and the other -$G_1$-G;

G is a group of Formula IIa or IIb:

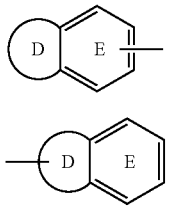

IIa

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, herein the 5–6 membered heterocycle is substituted with 0–2 carbonyl groups and 1–2 R and there are 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, C(=$NR^8$)$NR^7R^9$, NHC(=$NR^8$)$NR^7R^9$, ONHC(=$NR^8$)$NR^7R^9$, $NR^8$CH(=$NR^7$), $NH_2$, NH($C_{1-3}$ alkyl), N($C_{1-3}$ alkyl)$_2$, C(=NH)$NH_2$, $CH_2NH_2$, $CH_2$NH($C_{1-3}$ alkyl), $CH_2$N($C_{1-3}$ alkyl)$_2$, $CH_2CH_2NH_2$, $CH_2CH_2$NH($C_{1-3}$ alkyl), $CH_2CH_2$N($C_{1-3}$ alkyl)$_2$, $(CR^8R^9)_t$C(O)H, $(CR^8R^9)_t$C(O)$R^{2c}$, $(CR^8R^9)_t$$NR^7R^8$, $(CR^8R^9)_t$C(O)$NR^7R^8$, $(CR^8R^9)_t$$NR^7$C(O)$R^7$, $(CR^8R^9)_t$$OR^3$, $(CR^8R^9)_t$S(O)$_p$$NR^7R^8$, $(CR^8R^9)_t$$NR^7$S(O)$_p$$R^7$, $(CR^8R^9)_t$$SR^3$, $(CR^8R^9)_t$S(O)$R^3$, $(CR^8R^9)_t$S(O)$_2R^3$, and $OCF_3$;

alternatively, when 2 R groups are attached to adjacent atoms, they combine to form methylenedioxy or ethylenedioxy;

A is 2–8 membered linear chain consisting of: carbon atoms, 0–2 carbonyl groups, and 0–3 heteroatoms selected from O, N, and $S(O)_p$, and A is substituted with 0–3 $R^{1a}$ and 0–2 $R^2$, and there are 0–2 double bonds and 0–1 triple bonds; provided other than an S—S, S—O, or O—O bond is present in A;

B is selected from —CN, $OR^3$, $NR^3R^{3a}$, Y, N($B^1$)C(O)C($R^3R^{3g}$)$_{1-4}$$NB^2B^3$,

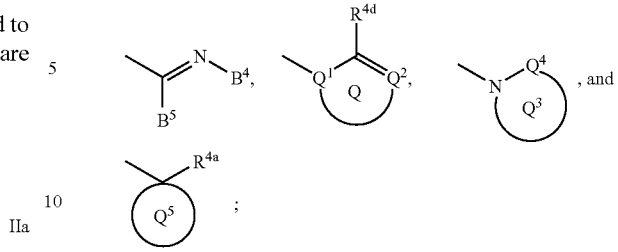

provided that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, C(O)$R^{2e}$, C(O)$OR^{2d}$, C(O)$NR^{2d}R^{2d}$, C(O)NH($CH_2$)$_2$$NR^{2d}R^{2d}$, $SO_2$$NR^{2d}R^{2d}$, C(O)$NHSO_2$—$C_{1-4}$ alkyl, and $S(O)_p$ $R^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

$B^4$ is selected from H, $SO_2R^{3b}$, C(O)$R^{3b}$, $SO_2NR^3R^{3b}$, C(O)$NR^3R^{3b}$, $OR^2$, $SR^2$, —CN, and $NO_2$;

$B^5$ is $NR^2R^{2f}$ or $CR^3R^2R^{2f}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–8 membered ring consisting of, in addition to the $Q^1$-$CR^{4d}$=$Q^2$ group shown, carbon atoms and 0–2 heteroatoms selected from N, O, and $S(O)_p$, and the ring is substituted with an additional 0–2 $R^{4d}$;

ring $Q^3$ is a 4–7 membered monocyclic or tricyclic ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

$Q^4$ is selected from C=O and $SO_2$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

Y is $CY^1Y^2R^{4a}$, and $Y^1$ and $Y^2$ are independently $C_{1-4}$ alkyl substituted with 0–2 $R^4$;

alternatively, Y is selected from: $C_{3-10}$ carbocycle substituted 0–2 $R^4$ and 0–1 $R^{4a}$, and, 3–10 membered heterocycle consisting of: carbon atoms and 1–4 heteroatoms selected from the group consisting of N, O, and $S(O)_p$ and substituted with 0–2 $R^4$ and 0–1 $R^{4a}$;

$G_1$ is absent or is selected from $(CR^3R^{3a})_{1-5}$, $(CR^3R^{3a})_{0-2}$ $CR^3$=$CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{3a})_w$, $(CR^3R^{3a})_uNRR^{3e}(CR^3R^{3a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(O)_2NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w total 0, 1, 2, 3, or 4 and the right side of $G_1$ is attached to ring G, provided that $G_1$ does not form an N—S, NCH$_2$N, NCH$_2$O, or NCH$_2$S bond with either group to which it is attached;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl$)$-$C_{3-10}$ carbocycle substituted with 0–3 $R^{1a}$, and —$(C_{0-4}$ alkyl$)$-5–10 membered heterocycle substituted with 0–3 $R^{1a}$ and consisting of: carbon atoms and 1–4 heteroatoms selected from the group consisting of N, O, and $S(O)_p$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—$C(O)$—$(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—C(=$NR^{1b}$)$NR^3R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5–10 membered saturated, partially saturated, or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $CR^2R^{2f}$ forms a 5–8 membered ring consisting of: carbon atoms and 0–2 heteroatoms selected from N, O, and $S(O)_p$, and this ring is substituted with 0–2 $R^{4b}$;

alternatively, $NR^2R^{2f}$ forms a 5–8 membered ring consisting of: carbon atoms and 0–2 additional heteroatoms selected from N, O, and $S(O)_p$, and this ring is substituted with 0–2 $R^{4b}$;

alternatively, when $B^4$ is $SO_2R^{3b}$ and $B^5$ is $NR^2R^{2f}$, $R^{3b}$ and $R^{2f}$ combine to form a 5–8 membered ring consisting of: carbon atoms and 0–2 additional heteroatoms selected from N, O, and $S(O)_p$, and this ring is substituted with 0–2 $R^{4b}$;

alternatively, when $B^4$ is $C(O)R^{3b}$ and $B^5$ is $NR^2R^{2f}$, $R^{3b}$ and $R^{2f}$ combine to form a 5–8 membered ring consisting of:

carbon atoms and 0–2 additional heteroatoms selected from N, O, and S(O)$_p$, and this ring is substituted with 0–2 R$^{4b}$;

alternatively, when B$^5$ is NR$^2$R$^{2f}$, B$^4$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$ and the R$^2$ group of NR$^2$R$^{2f}$, in addition to the groups recited below, is selected from SO$_2$R$^{3b}$, C(O)R$^{3b}$, and —CN;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, C(CH$_3$)$_3$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

alternatively, NR$^3$R$^{3a}$ forms a 5 or 6 membered saturated, partially unsaturated, or unsaturated ring consisting of: carbon atoms, the nitrogen atom to which R$^3$ and R$^{3a}$ are attached, and 0–1 additional heteroatoms selected from the group consisting of N, O, and S(O)$_p$;

R$^{3b}$, at each occurrence, is selected from H, C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, C(CH$_3$)$_3$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C$_{1-4}$ alkyl-phenyl, and C(=O)R$^{3c}$;

R$^{3e}$, at each occurrence, is selected from H, SO$_2$NHR$^3$, SO$_2$NR$^3$R$^3$, C(O)R$^3$, C(O)NHR$^3$, C(O)OR$^{3f}$, S(O)R$^{3f}$, S(O)$_2$ R$^{3f}$, C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3f}$, at each occurrence, is selected from: C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3g}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —(CH$_2$)$_r$-3–6 membered carbocycle, and —(CH$_2$)$_r$-5–6 membered heterocycle consisting of: carbon atoms and 1–4 heteroatoms selected from the group consisting of N, O, and S(O)$_p$;

alternatively, when R$^3$ and R$^{3g}$ are attached to the same carbon atom, they combine with the attached carbon atom to form a cyclopropyl group;

R$^4$, at each occurrence, is selected from H, =O, (CR$^3$R$^{3a}$)$_r$ OR$^2$, (CR$^3$R$^{3a}$)$_r$F, (CR$^3$R$^{3a}$)$_r$Cl, (CR$^3$R$^{3a}$)$_r$Br, (CR$^3$R$^{3a}$)$_r$I, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$C(O)R$^{2c}$, (CR$^3$R$^{3a}$)$_r$NR$^2$C(O) R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$C(=NS(O)$_2$R$^5$) NR$^2$R$^{2a}$, (CR$^3$R$^{3a}$)$_r$NR$^2$C(=NR$^2$)NR$^2$R$^{2a}$, (CR$^3$R$^{3a}$)$_r$C(O) NR$^2$C(=NR$^2$)NR$^2$R$^{2a}$, (CR$^3$R$^{3a}$)$_r$SO$_2$NR$^2$R$^{2a}$, (CR$^3$R$^{3a}$)$_r$ NR$^2$SO$_2$NR$^2$R$^{2a}$, (CR$^3$R$^{3a}$)$_r$NR$^2$SO$_2$—C$_{1-4}$ alkyl, (CR$^3$ R$^{3a}$)$_r$ NR$^2$SO$_2$R$^5$, (CR$^3$R$^{3a}$)$_r$S(O)$_p$R$^{5a}$, (CR$^3$R$^{3a}$)$_r$(CF$_2$)$_r$ CF$_3$, NHCH$_2$R$^{1b}$, OCH$_2$R$^{1b}$, SCH$_2$R$^{1b}$, NH(CH$_2$)$_2$(CH$_2$)$_t$ R$^{1b}$, O(CH$_2$)$_2$(CH$_2$)$_t$R$^{1b}$, S(CH$_2$)$_2$(CH$_2$)$_t$R$^{1b}$, (CR$^3$R$^{3a}$)$_r$-5–6 membered carbocycle substituted with 0–1 R$^5$, and a (CR$^3$R$^{3a}$)$_r$-5–6 membered heterocycle consisting of: carbon atoms and 1–4 heteroatoms selected from the group consisting of N, O, and S(O)$_p$ and substituted with 0–1 R$^5$;

R$^{4a}$ is selected from C$_{1-6}$ alkyl substituted with 0–2 R$^{4c}$, C$_{2-6}$ alkenyl substituted with 0–2 R$^{4c}$, C$_{2-6}$ alkynyl substituted with 0–2 R$^{4c}$, —(CR$^3$R$^{3g}$)$_r$—C$_{5-10}$ membered carbocycle substituted with 0–3 R$^{4c}$, —(CR$^3$R$^{3g}$)$_r$-5–10 membered heterocycle substituted with 0–3 R$^{4c}$ and consisting of: carbon atoms and 1–4 heteroatoms selected from the group consisting of N, O, and S(O)$_p$, (CR$^3$R$^{3g}$)$_r$CN, (CR$^3$R$^{3g}$)$_r$C (=NR$^{2d}$)NR$^{2d}$R$^{2d}$, (CR$^3$R$^{3g}$)$_r$NR$^{2d}$C(=NR$^{2d}$)NR$^{2d}$R$^{2d}$, (CR$^3$R$^{3g}$)$_r$NR$^{2d}$C(R$^{2e}$)(=NR$^{2d}$), (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$ NR$^{2d}$C(O)R$^{2e}$, (CR$^3$R$^{3g}$)$_r$C(O)R$^{2e}$, (CR$^3$R$^{3g}$)$_r$OC(O)R$^{2e}$, (CR$^3$R$^{3g}$)$_r$C(O)NR$^{2d}$R$^{2d}$, (CR$^3$R$^{3g}$)$_r$C(O)OR$^{2d}$, (CR$^3$R$^{3g}$)$_r$ NR$^{2d}$C(O)NR$^{2d}$R$^{2d}$, (CR$^3$R$^{3g}$)$_r$OC(O)NR$^{2d}$R$^{2d}$, (CR$^3$R$^{3g}$)$_r$ NR$^{2d}$C(O)OR$^{2d}$, (CR$^3$R$^{3g}$)$_r$SO$_2$NR$^{2d}$R$^{2d}$, (CR$^3$R$^{3g}$)$_r$ NR$^{2d}$SO$_2$NR$^{2d}$R$^{2d}$, (CR$^3$R$^{3g}$)$_r$C(O)NR$^{2d}$SO$_2$R$^{2d}$, (CR$^3$R$^{3g}$)$_r$ NR$^{2d}$SO$_2$R$^{2d}$, and (CR$^3$R$^{3g}$)$_r$S(O)$_p$R$^{2d}$, provided that S(O)$_p$ R$^{2d}$ forms other than S(O)$_2$H or S(O)H and further provided that R$^{4a}$ is other than a hydroxamic acid;

R$^{4b}$, at each occurrence, is selected from H, =O, (CH$_2$)$_r$ OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O) NR$^3$R$^{3a}$, (CH$_2$)$_r$NR$^3$C(O)NR$^3$R$^{3a}$, (CH$_2$)$_r$C(=NR$^3$) NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$ NR$^3$SO$_2$CF$_3$, (CH$_2$)$_r$NR$^3$SO$_2$-phenyl, (CH$_2$)$_r$S(O)$_p$ CF$_3$, (CH$_2$)$_r$S(O)$_p$—C$_{1-4}$ alkyl, (CH$_2$)$_r$S(O)$_p$-phenyl, and (CH$_2$)$_r$(CF$_2$)$_r$CF$_3$;

R$^{4c}$, at each occurrence, is selected from =O, (CR$^3$R$^{3a}$)$_r$ OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$ CF$_3$, C$_{1-4}$ alkyl, C$_{2-6}$ alkenyl, C$_{2-6}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O) R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$N=CHOR$^3$, (CR$^3$R$^{3a}$)$_r$ C(O)NR$^2$(CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$NR$^2$C(=NR$^2$) NR$^2$R$^{2a}$, (CR$^3$R$^{3a}$)$_r$SO$_2$NR$^2$R$^{2a}$, (CR$^3$R$^{3a}$)$_r$ NR$^2$SO$_2$NR$^2$R$^{2a}$, (CR$^3$R$^{3a}$)$_r$C(O)NR$^2$SO$_2$—C$_{1-4}$ alkyl, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_{3-10}$ carbocycle substituted with 0–2 R$^{4b}$, and (CR$^3$R$^{3a}$)$_r$4–10 membered heterocycle substituted with 0–2 R$^{4b}$ and consisting of carbon atoms and from 1–4 heteroatoms selected from the group consisting of N, O, and S(O)$_p$;

R$^{4d}$, at each occurrence, is selected from H, (CR$^3$R$^{3a}$)$_r$ OR$^2$, (CR$^3$R$^{3a}$)$_r$F, (CR$^3$R$^{3a}$)$_r$Br, (CR$^3$R$^{3a}$)$_r$Cl, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C (O)NR$^2$R$^{2a}$, (CR$^3$R$^{3a}$)$_r$N=CHOR$^3$, (CR$^3$R$^{3a}$)$_r$C(O)NH (CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C (=NR$^2$)NR$^2$R$^{2a}$, (CR$^3$R$^{3a}$)$_r$NHC(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$_3$R$^{3a}$)$_r$NR$^2$SO$_2$—C$_{1-4}$ alkyl, (CR$_3$R$^{3a}$)$_r$C(O)NHSO$_2$— C$_{1-4}$ alkyl, (CR$^3$R$^{3a}$)$_r$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5–6 membered carbocycle substituted with 0–1 R$^5$, and a (CR$^3$R$^{3a}$)$_r$-5–6 membered heterocycle consisting of: carbon atoms and 1–4 heteroatoms selected from the group consisting of N, O, and S(O)$_p$ and substituted with 0–1 R$^5$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

R$^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond;

R$^6$, at each occurrence, is selected from H, OH, (CH$_2$)$_r$OR$^2$, halo, C$_{1-4}$ alkyl, —CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl-C$_{1-4}$ alkyl-C(O)—;

R$^8$, at each occurrence, is selected from H, C$_{1-6}$ alkyl, and (CH$_2$)$_n$-phenyl;

alternatively, R$^7$ and R$^8$, when attached to the same nitrogen, combine to form a 5–10 membered heterocyclic ring consisting of carbon atoms and 0–2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

In a second embodiment, the present invention provides a novel compound of Formula II:

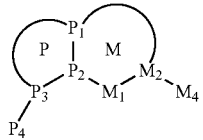

II or a stereoisomer or pharmaceutically acceptable salt thereof, wherein;

ring M, including P$_1$, P$_2$, M$_1$, and M$_2$, is a 5, 6, or 7 membered carbocycle or a 5, 6, or 7 membered heterocycle, consisting of: carbon atoms and 1–3 heteroatoms selected from O, S(O)$_p$, N, and NZ$^2$;

ring M is substituted with 0–2 R$^{1a}$ and 0–2 carbonyl groups, and there are 0–3 ring double bonds;

ring P, including P$_1$, P$_2$, and P$_3$, is a 5 or 6 membered aromatic or dihydro-aromatic heterocycle, consisting of: carbon atoms and 1–3 heteroatoms selected from O, S(O)$_p$, and N;

ring P is substituted with 0–2 R$^{1a}$;

one of P$_4$ and M$_4$ is -A-B and the other -G$_1$-G;

G is a group of Formula IIa or IIb:

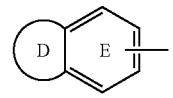

IIa

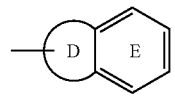

IIb ring D, including the two atoms of Ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, and thienyl, and ring E is substituted with 1–3 R;

alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and S(O)$_p$, wherein the 5–6 membered heterocycle is substituted with 0–2 carbonyl groups and 1–2 R and there are 0–3 ring double bonds;

R is selected from H, C$_{1-4}$ alkyl, F, Cl, OH, OCH$_3$, OCH$_2$CH$_3$, OCH(CH$_3$)$_2$, —CN, C(=NH)NH$_2$, C(=NH)NHOH, C(=NH)NHOCH$_3$, NH$_2$, NH(C$_{1-3}$ alkyl), N(C$_{1-3}$ alkyl)$_2$, C(=NH)NH$_2$, CH$_2$NH$_2$, CH$_2$NH(C$_{1-3}$ alkyl), CH$_2$N(C$_{1-3}$ alkyl)$_2$, (CR$^8$R$^9$)$_t$NR$^7$R$^8$, C(O)NR$^7$R$^8$, CH$_2$C(O)NR$^7$R$^8$, S(O)$_p$NR$^7$R$^8$, CH$_2$S(O)$_p$NR$^7$R$^8$, SO$_2$R$^3$, and OCF$_3$;

alternatively, when 2 R groups are attached to adjacent atoms, they combine to form methylenedioxy or ethylenedioxy;

A is 2–6 membered linear chain consisting of: carbon atoms, 0–2 carbonyl groups, and 0–3 heteroatoms selected from O, N, and S(O)$_p$, and A is substituted with 0–2 R$^{1a}$ and 0–2 R$^2$, and there are 0–1 double bonds and 0–1 triple bonds; provided that other than an S—S, S—O, or O—O bond is present in A;

B is selected from —CN, OR$^3$, NR$^3$R$^{3a}$, Y, N(B$^1$)C(O)C(R$^3$R$^{3g}$)NB$^2$B$^3$, N(B$^1$)C(O)C(R$^3$R$^{3g}$)C(R$^3$R$^{3g}$)NB$^2$B$^3$,

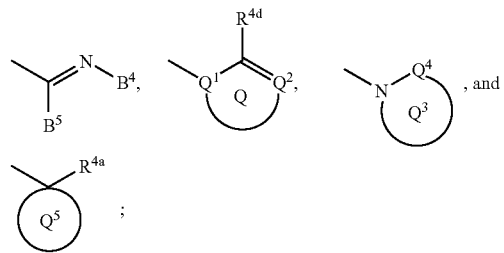

provided that the R$^{4d}$ shown is other than OH;

B$^1$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —(CH$_2$)$_{0-1}$—C$_{3-7}$ carbocycle substituted with 0–2 $R^{4b}$, and —(CH$_2$)$_{0-1}$-5–6 membered heterocycle consisting of: carbon atoms and 1–4 heteroatoms selected from the group consisting of N, O, and S(O)$_p$ and substituted with 0–2 $R^{4b}$;

$B^2$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^{2d}$R$^{2d}$, CH$_2$NR$^{2d}$R$^{2d}$, CH$_2$CH$_2$NR$^{2d}$R$^{2d}$, C(O)R$^{2e}$, C(O)NR$^{2d}$R$^{2d}$, SO$_2$NR$^{2d}$R$^{2d}$, and S(O)$_p$R$^{5a}$;

$B^3$ is selected from H, $C_{1-6}$ alkyl substituted with 0–1 $R^{4c}$, —(CH$_2$)$_{0-1}$-3–6 membered carbocycle substituted with 0–1 $R^5$, and a —(CH$_2$)$_{0-1}$-5–6 membered heterocycle consisting of: carbon atoms and 1–4 heteroatoms selected from the group consisting of N, O, and S(O)$_p$ and substituted with 0–1 $R^5$;

$B^4$ is selected from H, SO$_2$R$^{3b}$, C(O)R$^{3b}$, SO$_2$NR$^3$R$^{3b}$, C(O)NR$^3$R$^{3b}$, OR$^2$, and —CN;

$B^5$ is NR$^2$R$^{2f}$ or CR$^3$R$^2$R$^{2f}$;

ring Q is a 5–6 membered ring consisting of, in addition to the $Q^1$-CR$^{4d}$=Q$^2$ group shown, carbon atoms and 0–2 heteroatoms selected from N, O, and S(O)$_p$, and the ring is substituted with an additional 0–2 $R^{4d}$;

$Q^1$ and $Q^2$ are each N;

alternatively, $Q^1$ is CR$^3$ and $R^{4d}$ is NR$^2$R$^{2a}$ or NR$^{3a}$B$^4$, provided that when $Q^1$ is CR$^3$, then this R$^3$ group optionally forms a ring with the R$^2$ group of R$^{4d}$, this ring is a 5–6 membered ring consisting of, in addition to the C—C—N shown, carbon atoms and from 0–1 additional heteroatoms selected from N, O, and S(O)$_p$, and this ring is substituted with 0–1 $R^5$;

$Q^4$ is selected from C=O and SO$_2$;

ring $Q^3$ is a 4–7 membered monocyclic or tricyclic ring consisting of, in addition to the N-Q$^4$ group shown, carbon atoms and 0–2 heteroatoms selected from NR$^{4c}$, O, S, S(O), and S(O)$_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from NR$^{4c}$, O, S, S(O), and S(O)$_2$ and 0–1 double bonds are present within the ring; the fusion ring is phenyl or a 5–6 membered heteroaromatic consisting of carbon atoms and 1–2 heteroatoms selected from NR$^{4c}$, O, and S;

ring $Q^3$, which includes the 4–7 membered ring and the fusion ring, is substituted with 0–3 $R^4$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and S(O)p, the carbocycle or heterocycle further comprises 0–2 double bonds and 0–2 carbonyl groups, and the carbocycle or heterocycle is substituted with 0–2 $R^4$;

Y is CY$^1$Y$^2$R$^{4a}$, and Y$^1$ and Y$^2$ are independently $C_{1-3}$ alkyl substituted with 0–1 $R^4$;

alternatively, Y is selected from one of the following carbocycles and heterocycles that are substituted with 1 $R^{4a}$ and 0–2 $R^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

$Z^2$ is selected from H, $C_{1-4}$ alkyl, phenyl, benzyl, C(O)R$^{3b}$, S(O)R$^{3f}$, and S(O)$_2$R$^{3f}$;

$R^{1a}$, at each occurrence, is selected from H, —(CH$_2$)$_r$—R$^{1b}$, —(CH(CH$_3$))$_r$—R$^{1b}$, —(C(CH$_3$)$_2$)$_r$—R$^{1b}$, —O—(CR$^3$R$^{3a}$)$_r$—R$^{1b}$, —NR$^2$—(CR$^3$R$^{3a}$)$_r$—R$^{1b}$, and —S—(CR$^3$R$^{3a}$)$_r$—R$^{1b}$, provided that R$^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and S(O)$_p$, this ring being substituted with 0–2 $R^{4b}$ and 0–3 ring double bonds;

$R^{1b}$ is selected from H, CH$_3$, CH$_2$CH$_3$, CH$_2$CH$_2$CH$_3$, CH(CH$_3$)$_2$, F, Cl, Br, I, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^{2b}$, NR$^2$(CH$_2$)$_r$OR$^2$, NR$^2$C(O)R$^{2b}$, NR$^2$C(O)NHR$^2$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, $C_{5-6}$ carbocycle substituted with 0–2 $R^{4b}$, and 5–6 membered heterocycle consisting of carbon atoms and from 1–4 heteroatoms selected from the group consisting of N, O, and S(O)$_p$, and substituted with 0–2 $R^{4b}$, provided that $R^{1b}$ forms other than an O—O, N-halo, N—S, or N—CN bond;

$R^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 $R^{4b}$, $C_{5-6}$ carbocycle substituted with 0–2 $R^{4b}$, a CH$_2$—$C_{5-6}$ carbocycle substituted with 0–2 $R^{4b}$, and 5–6 membered heterocycle consisting of: carbon atoms and 1–4 heteroatoms selected from the group consisting of N, O, and S(O)$_p$, and substituted with 0–2 $R^{4b}$;

$R^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and S(O)$_p$, and substituted with 0–2 $R^{4b}$;

alternatively, NR$^2$R$^{2a}$ forms a 5 or 6 membered saturated, partially saturated, or unsaturated ring substituted with 0–2 $R^{4b}$ and consisting of: 0–1 additional heteroatoms selected from the group consisting of N, O, and S(O)$_p$;

$R^{2b}$, at each occurrence, is selected from CF$_3$, $C_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 $R^{4b}$, $C_{5-6}$ carbocycle substituted with 0–2 $R^{4b}$, and 5-6 membered heterocycle consisting of: carbon atoms and 1–4 heteroatoms selected from the group consisting of N, O, and S(O)$_p$, and substituted with 0–2 $R^{4b}$;

$R^{2c}$, at each occurrence, is selected from CF$_3$, OH, $C_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and S(O)$_p$, and substituted with 0–2 $R^{4b}$;

$R^{2d}$, at each occurrence, is selected from H, $R^{4c}$, $C_{1-4}$ alkyl substituted with 0–2 $R^{4c}$, —(CR$^3$R$^{3a}$)$_r$—$C_{3-6}$ carbocycle substituted with 0–2 $R^{4c}$, and —(CR$^3$R$^{3a}$)$_r$-5–6 membered heterocycle substituted with 0–2 $R^{4c}$ and consisting of: carbon atoms and 1–4 heteroatoms selected from the group consisting of N, O, and S(O)$_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

alternatively, $CR^2R^{2f}$ forms a 5–6 membered ring consisting of: carbon atoms and 0–2 heteroatoms selected from N, O, and $S(O)_p$, and this ring is substituted with 0–2 $R^{4b}$;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, when $B^5$ is $NR^2R^{2f}$, $B^4$ and $R^{2f}$ combine to form a 5–6 membered ring consisting of: carbon atoms and 0–2 additional heteroatoms selected from N, O, and $S(O)_p$, and this ring is substituted with 0–2 $R^{4b}$ and the $R^2$ group of $NR^2R^{2f}$, in addition to the groups recited below, is selected from $SO_2R^{3b}$ and $C(O)R^{3b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5–6 membered carbocycle substituted with 0–1 $R^{1a}$, and —$(C_{0-1}$ alkyl)-5–6 membered heterocycle substituted with 0–1 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2NR^2R^{2a}$, $S(O)_pR^{5a}$, $NR^2SO_2$—$C_{1-4}$ alkyl, $NR^2SO_2R^5$, $CF_3$, $CF_2CF_3$, 5–6 membered carbocycle substituted with 0–1 $R^5$, and a 5–6 membered heterocycle consisting of carbon atoms and 1–4 heteroatoms selected from the group consisting of N, O, and S $(O)_p$, and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-3}$ alkenyl, $C_{2-3}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OR^2$, $CH_2OR^2$, $C_{1-4}$ alkyl, —CN, $CH_2CN$, $NO_2$, $CH_2NO_2$, $NR^2R^{2a}$, $CH_2NR^2R^{2a}$, $CH_2C(O)R^{2c}$, $C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2R^5$, $(CH_2)_rS(O)_pR^{5a}$, $CH_2CF_3$, $CF_3$, 5–6 membered carbocycle substituted with 0–1 $R^5$, $CH_2$-5–6 membered carbocycle substituted with 0–1 $R^5$, a 5–6 membered heterocycle consisting of: carbon atoms and 1–4 heteroatoms selected from the group consisting of N, O, and $S(O)_p$ and substituted with 0–1 $R^5$, and a $CH_2$-5–6 membered heterocycle consisting of: carbon atoms and 1–4 heteroatoms selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^{5a}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

In a third embodiment, the present invention provides a novel compound, wherein:
ring M is substituted with 0–2 $R^{1a}$ and is selected from the group:
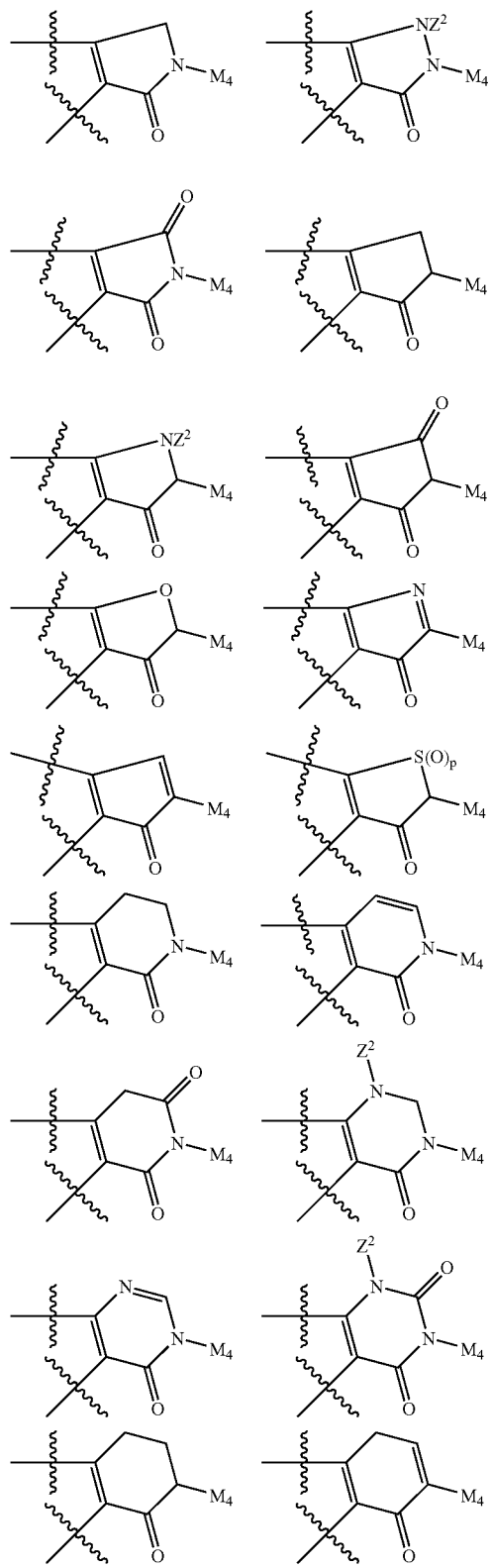
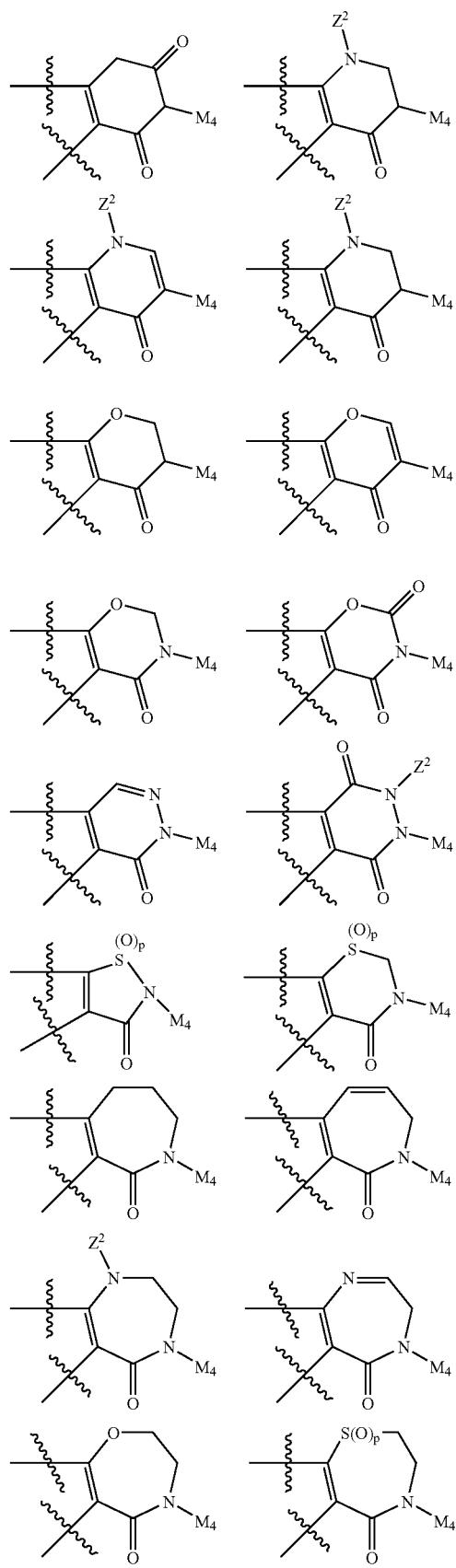

-continued
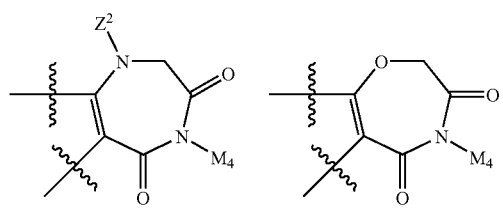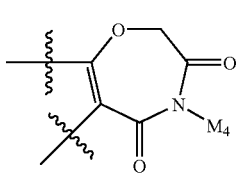
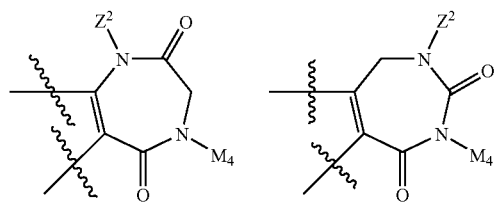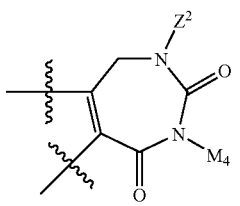
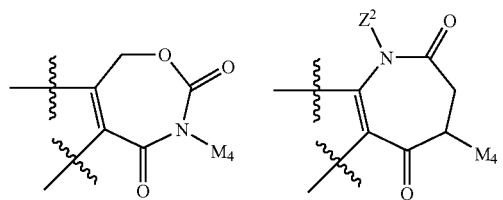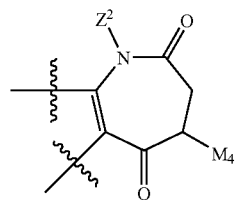
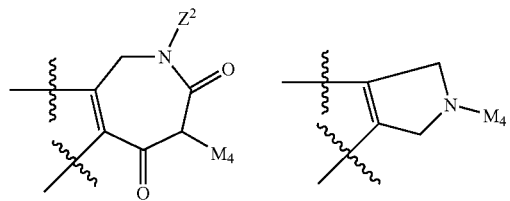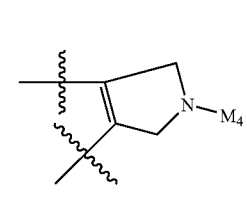
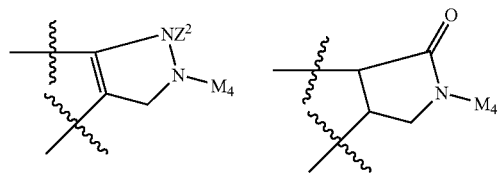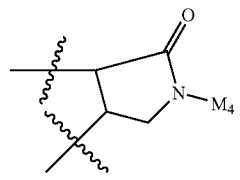
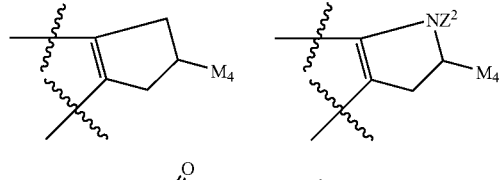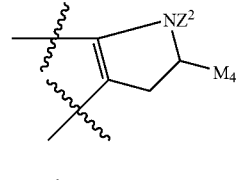
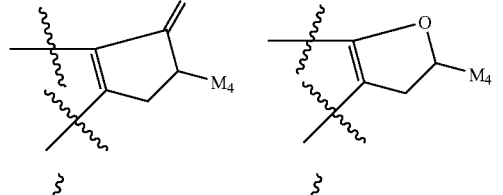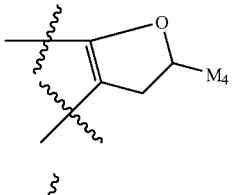
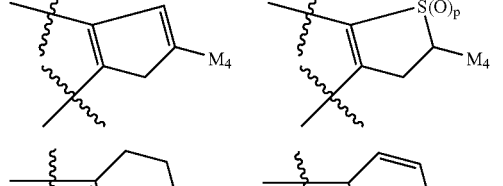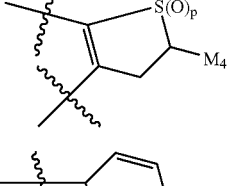
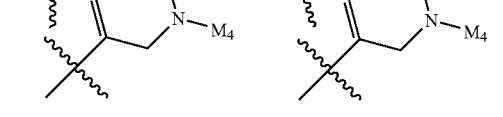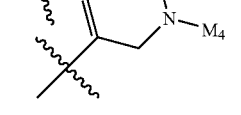
-continued
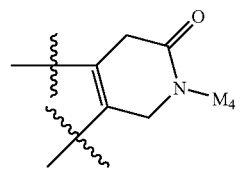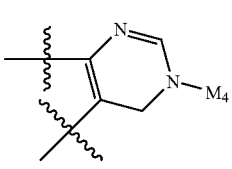
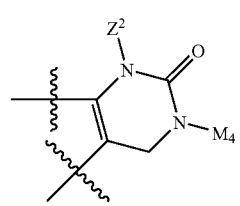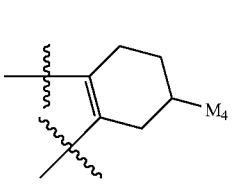
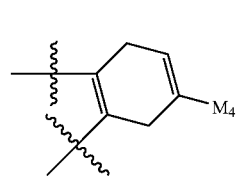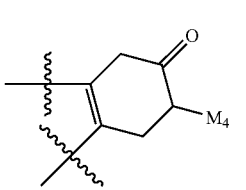
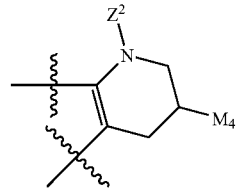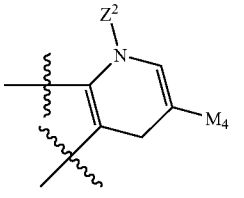
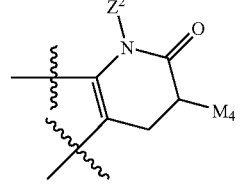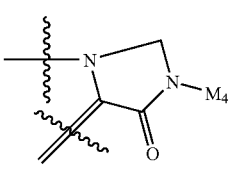
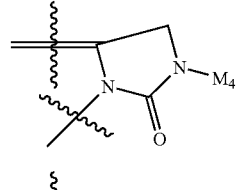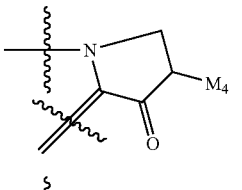
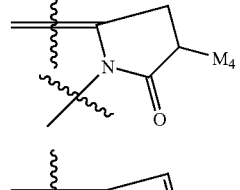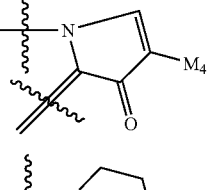
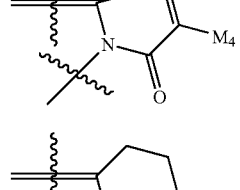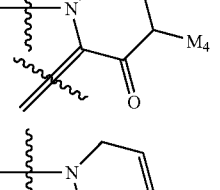
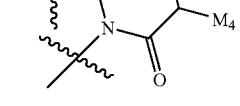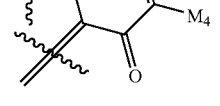

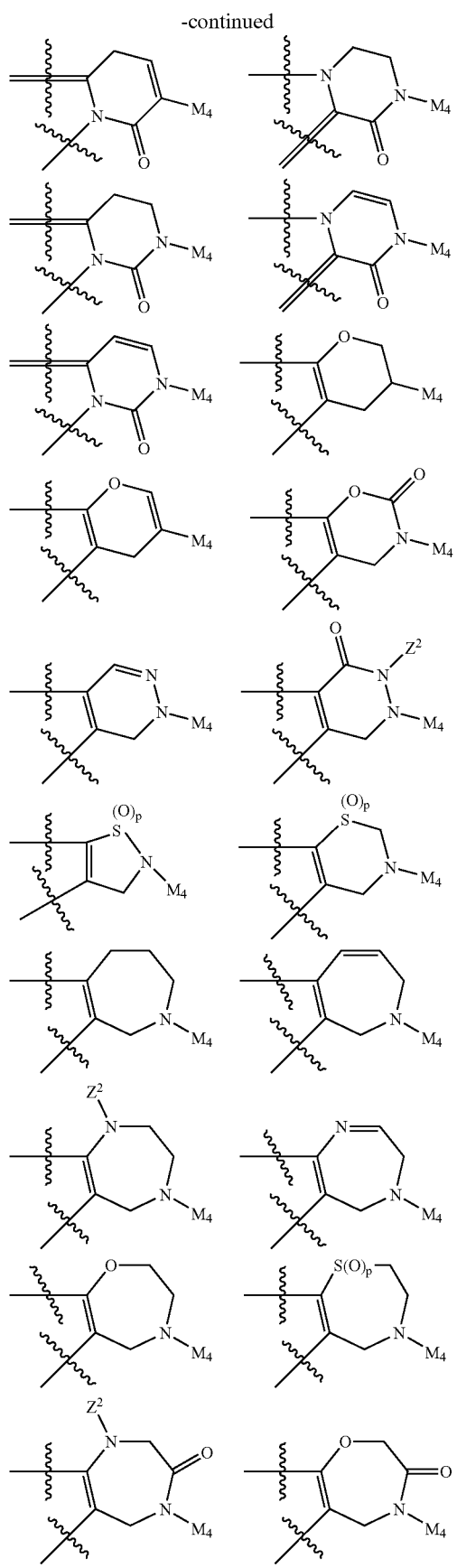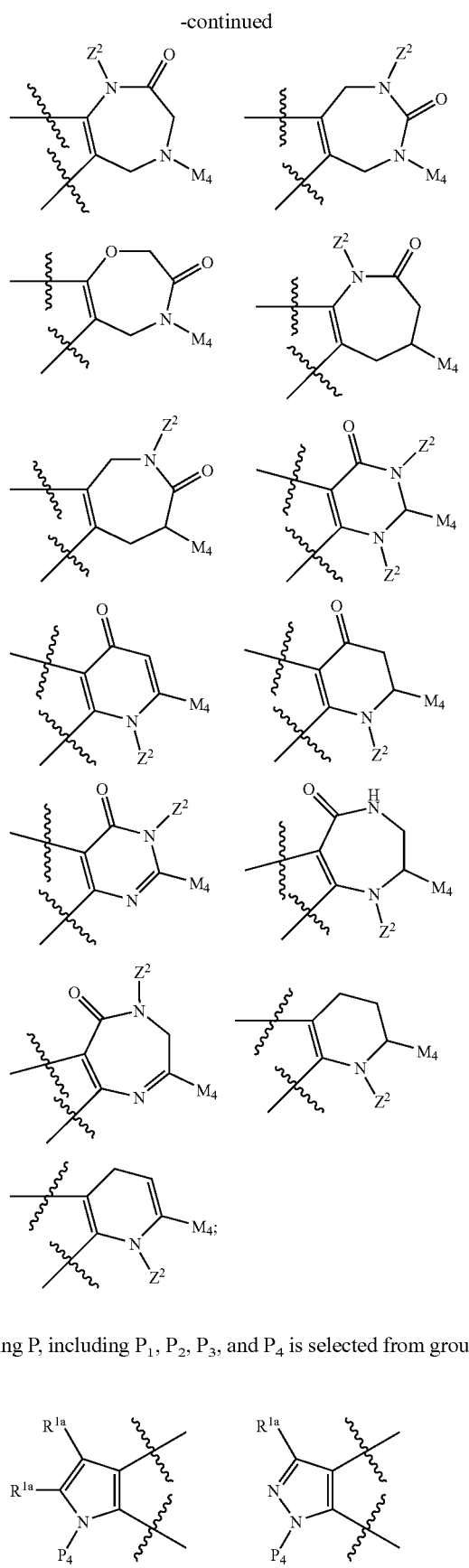
ring P, including $P_1$, $P_2$, $P_3$, and $P_4$ is selected from group:
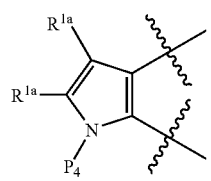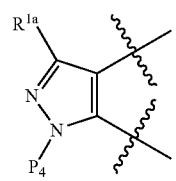

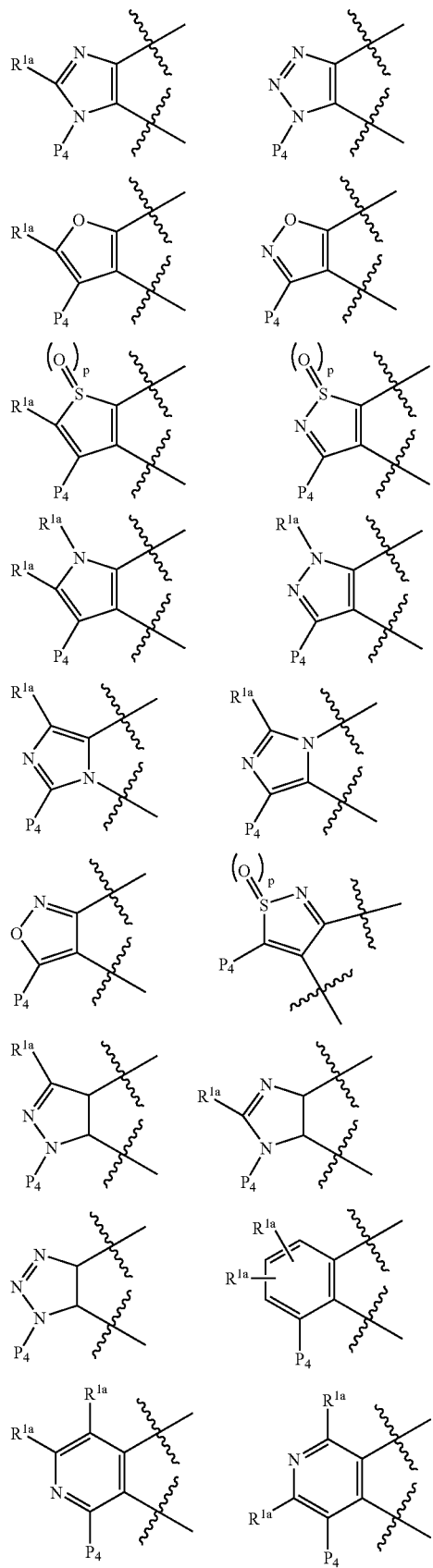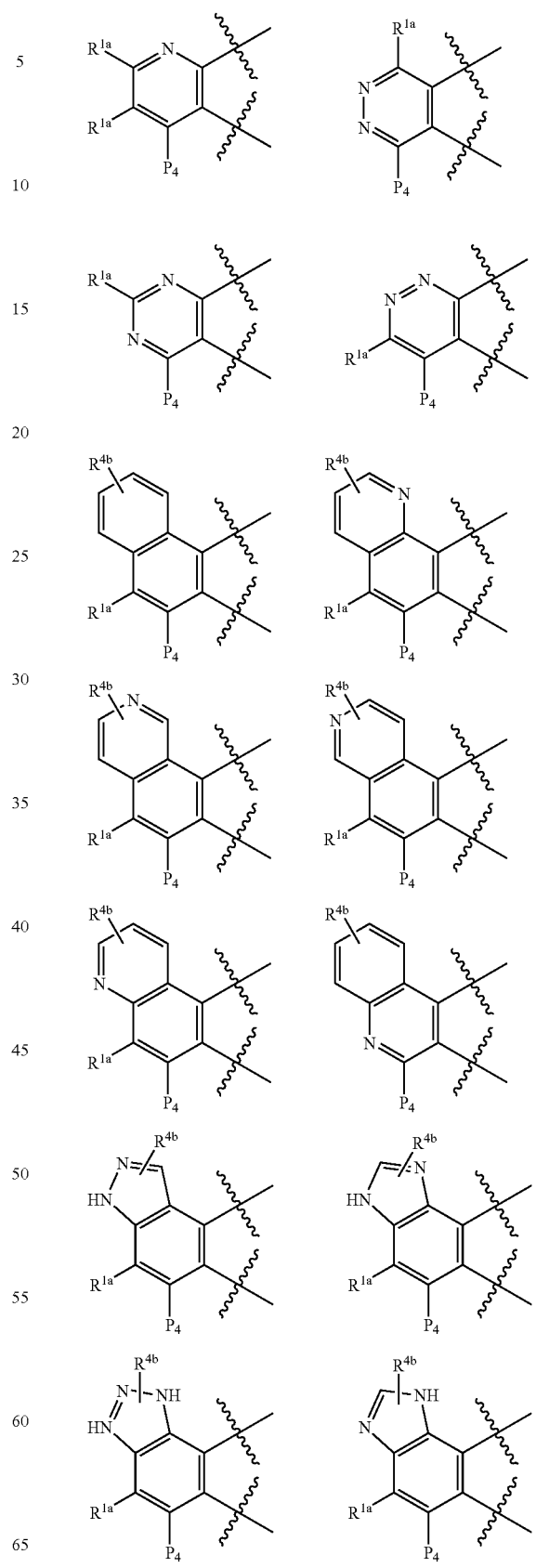

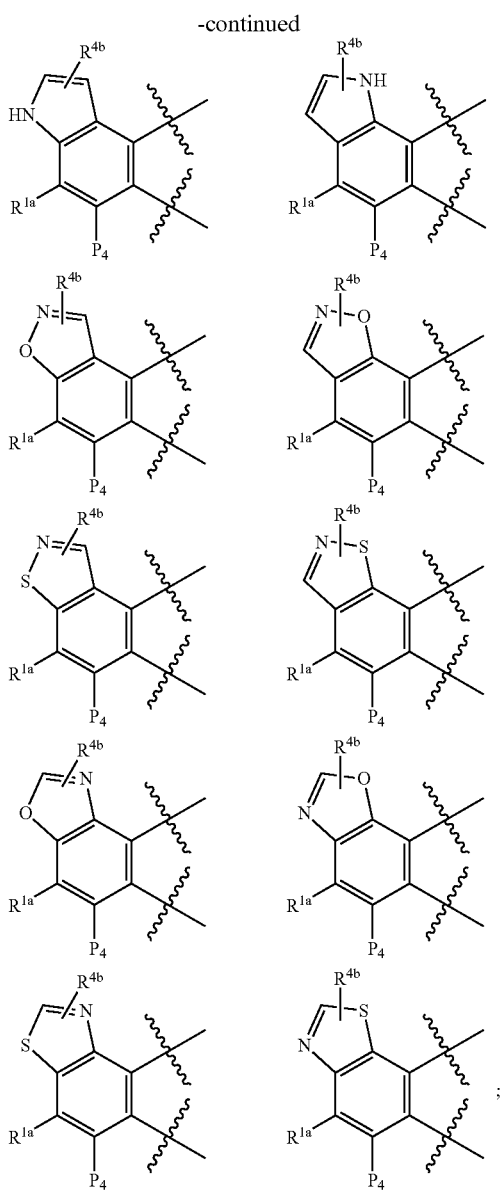

one of $P_4$ and $M_4$ is -A-B and the other -$G_1$-G;

G is selected from the group: phenyl; 4-ethyl-phenyl; 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4-chloro-phenyl; 3-aminomethyl-phenyl; 3-amino-phenyl; 3-chloro-4-fluoro-phenyl; 3-chloro-phenyl; 3-hydroxy-4-methoxy-phenyl; 4-(N,N-dimethylamino)-5-chloro-thien-2-yl; 4-(N-methylamino)-5-chloro-thien-2-yl; 4-amino-5-chloro-thien-2-yl; 4-amino-pyrid-2-yl; 4-chloro-3-fluoro-phenyl; 4-chloro-phenyl; 4-chloro-pyrid-2-yl; 4-methoxy-2-methylsulfonyl-phenyl; 4-methoxy-phenyl; 2-methoxy-pyridyl-5-yl; 5-(N,N-dimethylamino)-4-chloro-thien-2-yl; 5-(N-methylamino)-4-chloro-thien-2-yl; 5-amino-4-chloro-thien-2-yl; 5-chloro-2-aminosulfonyl-phenyl; 5-chloro-2-methylsulfonyl-phenyl; 5-chloro-pyrid-2-yl; 5-chloro-thien-2-yl; 6-amino-5-chloro-pyrid-2-yl; 6-amino-pyrid-2-yl;

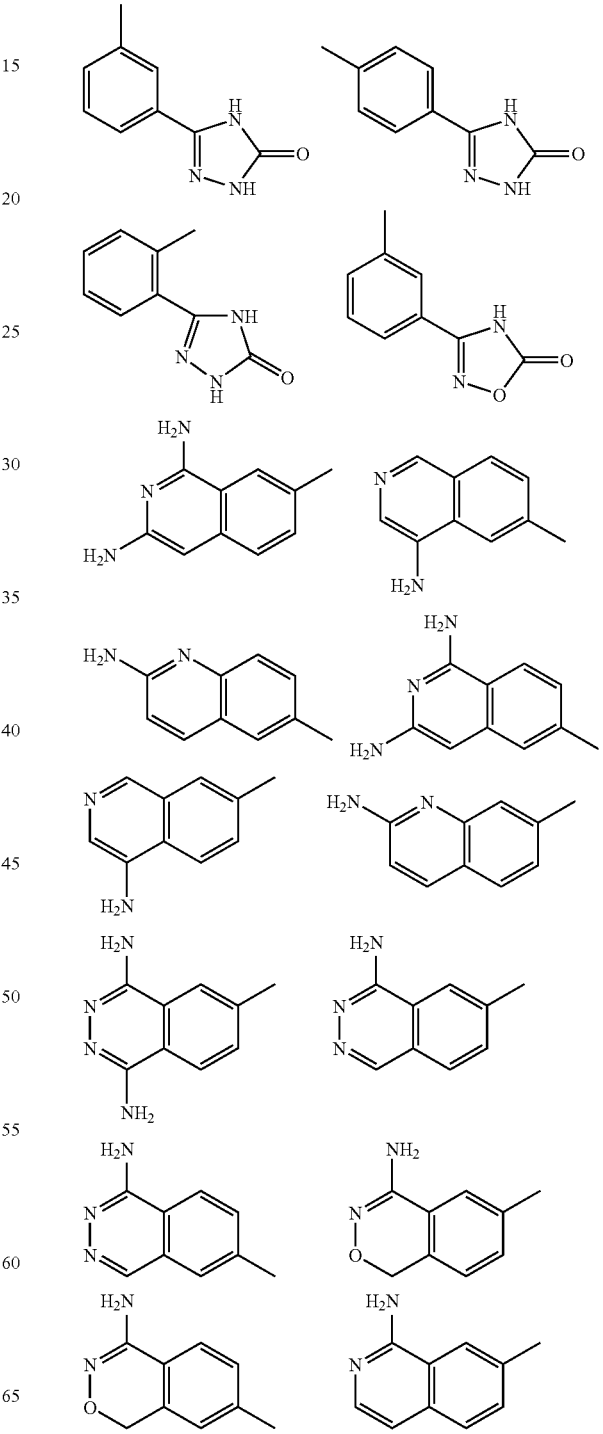

-continued
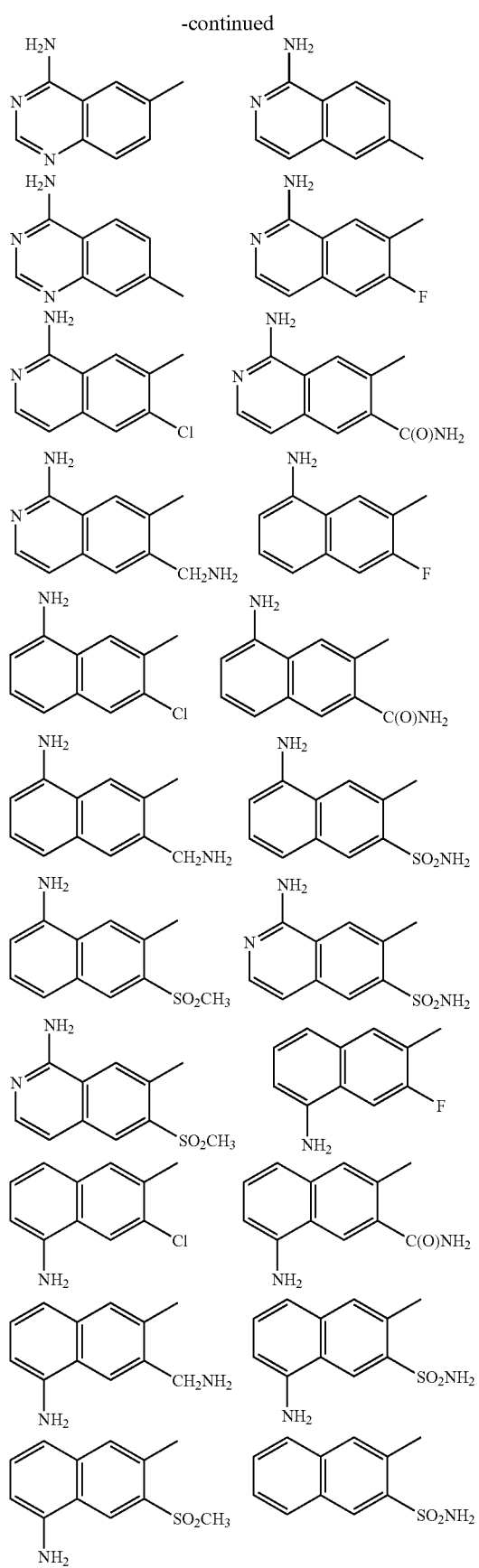
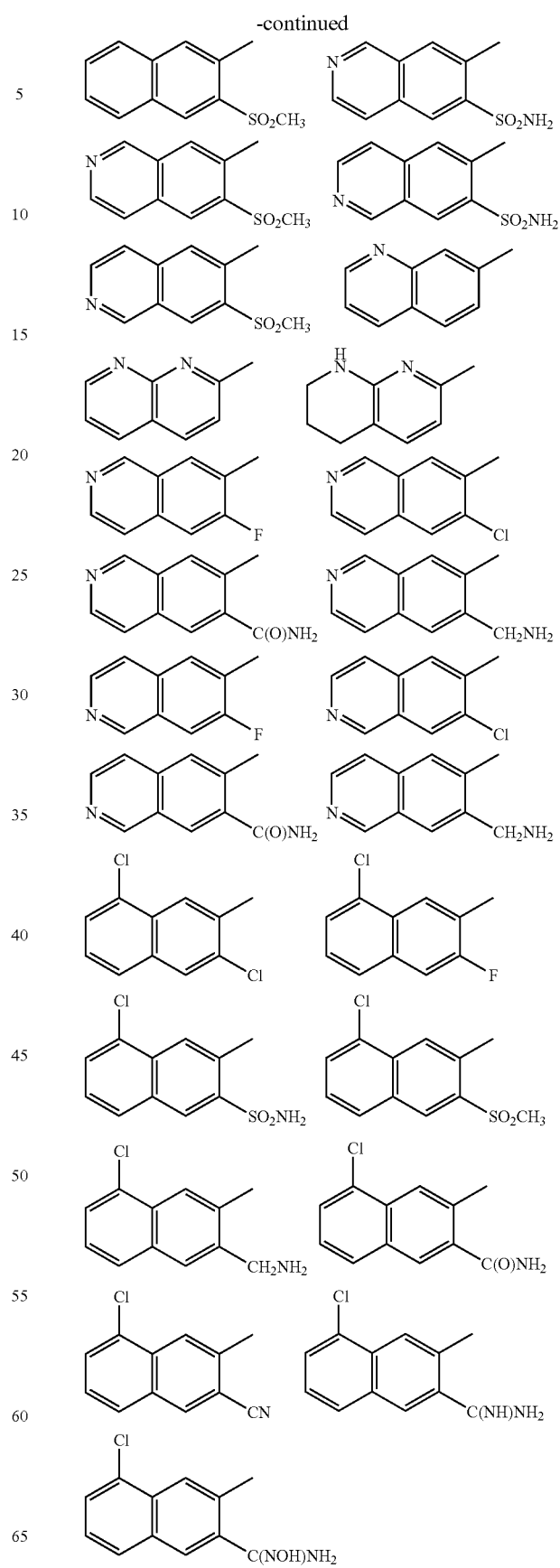

-continued
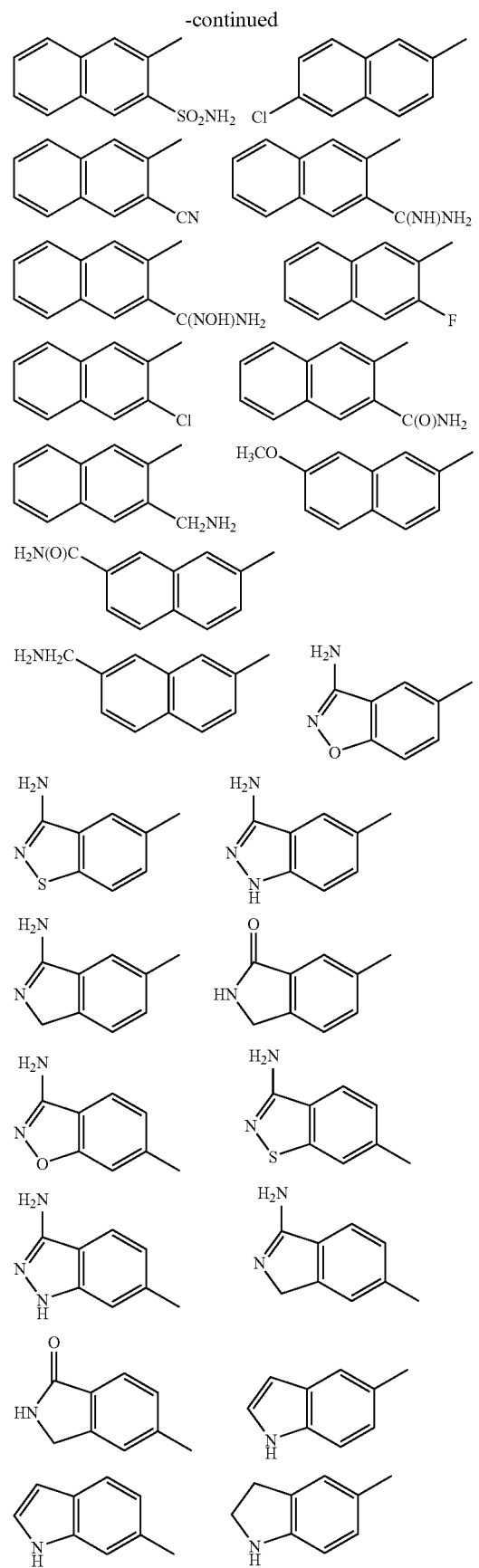
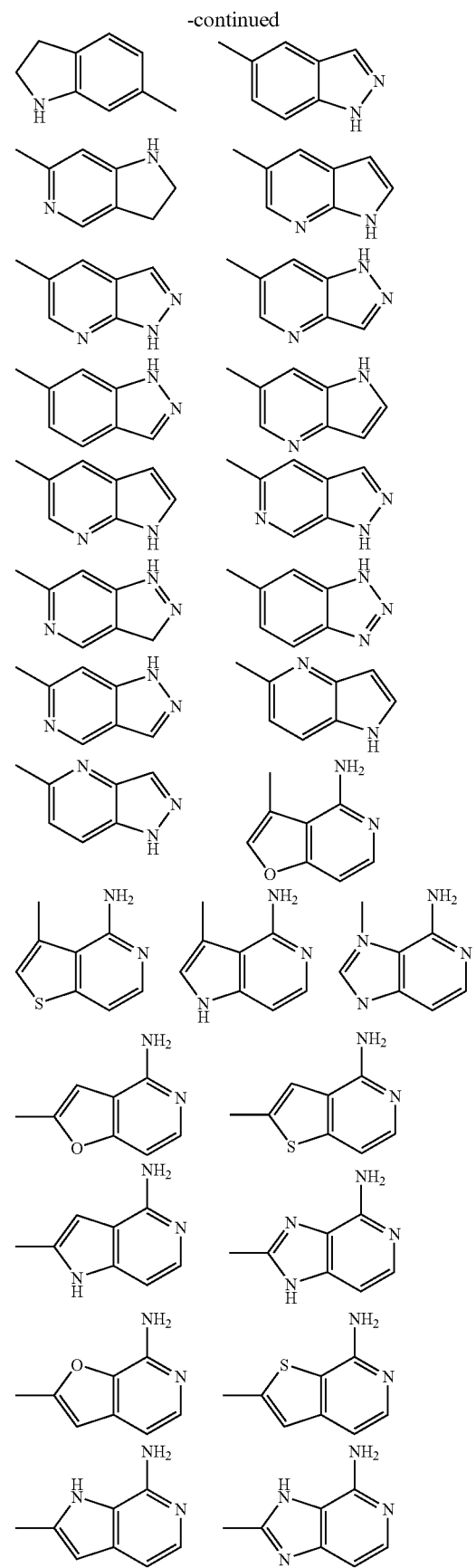

-continued

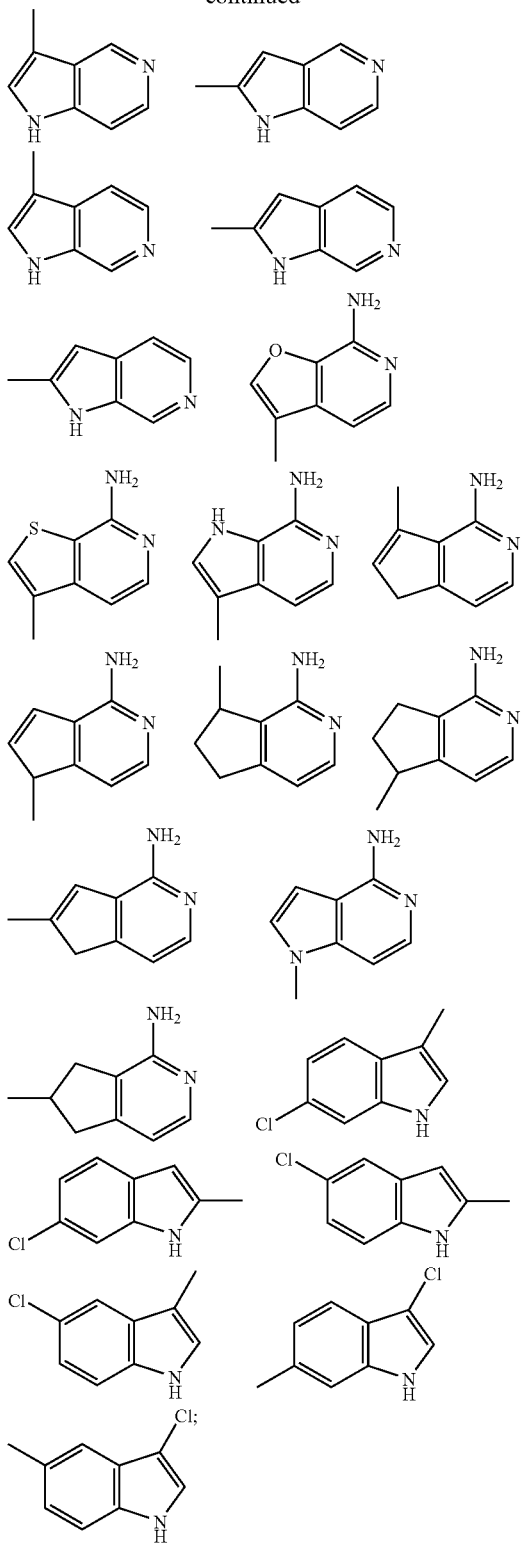

$G_1$ is absent or is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, and $(CR^3R^{3a})_uS(O)_2NR^{3b}(CR^3R^{3a})_w$, wherein u+w total 0, 1, or 2 and the right side of $G_1$ is attached to ring G, provided that $G_1$ does not form a N—S, NCH$_2$N, NCH$_2$O, or NCH$_2$S bond with either group to which it is attached;

A is 2–6 membered linear chain consisting of: carbon atoms, 0–2 carbonyl groups, and 0–2 heteroatoms selected from O, N, and $S(O)_p$, and A is substituted with 0–2 $R^{1a}$ and 0–2 $R^2$, and there are 0–1 double bonds and 0–1 triple bonds; provided that other than an S—S, S—O, or O—O bond is present in A;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$ and $OR^2$;

$B^5$ is $NR^2R^{2f}$;

ring Q is a 5–6 membered ring consisting of, in addition to the N—$CR^{4d}$=N group shown, carbon atoms and 0–2 heteroatoms selected from N, O, and $S(O)_p$, and the ring is substituted with an additional 0–2 $R^{4d}$;

$Q^4$ is selected from C=O and $SO_2$;

ring $Q^3$ is a 5–7 membered ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^{4a}$;

alternatively, ring $Q^3$ is a 5–7 membered ring to which another ring is fused, wherein: the 5–7 membered ring consists of, in addition to the shown amide group, carbon atoms and 0–2 heteroatoms selected from $NR^{4c}$, O, S, S(O), and $S(O)_2$, and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 5–7 membered ring and the fusion ring, is substituted with 0–3 $R^{4a}$;

ring $Q^5$, is a $C_{3-6}$ monocyclic carbocycle or 5–6 membered monocyclic heterocycle, wherein the carbocycle or heterocycle consists of: carbon atoms and 0–2 heteroatoms selected from N, O, and S(O)p, the carbocycle or heterocycle further comprises 0–1 double bonds and 0–1 carbonyl groups, and the carbocycle or heterocycle is substituted with 0–2 $R^4$;

Y is $CY^1Y^2R^{4a}$, and $Y^1$ and $Y^2$ are independently $C_{1-2}$ alkyl substituted with 0–1 $R^4$;

alternatively, Y is selected from one of the following carbocycles and heterocycles that are substituted with 1 $R^{4a}$ and 0–1 $R^4$: cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4- thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzimidazolonyl, benzoxazolyl, benzthiazolyl, indazolyl, benzisoxazolyl, benzisothiazolyl, and isoindazolyl;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $CH_3$, $CH_2CH_3$, $CH_2CH_2CH_3$, $CH(CH_3)_2$, $OCH_3$, and benzyl;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, $B^4$ and $R^{2f}$ combine to form a 5–6 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_3$, $CH_2CH(CH_3)_2$, $CH(CH_3)$ $CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_rNR^{2d}C(O)R^{2e}$, $(CR^3R^{3g})_rC(O)R^{2e}$, $(CR^3R^{3g})_rOC(O)R^{2e}$, $(CR^3R^{3g})_rC(O)NR^{2d}R^{2d}$, $(CR^3R^{3g})_rC(O)OR^{2d}$, $(CR^3R^{3g})_rNR^{2d}C(O)NR^{2d}R^{2d}$, $(CR^3R^{3g})_rNR^{2d}C(O)OR^{2d}$, $(CR^3R^{3g})_rSO_2NR^{2d}R^{2d}$, $(CR^3R^{3g})_rNR^{2d}SO_2R^{2d}$, and $(CR^3R^{3g})_rS(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)$ $R^{3a}$, $C(O)NR^3R^{3a}$, $CH_2C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, $C_{2-3}$ alkenyl, $C_{2-3}$ alkynyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OR^2$, $CH_2OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6 membered carbocycle substituted with 0–1 $R^5$, and a 5–6 membered heterocycle consisting of: carbon atoms and 1–2 heteroatoms selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

In a fourth embodiment, the present invention provides a novel compound, wherein:

ring M is substituted with 0–2 $R^{1a}$ and is selected from the group:

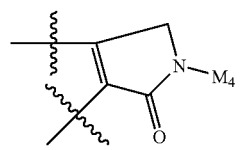
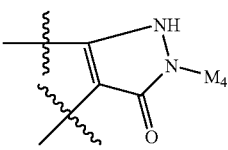
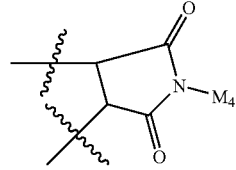
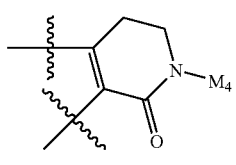
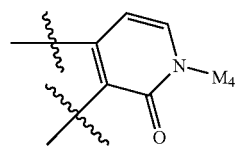
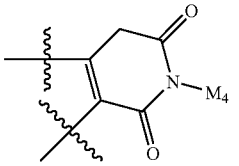
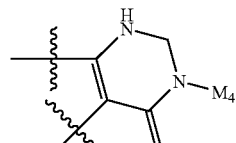
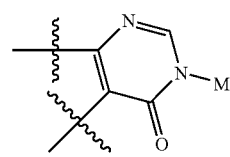
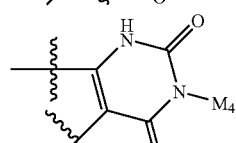
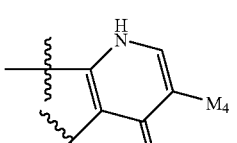
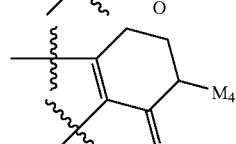
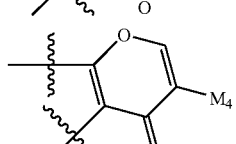

-continued

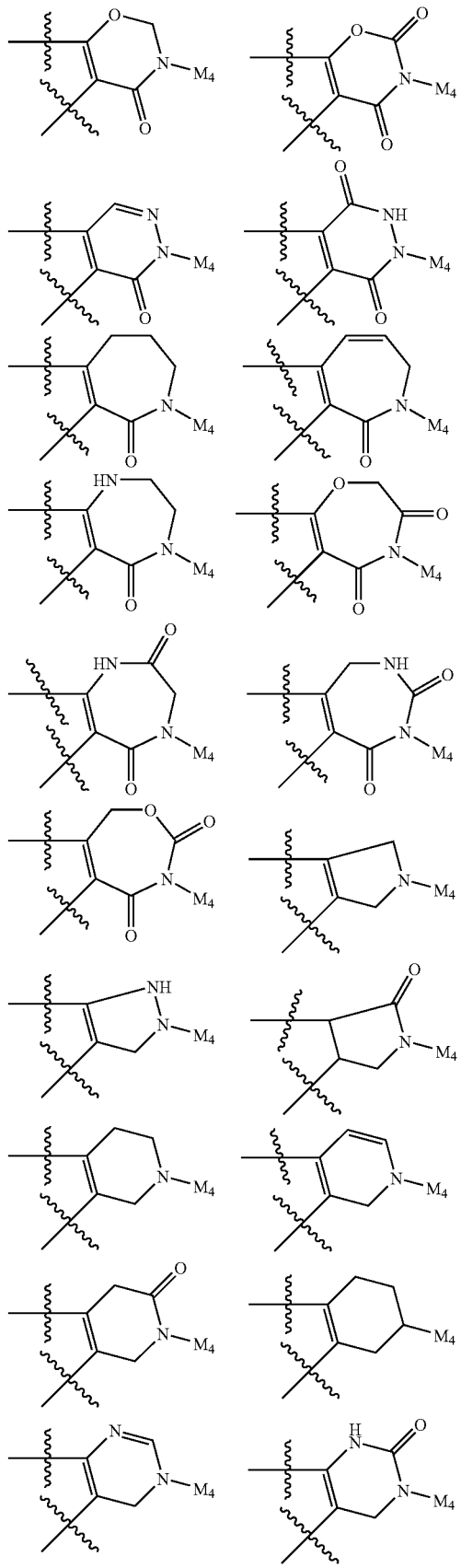

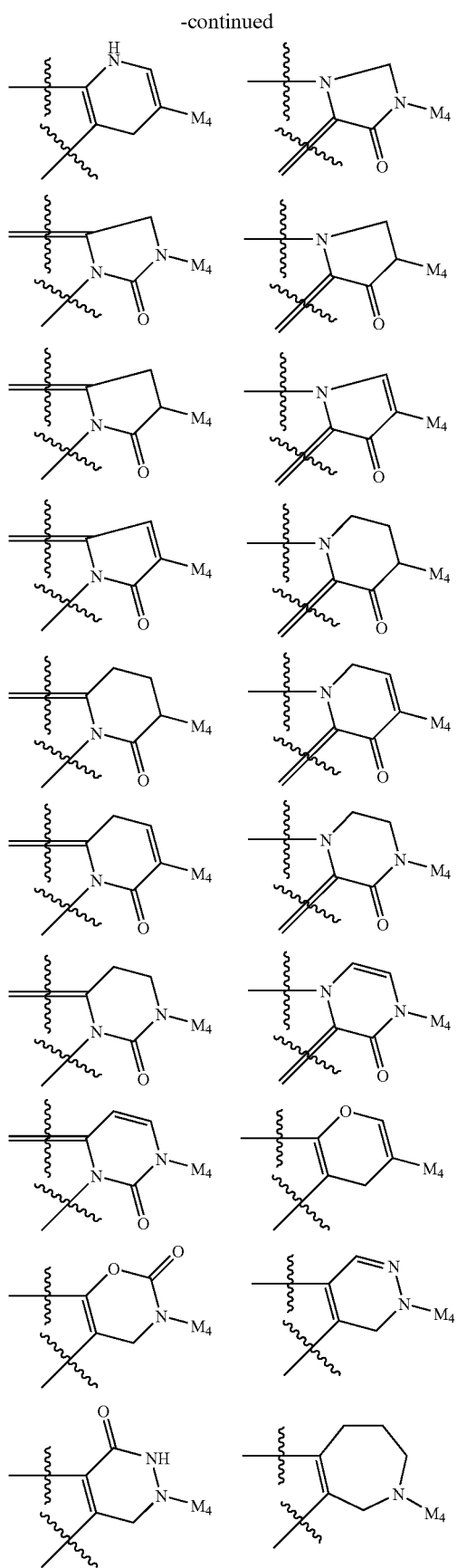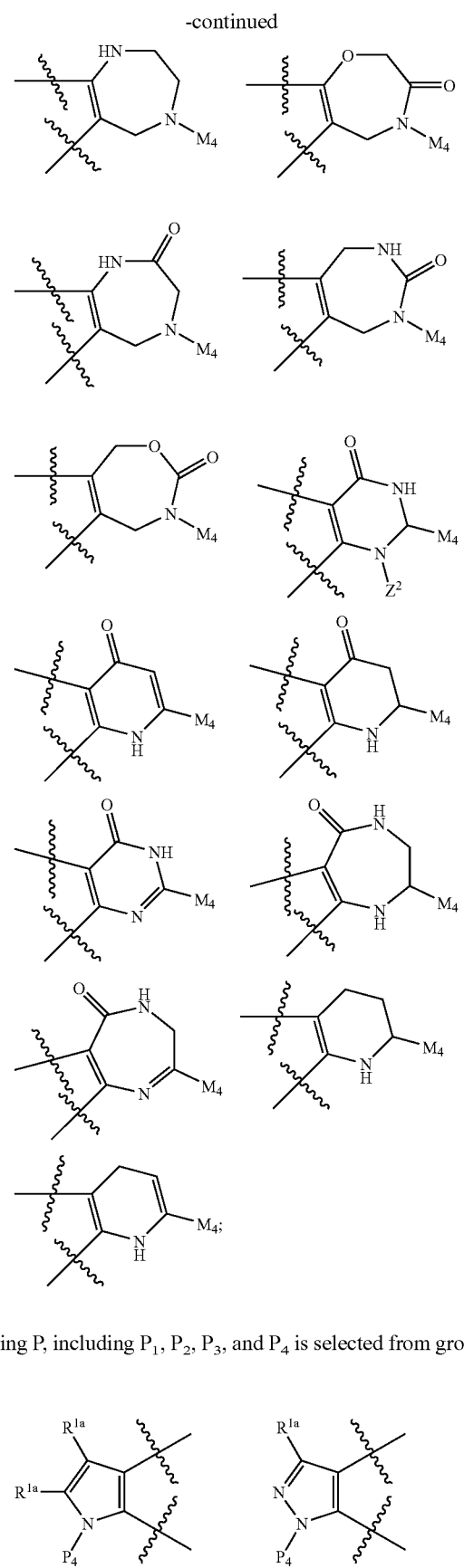
ring P, including $P_1$, $P_2$, $P_3$, and $P_4$ is selected from group:
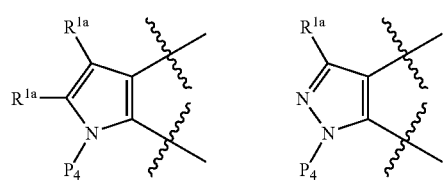

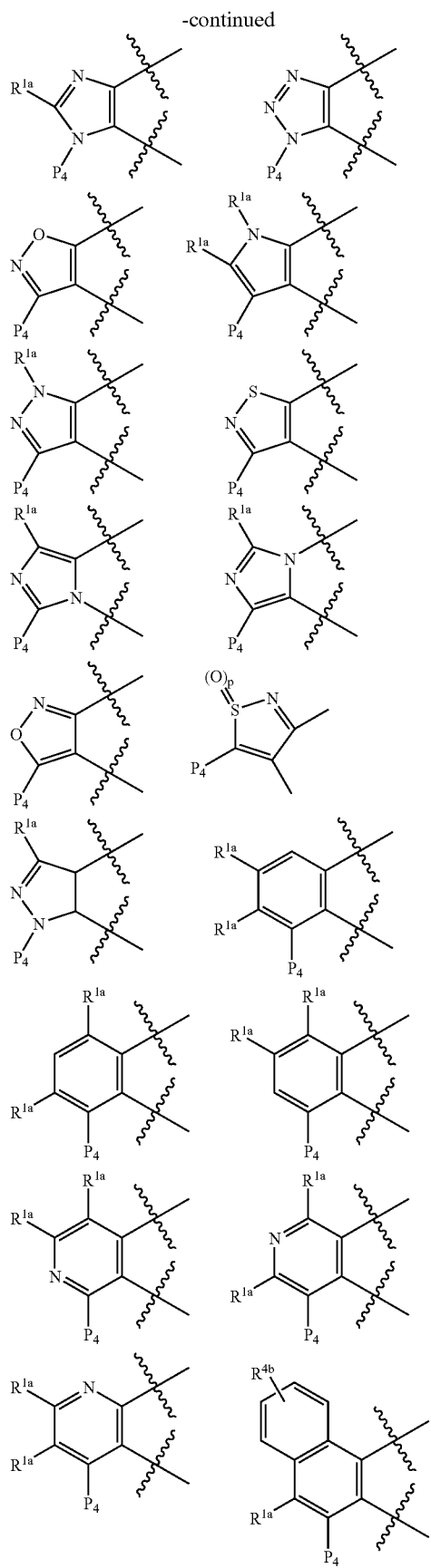

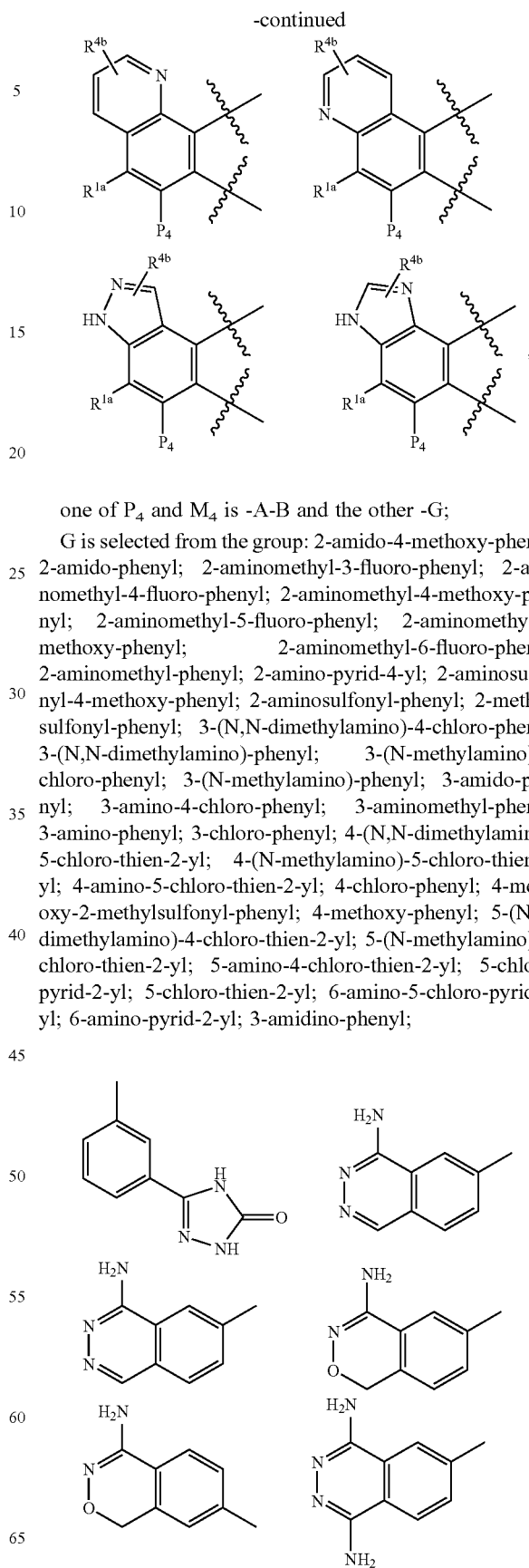

one of $P_4$ and $M_4$ is -A-B and the other -G;

G is selected from the group: 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-5-chloro-thien-2-yl; 4-(N-methylamino)-5-chloro-thien-2-yl; 4-amino-5-chloro-thien-2-yl; 4-chloro-phenyl; 4-methoxy-2-methylsulfonyl-phenyl; 4-methoxy-phenyl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 6-amino-5-chloro-pyrid-2-yl; 6-amino-pyrid-2-yl; 3-amidino-phenyl;

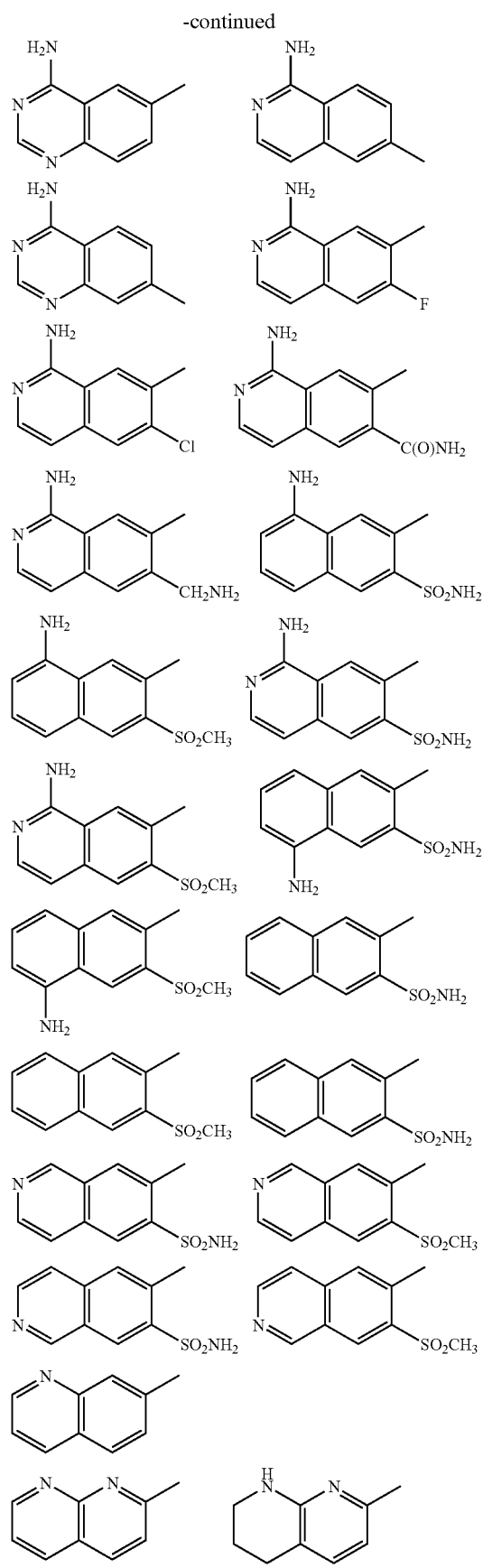
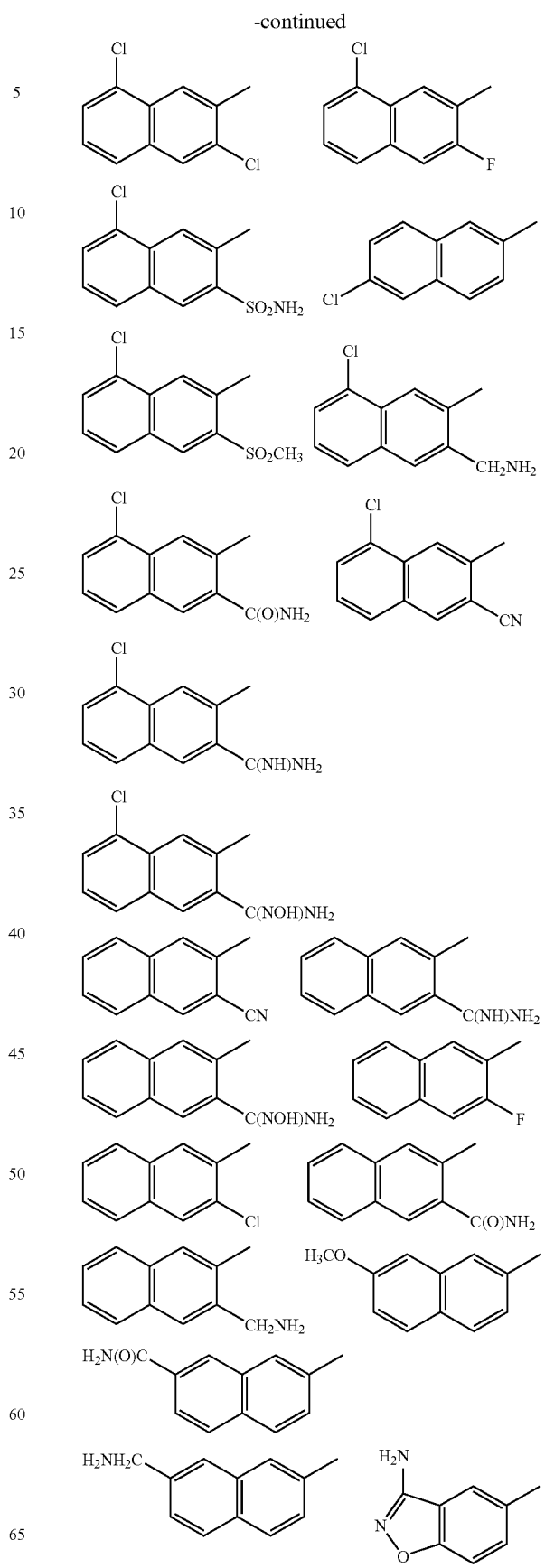

-continued

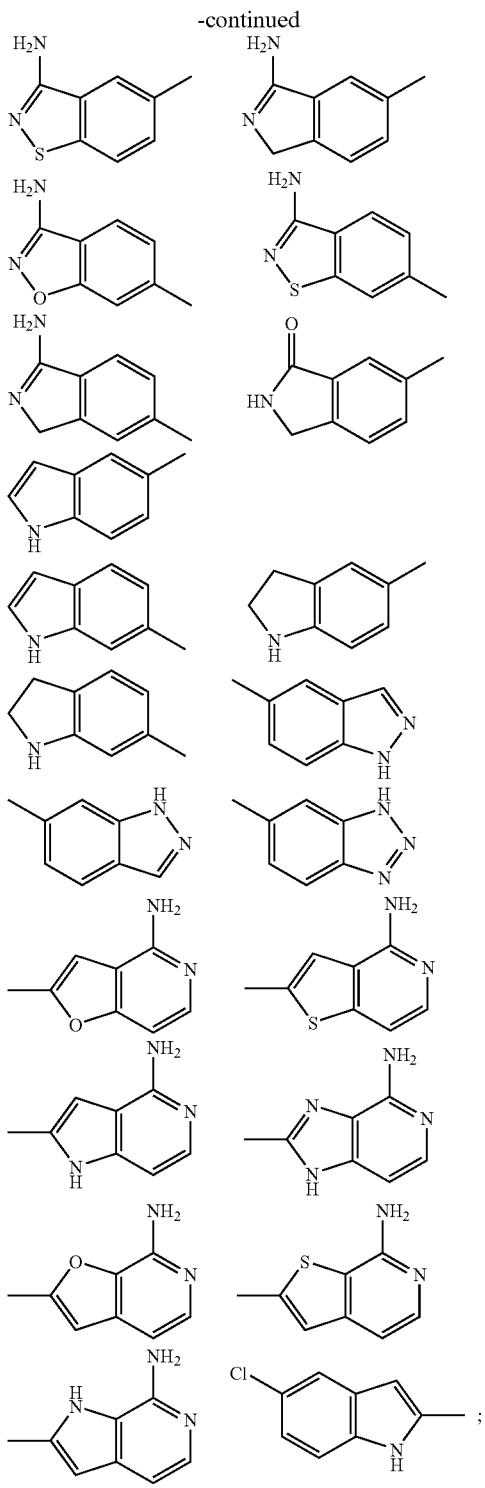

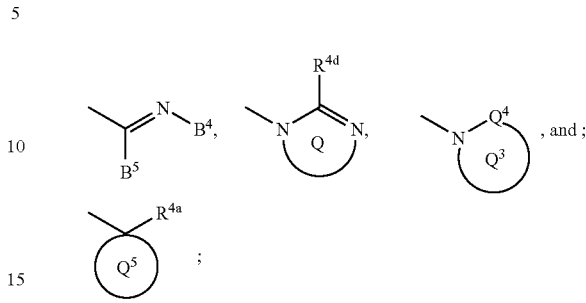

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $CH_2S(O)_2$, $S(O)_2(CH_2)$, $SO_2NH$, and $NHSO_2$, wherein the right side of $G_1$ is attached to ring G, provided that $G_1$ does not form a N—S, $NCH_2N$, $NCH_2O$, or $NCH_2S$ bond with either group to which it is attached;

A is 2–6 membered linear chain consisting of: carbon atoms, 0–1 carbonyl groups, and 0–1 heteroatoms selected from O, N, and $S(O)_p$, and A is substituted with 0–1 $R^{1a}$ and 0–2 $R^2$, and there are 0–1 double bonds; provided that other than an S—S, S—O, or O—O bond is present in A;

B is selected from Y, $N(B^1)C(O)C(R^3R^{3g})NB^2B^3$, provided that the $R^{4d}$ shown is other than OH;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$ and $OR^2$;

$B^5$ is $NR^2R^{2f}$;

ring Q is a 5–6 membered ring consisting of, in addition to the N—$CR^{4d}$=N group shown, carbon atoms and 0–1 heteroatoms selected from N, O, and $S(O)_p$, and the ring is substituted with an additional 0–2 $R^{4d}$;

$Q^4$ is selected from C=O and $SO_2$;

ring $Q^3$ is a 6–7 membered ring consisting of, in addition to the N-$Q^4$ group shown, carbon atoms and 0–1 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 5–7 membered ring to which another ring is fused, wherein: the 5–7 membered ring consists of, in addition to the shown amide group, carbon atoms and 0–1 heteroatoms selected from $NR^{4c}$, O, S, S(O), and $S(O)_2$, and 0–1 double bonds are present within the ring; the fusion ring is phenyl;

ring $Q^3$, which includes the 5–7 membered ring and the fusion ring, is substituted with 0–2 $R^4$;

ring $Q^5$ is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and is substituted with 0–1 $R^4$;

Y is selected from $C(CH_3)_2R^{4a}$ and $C(CH_2CH_3)_2R^{4a}$;

alternatively, Y is selected from phenyl, pyridyl, pyrrolidino, morpholino, 1,2,3-triazolyl, imidazolyl, and benzimidazolyl, and is substituted with 1 $R^{4a}$ and 0–1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^{2b}$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5–6 membered aromatic heterocycle consisting of: carbon atoms and 1–4 heteroatoms selected from the group consisting of N, O, and S(O)$_p$, and substituted with 0–1 R$^{4b}$;

R$^{2a}$, at each occurrence, is selected from H, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle consisting of: carbon atoms and 1–4 heteroatoms selected from the group consisting of N, O, and S(O)$_p$, and substituted with 0–1 R$^{4b}$;

alternatively, NR$^2$R$^{2a}$ forms a 5 or 6 membered saturated, partially saturated, or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle consisting of: carbon atoms and 1–4 heteroatoms selected from the group consisting of N, O, and S(O)$_p$, and substituted with 0–1 R$^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle containing from 1–4 heteroatoms selected from the group consisting of N, O, and S(O)$_p$, and substituted with 0–1 R$^{4b}$;

R$^{2d}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CH$_2$)-5–6 membered heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CH$_2$)-5–6 membered heterocycle and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CH$_3$, CH$_2$CH$_3$, OCH$_3$, and benzyl;

alternatively, NR$^2$R$^{2f}$ forms a 5–6 membered ring consisting of: carbon atoms and 0–1 additional heteroatoms selected from N, O, and S(O)$_p$, and this ring is substituted with 0–1 R$^{4b}$;

alternatively, B$^4$ and R$^{2f}$ combine to form a 5 membered ring consisting of: carbon atoms and 0–1 additional heteroatoms selected from N, O, and S(O)$_p$, and this ring is substituted with 0–2 R$^{4b}$ and the R$^2$ group of NR$^2$R$^{2f}$, in addition to the groups recited below, can be SO$_2$R$^{3b}$;

R$^{3b}$, at each occurrence, is selected from H and CH$_3$;

R$^4$, at each occurrence, is selected from H, =O, OH, OR$^2$, CH$_2$OR$^2$, (CH$_2$)$_2$OR$^2$, F, Br, Cl, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

R$^{4a}$ is selected from —(CR$^3$R$^{3g}$)$_r$-5–6 membered carbocycle substituted with 0–3 R$^{4c}$, —(CR$^3$R$^{3g}$)$_r$-5–6 membered heterocycle substituted with 0–3 R$^{4c}$ and consisting of: carbon atoms and 1–4 heteroatoms selected from the group consisting of N, O, and S(O)$_p$, (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$NR$^{2d}$C(O)R$^{2e}$, (CR$^3$R$^{3g}$)$_r$C(O)R$^{2e}$, (CR$^3$R$^{3g}$)$_r$C(O)NR$^{2d}$R$^{2d}$, (CR$^3$R$^{3g}$)$_r$NR$^{2d}$C(O)NR$^{2d}$R$^{2d}$, (CR$^3$R$^{3g}$)$_r$NR$^{2d}$C(O)OR$^{2d}$, (CR$^3$R$^{3g}$)$_r$NR$^{2d}$SO$_2$R$^{2d}$, and (CR$^3$R$^{3g}$)$_r$S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-3}$ alkenyl, C$_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a fifth embodiment, the present invention provides a novel compound, wherein:

ring M is substituted with 0–1 R$^{1a}$ and is selected from the group:

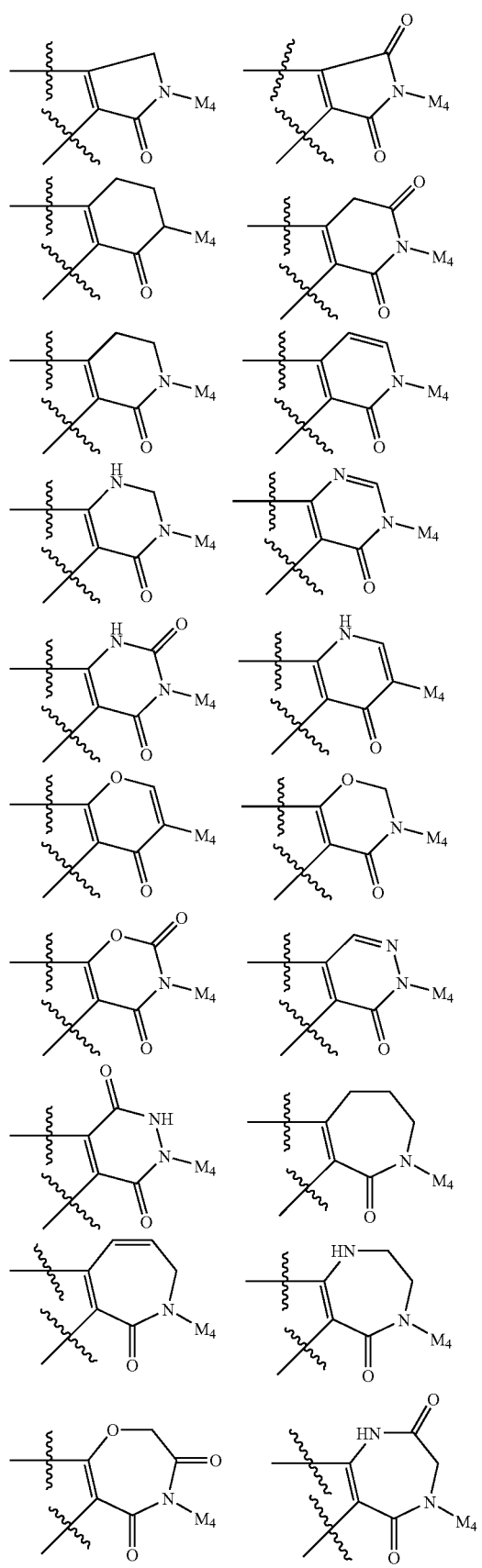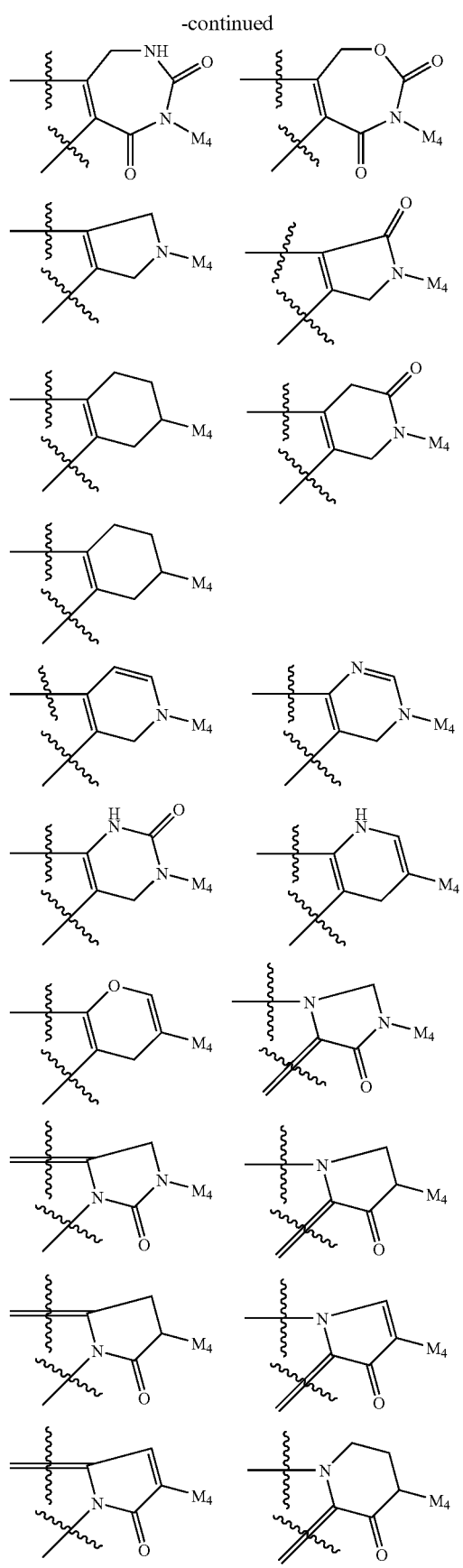

-continued

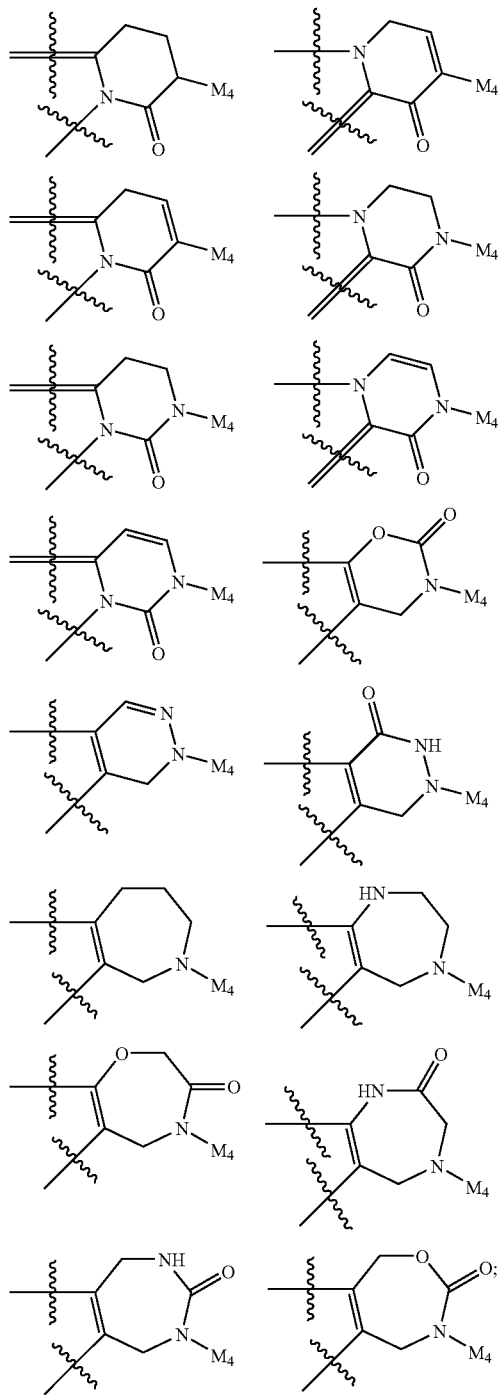
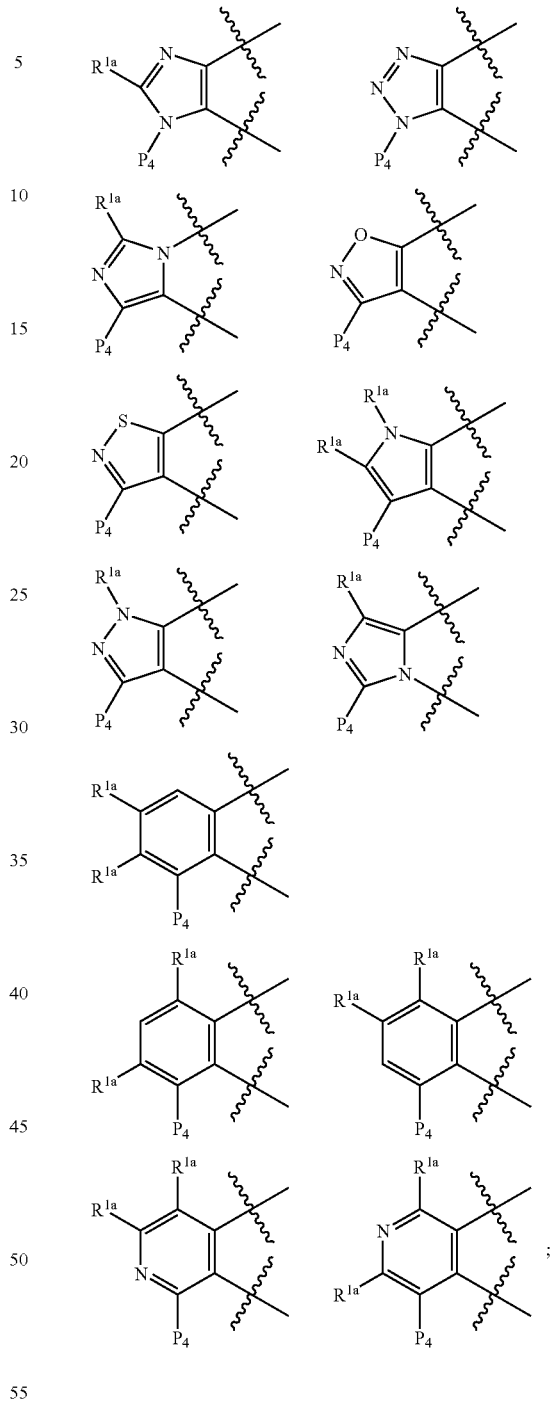

ring P, including $P_1$, $P_2$, $P_3$, and $P_4$ is selected from group:

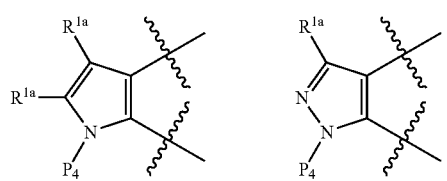

one of $P_4$ and $M_4$ is -A-B and the other -G;

G is selected from: 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 5-chloro-pyrid-2-yl; 5-chloro-thien-2-yl; 6-amino-5-chloro-pyrid-2-yl; 6-amino-pyrid-2-yl; 3-amidino-phenyl;

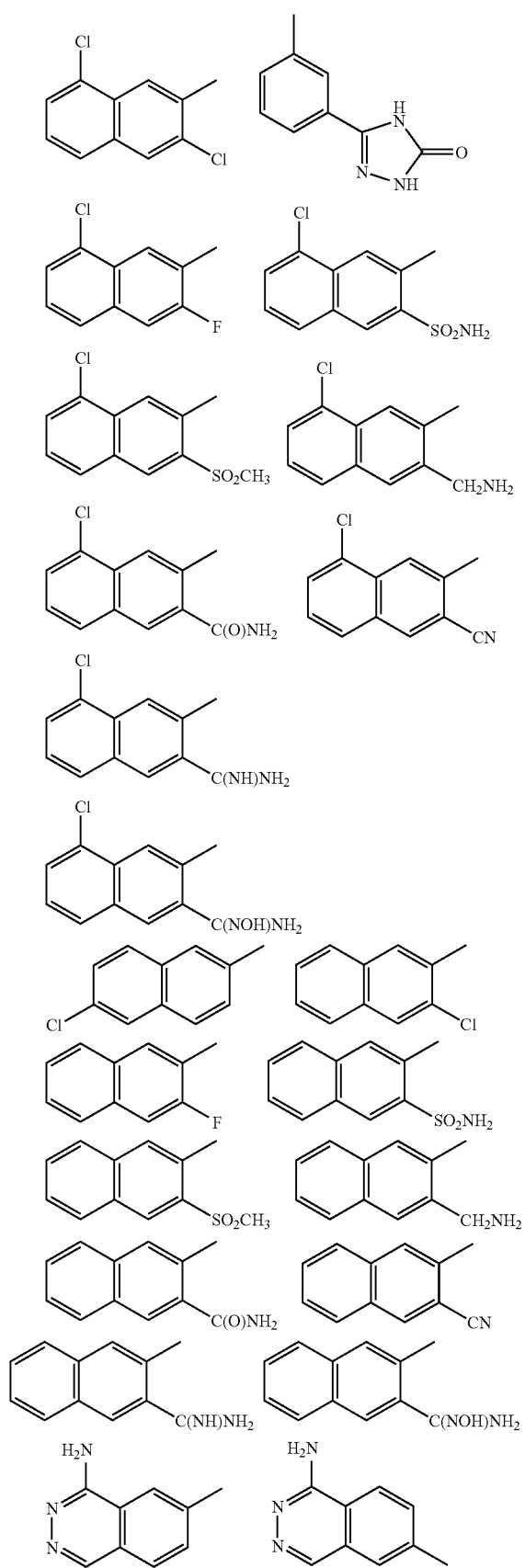
-continued
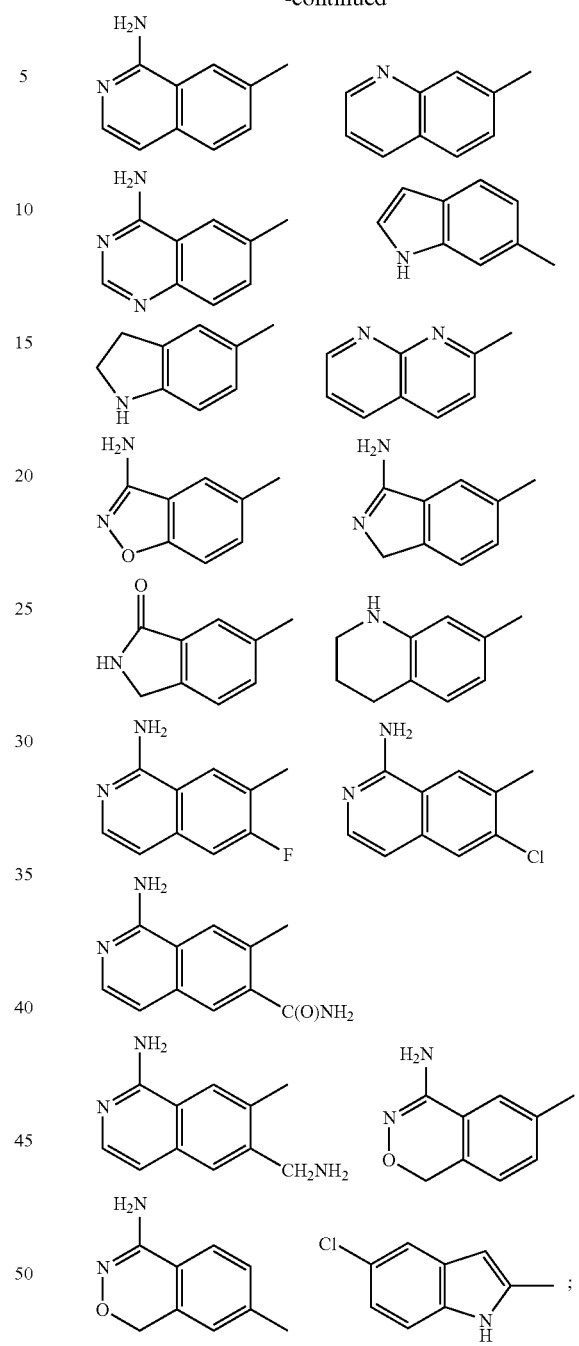
A is 2–6 membered linear chain consisting of: carbon atoms, 0–1 carbonyl groups, and A is substituted with 0–1 $R^{1a}$ and 0–2 $R^2$, and there are 0–1 double bonds;
B is selected from Y, $N(B^1)C(O)C(R^3R^{3g})NB^2B^3$,
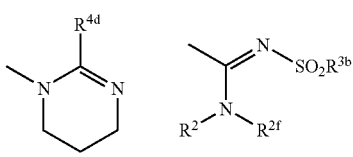

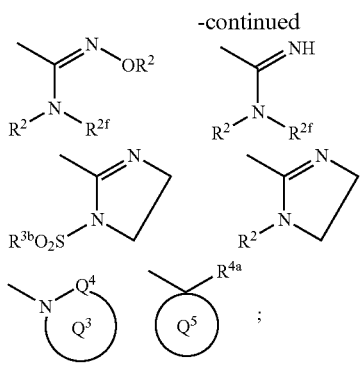

provided that the $R^{4d}$ shown is other than OH;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, cyclohexyl, and $CH_2$-cyclopropyl;

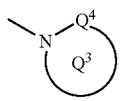

is attached to a different atom on A than M and is selected from the group:

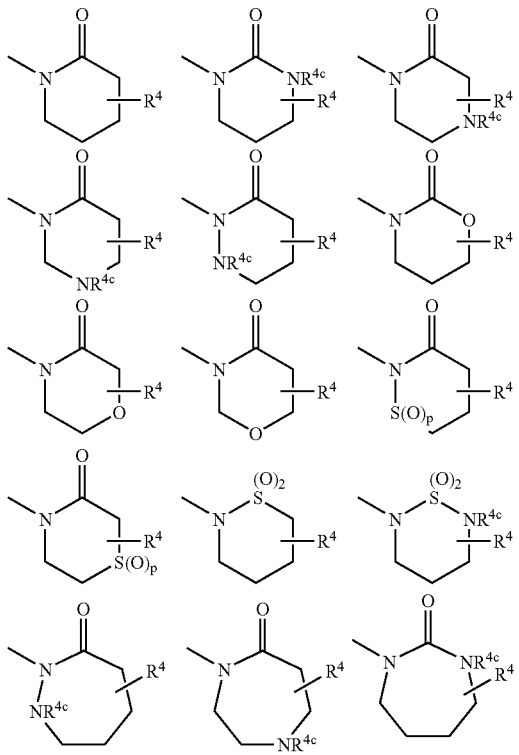

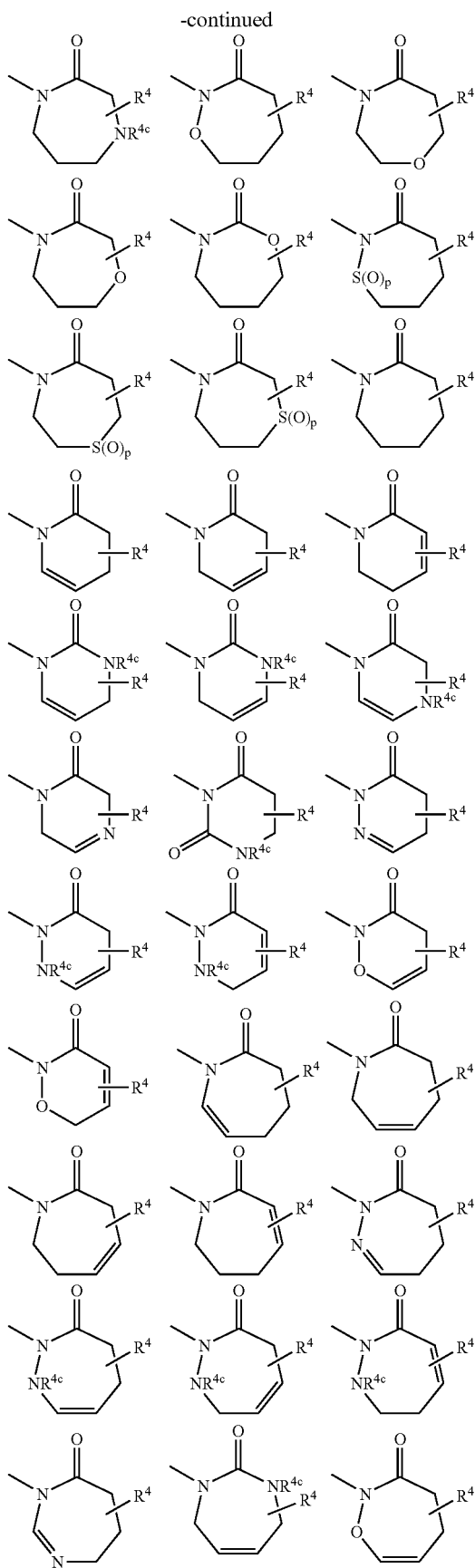

-continued

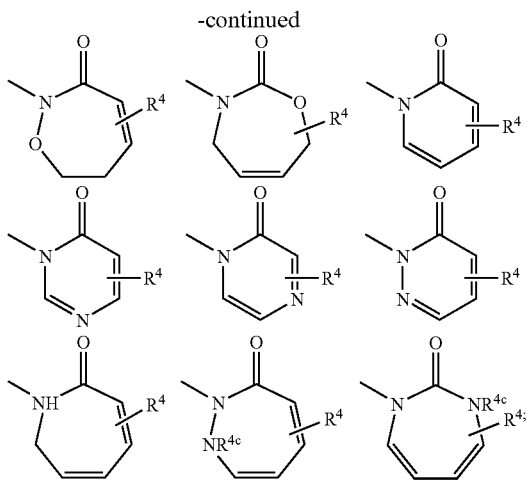

ring Q⁵ is selected from cyclopropyl, cyclobutyl, cyclopentyl, 2-cyclopentanonyl, cyclohexyl, 2-cyclohexanonyl, pyrrolidinyl (attached to A and R⁴ᵃ at the 2-position), pyrrolidinyl (attached to A and R⁴ᵃ at the 3-position), 2-pyrrolidinonyl (attached to A and R⁴ᵃ at the 3-position), piperidinyl (attached to A and R⁴ᵃ at the 4-position), 4-piperdinonyl (attached to A and R⁴ᵃ at the 3-position), tetrahydrofuranyl, and tetrahydropyranyl (attached to A and R⁴ᵃ at the 4-position);

Y is selected from $C(CH_3)_2R^{4a}$ and $C(CH_2CH_3)_2R^{4a}$;

alternatively, Y is selected from phenyl, pyridyl, 1,2,3-triazolyl, imidazolyl, and benzimidazolyl, and is substituted with 1 R⁴ᵃ;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

R², at each occurrence, is selected from H, $CH_3$, $CH_2CH_3$, $CH_2CH_2CH_3$, $CH(CH_3)_2$, phenyl substituted with 0–1 R⁴ᵇ, benzyl substituted with 0–1 R⁴ᵇ, and 5 membered aromatic heterocycle consisting of: carbon atoms and 1–4 heteroatoms selected from the group consisting of N, O, and $S(O)_p$, and substituted with 0–1 R⁴ᵇ;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 R⁴ᵇ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, R⁴ᶜ, $C_{1-4}$ alkyl substituted with 0–2 R⁴ᶜ, $C_{3-6}$ cycloalkyl substituted with 0–2 R⁴ᶜ, phenyl substituted with 0–2 R⁴ᶜ, and 5–6 membered aromatic heterocycle substituted with 0–2 R⁴ᶜ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, R⁴ᶜ, $C_{1-4}$ alkyl substituted with 0–2 R⁴ᶜ, $C_{3-6}$ cycloalkyl substituted with 0–2 R⁴ᶜ, phenyl substituted with 0–2 R⁴ᶜ, and 5–6 membered aromatic heterocycle substituted with 0–2 R⁴ᶜ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, and $OCH_3$;

alternatively, $NR^2R^{2f}$ forms a ring selected from morpholine, piperazine, piperidine, and pyrrolidine;

R⁴, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from —$(CH_2)_r$-5–6 membered carbocycle substituted with 0–3 R⁴ᶜ, —$(CH_2)_r$-5–6 membered heterocycle substituted with 0–3 R⁴ᶜ and consisting of: carbon atoms and 1–4 heteroatoms selected from the group consisting of N, O, and $S(O)_p$, $(CH_2)_rNR^{2d}R^{2d}$, $(CH_2)_rN(→O)R^{2d}R^{2d}$, $(CH_2)_rOR^{2d}$, $(CH_2)_rC(O)NR^{2d}R^{2d}$, $(CH_2)_rNR^{2d}C(O)R^{2e}$, $(CH_2)_rC(O)R^{2e}$, $(CH_2)_rNR^{2d}C(O)NR^{2d}R^{2d}$, $(CH_2)_rNR^{2d}C(O)OR^{2d}$, $(CH_2)_rNR^{2d}SO_2R^{2d}$, and $(CH_2)_rS(O)_pR^{2d}$, provided that $S(O)_pR^{2d}$ forms other than $S(O)_2H$ or $S(O)H$;

$R^{4b}$, at each occurrence, is selected from H, =O, OR³, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(→O)R^2R^{2a}$, $CH_2N(→O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 R⁴ᵇ, cyclobutyl substituted with 0–1 R⁴ᵇ, cyclopentyl substituted with 0–1 R⁴ᵇ, phenyl substituted with 0–1 R⁴ᵇ, —$CH_2$-cyclopropyl substituted with 0–1 R⁴ᵇ, —$CH_2$-cyclobutyl substituted with 0–1 R⁴ᵇ, —$CH_2$-cyclopentyl substituted with 0–1 R⁴ᵇ, benzyl substituted with 0–2 R⁴ᵇ, 5–6 membered aromatic heterocycle consisting of carbon atoms and from 1–4 heteroatoms selected from the group consisting of N, O, and $S(O)_p$ and substituted with 0–2 R⁴ᵇ, and $(CH_2)$-5–6 membered aromatic heterocycle consisting of carbon atoms and from 1–4 heteroatoms selected from the group consisting of N, O, and $S(O)_p$ and substituted with 0–2 R⁴ᵇ;

$R^{4d}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

R⁵, at each occurrence, is selected from H, =O, $CH_3$, $CH_2CH_3$, OR³, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR_3SO_2$—$C_{1-4}$ alkyl, $NR^3SO_2$-phenyl, $S(O)_2$—$CH_3$, $S(O)_2$-phenyl, $CF_3$, phenyl substituted with 0–2 R⁶, naphthyl substituted with 0–2 R⁶, and benzyl substituted with 0–2 R⁶; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.
In a sixth embodiment, the present invention provides a novel compound, wherein the compound is selected from:
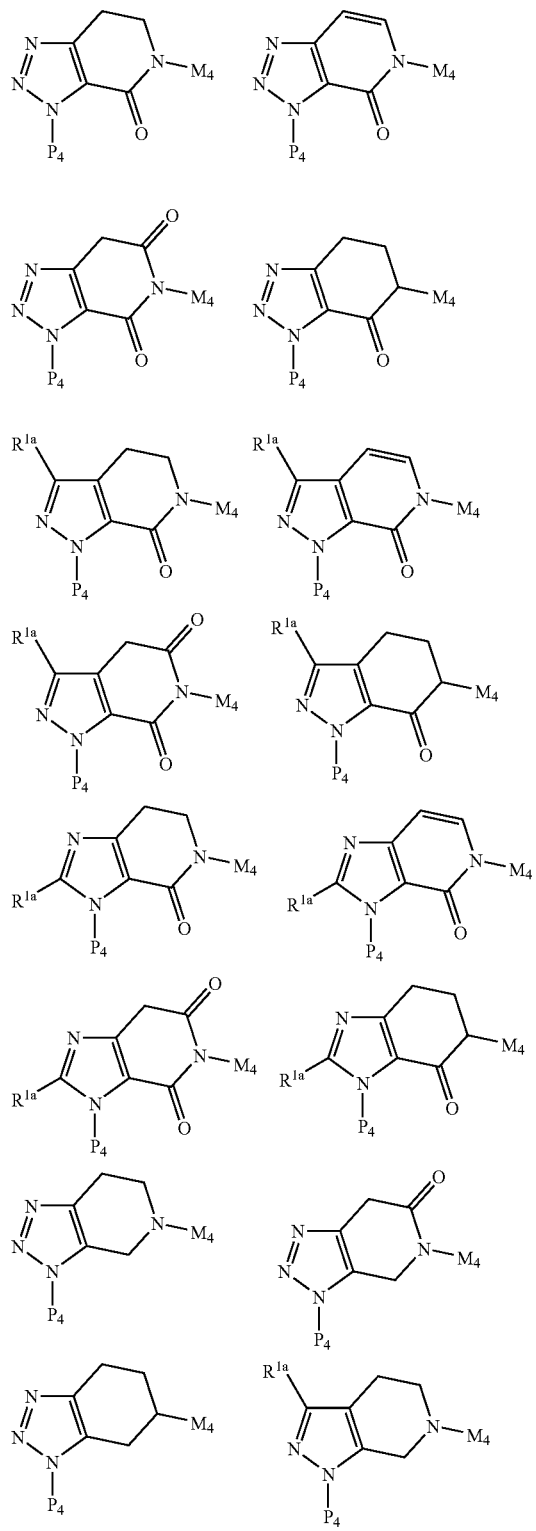
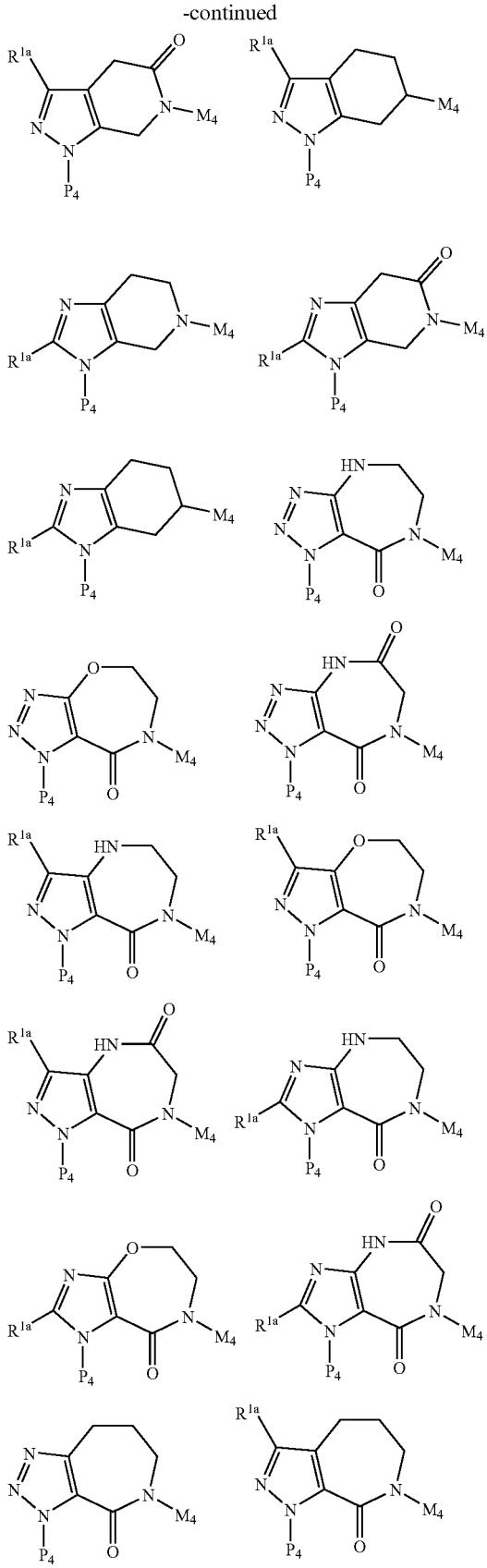
-continued -continued
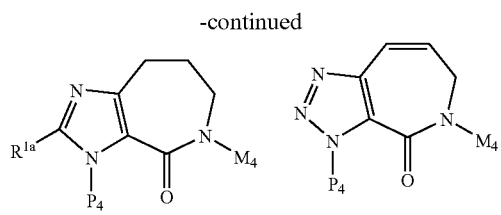
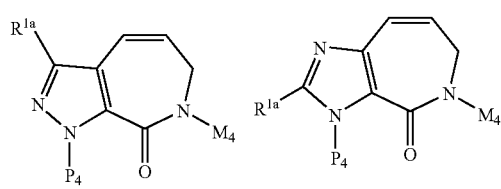
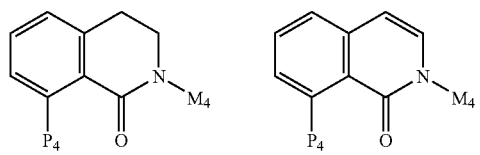
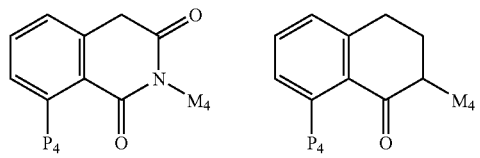
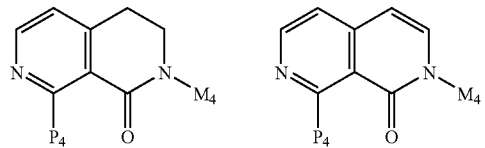
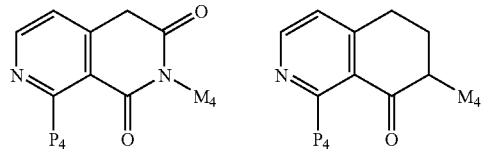
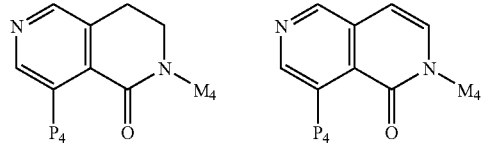
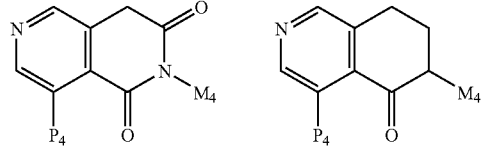
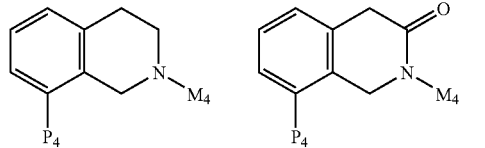
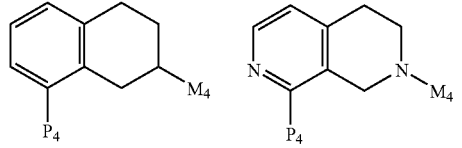
-continued
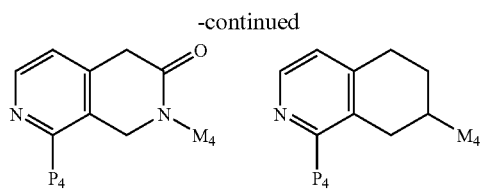
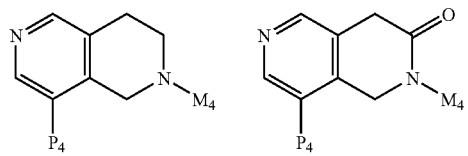
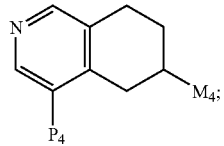
$P_4$ is -G;
$M_4$ is -A-B;
G is selected from:
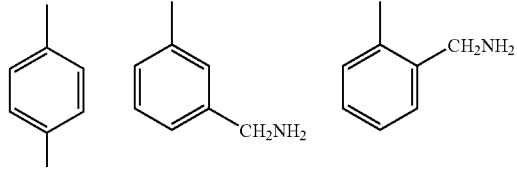
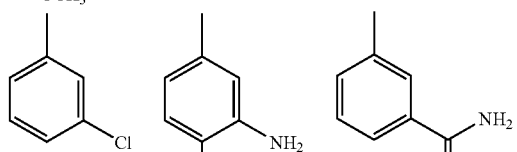
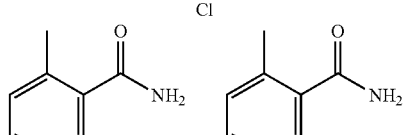
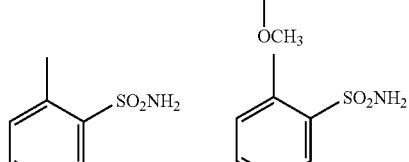
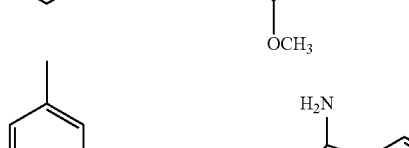
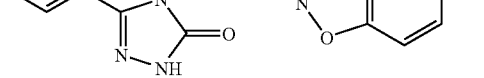

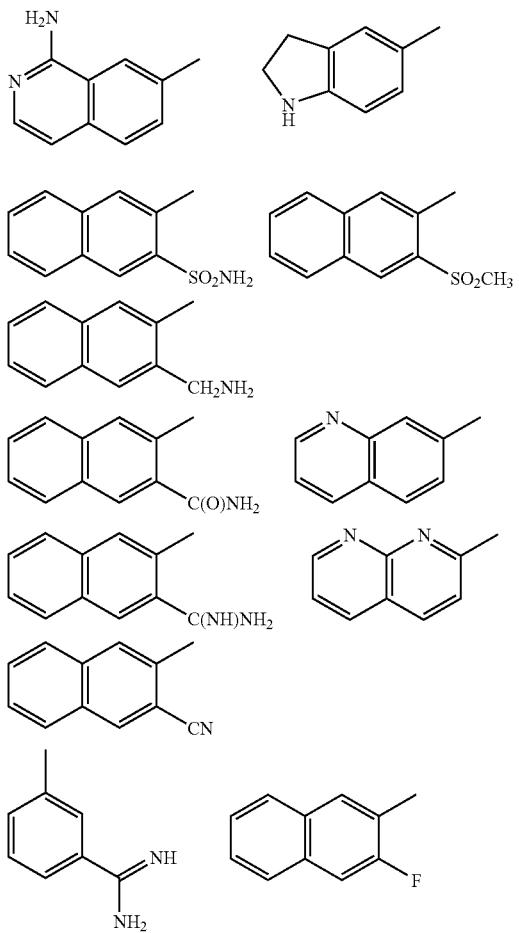
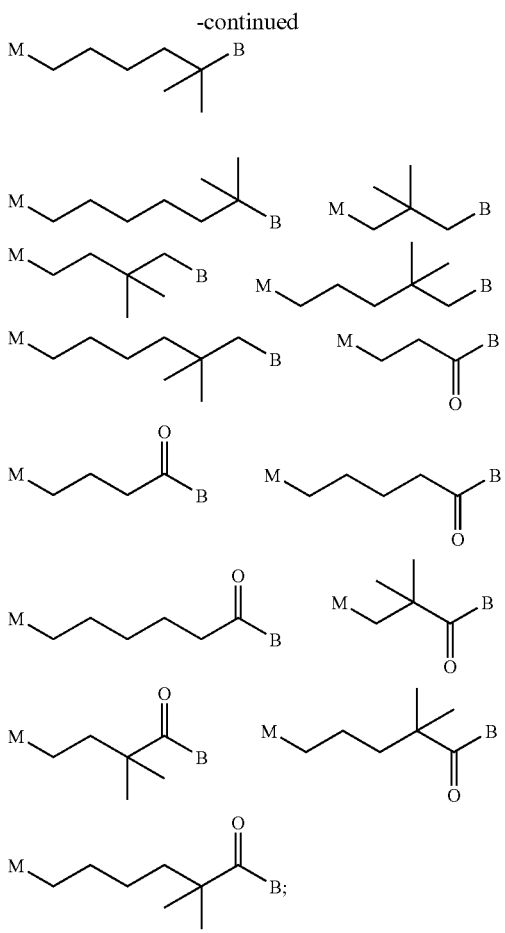
A is selected from:
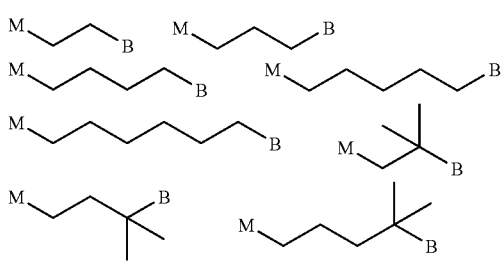
B is selected from:
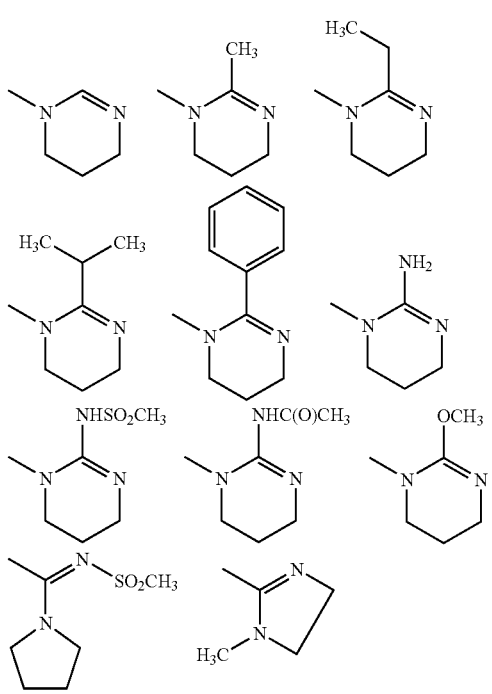

-continued

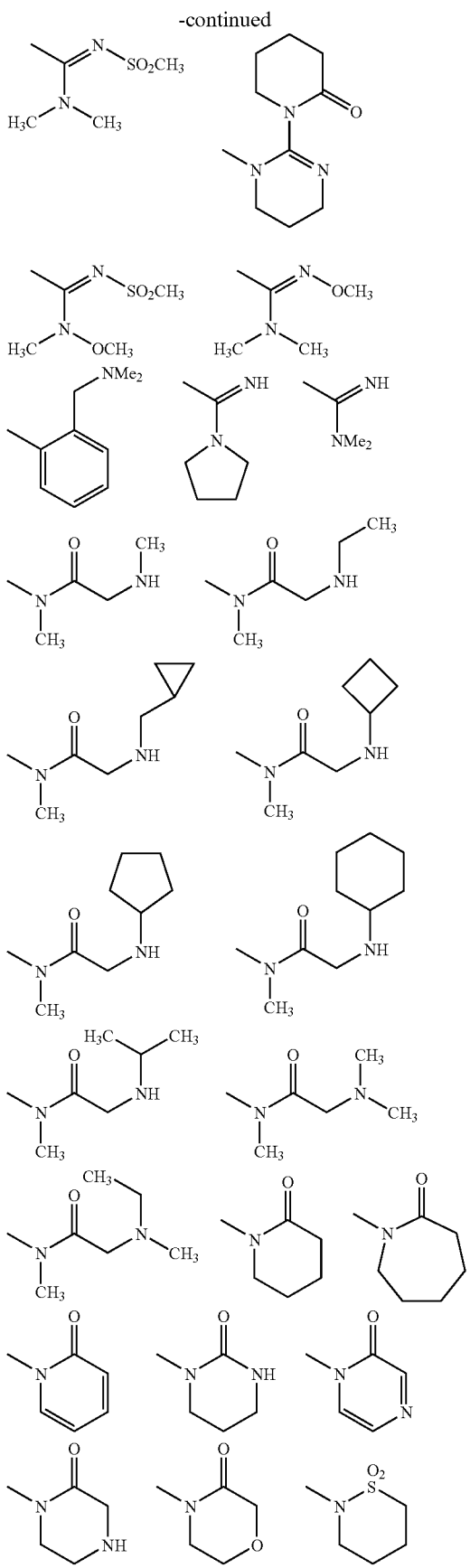

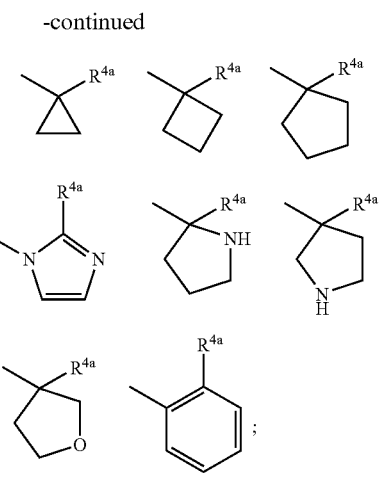

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —($CH_2$)-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or S(O)H; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a seventh embodiment, the present invention provides a novel compound, wherein the compound is selected from:

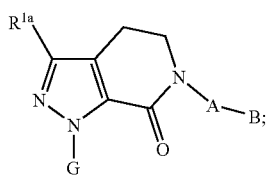
A is selected from:
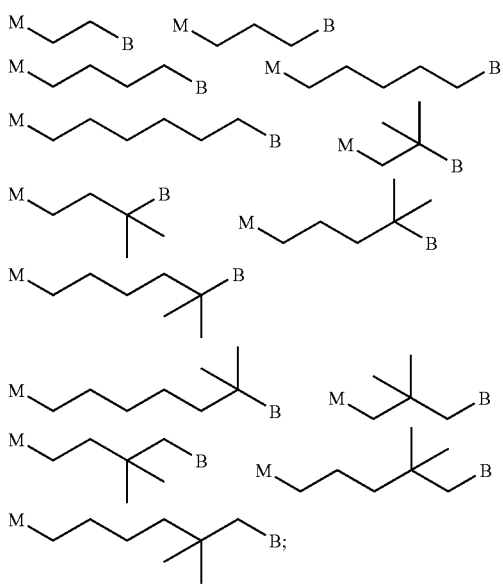
B is selected from:
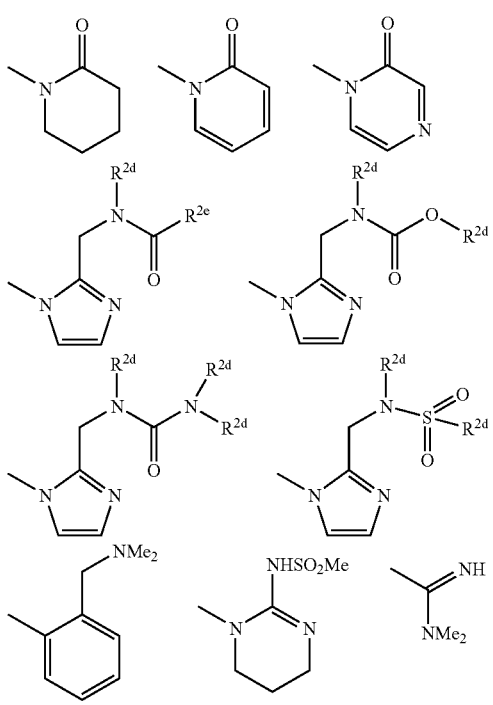
-continued
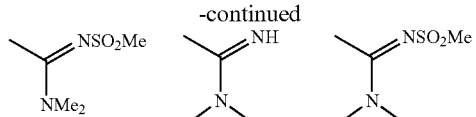
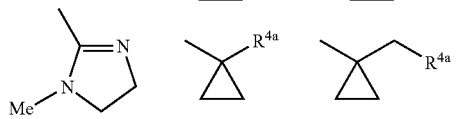
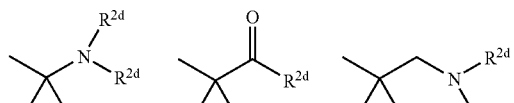
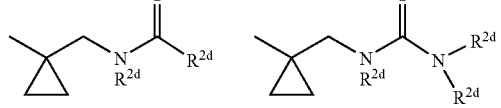
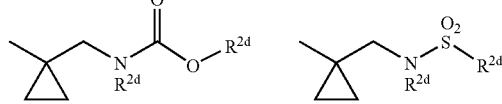
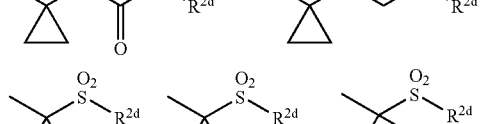
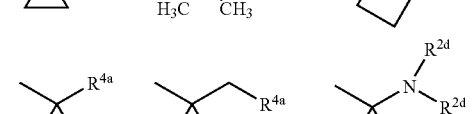
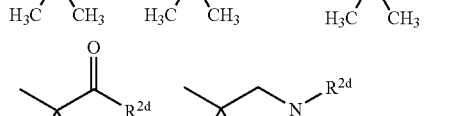
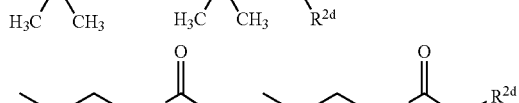
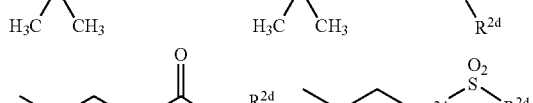
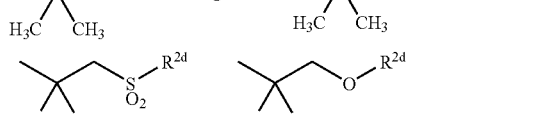
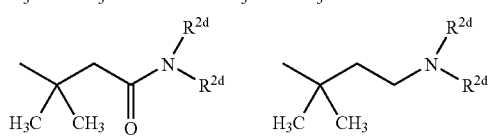

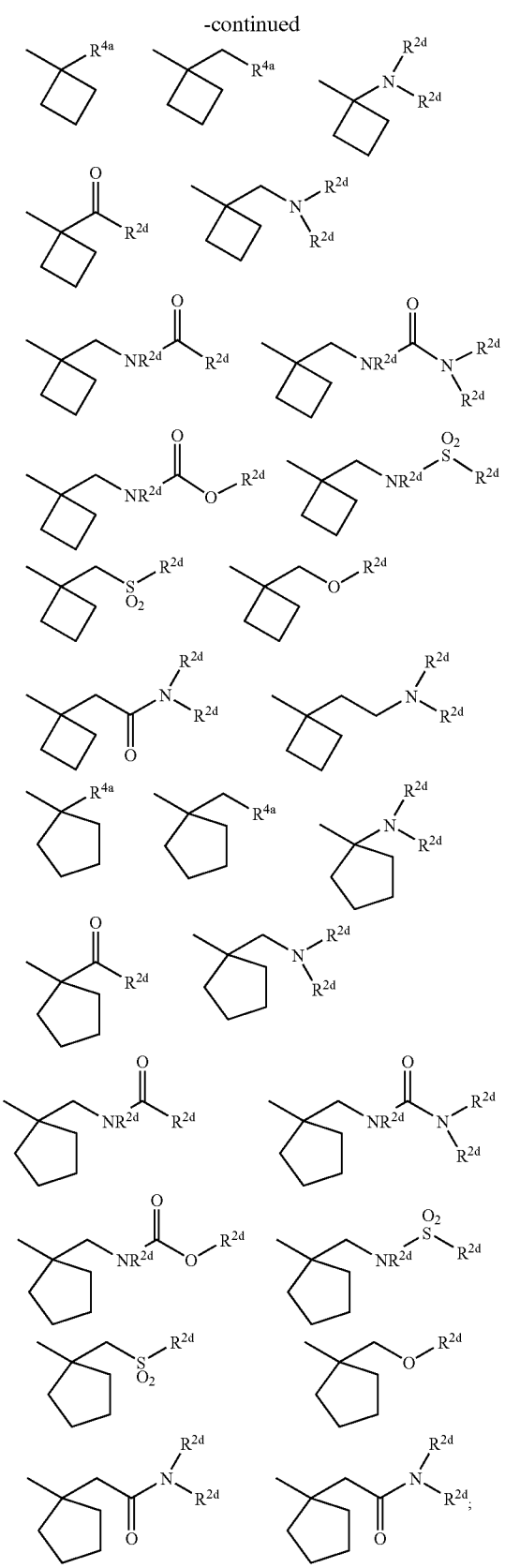

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NH$_2$, cyclopropyl, CH$_2$-cyclopropyl, cyclobutyl, cyclopentyl, and thiazolyl;

$R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazolyl, imidazoline, imidazolidine, oxazoline, and thiazoline; and $R^{4c}$ is selected from =O, OH, OCH$_3$, and CH$_3$.

In an eighth embodiment, the present invention provides a novel compound selected from Examples 1–85 or a pharmaceutically acceptable salt form thereof.

In a ninth embodiment, the present invention provides a novel compound, wherein the compound is of Formula IIIa, IIIb, or IIIc:

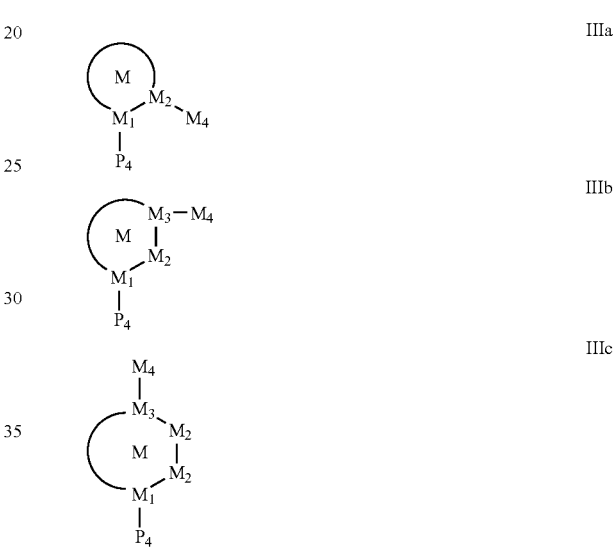

or a stereoisomer or pharmaceutically acceptable salt thereof, wherein;

ring M, including M$_1$, M$_2$, and, if present, M$_3$, is phenyl or a 3–10 membered carbocycle or 4–10 membered heterocycle consisting of: carbon atoms and 1–4 heteroatoms selected from O, S(O)$_p$, N, and NZ$^2$;

ring M is substituted with 0–3 $R^{1a}$ and 0–2 carbonyl groups, and there are 0–3 ring double bonds;

one of P$_4$ and M$_4$ is -A-B and the other -G$_1$-G;

G is a group of Formula IIa or IIb:

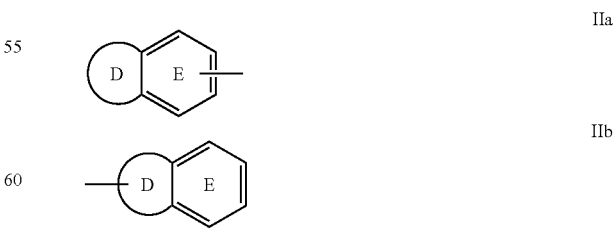

ring D, including the two atoms of Ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, and thienyl, and ring E is substituted with 1–3 R;

alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyl groups and 1–2 R and there are 0–3 ring double bonds;

R is selected from H, $C_{1-4}$ alkyl, F, Cl, OH, $OCH_3$, $OCH_2CH_3$, $OCH(CH_3)_2$, —CN, $C(=NH)NH_2$, $C(=NH)NHOH$, $C(=NH)NHOCH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is 2–6 membered linear chain consisting of: carbon atoms, 0–2 carbonyl groups, and 0–3 heteroatoms selected from O, N, and $S(O)_p$, and A is substituted with 0–2 $R^{1a}$ and 0–2 $R^2$, and there are 0–1 double bonds and 0–1 triple bonds; provided that other than an S—S, S—O, or O—O bond is present in A;

B is selected from —CN, $OR^3$, $NR^3R^{3a}$, Y, $N(B^1)C(O)C(R^3R^{3g})NB^2B^3$, $N(B^1)C(O)C(R^3R^{3g})C(R^3R^{3g})NB^2B^3$,

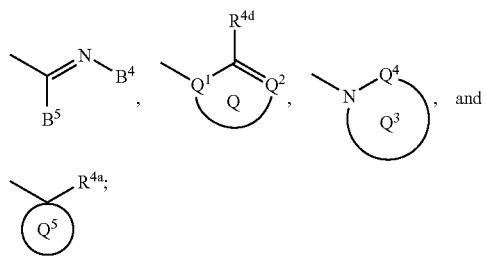

and provided that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2NR^{2d}R^{2d}$, $CH_2CH_2NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$, $C(O)R^{3b}$, $SO_2NR^3R^{3b}$, $C(O)NR^3R^3b$, $OR^2$, and —CN;

$B^5$ is $NR^2R^{2f}$ or $CR^3R^2R^{2f}$;

ring Q is a 5–6 membered ring consisting of, in addition to the $Q^1$-$CR^{4d}=Q^2$ group shown, carbon atoms and 0–2 heteroatoms selected from N, O, and $S(O)_p$, and the ring is substituted with an additional 0–2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

$Q^4$ is selected from C=O and $SO_2$;

ring $Q^3$ is a 4–7 membered monocyclic or tricyclic ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and S(O)p, the carbocycle or heterocycle further comprises 0–2 double bonds and 0–2 carbonyl groups, and the carbocycle or heterocycle is substituted with 0–2 $R^4$;

Y is $CY^1Y^2R^{4a}$, and $Y^1$ and $Y^2$ are independently $C_{1-3}$ alkyl substituted with 0–1 $R^4$;

alternatively, Y is selected from one of the following carbocycles and heterocycles that are substituted with 1 $R^{4a}$ and 0–2 $R^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR_{2b}$, $NR^2(CH_2)_rOR^2$, $NR^2C(O)R^{2b}$, $NR^2C(O)NHR^2$, $NR^2C(O)_2R^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, C$_{5-6}$ carbocycle substituted with 0–2 R$^{4b}$, and 5–6 membered heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, a —CH$_2$—C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$, and substituted with 0–2 R$^{4b}$;

R$^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$, and substituted with 0–2 R$^{4b}$;

alternatively, NR$^2$R$^{2a}$ forms a 5 or 6 membered saturated, partially saturated, or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{56}$ carbocycle substituted with 0–2 R$^{4b}$, and 5–6 membered heterocycle consisting of: carbon atoms and 1–4 heteroatoms selected from the group consisting of N, O, and S(O)$_p$, and substituted with 0–2 R$^{4b}$;

R$^{2c}$, at each occurrence, is selected from CF$_3$, OH, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, and 5–6 membered heterocycle containing from 1–4 heteroatoms selected from the group consisting of N, O, and S(O)$_p$, and substituted with 0–2 R$^{4b}$;

R$^{2d}$, at each occurrence, is selected from H, R$^{4c}$, C$_{1-4}$ alkyl substituted with 0–2 R$^{4c}$, —(CR$^3$R$^{3a}$)$_r$—C$_{3-6}$ carbocycle substituted with 0–2 R$^{4c}$, and —(CR$^3$R$^{3a}$)$_r$-5–6 membered heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5 or 6 membered saturated, partially saturated, or unsaturated ring substituted with 0–2 R$^{4b}$ and consisting of: 0–1 additional heteroatoms selected from the group consisting of N, O, and S(O)$_p$;

R$^{2e}$, at each occurrence, is selected from H, R$^{4c}$, C$_{1-4}$ alkyl substituted with 0–2 R$^{4c}$, —(CR$^3$R$^{3a}$)$_r$—C$_{3-6}$ carbocycle substituted with 0–2 R$^{4c}$, and —(CR$^3$R$^{3a}$)$_r$-5–6 membered heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CF$_3$, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, and 5–6 membered heterocycle containing from 1–4 heteroatoms selected from the group consisting of N, O, and S(O)$_p$ and substituted with 0–2 R$^{4b}$;

alternatively, CR$^2$R$^{2f}$ forms a 5–6 membered ring consisting of: carbon atoms and 0–2 heteroatoms selected from N, O, and S(O)$_p$, and this ring is substituted with 0–2 R$^{4b}$;

alternatively, NR$^2$R$^{2f}$ forms a 5–6 membered ring consisting of: carbon atoms and 0–2 additional heteroatoms selected from N, O, and S(O)$_p$, and this ring is substituted with 0–2 R$^{4b}$;

alternatively, when B$^5$ is NR$^2$R$^{2f}$, B$^4$ and R$^{2f}$ combine to form a 5–6 membered ring consisting of: carbon atoms and 0–2 additional heteroatoms selected from N, O, and S(O)$_p$, and this ring is substituted with 0–2 R$^{4b}$ and the R$^2$ group of NR$^2$R$^{2f}$, in addition to the groups recited below, is selected from SO$_2$R$^{3b}$ and C(O)R$^{3b}$;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, NR$^3$R$^{3a}$ forms a 5 or 6 membered saturated, partially unsaturated, or unsaturated ring consisting of: carbon atoms and the nitrogen atom to which R$^3$ and R$^{3a}$ are attached;

R$^{3b}$, at each occurrence, is selected from H, CF$_3$, CH$_3$, CH$_2$CH$_3$, CH$_2$CH$_2$CH$_3$, CH(CH$_3$)$_2$, —(C$_{0-1}$ alkyl)-5–6 membered carbocycle substituted with 0–1 R$^{1a}$, and —(C$_{0-1}$ alkyl)-5–6 membered heterocycle substituted with 0–1 R$^{1a}$ and consisting of: carbon atoms and 1–4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, NR$^2$SO$_2$NR$^2$R$^{2a}$, S(O)$_p$R$^{5a}$, NR$^2$SO$_2$—C$_{1-4}$ alkyl, NR$^2$SO$_2$R$^5$, CF$_3$, CF$_2$CF$_3$, 5–6 membered carbocycle substituted with 0–1 R$^5$, and a 5–6 membered heterocycle consisting of: carbon atoms and 1–4 heteroatoms selected from the group consisting of N, O, and S(O)$_p$, and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$CF$_3$;

R$^{4c}$, at each occurrence, is selected from =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-3}$ alkenyl, C$_{2-3}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_{3-10}$ carbocycle substituted with 0–2 R$^{4b}$, and (CR$^3$R$^{3a}$)$_r$5–10 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OR$^2$, CH$_2$OR$^2$, C$_{1-4}$ alkyl, —CN, CH$_2$CN, NO$_2$, CH$_2$NO$_2$, NR$^2$R$^{2a}$, CH$_2$NR$^2$R$^{2a}$, CH$_2$C(O)R$^{2c}$, C(O)R$^{2c}$, NR$^2$C(O) R$^{2b}$, (CH$_2$)$_r$C(O)NR$^2$R$^{2a}$, NR$^2$C(O)NR$^2$R$^{2a}$, (CH$_2$)$_r$ SO$_2$NR$^2$R$^{2a}$, NR$^2$SO$_2$NR$^2$R$^{2a}$, NR$^2$SO$_2$R$^5$, (CH$_2$)$_r$S(O)$_p$ R$^{5a}$, CH$_2$CF$_3$, CF$_3$, 5–6 membered carbocycle substituted with 0–1 R$^5$, CH$_2$-5–6 membered carbocycle substituted with 0–1 R$^5$, a 5–6 membered heterocycle consisting of: carbon atoms and 1–4 heteroatoms selected from the group consisting of N, O, and S(O)$_p$ and substituted with 0–1 R$^5$, and a CH$_2$-5–6 membered heterocycle consisting of: carbon atoms and 1–4 heteroatoms selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$) NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^{5a}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, C(CH$_3$)$_3$, OR$^3$, CH$_2$OR$^3$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O) NR$^3$R$^{3a}$, CH$_2$C(O)NR$^3$R$^{3a}$, CF$_3$, CF$_2$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH) NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

In a tenth embodiment, the present invention provides a novel compound, wherein:

ring M, including M$_1$, M$_2$, and, if present, M$_3$, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran-1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran-1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopropane, cyclobutane, cyclopentene, cyclopentane, cyclohexene, cyclohexane, cycloheptane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, tetrahydro-1,2,3,4-tetrazine, piperidine, indan, 1,2,3,4-tetrahydro-naphthalene, 7,8-dimethyl-1-oxa-spiro[4.4]nonane, 6,7-dihydro-5H-[1]pyrindine, 6,7-dihydro-5H-[2]pyrindine, 5,6,7,8-tetrahydro-quinoline, 5,6,7,8-tetrahydro-isoquinoline, 5,6,7,8-tetrahydro-quinoxaline, 6,7-dihydro-5H-cyclopentapyrazine, 4,5,6,7-tetrahydro-1H-benzoimidazole, 4,5,6,7-tetrahydro-benzothiazole, 4,5,6,7-tetrahydro-benzooxazole, 4,5,6,7-tetrahydro-benzo[c]isothiazole, 4,5,6,7-tetrahydro-benzo[c] isoxazole, 4,5,6,7-tetrahydro-2H-indazole, 4,5,6,7-tetrahydro-2H-isoindole, and 4,5,6,7-tetrahydro-1H-indole;

ring M is substituted with 0–3 R$^{1a}$ and 0–1 carbonyl group;

G is selected from the group: 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4-chloro-phenyl; 3-amino-4-chloro-phenyl; 3-aminomethyl-phenyl; 3-amino-phenyl; 3-chloro-4-fluoro-phenyl; 3-chloro-phenyl; 3-hydroxy-4-methoxy-phenyl; 4-(N,N-dimethylamino)-5-chloro-thien-2-yl; 4-(N-methylamino)-5-chloro-thien-2-yl; 4-amino-5-chloro-thien-2-yl; 4-amino-pyrid-2-yl; 4-chloro-3-fluoro-phenyl; 4-chloro-phenyl; 4-chloro-pyrid-2-yl; 4-methoxy-2-methylsulfonyl-phenyl; 4-methoxy-phenyl; 5-(N,N-dimethylamino)-4-chloro-thien-2-yl; 5-(N-methylamino)-4-chloro-thien-2-yl; 5-amino-4-chloro-thien-2-yl; 5-chloro-2-aminosulfonyl-phenyl; 5-chloro-2-methylsulfonyl-phenyl; 5-chloro-pyrid-2-yl; 5-chloro-thien-2-yl; 6-amino-5-chloro-pyrid-2-yl; 6-amino-pyrid-2-yl;

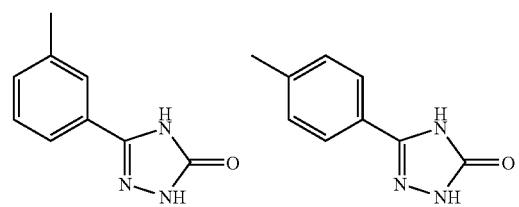

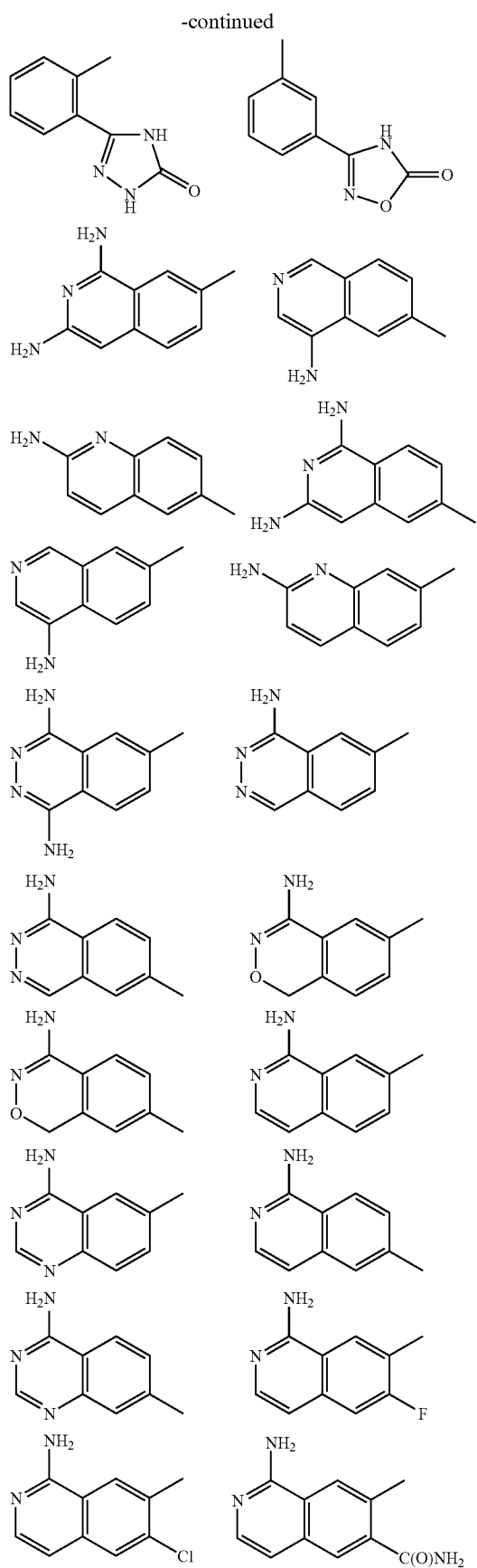
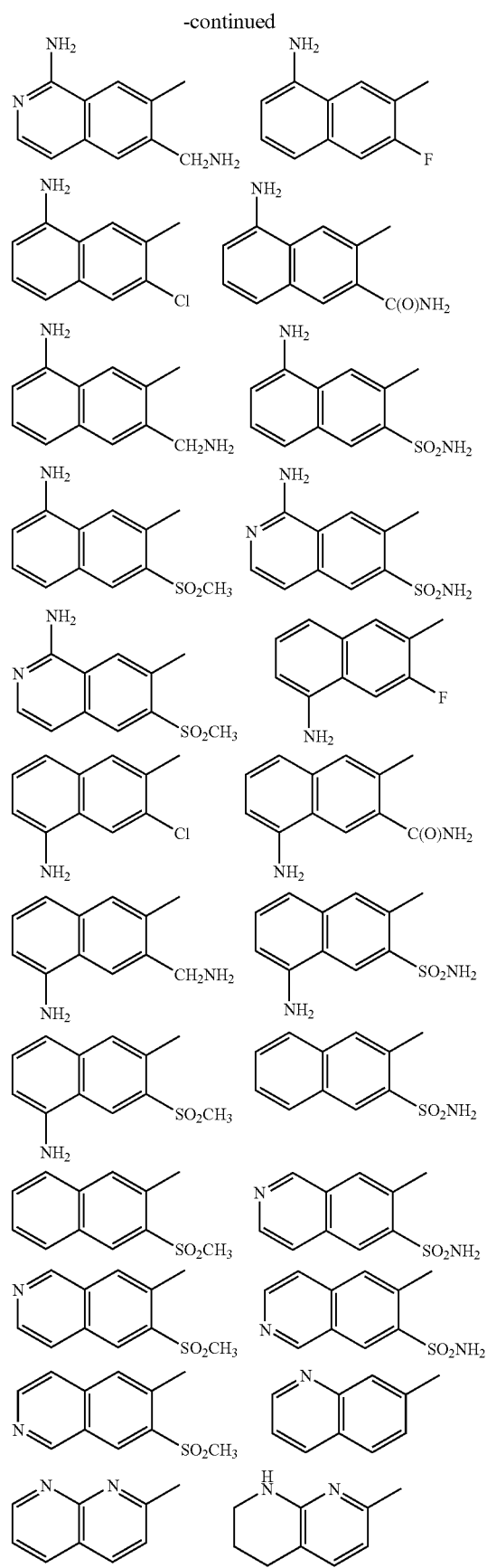

-continued
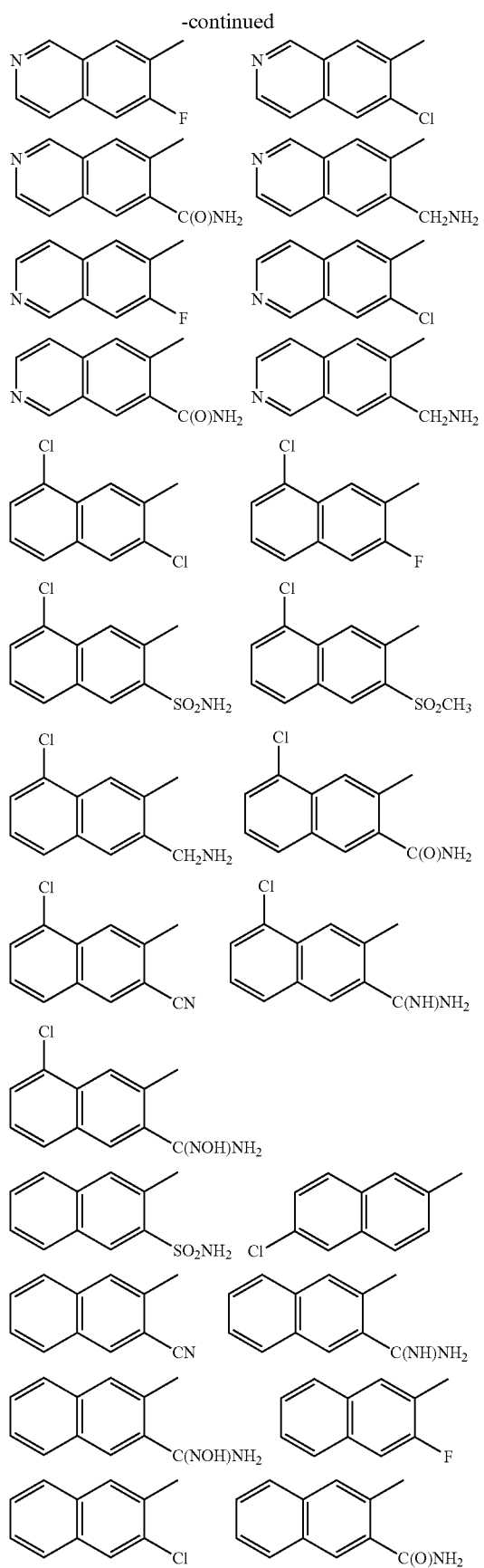
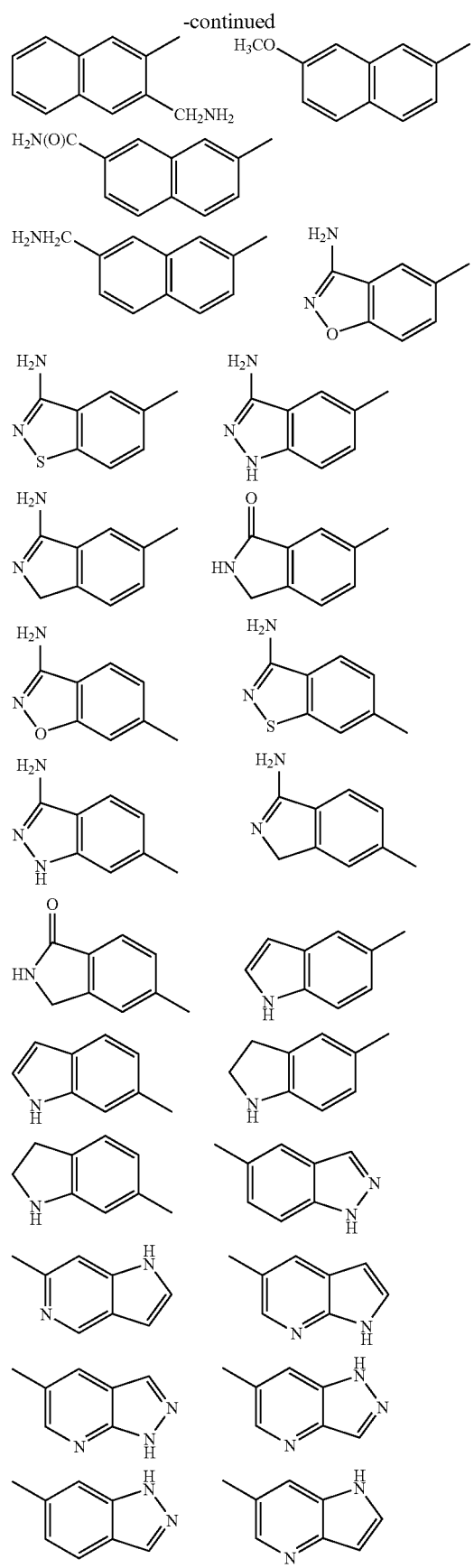

-continued
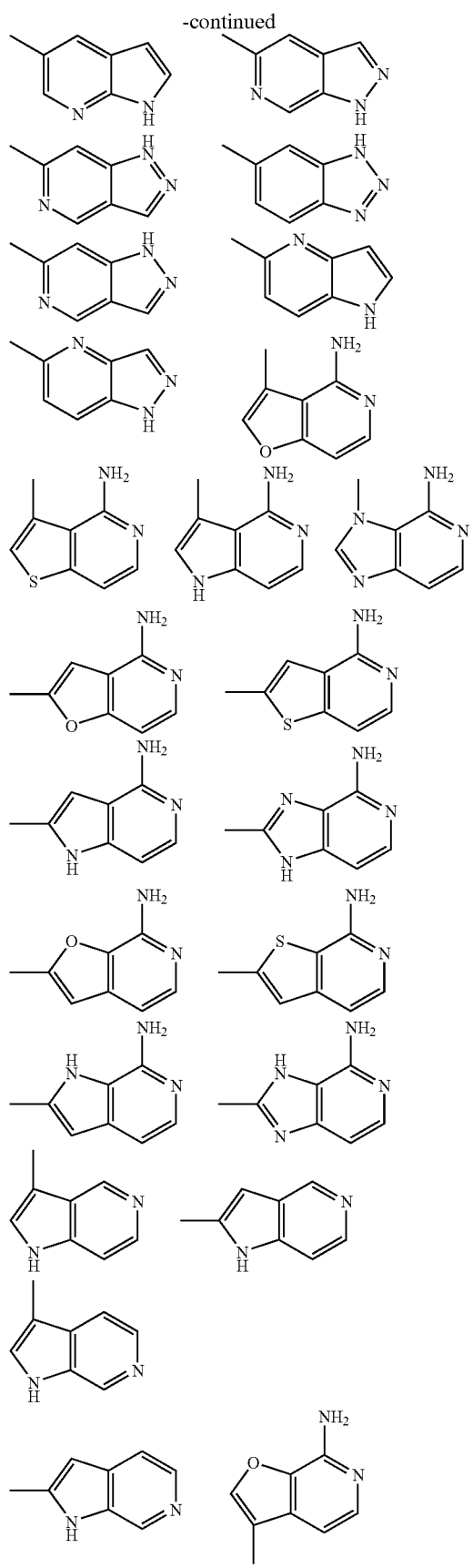
-continued
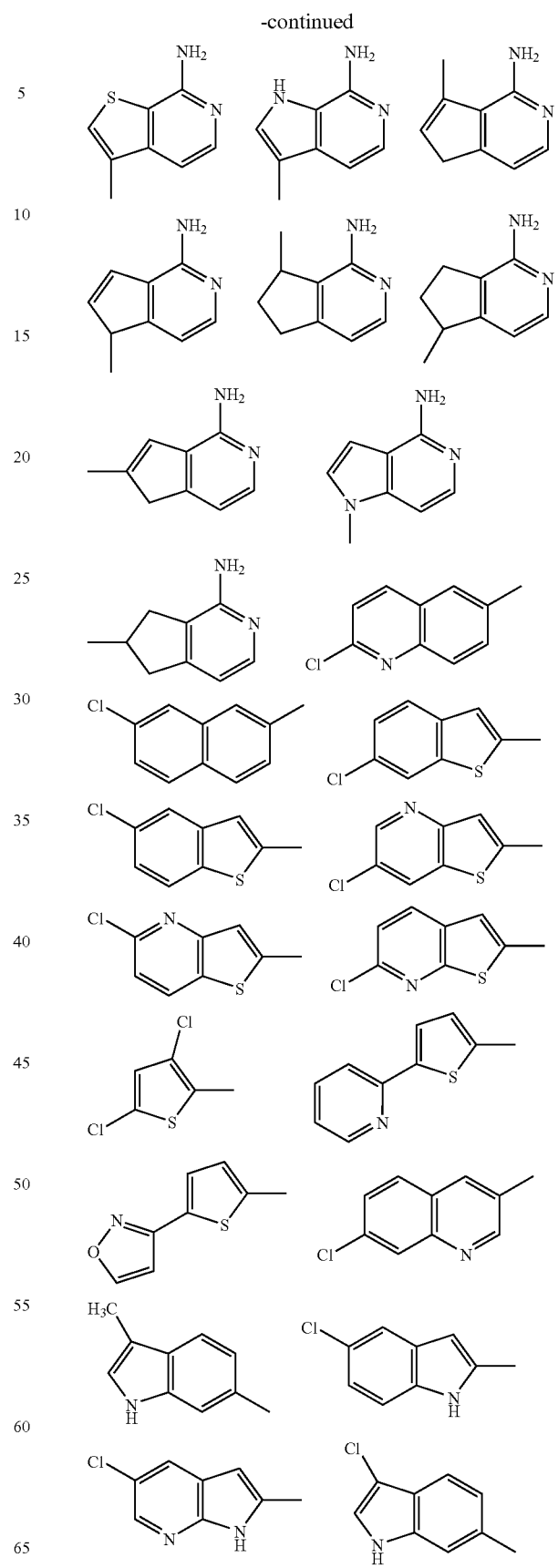

-continued

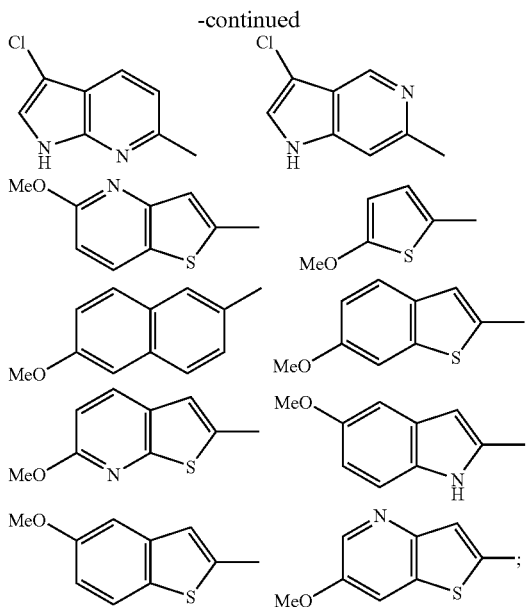

G₁ is absent or is selected from $(CR^3R^{3a})_{1-3}$, $CR^3=CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, and $(CR^3R^{3a})_uC(O)NR^{3b}S(O)_2(CR^3R^{3a})_w$, wherein u+w total 0, 1, or 2 and the right side of G₁ is attached to ring G, provided that G₁ does not form a N—S, NCH₂N, NCH₂O, or NCH₂S bond with either group to which it is attached;

A is 2–6 membered linear chain consisting of: carbon atoms, 0–2 carbonyl groups, and 0–2 heteroatoms selected from O, N, and $S(O)_p$, and A is substituted with 0–2 $R^{1a}$ and 0–2 $R^2$, and there are 0–1 double bonds and 0–1 triple bonds; provided that other than an S—S, S—O, or O—O bond is present in A;

B¹ is selected from H, CH₃, CH₂CH₃, CH₂CH₂CH₃, CH(CH₃)₂, —(CH₂)₀₋₁—$C_{5-6}$ carbocycle substituted with 0–2 $R^{4b}$, and —(CH₂)₀₋₁-5–6 membered heterocycle consisting of: carbon atoms and 1–4 heteroatoms selected from the group consisting of N, O, and $S(O)_p$ and substituted with 0–2 $R^{4b}$;

B² is selected from H, CH₃, CH₂CH₃, CH₂CH₂CH₃, CH(CH₃)₂, $C(O)R^{2e}$, $C(O)NR^{2d}R^{2d}$, $SO_2NR^{2d}R^{2d}$, and $S(O)_pR^{5a}$;

B³ is selected from H, $C_{1-6}$ alkyl substituted with 0–1 $R^{4c}$, —(CH₂)₀₋₁-3–6 membered carbocycle substituted with 0–1 R⁵, and a —(CH₂)₀₋₁-5–6 membered heterocycle consisting of: carbon atoms and 1–4 heteroatoms selected from the group consisting of N, O, and $S(O)_p$ and substituted with 0–1 R⁵;

B⁴ is selected from H, $SO_2R^{3b}$ and $OR^2$;

B⁵ is $NR^2R^{2f}$;

ring Q is a 5–6 membered ring consisting of, in addition to the N—$CR^{4d}$=N group shown, carbon atoms and 0–2 heteroatoms selected from N, O, and $S(O)_p$, and the ring is substituted with an additional 0–2 $R^{4d}$;

Q⁴ is selected from C=O and SO₂;

ring Q³ is a 5–7 membered ring consisting of, in addition to the N-Q⁴ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^{4a}$;

alternatively, ring Q³ is a 5–7 membered ring to which another ring is fused, wherein: the 5–7 membered ring consists of, in addition to the shown amide group, carbon atoms and 0–2 heteroatoms selected from $NR^{4c}$, O, S, S(O), and $S(O)_2$, and 0–1 double bonds are present within the ring; the fusion ring is phenyl or a 5–6 membered heteroaromatic consisting of carbon atoms and 1–2 heteroatoms selected from $NR^{4c}$, O, and S;

ring Q³, which includes the 5–7 membered ring and the fusion ring, is substituted with 0–3 $R^{4a}$;

ring Q⁵, is a $C_{3-6}$ monocyclic carbocycle or 5–6 membered monocyclic heterocycle, wherein the carboocycle or heterocycle consists of: carbon atoms and 0–2 heteroatoms selected from N, O, and S(O)p, the carbocycle or heterocycle further comprises 0–1 double bonds and 0–1 carbonyl groups, and the carbocycle or heterocycle is substituted with 0–2 R⁴;

Y is $CY^1Y^2R^{4a}$, and Y¹ and Y² are independently $C_{1-2}$ alkyl substituted with 0–1 R⁴;

alternatively, Y is selected from one of the following carbocycles and heterocycles that are substituted with 1 $R^{4a}$ and 0–1 R⁴; cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzimidazolonyl, benzoxazolyl, benzthiazolyl, indazolyl, benzisoxazolyl, benzisothiazolyl, and isoindazole;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, CH₃, CH₂CH₃, F, Cl, Br, —CN, —CHO, CF₃, OR², $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

R², at each occurrence, is selected from H, CF₃, CH₃, CH₂CH₃, CH₂CH₂CH₃, CH(CH₃)₂, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, CF₃, CH₃, CH₂CH₃, CH₂CH₂CH₃, CH(CH₃)₂, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $CH_3$, $CH_2CH_3$, $CH_2CH_2CH_3$, $CH(CH_3)_2$, $OCH_3$, and benzyl;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, $B^4$ and $R^{2f}$ combine to form a 5–6 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)$ $CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r NR^{2d}C(O)R^{2e}$, $(CR^3R^{3g})_rC(O)R^{2e}$, $(CR^3R^{3g})_rOC(O)R^{2e}$, $(CR^3R^{3g})_rC(O)NR^{2d}R^{2d}$, $(CR^3R^{3g})_rC(O)OR^{2d}$, $(CR^3R^{3g})_r NR^{2d}C(O)NR^{2d}R^{2d}$, $(CR^3R^{3g})_rNR^{2d}C(O)OR^{2d}$, $(CR^3R^{3g})_r SO_2NR^{2d}R^{2d}$, $(CR^3R^{3g})_rNR^{2d}SO_2R^{2d}$, and $(CR^3R^{3g})_rS(O)_p R^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)$ $R^{3a}$, $C(O)NR^3R^{3a}$, $CH_2C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})$ Cl, $CF_3$, $(CR^3R^{3a})CF_3$, $C_{1-4}$ alkyl, $C_{2-3}$ alkenyl, $C_{2-3}$ alkynyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C$ $(O)R^{2b}$, $C(O)NR^2R^{2a}$, $(CR^3R^{3a})C(O)NR^2R^{2a}$, $NR^2C(O)$ $NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})$ $NR^2SO_2NR^2R^{2a}$, $NR^2SO_2R^{5a}$, $(CR^3R^{3a})NR^2SO_2R^{5a}$, $S(O)_p R^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OR^2$, $CH_2OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6 membered carbocycle substituted with 0–1 $R^5$, and a 5–6 membered heterocycle consisting of: carbon atoms and 1–2 heteroatoms selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R_{2b}$, $CH_2C(O)R^{2b}$, $NR^2C(O)$ $R^{2b}$, $SO_2NR^2R^{2a}$, and $NR^2SO_2C_{1-4}$ alkyl.

In an eleventh embodiment, the present invention provides a novel compound, wherein the compound is selected from:

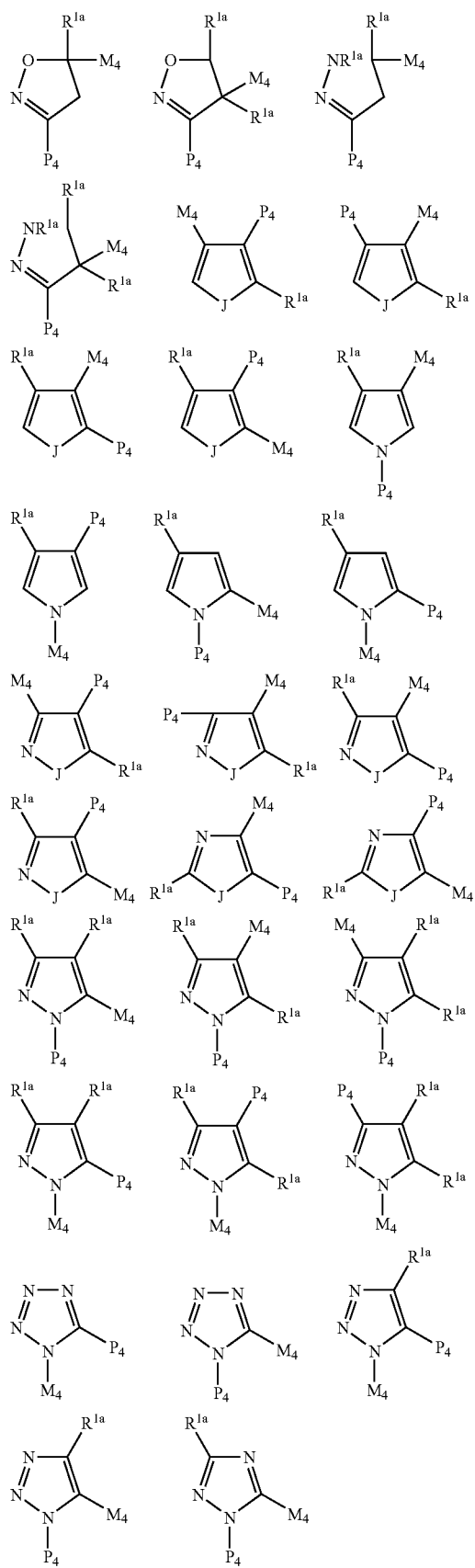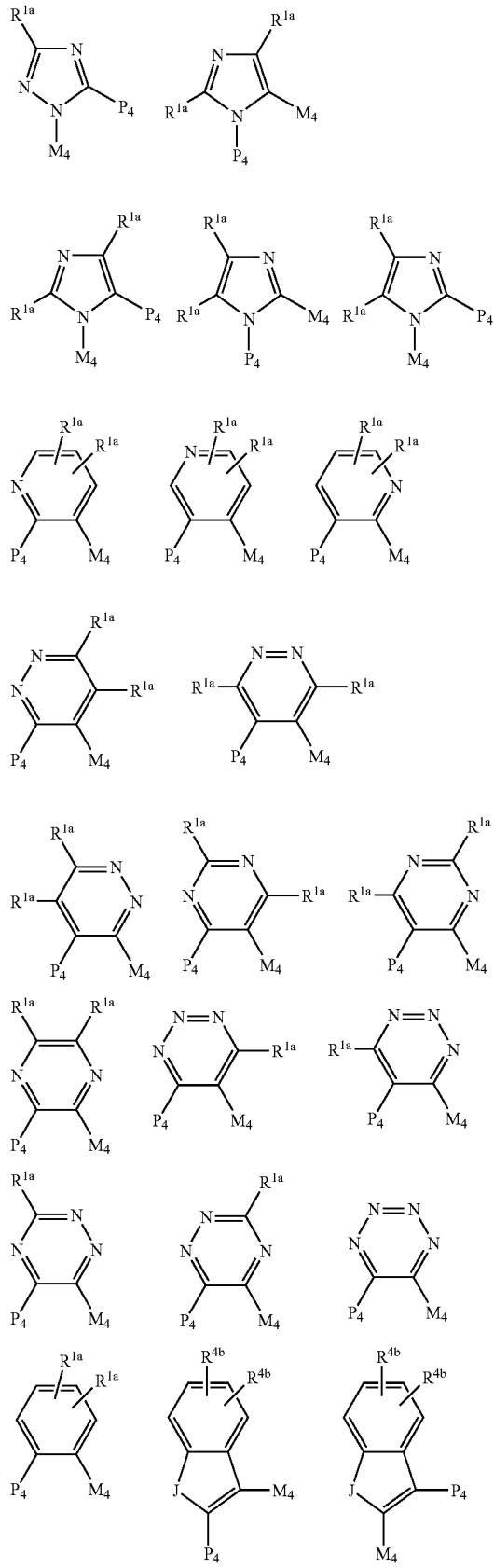

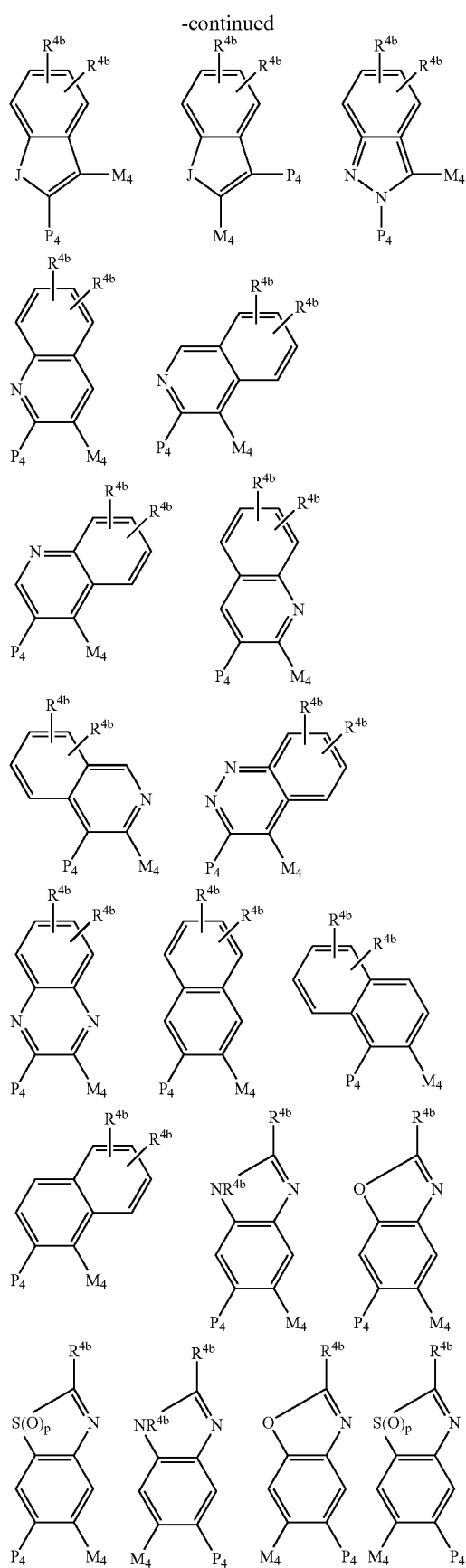
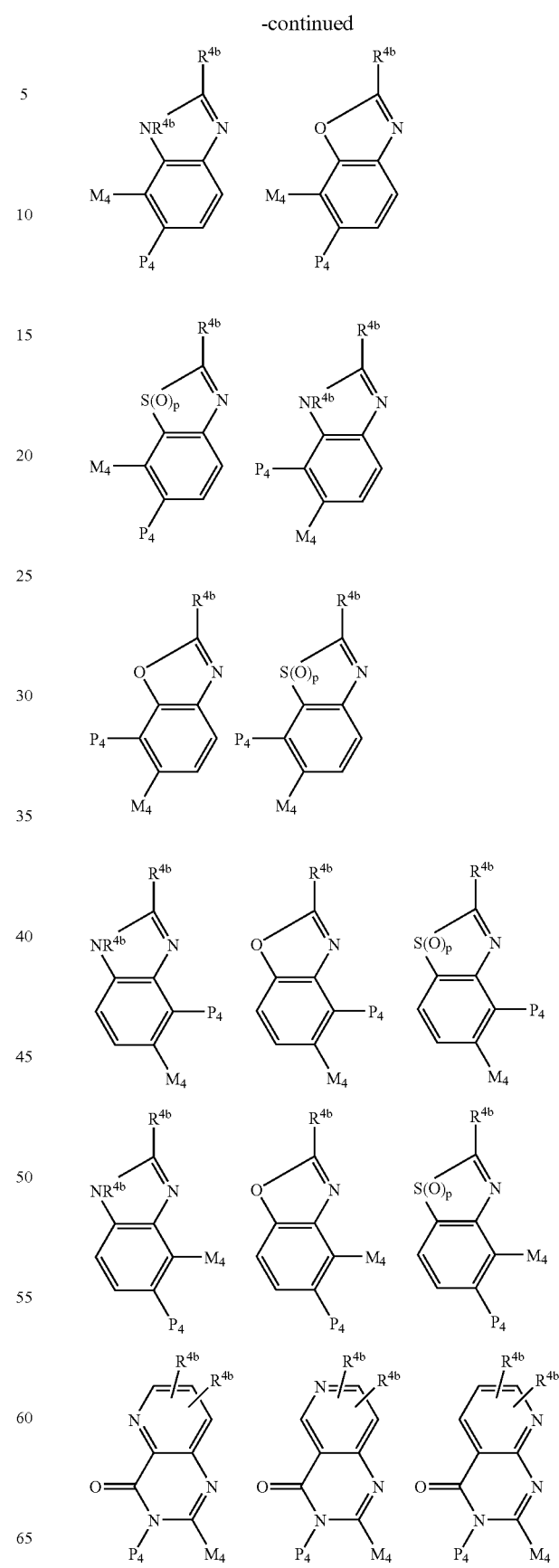

-continued
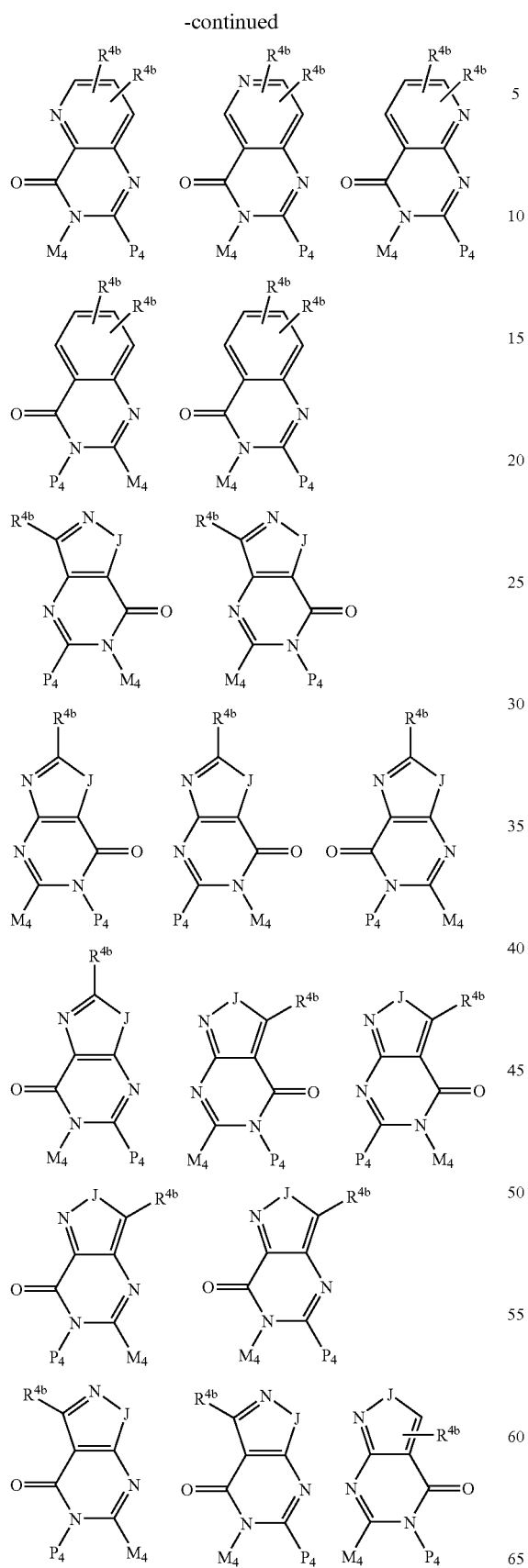
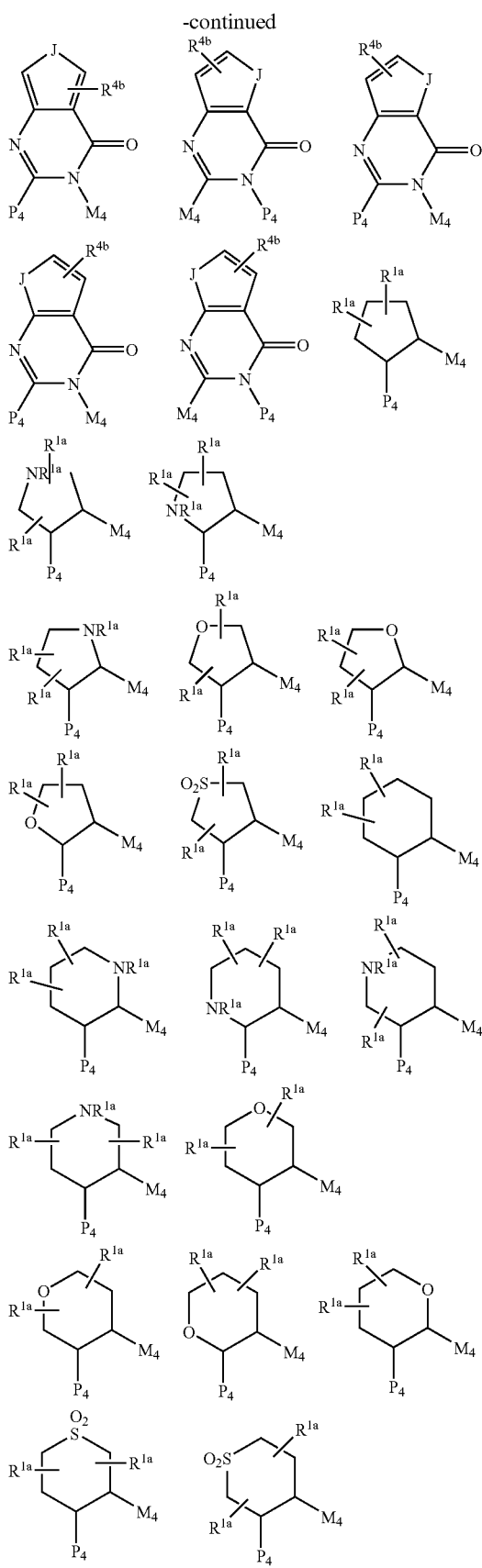

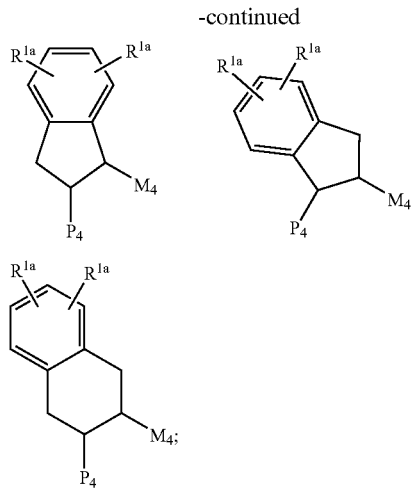

J is selected from O, S, NH, and $NR^{1a}$;

G is selected from the group: 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-5-chloro-thien-2-yl; 4-(N-methylamino)-5-chloro-thien-2-yl; 4-amino-5-chloro-thien-2-yl; 4-chloro-phenyl; 4-methoxy-2-methylsulfonyl-phenyl; 4-methoxy-phenyl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 6-amino-5-chloro-pyrid-2-yl; 6-amino-pyrid-2-yl; 3-amidino-phenyl;

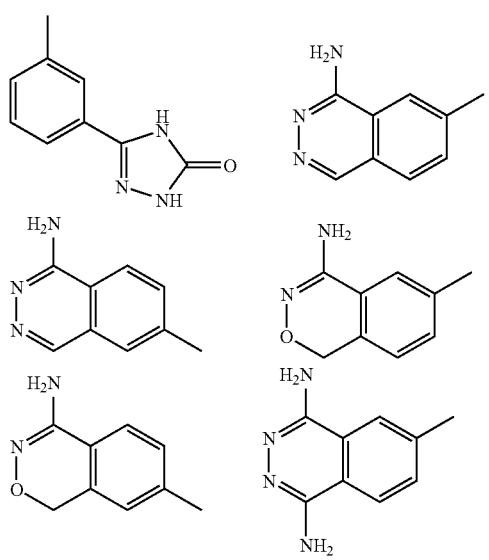

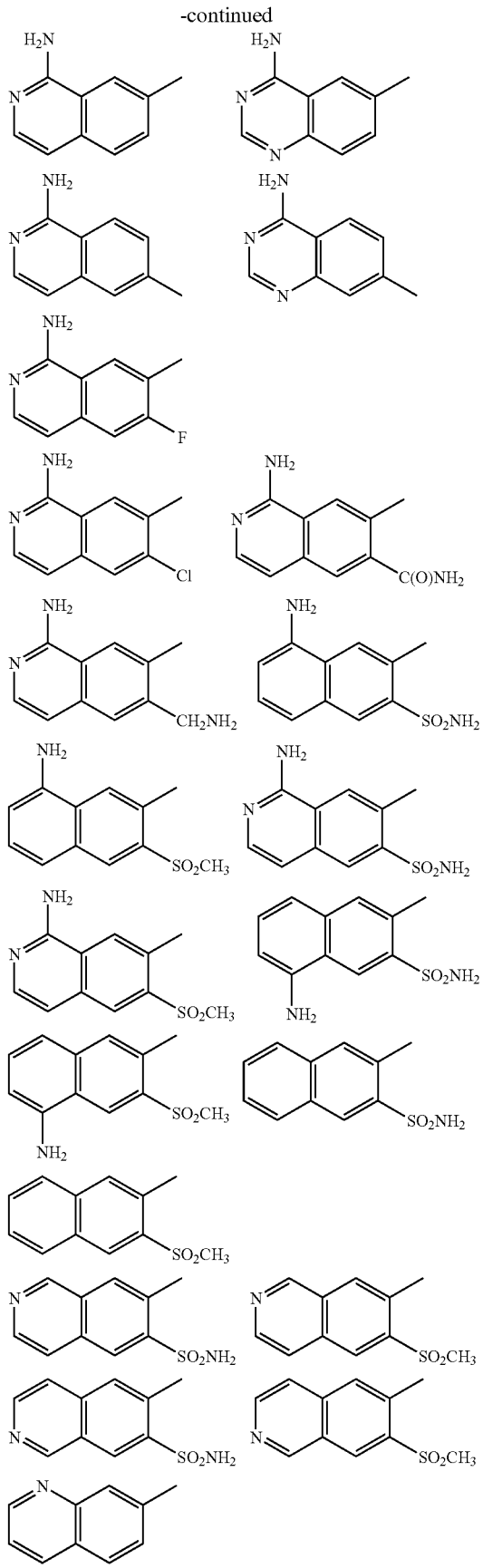

-continued
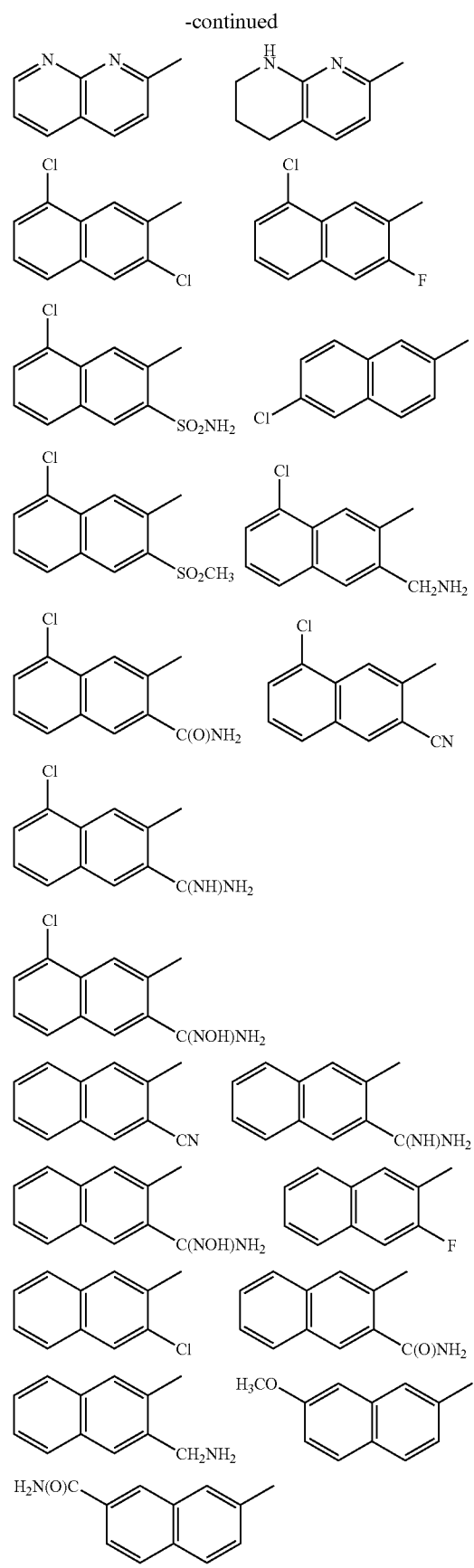
-continued
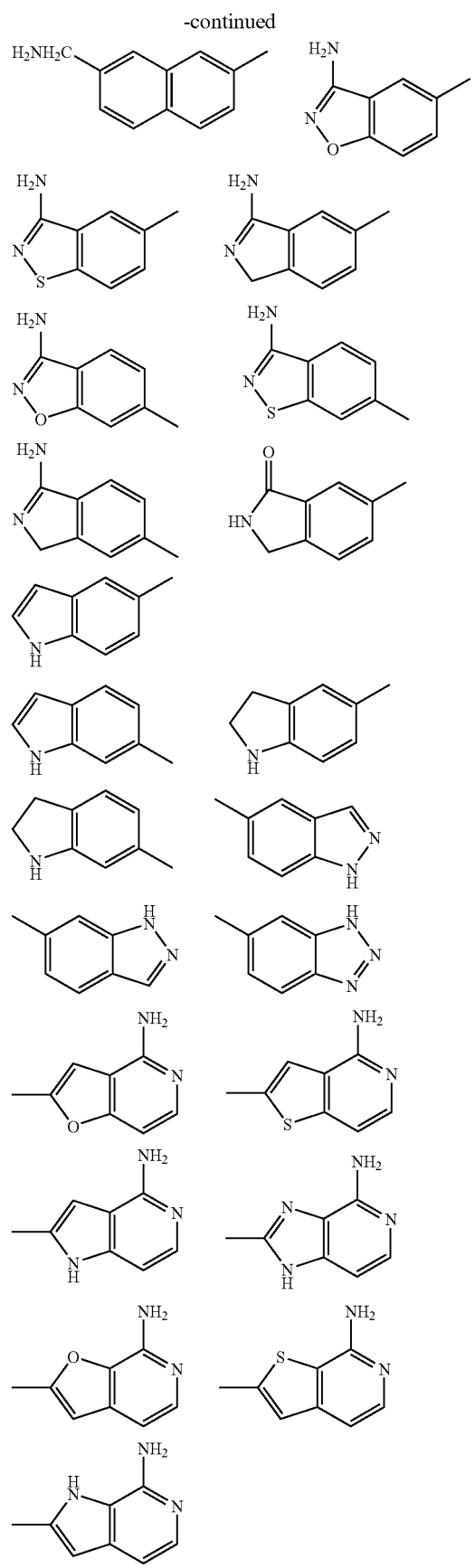

-continued

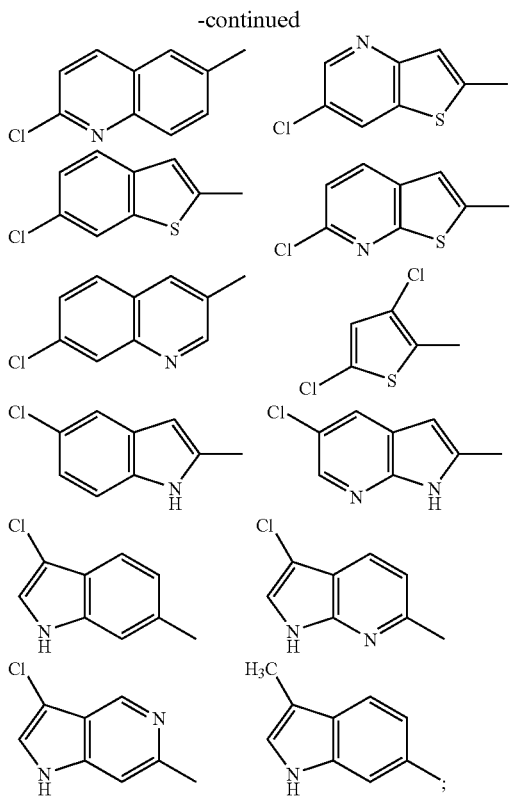

$G_1$ is absent or is selected from $CH_2$, $CH_2CH_2$, $CH_2O$, $OCH_2$, $NH$, $CH_2NH$, $NHCH_2$, $CH_2C(O)$, $C(O)CH_2$, $C(O)NH$, $NHC(O)$, $NHC(O)NH$, $C(O)NHS(O)_2$, $CH_2S(O)_2$, $S(O)_2(CH_2)$, $SO_2NH$, and $NHSO_2$, wherein the right side of $G_1$ is attached to ring G, provided that $G_1$ does not form a N—S, $NCH_2N$, $NCH_2O$, or $NCH_2S$ bond with either group to which it is attached;

A is 2–6 membered linear chain consisting of: carbon atoms, 0–1 carbonyl groups, and 0–1 heteroatoms selected from O, N, and $S(O)_p$, and A is substituted with 0–1 $R^{1a}$ and 0–2 $R^2$, and there are 0–1 double bonds; provided that other than an S—S, S—O, or O—O bond is present in A;

B is selected from Y, $N(B^1)C(O)C(R^3R^{3g})NB^2B^3$,

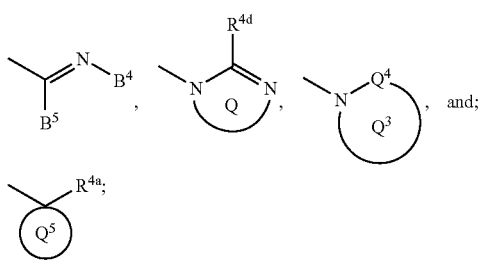

provided that the $R^{4d}$ shown is other than OH;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$ and $OR^2$;

$B^5$ is $NR^2R^{2f}$;

ring Q is a 5–6 membered ring consisting of, in addition to the N—$CR^{4d}$=N group shown, carbon atoms and 0–1 heteroatoms selected from N, O, and $S(O)_p$, and the ring is substituted with an additional 0–2 $R^{4d}$;

$Q^4$ is selected from C=O and $SO_2$;

ring $Q^3$ is a 6–7 membered ring consisting of, in addition to the N-$Q^4$ group shown, carbon atoms and 0–1 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 5–7 membered ring to which another ring is fused, wherein: the 5–7 membered ring consists of, in addition to the shown amide group, carbon atoms and 0–1 heteroatoms selected from $NR^{4c}$, O, S, S(O), and $S(O)_2$, and 0–1 double bonds are present within the ring; the fusion ring is phenyl;

ring $Q^3$, which includes the 5–7 membered ring and the fusion ring, is substituted with 0–2 $R^4$;

ring $Q^5$ is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and is substituted with 0–1 $R^4$;

Y is selected from $C(CH_3)_2R^{4a}$ and $C(CH_2CH_3)_2R^{4a}$;

alternatively, Y is selected from phenyl, pyridyl, pyrrolidino, morpholino, 1,2,3-triazolyl, imidazolyl, and benzimidazolyl, and is substituted with 1 $R^{4a}$ and 0–1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^{2b}$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O , N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated, or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0'- $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle containing from 1–4 heteroatoms selected from the group consisting of N, O, and S(O)$_p$, and substituted with 0–1 R$^{4b}$;

R$^{2d}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CH$_2$)-5–6 membered heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_1$-4 alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CH$_2$)-5–6 membered heterocycle and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CH$_3$, CH$_2$CH$_3$, OCH$_3$, and benzyl;

alternatively, NR$^2$R$^{2f}$ forms a 5–6 membered ring consisting of: carbon atoms and 0–1 additional heteroatoms selected from N, O, and S(O)$_p$, and this ring is substituted with 0–1 R$^{4b}$;

alternatively, B$^4$ and R$^{2f}$ combine to form a 5 membered ring consisting of: carbon atoms and 0–1 additional heteroatoms selected from N, O, and S(O)$_p$, and this ring is substituted with 0–2 R$^{4b}$ and the R$^2$ group of NR$^2$R$^{2f}$, in addition to the groups recited below, can be SO$_2$R$^{3b}$;

R$^{3b}$, at each occurrence, is selected from H and CH$_3$;

R$^4$, at each occurrence, is selected from H, =O, OH, OR$^2$, CH$_2$OR$^2$, (CH$_2$)$_2$OR$^2$, F, Br, Cl, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

R$^{4a}$ is selected from —(CR$^3$R$^{3g}$)$_r$-5–6 membered carbocycle substituted with 0–3 R$^{4c}$, —(CR$^3$R$^{3g}$)$_r$-5–6 membered heterocycle substituted with 0–3 R$^{4c}$ and consisting of: carbon atoms and 1–4 heteroatoms selected from the group consisting of N, O, and S(O)$_p$, (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$NR$^{2d}$C(O)R$^{2e}$, (CR$^3$R$^{3g}$)$_r$C(O)R$^{2e}$, (CR$^3$R$^{3g}$)$_r$C(O)NR$^{2d}$R$^{2d}$, (CR$^3$R$^{3g}$)$_r$NR$^{2d}$C(O)NR$_{2d}$R$^{2d}$, (CR$^3$R$^{3g}$)$_r$NR$^{2d}$C(O)OR$^{2d}$, (CR$^3$R$^{3g}$)$_r$NR$^{2d}$SO$_2$R$^{2d}$, and (CR$^3$R$_{3g}$)$_r$S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_3$, CH$_2$CH(CH$_3$)$_2$, CH(CH$_3$)CH$_2$CH$_3$, C(CH$_3$)$_3$, C$_{2-3}$ alkenyl, C$_{2-3}$ alkynyl, —CN, NO$_2$, NR$^2$R$^{2a}$, CH$_2$NR$^2$R$^{2a}$, N(→)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$_{2b}$, CH$_2$C(O)R$^{2b}$, NR$^2$C(O)R$^{2b}$, and SO$_2$NR$^2$R$^{2a}$.

In a twelfth embodiment, the present invention provides a novel compound, wherein the compound is selected from:

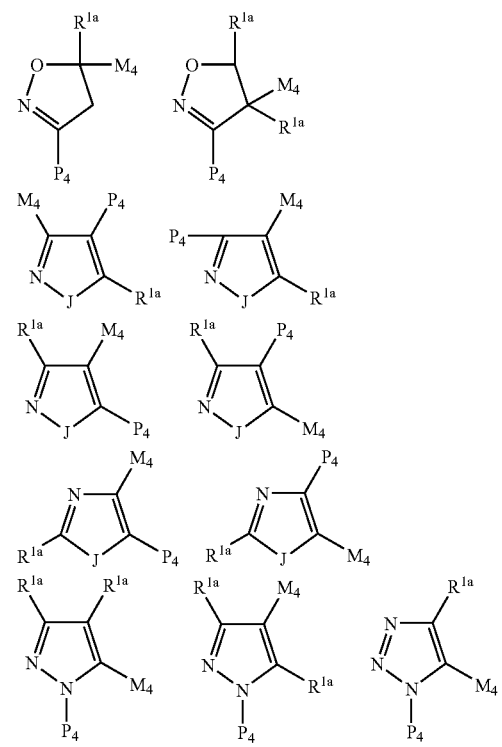

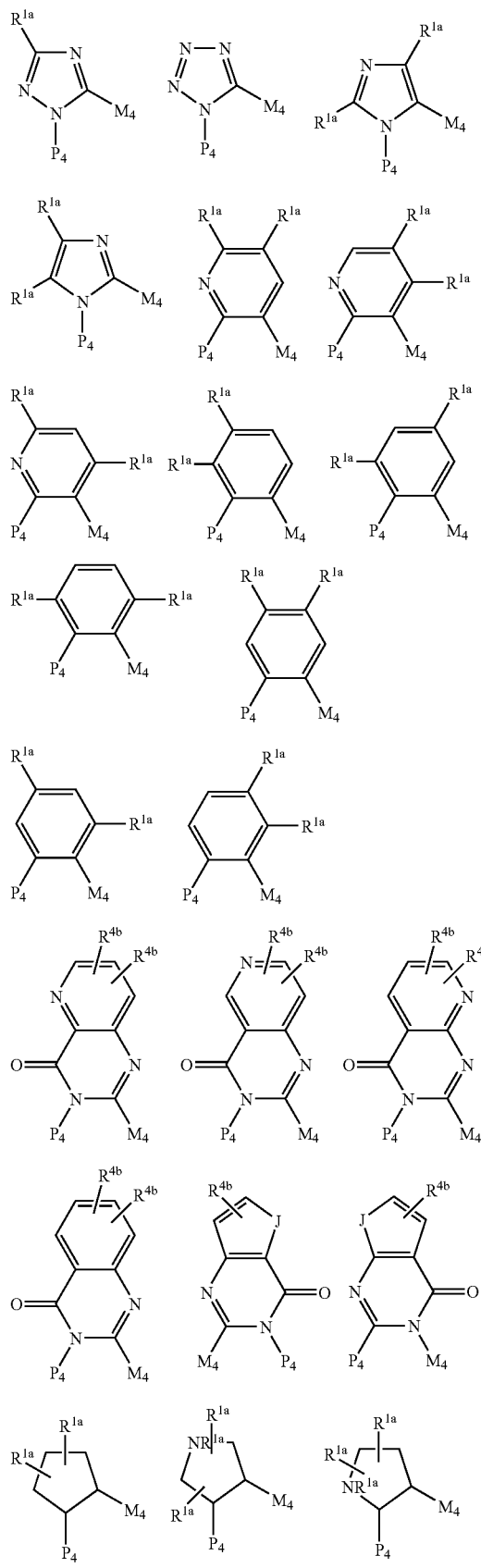
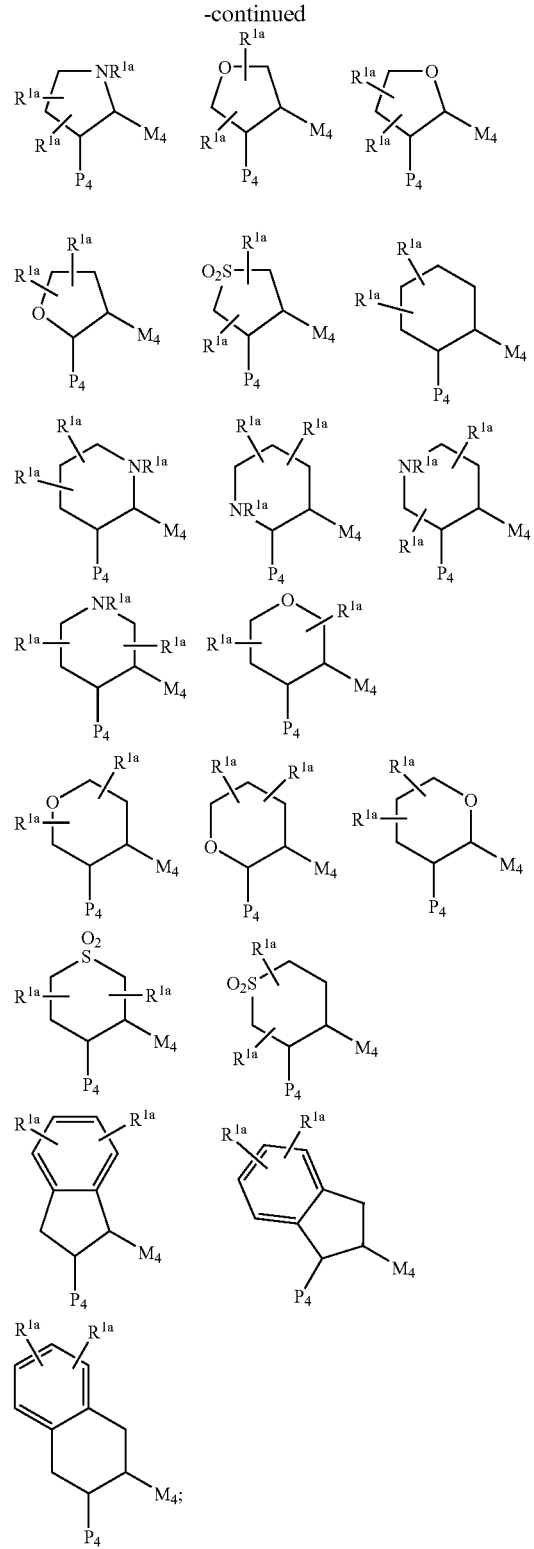
J is selected from O, S, NH, and NR$^{1a}$;
P$_4$ is -G;
M$_4$ is -A-B;
G is selected from: 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 5-chloro-pyrid-2-yl; 5-chloro-thien-2-yl; 6-amino-5-chloro-pyrid-2-yl; 6-amino-pyrid-2-yl; 3-amidino-phenyl;
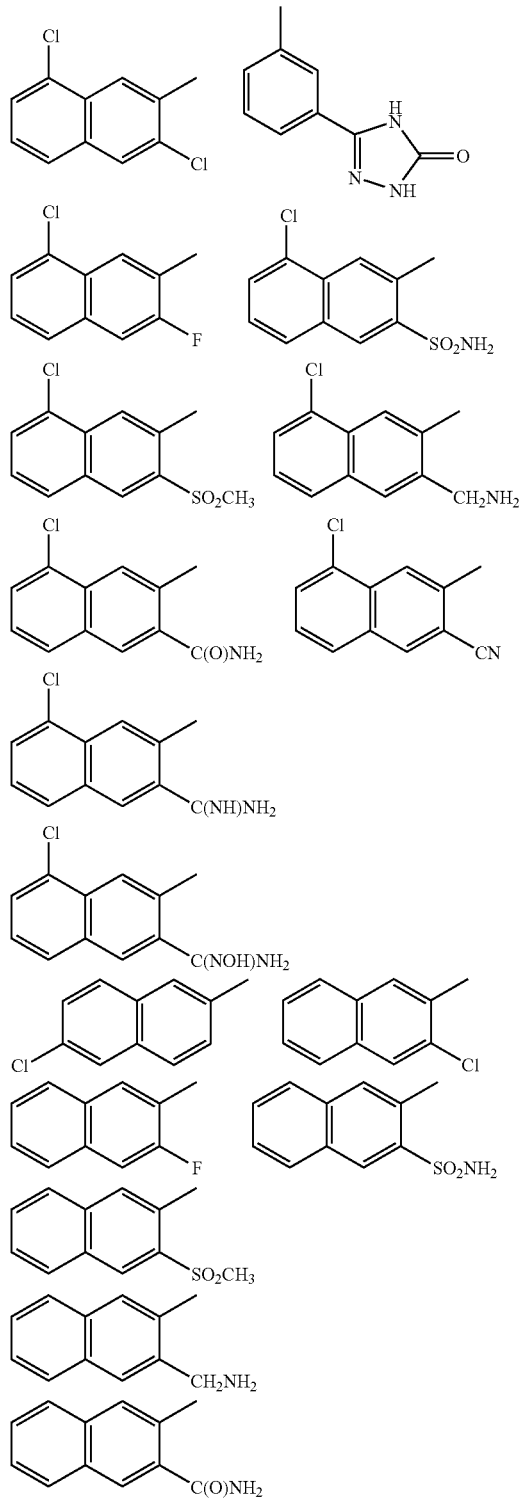
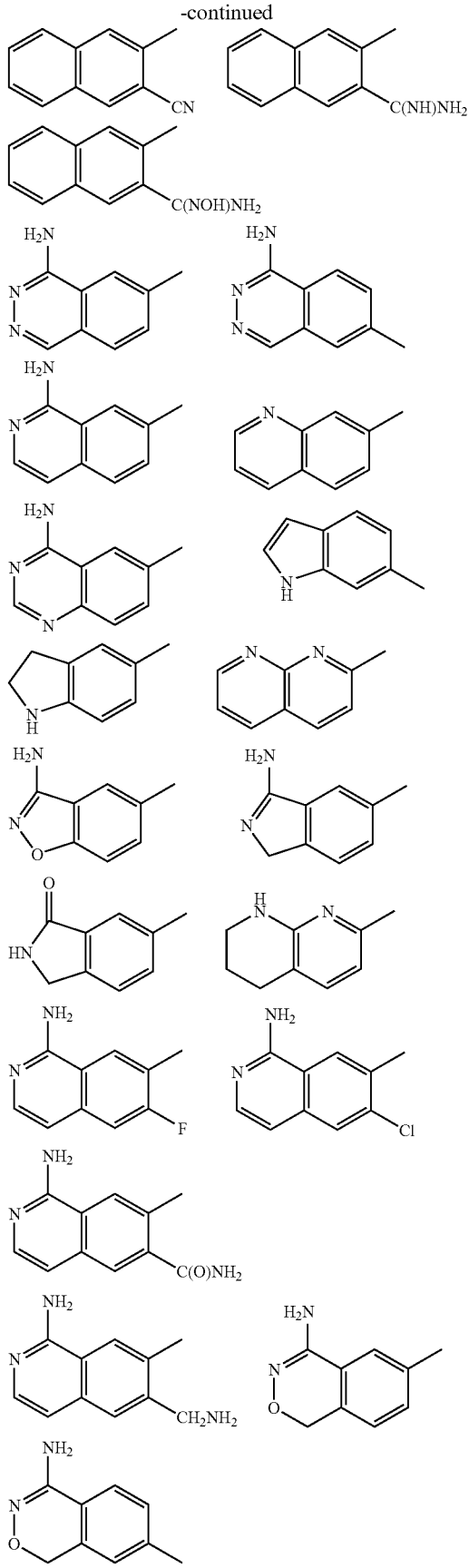

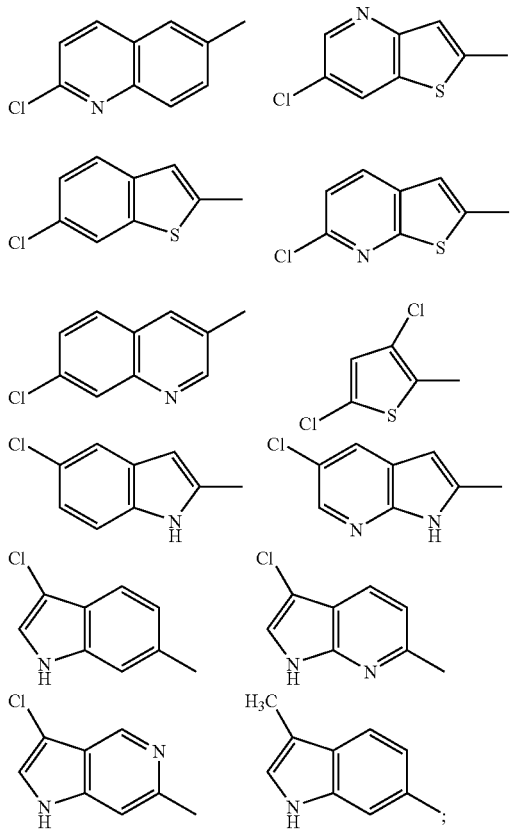

G₁ is absent or is selected from CH₂NH, NHCH₂, CH₂C(O), C(O)CH₂, C(O)NH, NHC(O), NHC(O)NH, CH₂S(O)₂, S(O)₂(CH₂), SO₂NH, and NHSO₂, wherein the right side of G₁ is attached to ring G, provided that G₁ does not form a N—S, NCH₂N, NCH₂O, or NCH₂S bond with either group to which it is attached;

A is 2–6 membered linear chain consisting of: carbon atoms, 0–1 carbonyl groups, and A is substituted with 0–1 $R^{1a}$ and 0–2 $R^2$, and there are 0–1 double bonds;

B is selected from Y, $N(B^1)C(O)C(R^3R^{3g})NB^2B^3$,

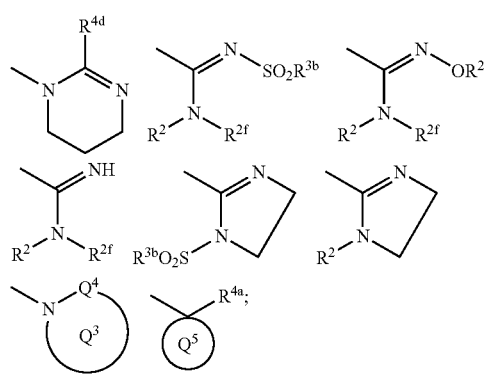

provided that the $R^{4d}$ shown is other than OH;

$B^1$ is selected from H, CH₃, CH₂CH₃, and CH₂CH₂CH₃;

$B^2$ is selected from H, CH₃, and CH₂CH₃;

$B^3$ is selected from CH₃, CH₂CH₃, CH₂CH₂CH₃, CH(CH₃)₂, CH₂CH₂CH₂CH₃, C(CH₃)₃, CH(CH₃)CH₂CH(CH₃)₂, CH₂CH₂OH, CH(CH₃)CH₂OH, CH(phenyl)CH₂CH₃, cyclopropyl, cyclobutyl, cyclopentyl, cyclohexyl, and CH₂-cyclopropyl;

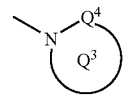

is attached to a different atom on A than M and is selected from the group:

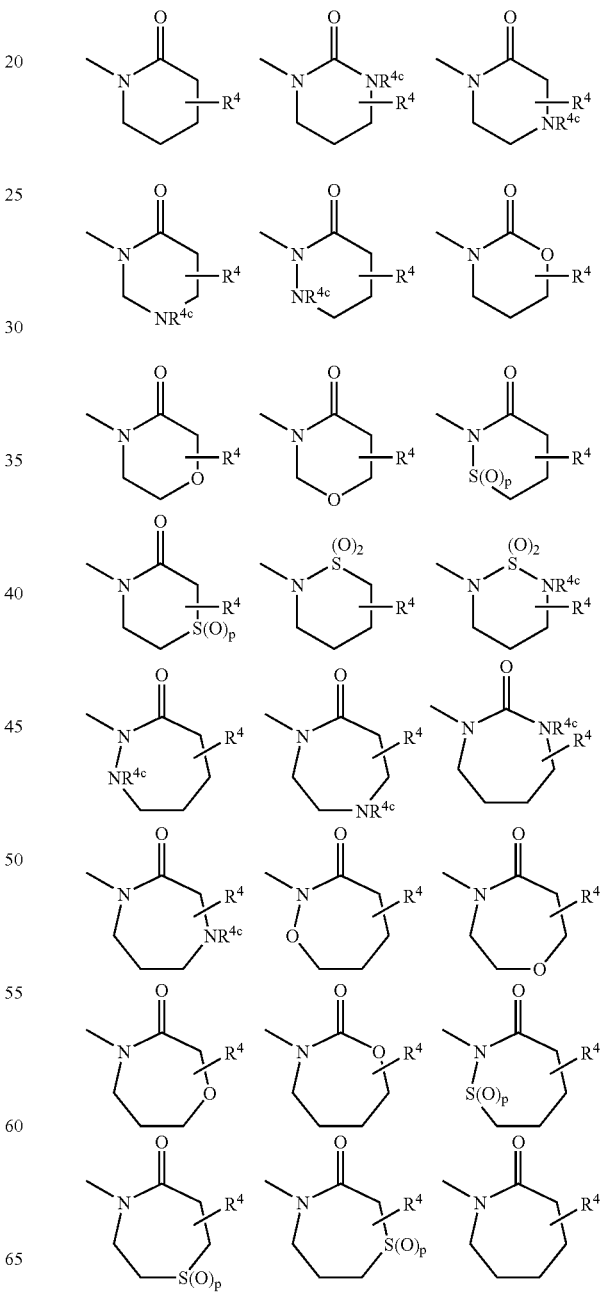

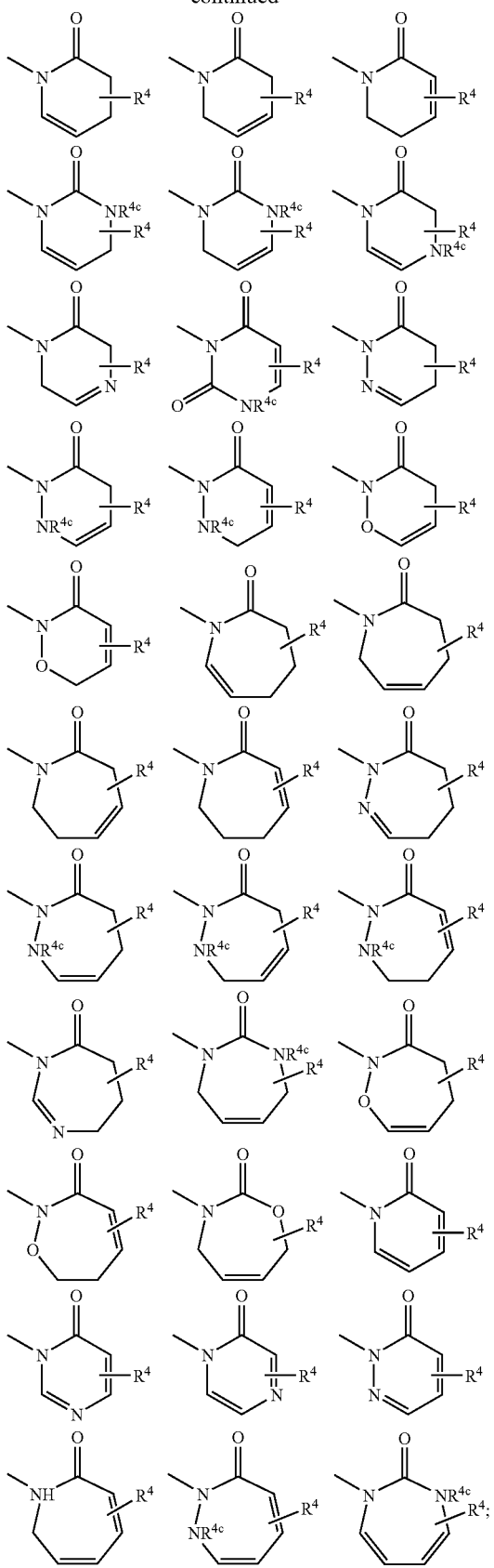

ring $Q^5$ is selected from cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

Y is selected from $C(CH_3)_2R^{4a}$ and $C(CH_2CH_3)_2R^{4a}$;

alternatively, Y is selected from phenyl, pyridyl, 1,2,3-triazolyl, imidazolyl, and benzimidazolyl, and is substituted with 1 $R^{4a}$;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, and $OCH_3$;

alternatively, $NR^2R^{2f}$ forms a ring selected from morpholine, piperazine, piperidine, and pyrrolidine;

$R^4$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from —$(CH_2)_r$-5–6 membered carbocycle substituted with 0–3 $R^{4c}$, —$(CH_2)_r$-5–6 membered heterocycle substituted with 0–3 $R^{4c}$ and consisting of: carbon atoms and 1–4 heteroatoms selected from the group consisting of N, O, and $S(O)_p$, $(CH_2)_r NR^{2d}R^{2d}$, $(CH_2)_r N(\to O)$ $R^{2d}R^{2d}$, $(CH_2)_r OR^{2d}$, $(CH_2)_r C(O)NR^{2d}R^{2d}$, $(CH_2)_r NR^{2d}C(O)R^{2e}$, $(CH_2)_r C(O)R^{2e}$, $(CH_2)_r NR^{2d}C(O)NR^{2d}R^{2d}$, $(CH_2)_r NR^{2d}C(O)OR^{2d}$, $(CH_2)_r NR^{2d}SO_2R^{2d}$, and $(CH_2)_r S(O)_p R^{2d}$, provided that $S(O)_p R_{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\to O)R^2R^{2a}$, $CH_2N(\to O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_p R^{5a}$, $CH_2S(O)_p R^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a thirteenth embodiment, the present invention provides a novel compound, wherein the compound is selected from:

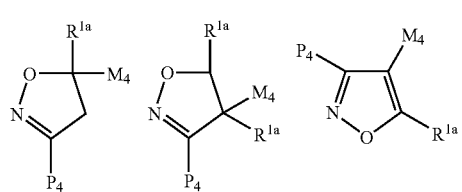

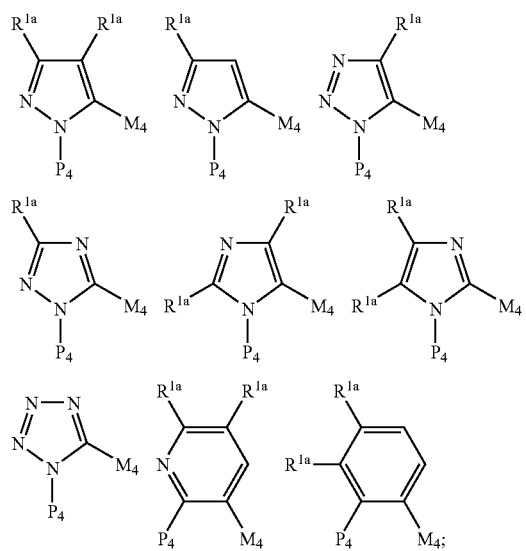

G is selected from:

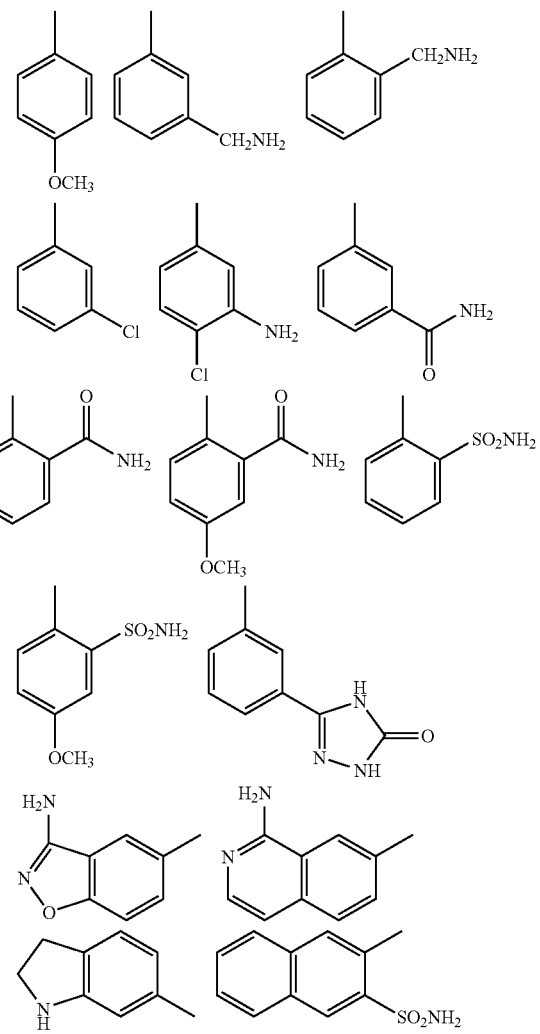

-continued
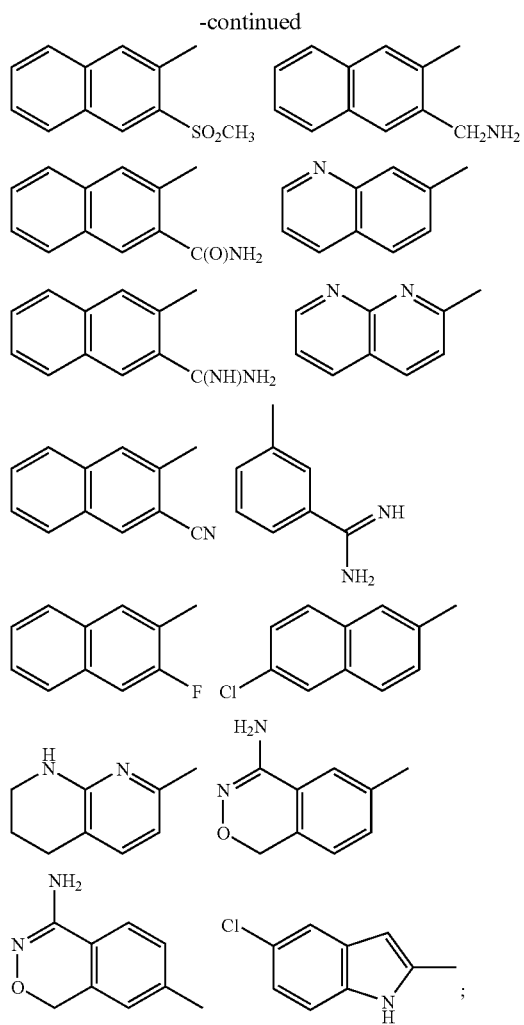
A is selected from:
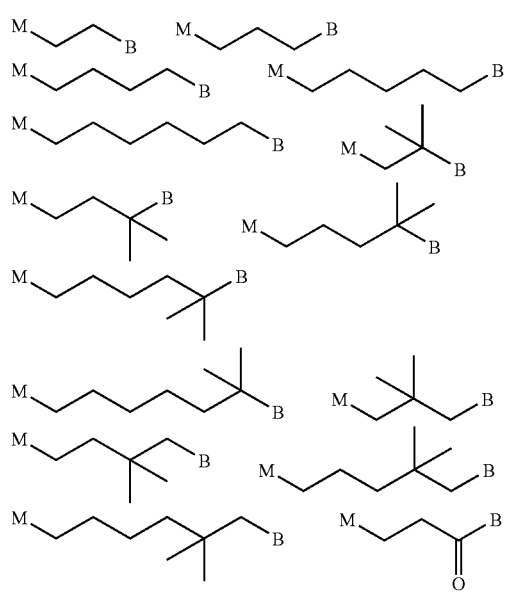
-continued
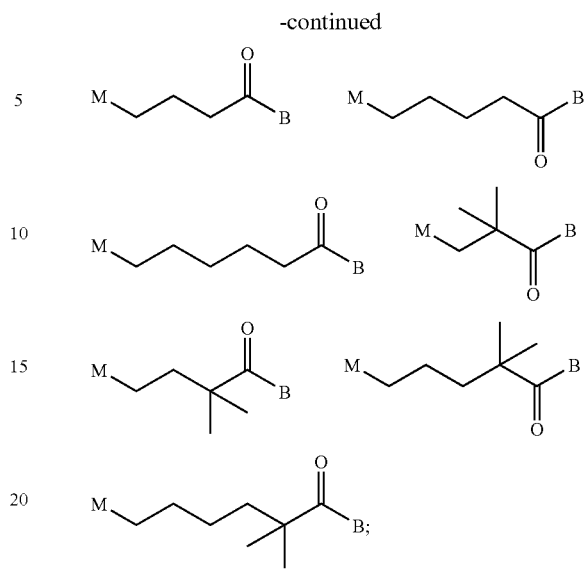
B is selected from:
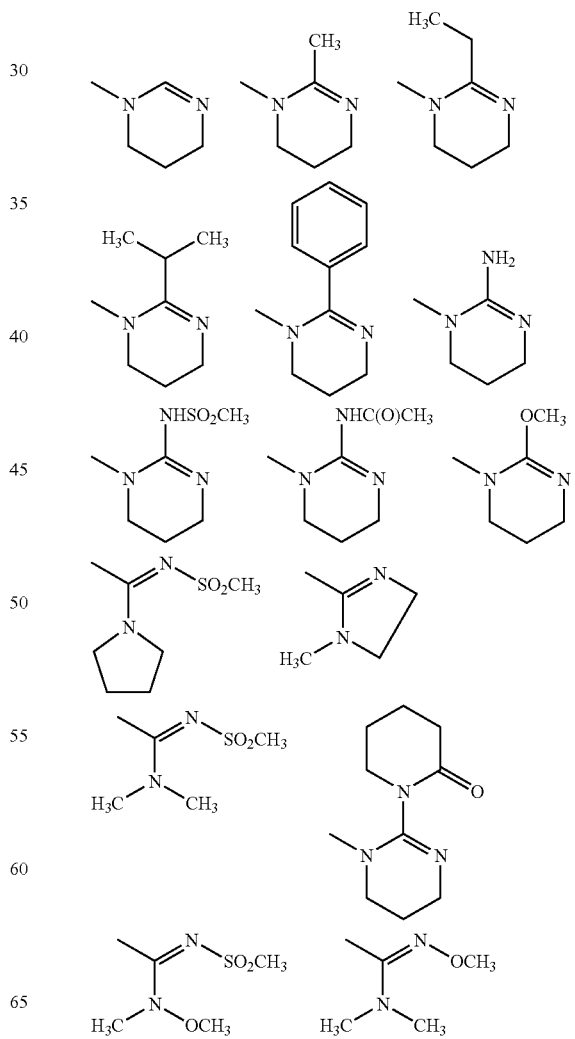

-continued

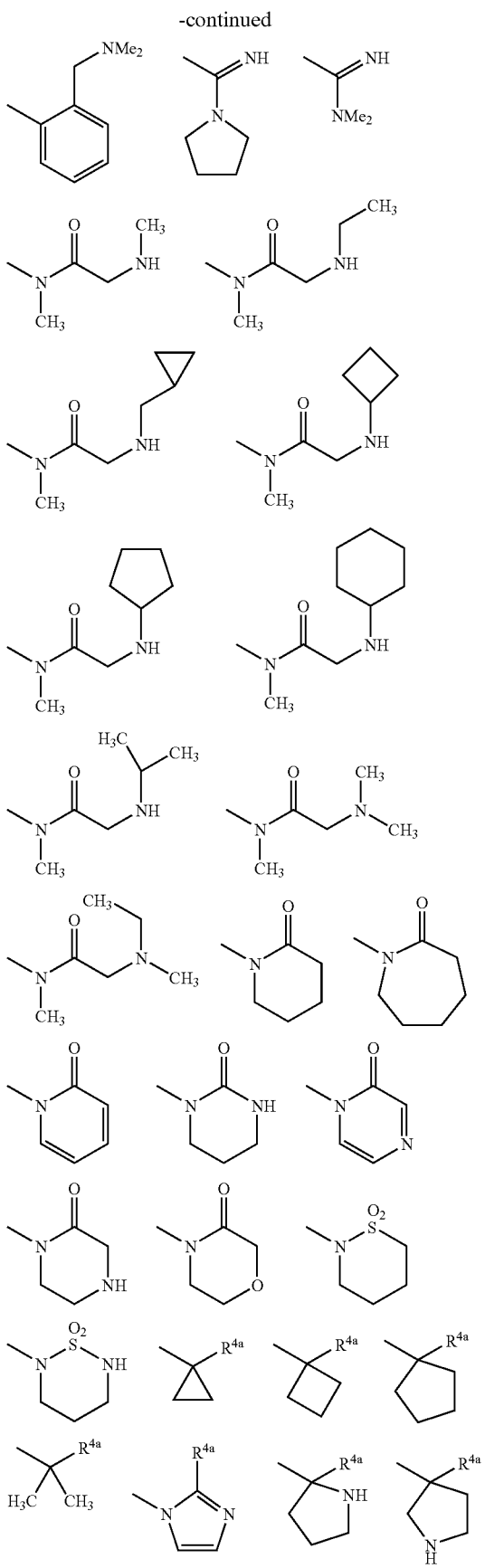

-continued

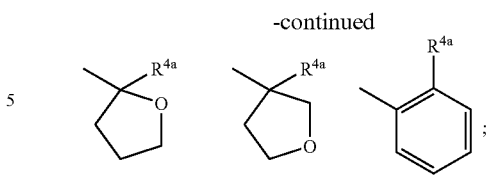

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —(CH$_2$)-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —(CH$_2$)-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a fourteenth embodiment, the present invention provides a novel compound, wherein the compound is selected from:

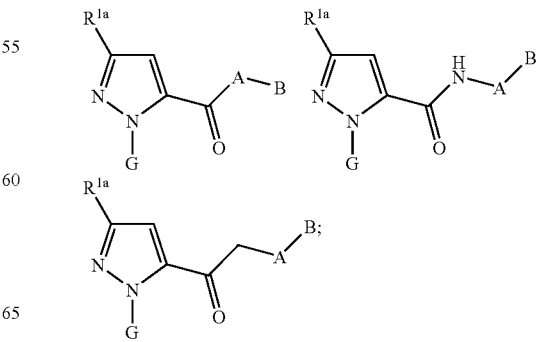

A is selected from:
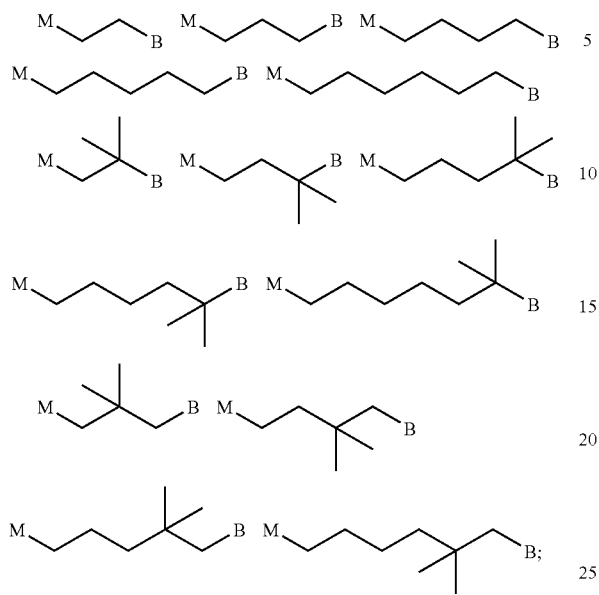
B is selected from:
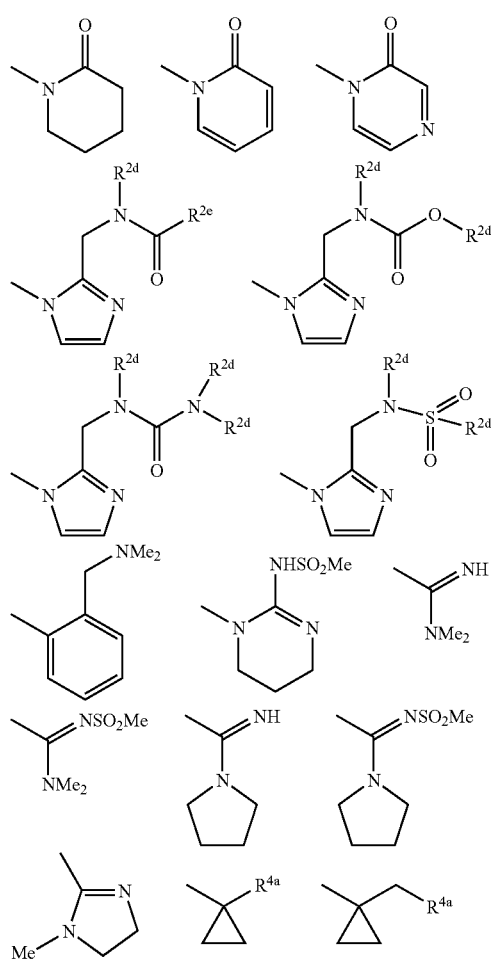
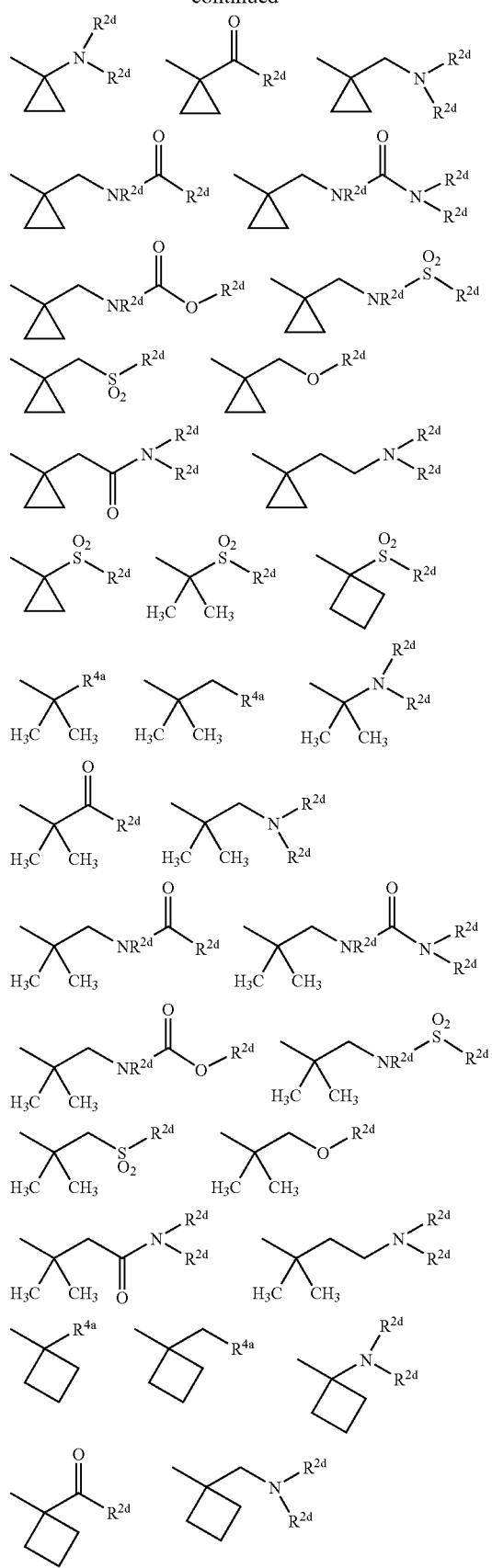

-continued

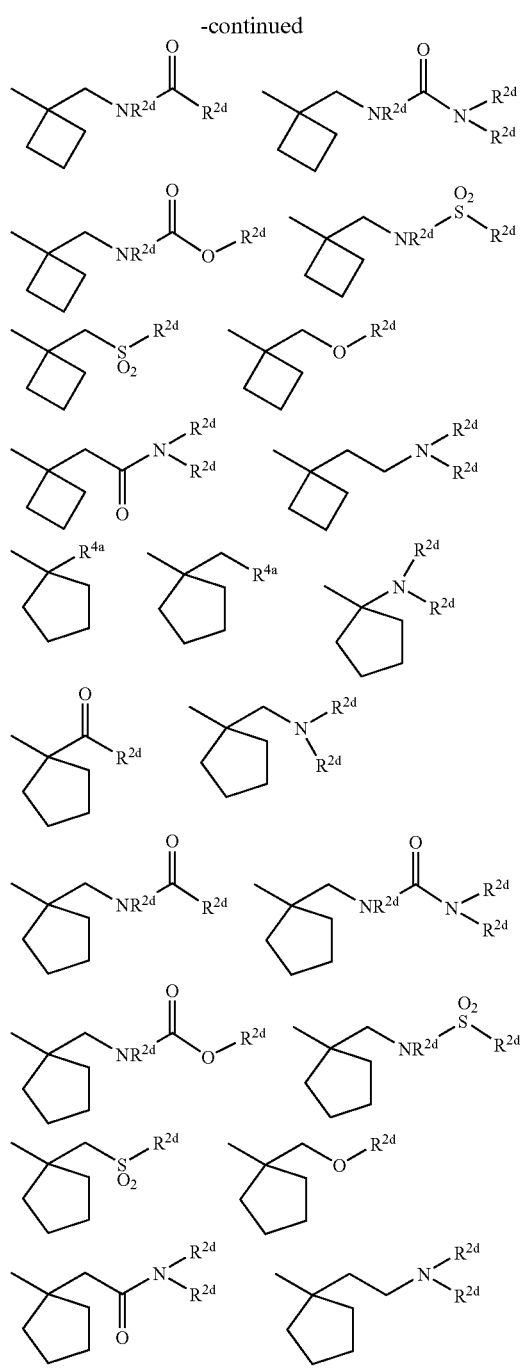

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NH$_2$, cyclopropyl, CH$_2$-cyclopropyl, cyclobutyl, cyclopentyl, and thiazolyl;

$R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazolyl, imidazoline, imidazolidine, oxazoline, and thiazoline; and $R^{4c}$ is selected from =O, OH, OCH$_3$, and CH$_3$.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "linear chain," as used herein to describe linker A, is intended to mean a series of atoms (i.e., carbon, oxygen, nitrogen, and sulfur) that are connected together one at a time to form a chain. Thus, a chain atom is connected to one other chain atom if it is a terminal atom or two other chain atoms if is non-terminal. The only way a chain atom is allowed to be part of a ring is if the ring is spirocyclic (i.e., the ring is attached to only one chain atom). Examples of a 5-membered linear chain include $C(O)NHCH_2NHC(O)$ and $NHC(O)CH_2S(O)_2NH$, but not 1-amino-2-carbamoyl-cyclohexane. The number of chain atoms is determined by counting each atom in the chain, but not any atom substituted thereon. Thus, the 3 oxygen atoms and 4 hydrogen atoms of the group $S(O)_2NHCH_2NHC(O)$ are not counted, and $S(O)_2NHCH_2NHC(O)$ is a 5-membered chain, not a 12-membered chain.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl, groups. "Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of: carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of: carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

All references cited herein are hereby incorporated in their entirety herein by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. Also, the functionality present on the molecule should be consistent with the transformations proposed. This will sometimes require a judgment to modify the order of the synthetic steps or to select one particular process scheme over another in order to obtain a desired compound of the invention.

Another major consideration in the planning of any synthetic route in this field is the judicious choice of the protecting group. An authoritative account describing the many alternatives to the trained practitioner is Greene and Wuts (*Protective Groups In Organic Synthesis*, Wiley and Sons, 1991).

The synthesis of compounds of the present invention involving intermediate A-B is accomplished via standard methods known to those skilled in the art. A general route that involves this type of methodology is outlined in Scheme 1. Construction of compounds with a general structure G-G$_1$-M-A-B (wherein G$_1$ is an optional linker) can be performed in two directions: 1) from G to G-G$_1$-M then to G-G$_1$-M-A-B or 2) from A-B to M-A-B then to G-G$_1$-M-A-B. During the synthesis of these compounds, it may be useful or necessary to use protecting groups to prevent cross-reaction during the coupling conditions. Examples of suitable protecting groups and their uses are described in "The Peptides: Analysis, Synthesis, Biology", Academic Press, Vol. 3 (Groii, et al Eds., 1981). Functional group transformations and coupling reactions that can be used to prepare compounds of the present invention are described in "Advanced Organic Chemistry: Reaction, Mechanism, and Structure" (March, et. al. fourth Ed.) and "Comprehensive Organic Transformations" (Larock, second Ed.).

Scheme 1

Formula I

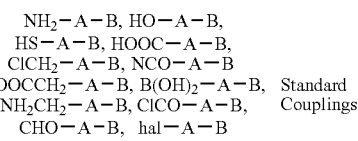

G—G$_1$—M— (acid chloride, acid, sulfonylchloride, amino, isocyanate, alkylhalide, aldehyde, alcohol, sulfonamide, etc)

Formula II or

Formula I

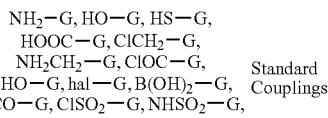

B—A—M— (acid chloride, acid, sulfonylchloride, amino, isocyanate, alkylhalide, aldehyde, alcohol, sulfonamide, etc)

Formula III

Compounds of the present invention wherein P is fused to M can be prepared from the readily accessible pyrazolo-piperidinone core (see Scheme 2). This can be accomplished by employing the [3+2] cycloaddition methodology. A suitably substituted phenyl, heteroaryl, naphthyl, or other carbocyclic hydrazone can be prepared by the condensation of an appropriate hydrazine with an appropriate aldehyde (or acetal thereof). Chlorination or bromination of the hydrazone should afford the desired halohydrazone. A useful dienophilic species can be obtained from commercially available δ-valerolactam by chlorination with PCl$_5$ and elimination to the chloro-olefinone dienophile or displacement with morpholine to the morpholino-enamine dienophile. The [3+2] cycloaddition can be accomplished in refluxing toluene containing excess triethylamine base to afford the desired pyrazolo-piperidinone.

Scheme 2

Synthesis of halo hydrazones

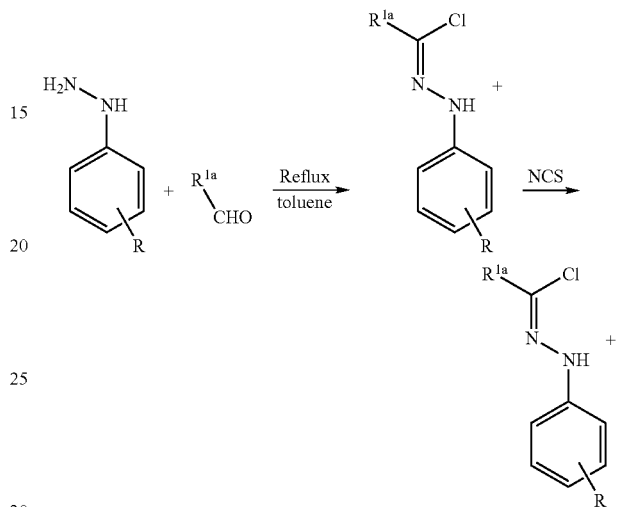

Synthesis of dienophiles

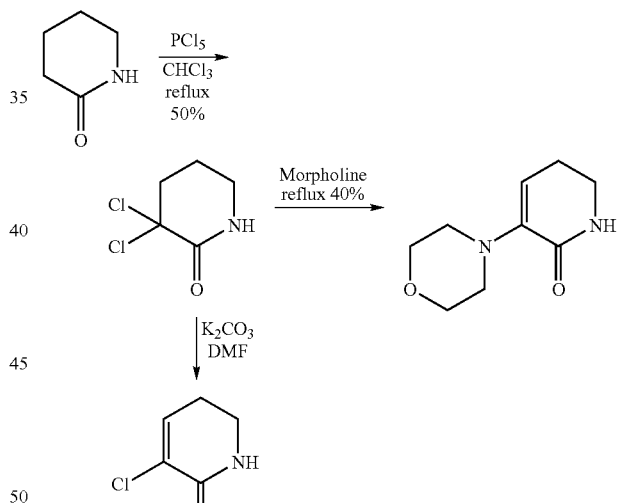

Synthesis of the pyrazolopiperidinone

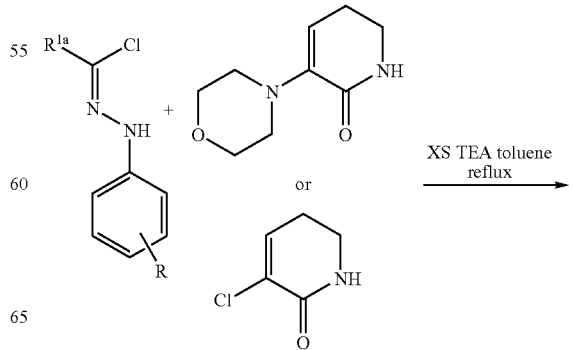

-continued

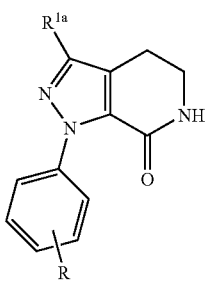

Treatment of the pyrazolo-piperidinone intermediate with commercially available alkyl halides with an appropriate terminal functional group, should afford various alkylated intermediates (see Scheme 3). When the terminal group is an ester, it can either be treated with amines under Weinreb conditions to afford amides or hydrolyzed to acids and reduced to the corresponding alcohols that can then serve as key intermediates to a variety of amino analogs. The alcohol analogs can be converted to halides and then aminated or can be alkylated with suitable amides or cyclic amides in the presence of sodium hydride to afford lactams or amide containing compounds. The ester and/or nitrile intermediates can be alkylated to the geminal methylated analogs, which in turn can be converted to numerous compounds of the present invention by methods known to those skilled in the art.

Scheme 3

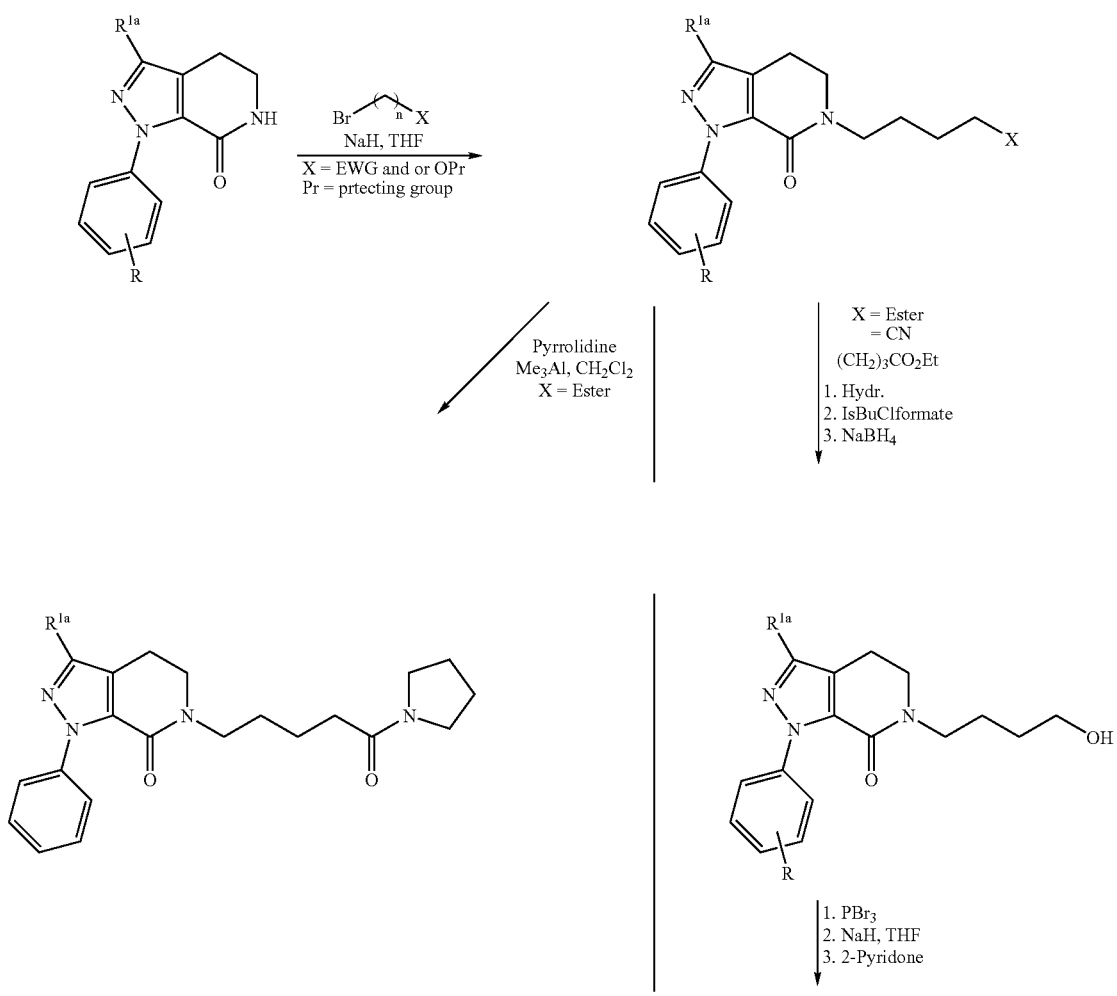

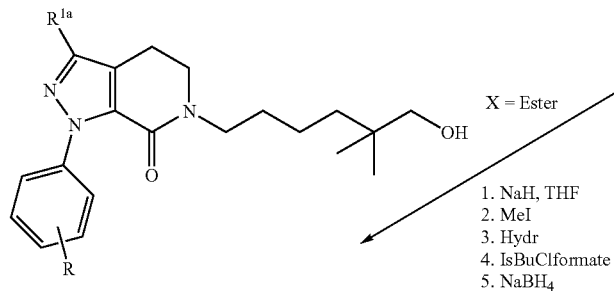

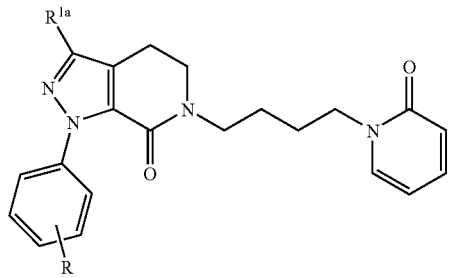

X = Ester

1. NaH, THF
2. MeI
3. Hydr
4. IsBuClformate
5. NaBH₄

1. PBr₃
2. NHMe₂

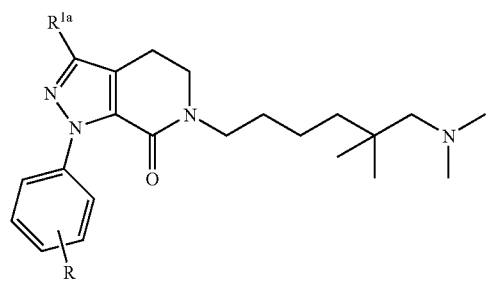

Compounds of present invention can be obtained by alkylation of the pyrazolo-piperidinone pharmacophore with a wide variety of electrophiles. Some useful electrophiles are illustrated in Scheme 4 below.

Scheme 4

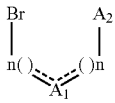

$A_2$ can be ester, nitrile, O—Pg, S—Pr, $NR^3R^{3a}$, etc.
$A_1$ can be O, $NR_2$, S, $SO_2$, aryl, heteroaryl, etc.
Pg = Protecting group
n = 1-6

Schemes 2–4 describe how to make the A-B moieties of the present invention and how to couple them to prepare compounds of the present invention. The remaining portions of the compounds of the present invention, $G-G_1-P-M$, $G-G_1-M-P$, and $G-G_1-M$, can be prepared using methods known to those of ordinary skill in the art.

All of the following patents and publications are incorporated herein by reference. For compounds wherein ring P is absent and ring M is a 5-, 6-, or 7-membered ring, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 5,998,424, U.S. Pat. No. 6,191,159, WO98/57951, WO99/32454, WO00/039108, WO00/059902, WO01/32628, WO01/005785, WO02/00651, WO02/102380, WO02/94197, and WO02/00647 for starting materials and intermediates to which the present B and/or A-B groups can be coupled. For compounds wherein ring P is fused to ring M (i.e., a bicyclic moiety is present), one of ordinary skill in the art can look to WO00/39131, WO02/94197, U.S. Ser. No. 10/104,467, U.S. Ser. No. 10/105,477 and WO02/00655 for starting materials and intermediates to which the present B and/or A-B groups can be coupled.

For compounds wherein G is a ring substituted with a basic moiety, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 6,191,159, WO98/57951, WO99/32454 WO00/059902, WO01/32628, WO00/39131, WO02/00651, WO02/102380, WO02/94197, U.S. Ser. No. 10/104,467, and U.S. Ser. No. 10/105,477 for starting materials and intermediates to which the present A and/or A-B groups can be coupled. For compounds wherein G is a ring substituted with a non-basic group, one of ordinary skill in the art can look to U.S. Pat. No. 5,998,424, WO00/39131, WO00/059902, WO01/32628, WO02/00651, WO02/102380, WO02/94197, U.S. Ser. No. 10/104,467, and U.S. Ser. No. 10/105,477 for starting materials and intermediates to which the present A and/or A-B groups can be coupled. For compounds wherein G is a bicyclic moiety, one of ordinary skill in the art can look to WO098/57951 WO00/039108, WO00/39131, WO02/00651, WO02/102380, WO02/94197, U.S. Ser. No. 10/104,467, and U.S. Ser. No. 10/105,477 for starting materials and intermediates to which the present A and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed.

Scheme 5 illustrates some of the numerous pyrrole intermediates that can be used to prepare compounds of the present invention ($R^z$ is the point of attachment for A-B and can be H, a protecting group, A, or a group modifiable to A). These intermediates are described in the above-noted patents and publications.

Scheme 5

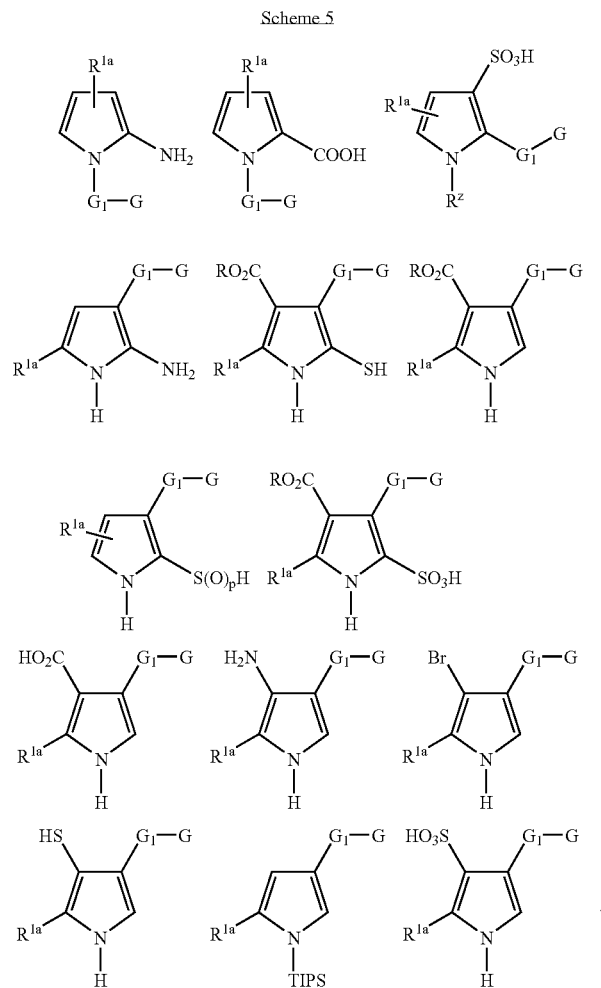

Scheme 6 illustrates some of the numerous imidazole, triazole, and tetrazole intermediates that can be used to prepare compounds of the present invention. These intermediates are described in the above-noted patents and publications. In Scheme 6, V is nitro, amino, thio, hydroxy, sulfonic acid, sulfonic ester, sulfonyl chloride, ester, acid, or halide; U is aldehyde, ester, acid, amide, amino, thiol, hydroxy, sulfonic acid, sulfonic ester, sulfonyl chloride, or methylene halide. A' is used to indicate that this group is a subset of A and when taken with an adjacent group (e.g., C=O) represents the A group of the present invention.

Scheme 6

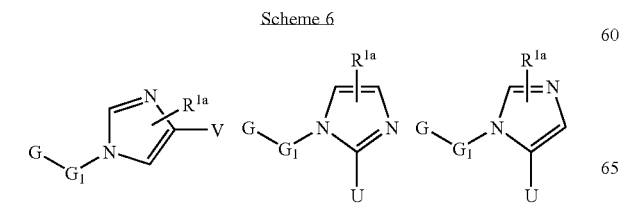

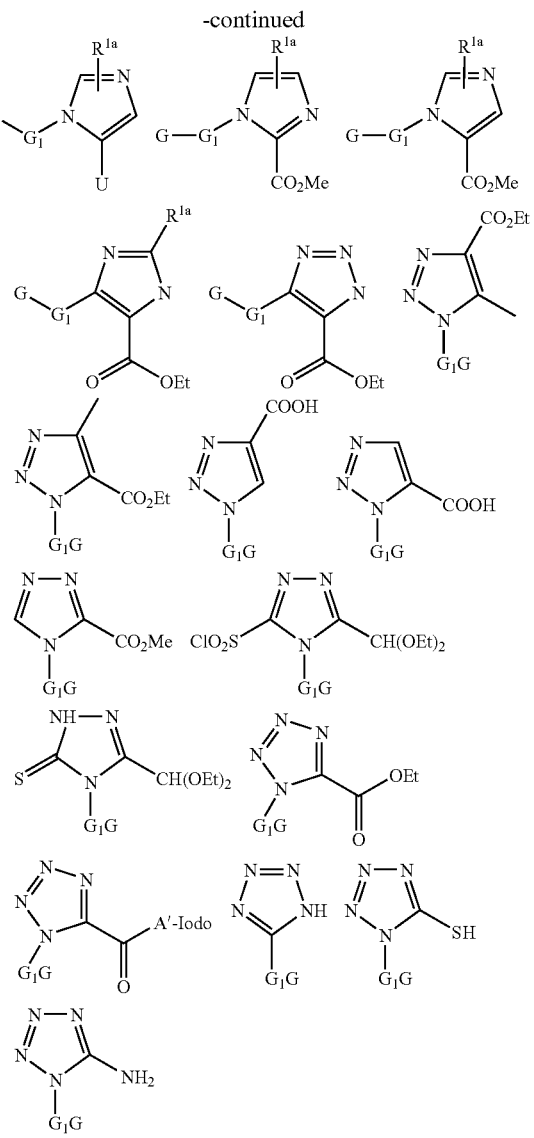

Scheme 7 shows some of the numerous pyrazole intermediates that can be used to prepare compounds of the present invention. These intermediates are described in the above-noted patents and publications.

Scheme 7

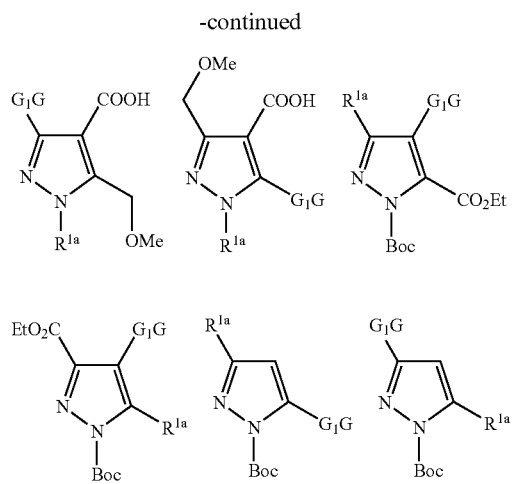

Scheme 8 depicts some of the numerous oxazole, thiazole, isoxazole, oxadiazole, and thiadiazole intermediates that can be used to prepare compounds of the present invention. These intermediates are described in the above-noted patents and publications. In Scheme 8, V is nitro, amino, ester, or acid.

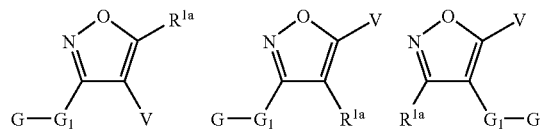

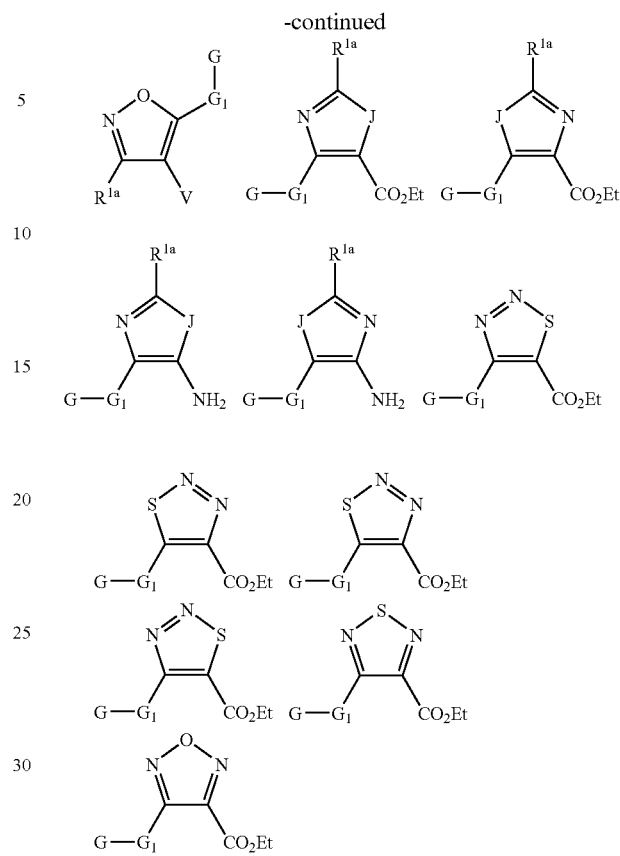

Scheme 9 illustrates intermediates useful for making a compound of the present invention wherein ring P is fused to ring M. These intermediates can be modified by those knowledgeable in the art to prepared other compounds of this invention.

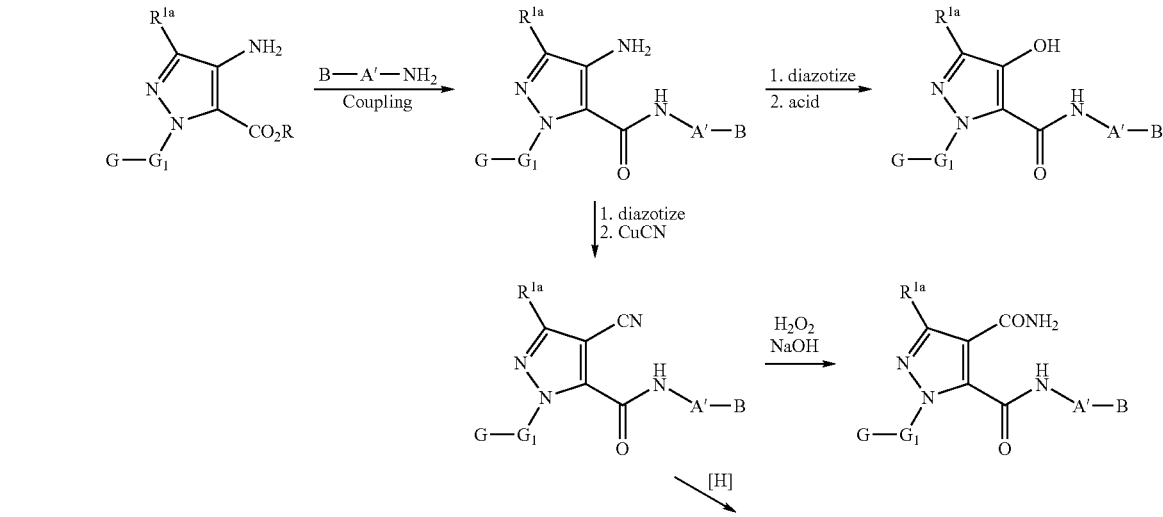

-continued

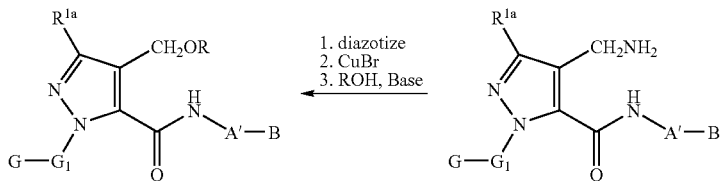

Scheme 10 shows some of the intermediate templates from this invention that can be obtained from compounds shown in Scheme 9.

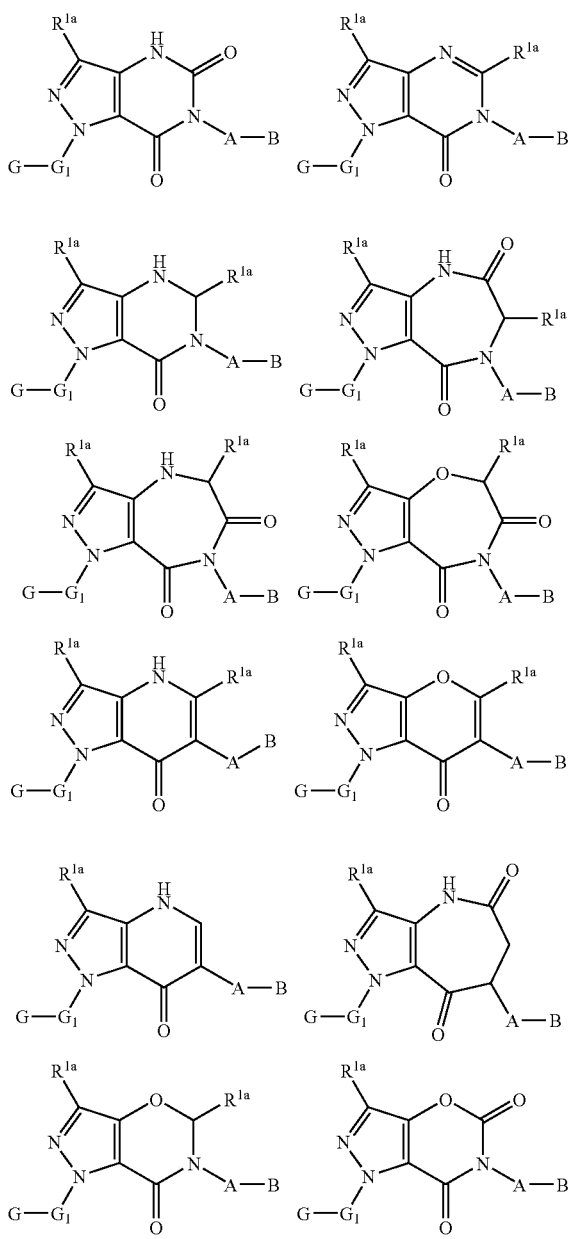

-continued

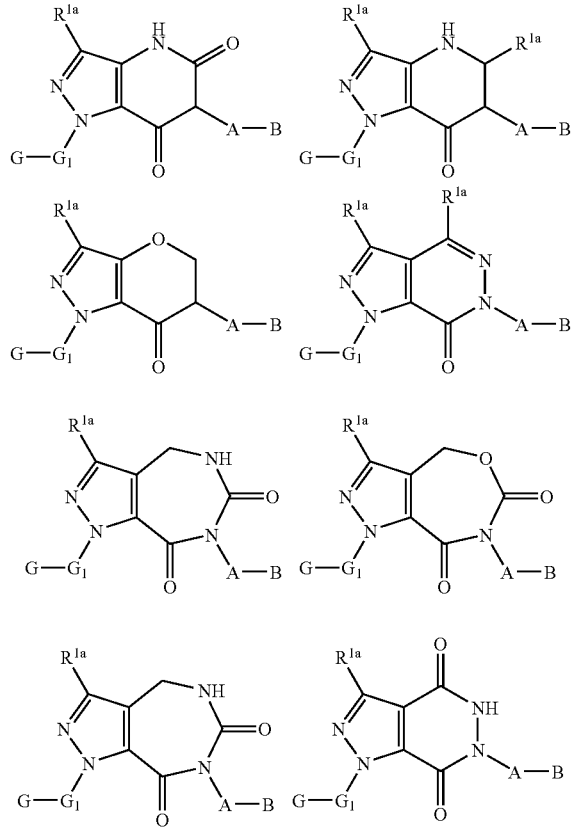

Scheme 11 depicts another intermediate useful for making a compound of the present invention wherein ring P is fused to ring M. Scheme 11 also illustrates a number of bicyclic compounds that can be made from this intermediate or derivatives thereof (e.g., the corresponding cyclohexenone). In Scheme 11, U is OH or morpholine and V is H or $C(O)R^{1a}$. This intermediate, derivatives thereof, and their modification are described in the above-noted patents and publications.

Scheme 11

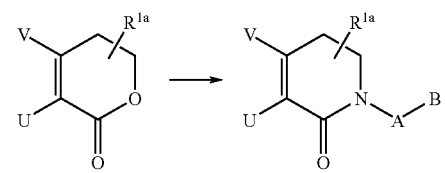

-continued

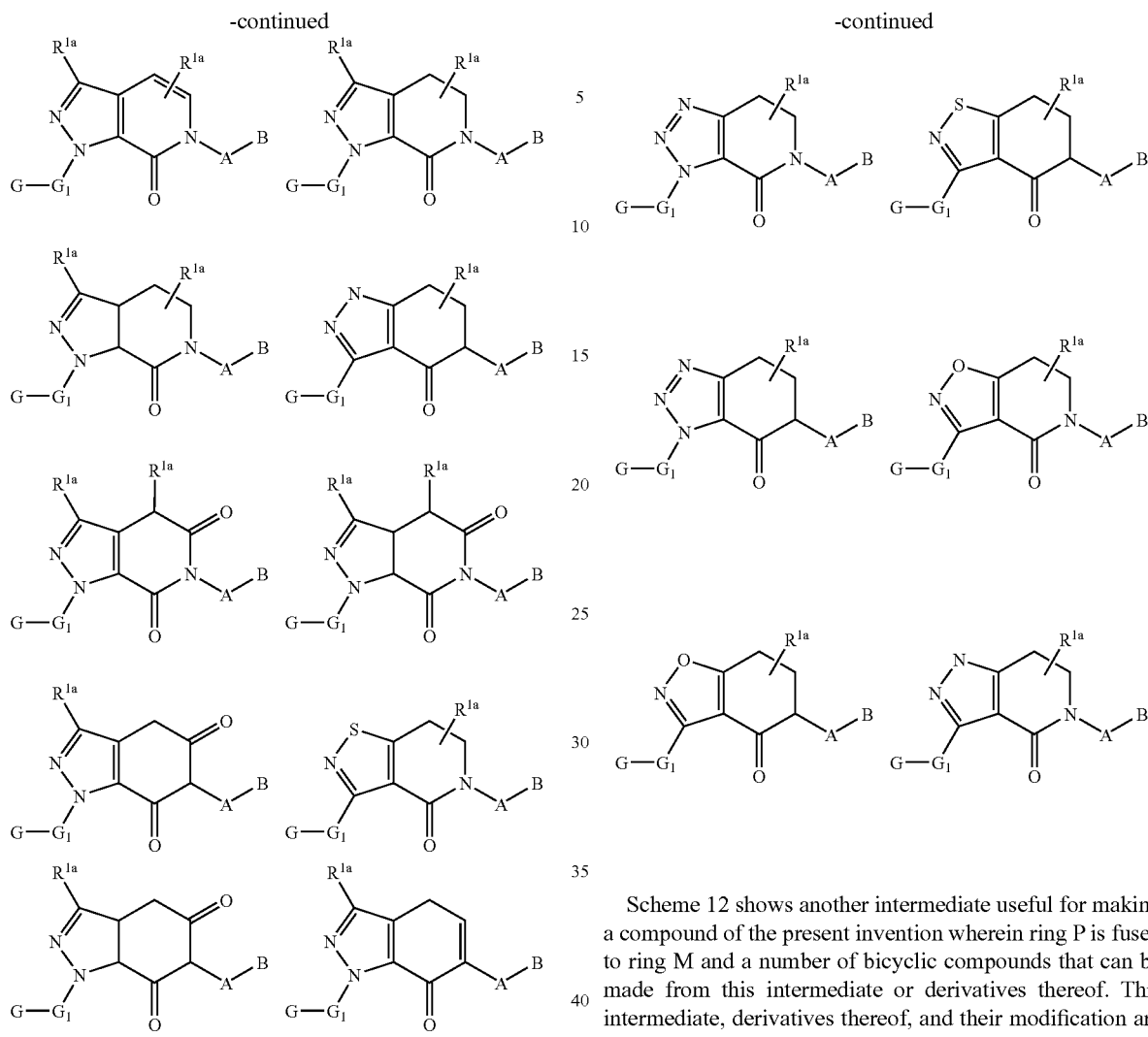

Scheme 12 shows another intermediate useful for making a compound of the present invention wherein ring P is fused to ring M and a number of bicyclic compounds that can be made from this intermediate or derivatives thereof. This intermediate, derivatives thereof, and their modification are described in the above-noted patents and publications.

Scheme 12

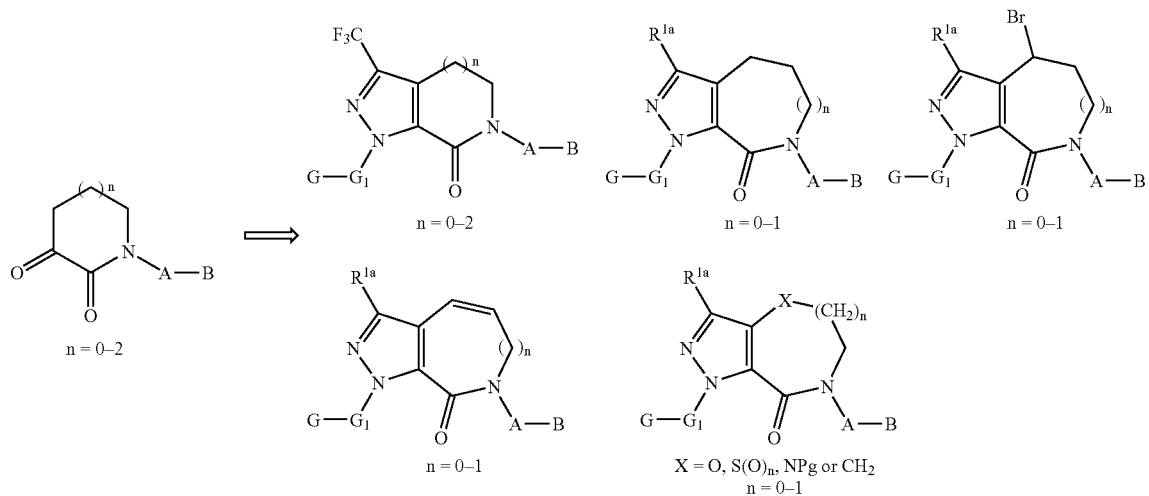

Scheme 13 illustrates a number of other bicyclic rings that are included in the present invention as rings P-M. Scheme 13 also describes a method of converting the shown rings to compounds of the present invention. This methodology is applicable to heterobicyclics not shown, but included in the present invention.
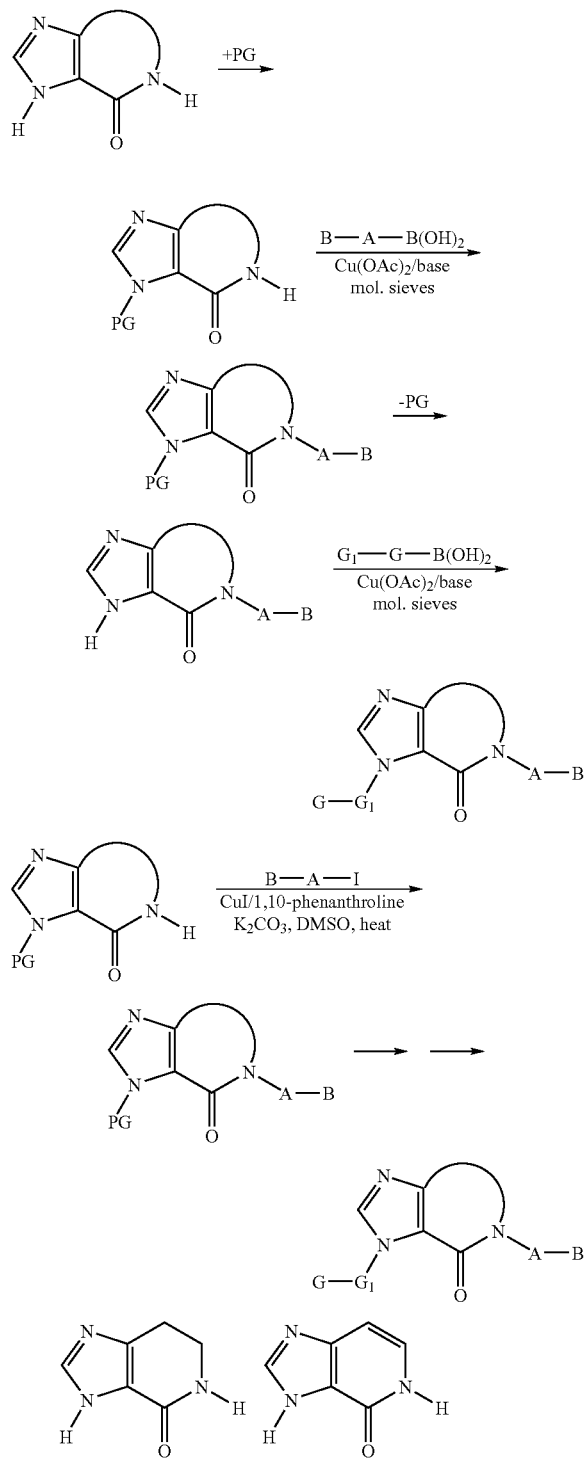
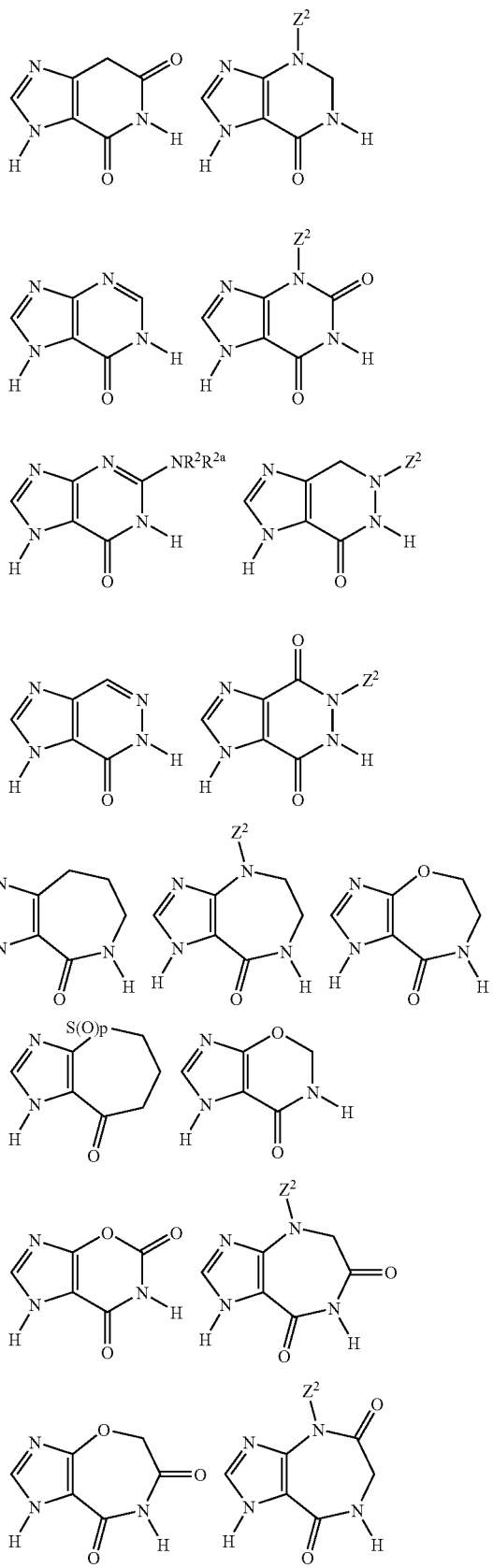

-continued

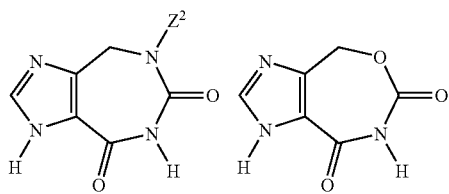

Scheme 14 depicts some of the numerous 6-membered aromatic ring intermediates that can be used to prepare compounds of the present invention. These intermediates are described in the above-noted patents and publications. In Scheme 14, V is nitro, sulfonic acid or carboxylic acid.

Scheme 14

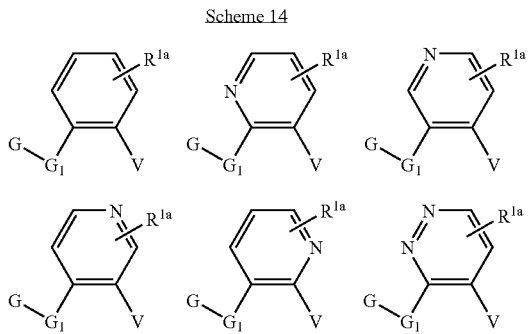

-continued

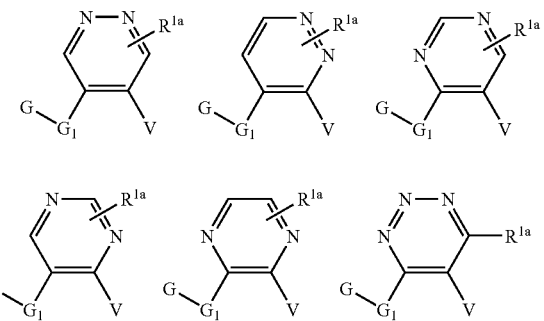

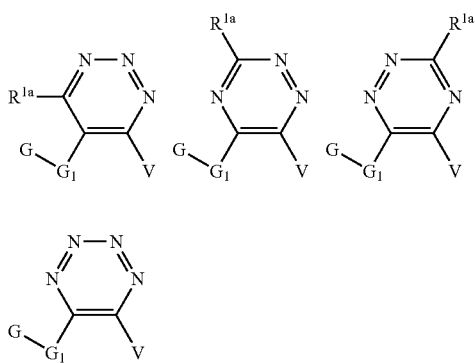

Benzo-bicyclics can also be obtained as shown in Schemes 15 and 16.

Scheme 15

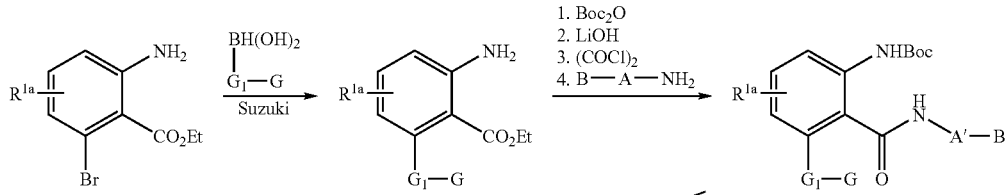

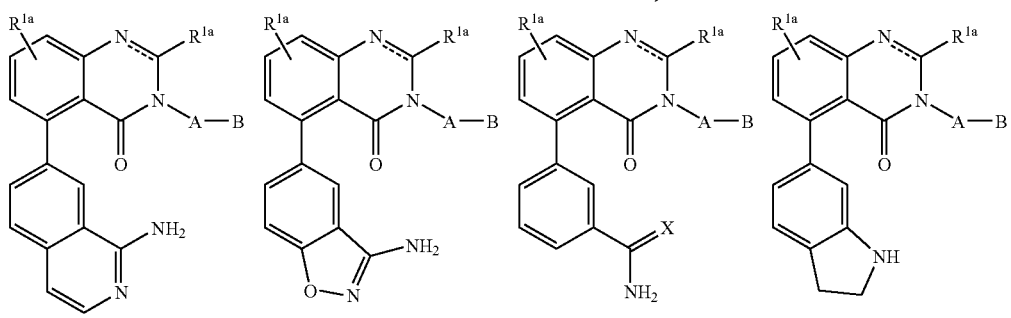

X = H, NH, O, S, $NR^7$

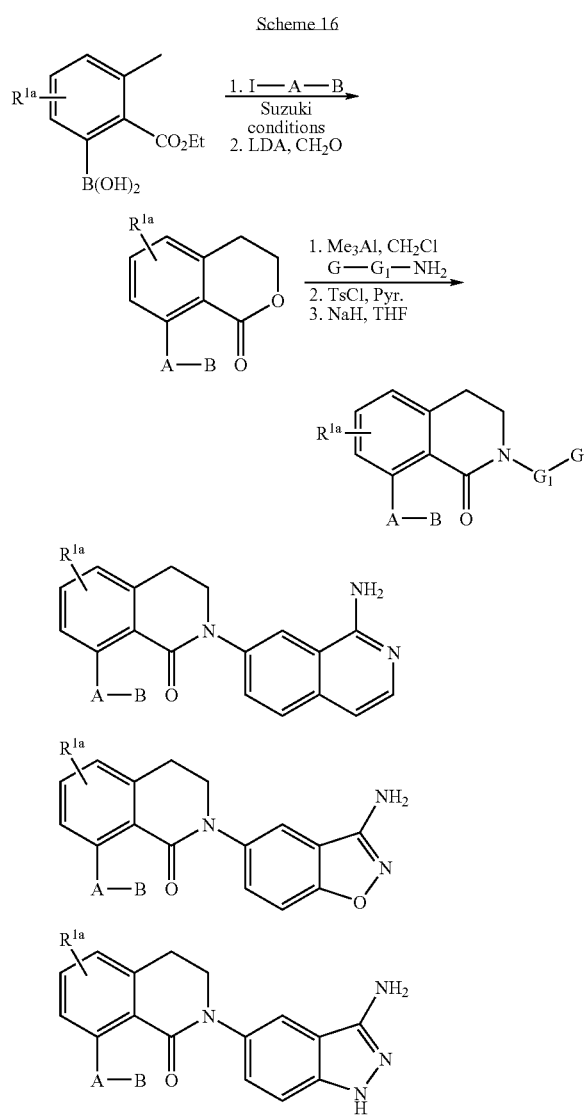

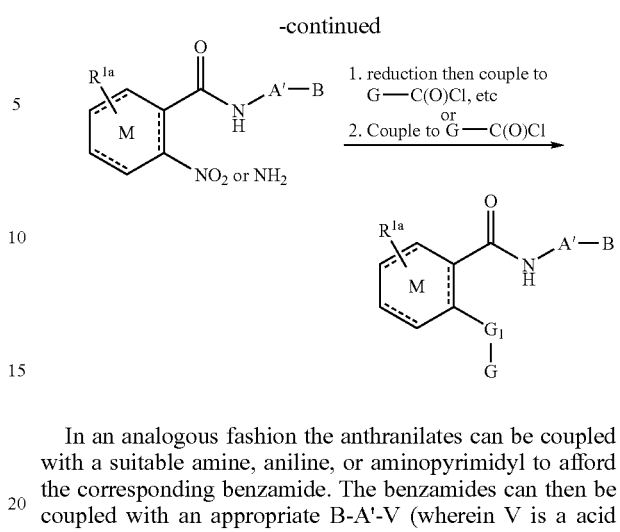

In an analogous fashion the anthranilates can be coupled with a suitable amine, aniline, or aminopyrimidyl to afford the corresponding benzamide. The benzamides can then be coupled with an appropriate B-A'-V (wherein V is a acid chloride derivative, an alkyl halide, or a sulfonyl chloride) to afford additional compounds of the present invention (see Scheme 18).

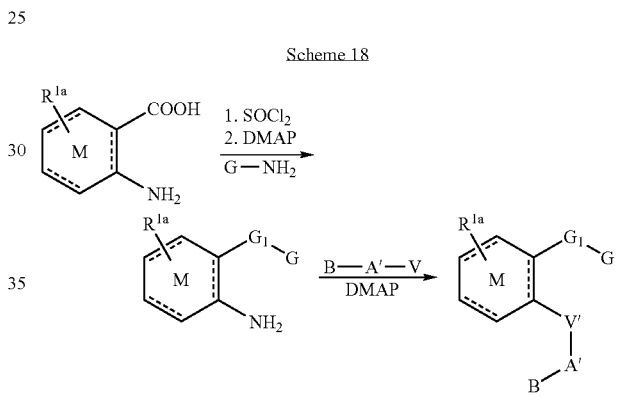

Commercially available ring M derivatives bearing a nitro and amino functionality can also be derivatized as shown in Scheme 19 to afford bisamide analogs. In this case, coupling of the aniline with B-A'-V (wherein V is an acid chloride, a sulfonyl chloride, or an alkylhalide) affords an intermediate that can be subjected to treatment with an appropriate G-U (wherein U is either an acid chloride or an alkyl halide) in presence of a suitable base such as DMAP. It should be noted that the order of addition of B-A'-V and G-U can be reversed to obtain other compounds of the present invention.

Compounds of the present invention wherein ring P is absent and ring M is a six-membered ring can be obtained as shown in Scheme 17. These types of compounds can be obtained from commercially available anthranilic acids or their anthranilates. Anthranilic acids or their nitro precursors can be coupled with a suitable B-A'-NH$_2$ in presence of a base such as triethyl amine, pyridine, or DMAP. Subsequent coupling with an appropriate acid chloride or aniline or aminopyridyl should afford compounds of the present invention.

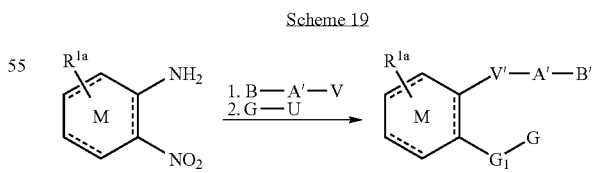

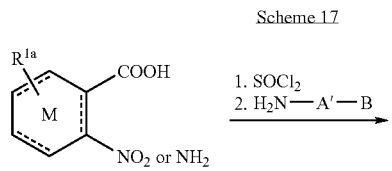

The syntheses shown above could be modified to use coupling intermediates such as Iodo-A-V, wherein V is an acid chloride, amino, alkylhalide, or sulfonyl chloride. These in turn could be coupled to a G-U group. The iodo intermediate could then be subjected to Ullman or Buchwald coupling as described previously to afford compounds of the present invention. The iodo intermediate could also be converted to an amine via standard Buchwald conditions to afford the corresponding anilino intermediate. This in turn could be coupled as previously described to afford compounds of the present invention.

The syntheses of bisamide compounds shown in Schemes 17–19 can also be applied to the syntheses of compounds wherein ring M is a 5-membered heterocycle. The bisamides can also be further converted into bicyclic pyrimidin-4-ones under acidic conditions as shown in Scheme 20.

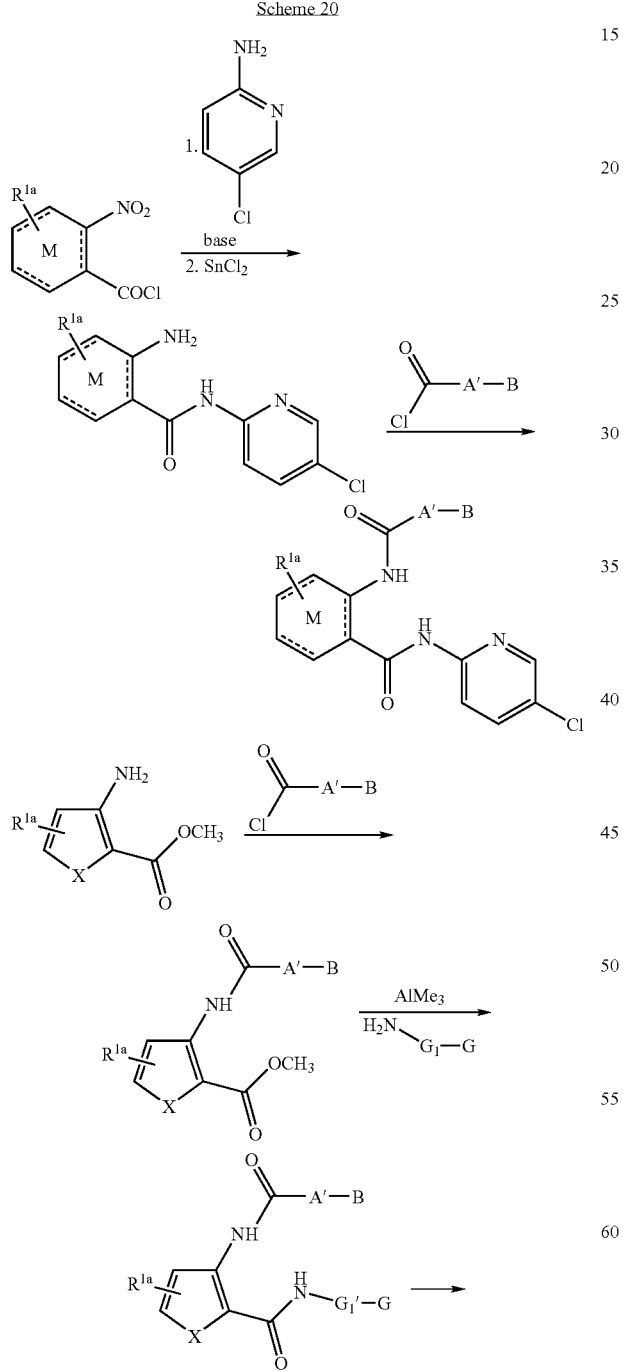

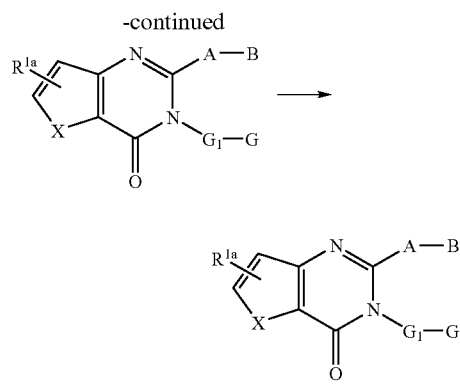

Scheme 21 illustrates the synthesis of piperidine derivatives by using the methods described above and known by those skilled in the art.

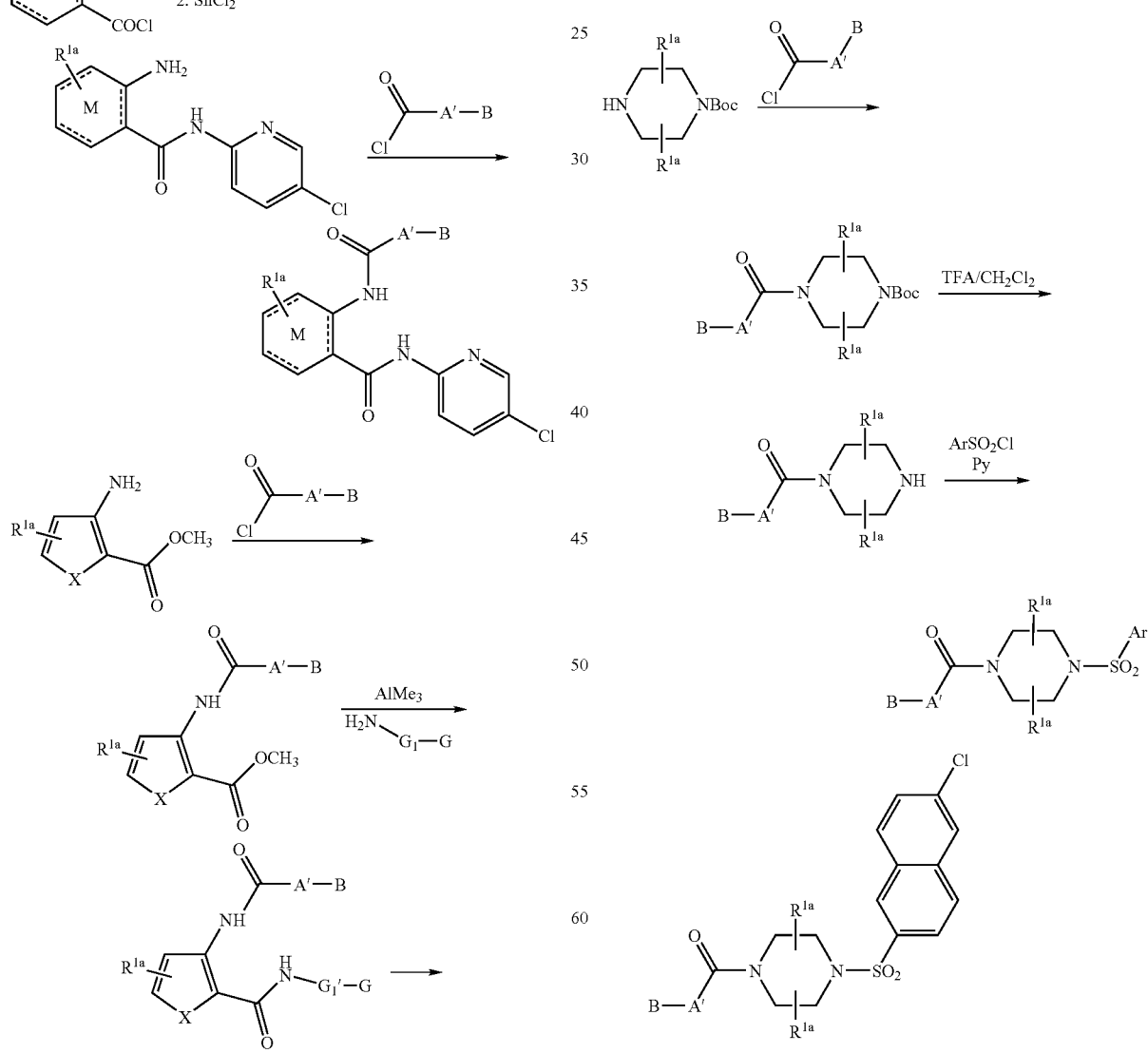

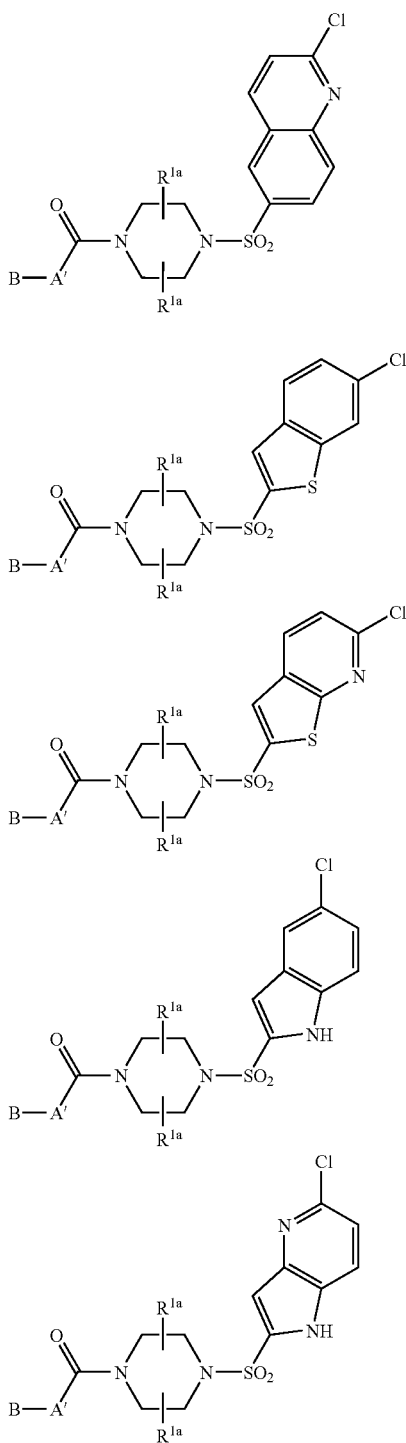

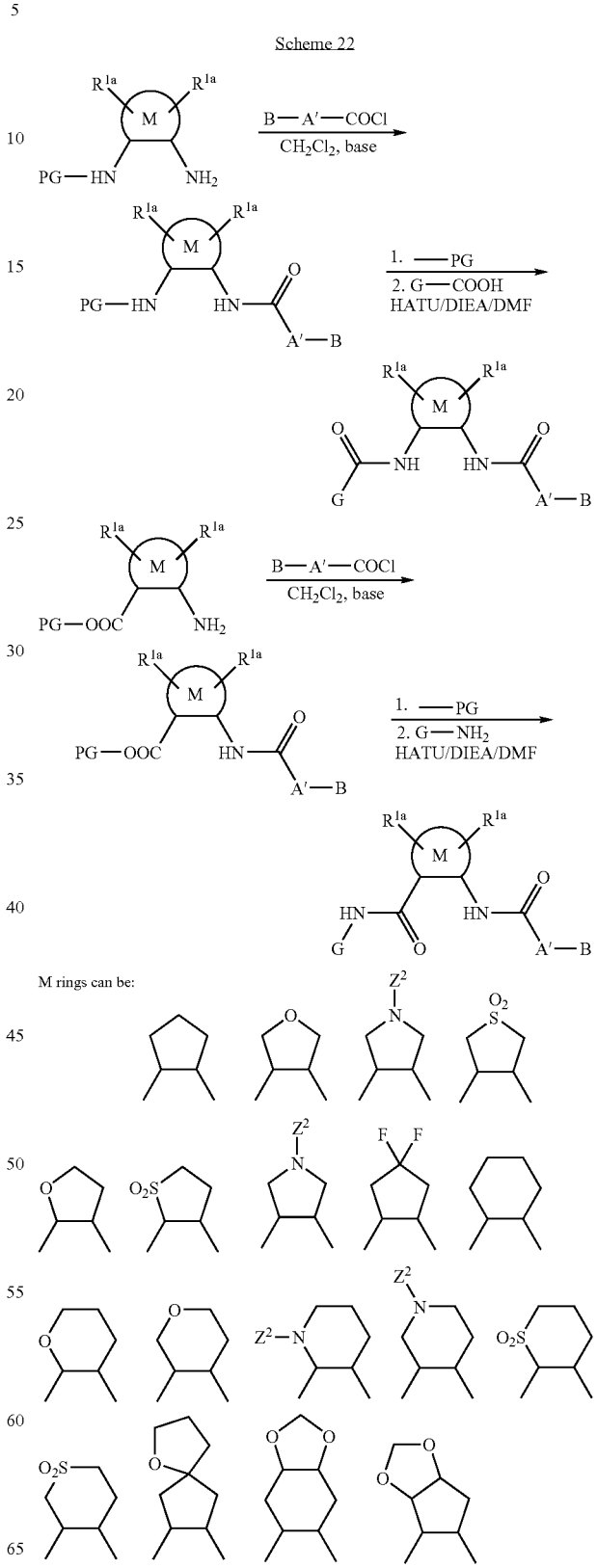

shown rings to compounds of the present invention. This methodology is also applicable to non-aromatic rings not shown, but within the present invention.

Compounds of the present invention wherein ring P is absent and ring M is a 3–10 membered non-aromatic carbocycle or heterocycle can also be prepared by using the methods described previously and known to those skilled in the art. Scheme 22 illustrates a number of non-aromatic M rings that are considered to be part of the present invention. Scheme 22 also describes general methods of converting the -continued

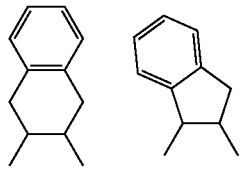

Properly protected, enantiomerically pure cyclic amino acid cores can be obtained via Davies' protocol (*J. Chem. Soc. Perkin Trans I*, 1994, 1411) or via the reduction of enamines (*J. Org. Chem.* 1996, 61, 5557). The corresponding diamino compounds can be obtained via saponification of the ester of the cyclic amino acids followed by Curtius rearrangement. On the other hand, the cyclic diamines can be prepared via literature methods. (See, for example, *Tetrahedron: Assymmetry*, 1997, 8, 1861 and *Tetrahedron Lett.* 1998, 39, 6921).

A series of compounds of formula I wherein $G_1$ is 1,1-dioxo-sulfonylmethyl group are prepared following the sequence outlined in Scheme 23.

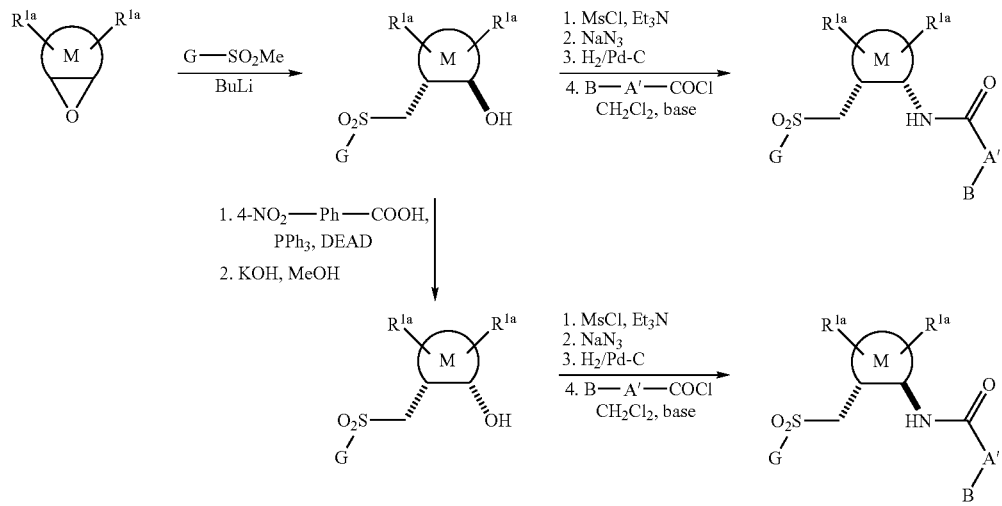

Scheme 23

One diastereomer of a compound of Formula I may be more potent against fXa than the others. Thus, when applicable (i.e., ring M or part of ring M is a non-aromatic ring), the following stereochemistries are considered to be a part of the present invention.

-continued

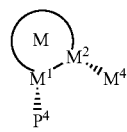 Ie

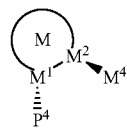 If

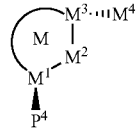 Ig

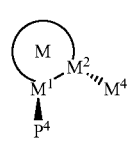 Ic

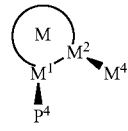 Id

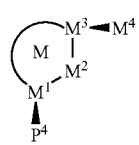 Ih

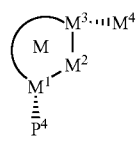 Ii

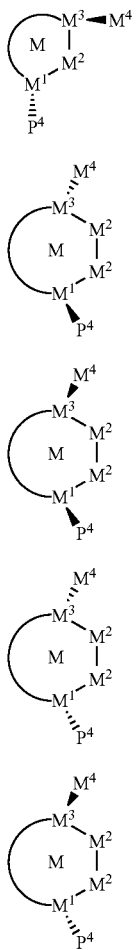

When required, separation of the racemic material can be achieved by HPLC using a chiral column or by a resolution using a resolving agent such as camphonic chloride (*Antimicrobial Agents and Chemotheraphy*, 1995, 2602–2605). A chiral compound of Formula I may also be directly synthesized using a chiral catalyst or a chiral ligand (see, for example, *Tetrahedron Lett*. 1995, 36, 8937–8940).

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM-1 mM) in the presence of inhibitor. Reactions were allowed to go for 30 min and the velocities (rate of absorbance change vs. time) were measured in the time frame of 25–30 min. The following relationship was used to calculate $K_i$ values:

$$(v_o - v_s)/v_s = I/(K_i(1+S/K_m))$$

where:

$v_o$ is the velocity of the control in the absence of inhibitor;
$v_s$ is the velocity in the presence of inhibitor;
I is the concentration of inhibitor;
$K_i$ is the dissociation constant of the enzyme:inhibitor complex;
S is the concentration of substrate;
$K_m$ is the Michaelis constant.

Compounds tested in the above assay are considered to be active if they exhibit a $K_i$ of ≦10 μM. Preferred compounds of the present invention have $K_i$'s of ≦1 μM. More preferred compounds of the present invention have $K_i$'s of ≦0.1 μM. Even more preferred compounds of the present invention have $K_i$'s of ≦0.01 μM. Still more preferred compounds of the present invention have $K_i$'s of ≦0.001 μM. Using the methodology described above, a number of compounds of the present invention were found to exhibit $K_i$'s of ≦10 μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin, for example LOVENOX™), synthetic pentasaccharide, direct acting thrombin inhibitors including hirudin and argatrobanas, factor VIIa, Ixa, XIa inhibitors, well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE. V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of The present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of The present invention and about 50 to 150 milligrams of the anti-platelet agent, preferably about 0.1 to 1 milligrams of the compound of The present invention and about 1 to 3 milligrams of antiplatelet agents, per kilogram of patient body weight.

Where the compounds of The present invention are administered in combination with thrombolytic agent, typically a daily dosage may be about 0.1 to 1 milligrams of the compound of The present invention, per kilogram of patient body weight and, in the case of the thrombolytic agents, the usual dosage of the thrombolyic agent when administered alone may be reduced by about 70–80% when administered with a compound of The present invention.

Where two or more of the foregoing second therapeutic agents are administered with the compound of The present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of The present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

[1-(4-Methoxy-phenyl)-7-oxo-3-trifluoromethyl-1,4,5,7-tetrahydro-pyrazolo[3,4-c]pyridin-6-yl]-acetic acid methyl ester

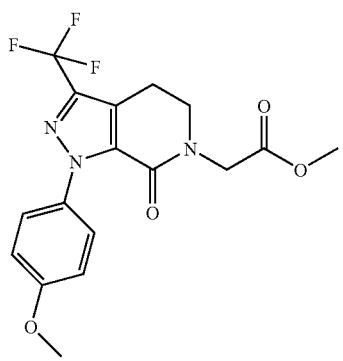

Part A. 2-piperidone (35.70 g, 360.2 mmol) was dissolved in chloroform (1 L). Phosphorus pentachloride (300 g, 1.44 mol) was added, and the reaction was heated at reflux for 4 hr. The reaction was cooled and poured over wet ice, extracted with chloroform (3×500 mL), washed with brine (1×250 mL), dried over MgSO$_4$, and concentrated to afford the alpha-dichloro valerolactam intermediate. The di-chloro intermediate was dissolved in morpholine (300 mL) and refluxed for 1.5 hr. The reaction was concentrated, quenched with water (500 mL), extracted into ethyl acetate (3×500 mL), washed with brine (1×250 mL), dried over MgSO$_4$, concentrated, and purified by flash chromatography using 0–100% ethyl acetate/hexanes afforded 36.76 g (56%): $^1$H NMR (CDCl$_3$) δ 5.92 (bs, 1H), 5.56 (t, j=4.6 Hz, 1H), 3.85–3.80(m, 4H), 3.33 (dt, j=7.0 Hz, 3.3 Hz, 2H), 2.89 (t, j=4.8 Hz, 2H), 2.37 (dt, j=7.0 Hz, 4.8 Hz, 2H) ppm.

Part B: p-Anisidine hydrochloride (23.14 g, 132.5 mmol) was dissolved in ethanol (400 mL) and trifluoroacetaldehyde ethyl hemiacetal (20 mL, 172.3 mmol) was added and refluxed overnight. The reaction was concentrated, and the crude compound was redissolved in N,N-dimethylformamide (150 mL) and cooled to 0° C. N-bromosuccinimide (23.59 g, 132.5 mmol) was added to the solution over five minutes. The reaction was warmed to rt and stirred overnight. The reaction was quenched with water (1000 mL) and ethyl acetate (5000 mL), extracted with ethyl acetate (3×500 mL), washed with brine (1×500 mL), dried over Na$_2$SO$_4$, concentrated, and purified by flash chromatography using 0–10% ethyl acetate/hexanes as eluent afforded 18.8 g (48%) of the hydrazone intermediate.

Part C. The hydrazone intermediate (18.8 g, 63.3 mmol), 3-morpholin-4-yl-5,6-dihydro-1H-pyridin-2-one (9.6 g, 52.7 mmol), and triethylamine (18.4 mL, 131.7 mmol) were dissolved in toluene (300 mL) and refluxed overnight. The reaction was quenched with water (300 mL), extracted with ethyl acetate (3×500), washed with brine (1×300 mL), dried over MgSO$_4$, concentrated, and purified by flash chromatography using 0–100% ethyl acetate/hexanes gradient as eluent. The intermediate was concentrated and redissolved in methylene chloride (250 mL) and trifluoroacetic acid (60 mL) and stirred overnight at rt. The reaction was quenched with water (250 mL), extracted into ethyl acetate (3×250 mL), washed with brine (1×250 mL), dried over MgSO$_4$, and concentrated to afford 1-(4-methoxy-phenyl)-3-trifluoromethyl-1,4,5,6-tetrahydro-pyrazolo[3,4-c]pyridin-7-one 11.8 g (72%): $^1$H NMR (CDCl$_3$) δ 7.47 (d, j=8.8 Hz, 2H), 6.94 (d, j=8.0 Hz, 2H), 3.83 (s, 3H), 3.90–3.78 (m, 1H), 3.72–3.60(m, 2H), 3.02 (t, j=6.6 Hz, 2H) ppm.

Part D: 1-(4-Methoxy-phenyl)-3-trifluoromethyl-1,4,5,6-tetrahydro-pyrazolo[3,4-c]pyridin-7-one (1.0 g, 3.213 mmol) was dissolved in N,N-dimethylformamide (20 mL) and cooled to 0° C. Sodium hydride (60%, 0.321 g, 8.032 mmol) was added followed by methyl bromoacetate (0.608 mL, 6.425 mmol). The reaction was stirred at rt overnight. The reaction was quenched with 1N hydrochloric acid (100 mL), extracted with ethyl acetate (3×100 mL), washed with water (2×100 mL), washed with brine (1×100 mL), dried over MgSO$_4$, concentrated, and purified by flash chromatography using 0–100% ethyl acetate/hexanes gradient as the eluent to afford the title compound (0.91 g, 74%): $^1$H NMR (CDCl$_3$) δ 7.45 (d, j=8.8 Hz, 2H), 6.96 (d, j=9.2 Hz, 2H), 4.25 (s, 2H), 3.84 (s, 3H), 3.78 (t, j=7.0 Hz, 2H), 3.75 (m, 3H), 3.02 (t, j=6.8 Hz, 2H) ppm.

Example 2

4-[1-(4-Methoxy-phenyl)-7-oxo-3-trifluoromethyl-1,4,5,7-tetrahydro-pyrazolo[3,4-c]pyridin-6-yl]-butyric acid ethyl ester

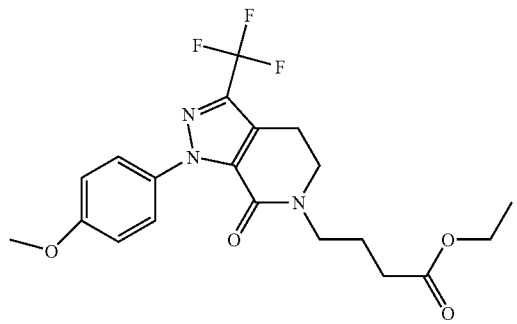

The title compound was prepared in a similar manner following the procedure outlined in Example 1. Mass Spec 426.2(M+H)+.

Example 3

5-[1-(4-Methoxy-phenyl)-7-oxo-3-trifluoromethyl-1,4,5,7-tetrahydro-pyrazolo[3,4-c]pyridin-6-yl]-pentanoic acid methyl ester

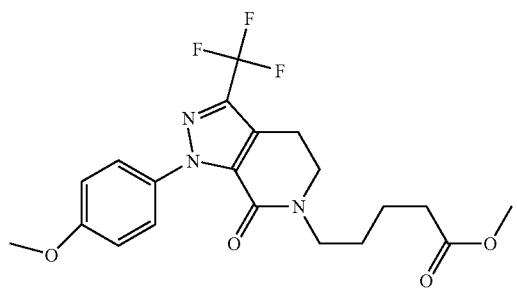

The title compound was prepared in a similar manner following the procedure outlined in Example 1. Mass Spec 424.3(M–H)−.

Example 4

6-[1-(4-Methoxy-phenyl)-7-oxo-3-trifluoromethyl-1,4,5,7-tetrahydro-pyrazolo[3,4-c]pyridin-6-yl]-hexanoic acid ethylester

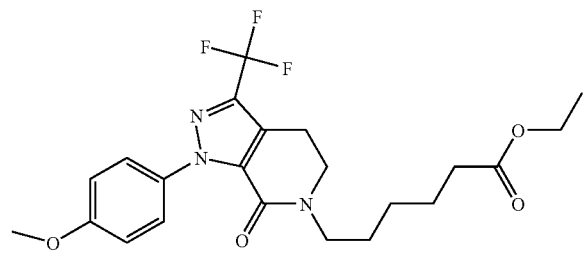

The title compound was prepared in a similar maner following the procedure outlined in Example 1. Mass Spec 476.3(M+H+Na)+.

Example 5

6-[1-(4-Methoxy-phenyl)-7-oxo-3-trifluoromethyl-1,4,5,7-tetrahydro-pyrazolo[3,4-c]pyridin-6-yl]-2,2-dimethyl-hexanoic acid methyl ester

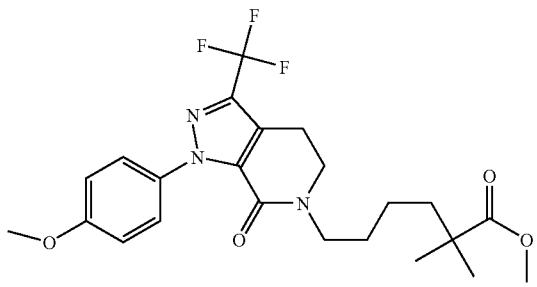

The title compound was prepared in a similar manner following the procedure outlined in Example 1. In this particular case 6-Bromo-2,2-dimethyl-hexanoic acid methyl ester was used as the electrophile in the alkylation step. Mass Spec 468.3(M+H+Na)+.

Example 6

1-(4-Methoxy-phenyl)-6-(2-oxo-2-pyrrolidin-1-yl-ethyl)-3-trifluoromethyl-1,4,5,6-tetrahydro-pyrazolo[3,4-c]pyridin-7-one

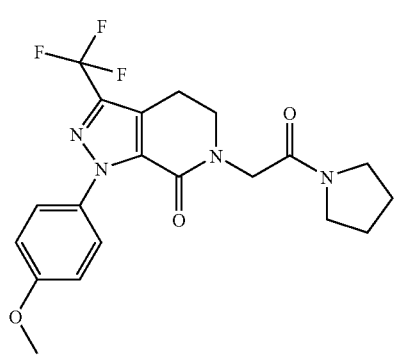

Part A: Pyrrolidine (0.152 mL, 1.826 mmol) was dissolved in methylene chloride (6 mL) and cooled to 0° C. 2M Trimethylaluminum (0.652 mL, 1.304 mmol) was added to the reaction and stirred for 30 min at 0° C. [1-(4-Methoxy-phenyl)-7-oxo-3-trifluoromethyl-1,4,5,7-tetrahydro-pyrazolo[3,4-c]pyridin-6-yl]-acetic acid methyl ester (0.100 g, 0.261 mmol) was added and the reaction was stirred overnight at rt. The reaction was quenched with water (100 mL), extracted into methylene chloride (3×50 mL), washed with brine (1×50 mL), dried over MgSO4, concentrated, and purified, by flash chromatography using 0–100% ethyl acetate/hexanes gradient and methanol flush as eluents, followed by further purification by reverse phase HPLC. Freeze-drying afforded 0.052 g (47%): $^1$H NMR (CDCl$_3$) δ 7.38 (d, j=8.8 Hz, 2H), 6.87 (d, j=9.1 Hz, 2H), 4.15 (s, 2H), 3.77 (t, j=6.8 Hz, 2H), 3.76 (s, 3H), 3.40(t, j=6.8 Hz, 2H), 3.33 (t, j=6.8 Hz, 2H), 3.00(t, j=6.8 Hz, 2H), 1.92–1.85 (m, 2H), 1.82–1.73 (m, 2H) ppm; Mass Spec 423.3(M+H)+.

Example 7

2-[1-(4-Methoxy-phenyl)-7-oxo-3-trifluoromethyl-1,4,5,7-tetrahydro-pyrazolo[3,4-c]pyridin-6-yl]-N,N-dimethyl-acetamide

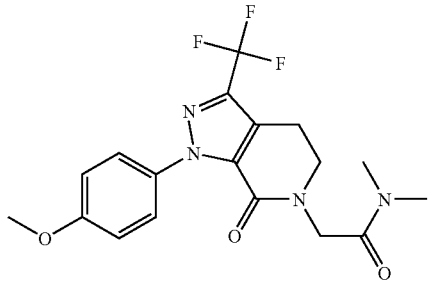

The title compound was prepared in a similar manner following the procedure outlined in Example 6. Mass Spec 395.3(M−H)⁻.

Example 8

N-Ethyl-2-[1-(4-methoxy-phenyl)-7-oxo-3-trifluoromethyl-1,4,5,7-tetrahydro-pyrazolo[3,4-c]pyridin-6-yl]-N-methyl-acetamide

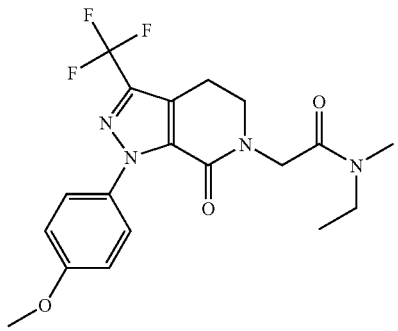

The title compound was prepared in a similar manner following the procedure outlined in Example 6. Mass Spec 409.3(M−H)⁻.

Example 9

1-(4-Methoxy-phenyl)-6-(2-morpholin-4-yl-2-oxo-ethyl)-3-trifluoromethyl-1,4,5,6-tetrahydro-pyrazolo[3,4-c]pyridin-7-one

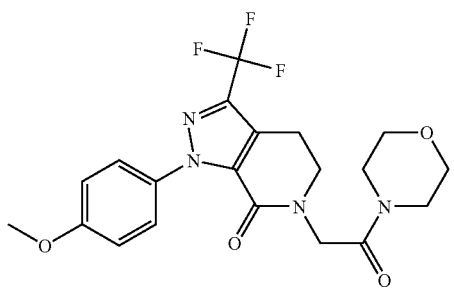

The title compound was prepared in a similar manner following the procedure outlined in Example 6. Mass Spec 439.3(M+H)⁺.

Example 10

N,N-Diethyl-2-[1-(4-methoxy-phenyl)-7-oxo-3-trifluoromethyl-1,4,5,7-tetrahydro-pyrazolo[3,4-c]pyridin-6-yl]-acetamide

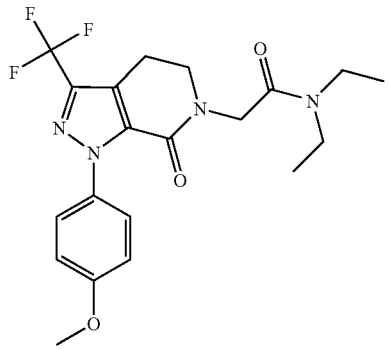

The title compound was prepared in a similar manner following the procedure outlined in Example 6. Mass Spec 425.3(M+H)⁺.

Example 11

1-(4-Methoxy-phenyl)-6-(2-oxo-2-piperidin-1-yl-ethyl)-3-trifluoromethyl-1,4,5,6-tetrahydro-pyrazolo[3,4-c]pyridin-7-one

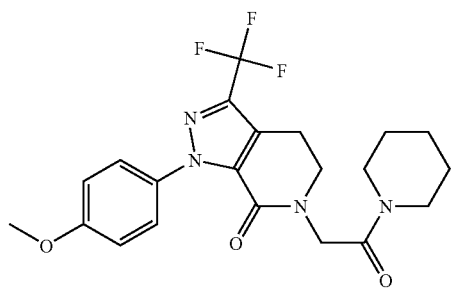

The title compound was prepared in a similar manner following the procedure outlined in Example 6. Mass Spec 437.3(M+H)⁺.

Example 12

1-(4-Methoxy-phenyl)-6-[2-(4-methyl-piperazin-1-yl)-2-oxo-ethyl]-3-trifluoromethyl-1,4,5,6-tetrahydro-pyrazolo[3,4-c]pyridin-7-one

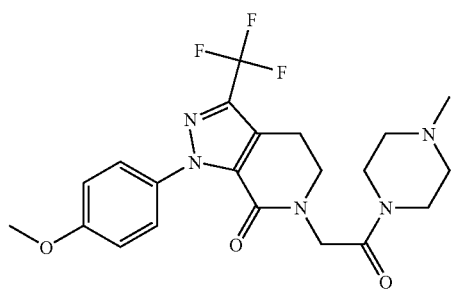

The title compound was prepared in a similar manner following the procedure outlined in Example 6. Mass Spec 52.3 (M+H)⁺.

Example 13

6-[2-(1,3-Dihydro-isoindol-2-yl)-2-oxo-ethyl]-1-(4-methoxy-phenyl)-3-trifluoromethyl-1,4,5,6-tetrahydro-pyrazolo[3,4-c]pyridin-7-one

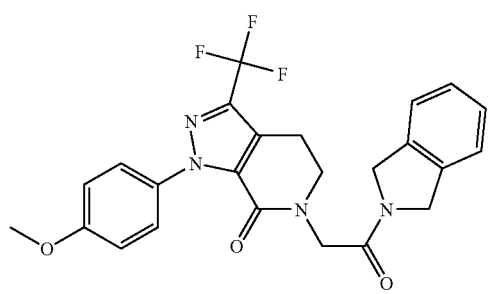

The title compound was prepared in a similar manner following the procedure outlined in Example 6. Mass Spec 471.3(M+H)⁺.

Example 14

6-[2-(3,4-Dihydro-1H-isoquinolin-2-yl)-2-oxo-ethyl]-1-(4-methoxy-phenyl)-3-trifluoromethyl-1,4,5,6-tetrahydro-pyrazolo[3,4-c]pyridin-7-one

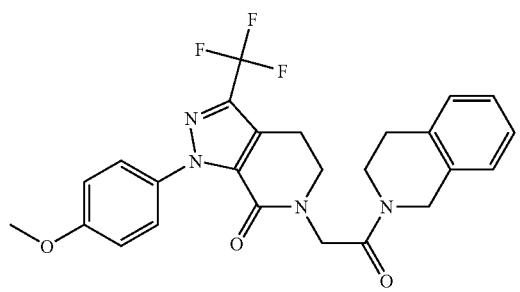

The title compound was prepared in a similar manner following the procedure outlined in Example 6. Mass Spec 485.3(M+H)⁺.

Example 15

6-[2-(3,4-Dihydro-2H-quinolin-1-yl)-2-oxo-ethyl]-1-(4-methoxy-phenyl)-3-trifluoromethyl-1,4,5,6-tetrahydro-pyrazolo[3,4-c]pyridin-7-one

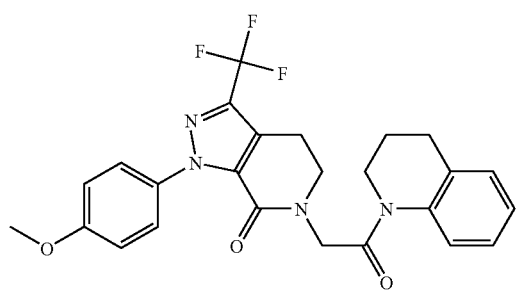

The title compound was prepared in a similar manner following the procedure outlined in Example 6. Mass Spec 485.4(M+H)⁺.

Example 16

N,N-Diethyl-3-[1-(4-methoxy-phenyl)-7-oxo-3-trifluoromethyl-1,4,5,7-tetrahydro-pyrazolo[3,4-c]pyridin-6-yl]-propionamide

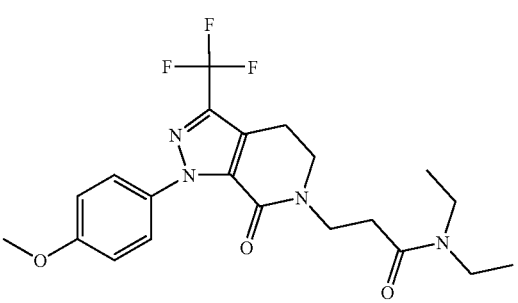

The title compound was prepared in a similar manner following the procedure outlined in Example 6, by the Weinreb reaction of diethylamine with 3-[1-(4-Methoxy-phenyl)-7-oxo-3-trifluoromethyl-1,4,5,7-tetrahydro-pyrazolo[3,4-c]pyridin-6-yl]-propionic acid methyl ester. Mass Spec 439.3(M+H)⁺.

Example 17

1-(4-Methoxy-phenyl)-6-(3-morpholin-4-yl-3-oxo-propyl)-3-trifluoromethyl-1,4,5,6-tetrahydro-pyrazolo[3,4-c]pyridin-7-one

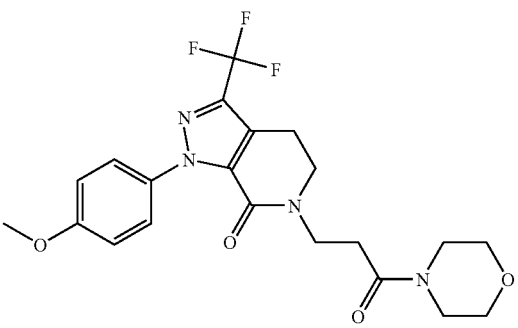

The title compound was prepared in a similar manner following the procedure outlined in Example 16. Mass Spec 453.3(M+H)⁺.

Example 18

1-(4-Methoxy-phenyl)-6-(3-oxo-3-piperidin-1-yl-propyl)-3-trifluoromethyl-1,4,5,6-tetrahydro-pyrazolo[3,4-c]pyridin-7-one

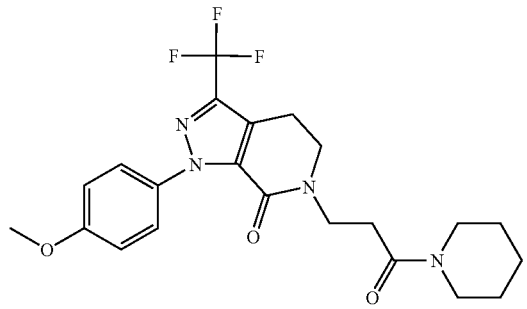

The title compound was prepared in a similar manner following the procedure outlined in Example 16. Mass Spec 451.3(M+H)$^+$.

Example 19

1-(4-Methoxy-phenyl)-6-(3-oxo-3-pyrrolidin-1-yl-propyl)-3-trifluoromethyl-1,4,5,6-tetrahydro-pyrazolo[3,4-c]pyridin-7-one

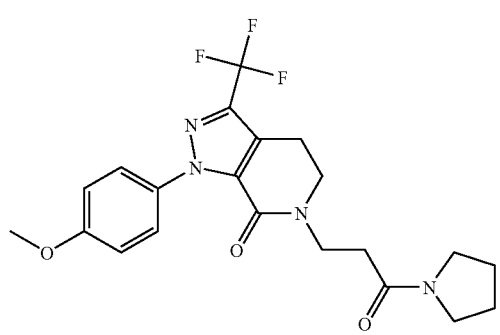

The title compound was prepared in a similar manner following the procedure outlined in Example 16. Mass Spec 437.3(M+H)$^+$.

Example 20

1-(4-Methoxy-phenyl)-6-[3-(4-methyl-piperazin-1-yl)-3-oxo-propyl]-3-trifluoromethyl-1,4,5,6-tetrahydro-pyrazolo[3,4-c]pyridin-7-one

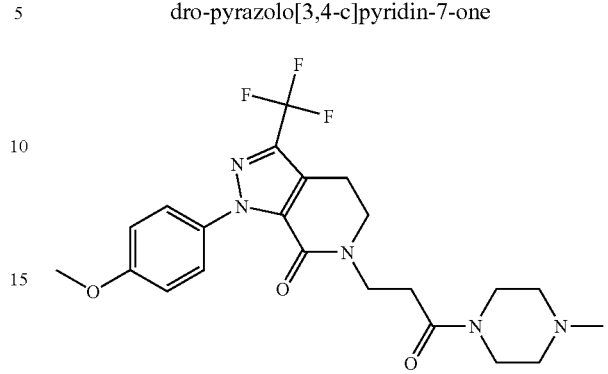

The title compound was prepared in a similar manner following the procedure outlined in Example 16. Mass Spec 466.3(M+H)$^+$.

Example 21

N-Ethyl-3-[1-(4-methoxy-phenyl)-7-oxo-3-trifluoromethyl-1,4,5,7-tetrahydro-pyrazolo[3,4-c]pyridin-6-yl]-N-methyl-propionamide

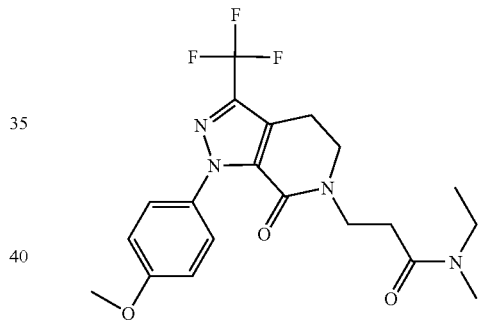

The title compound was prepared in a similar manner following the procedure outlined in Example 16. Mass Spec 425.3(M+H)$^+$.

Example 22

N-Benzyl-3-[1-(4-methoxy-phenyl)-7-oxo-3-trifluoromethyl-1,4,5,7-tetrahydro-pyrazolo[3,4-c]pyridin-6-yl]-N-methyl-propionamide

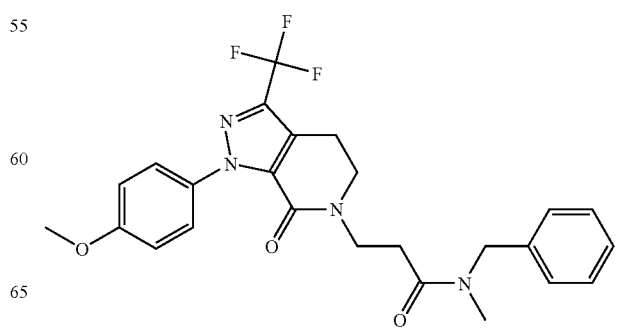

The title compound was prepared in a similar manner following the procedure outlined in Example 16. Mass Spec 487.4(M+H)+.

Example 23

4-[1-(4-Methoxy-phenyl)-7-oxo-3-trifluoromethyl-1,4,5,7-tetrahydro-pyrazolo[3,4-c]pyridin-6-yl]-N,N-dimethyl-butyramide

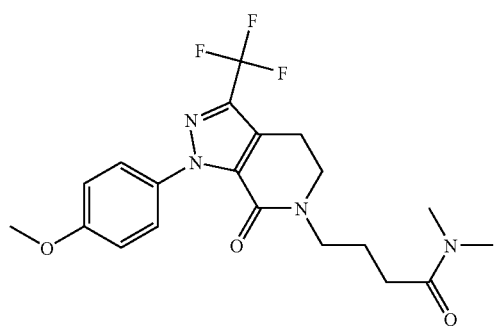

The title compound was prepared in a similar manner following the procedure outlined in Example 6 and 16. In this particular case 4-[1-(4-Methoxy-phenyl)-7-oxo-3-trifluoromethyl-1,4,5,7-tetrahydro-pyrazolo[3,4-c]pyridin-6-yl]-butyric acid methyl ester was the starting material used in the Weinreb reaction. Mass Spec 425.2(M+H)+.

Example 24

1-(4-Methoxy-phenyl)-6-(4-oxo-4-pyrrolidin-1-yl-butyl)-3-trifluoromethyl-1,4,5,6-tetrahydro-pyrazolo[3,4-c]pyridin-7-one

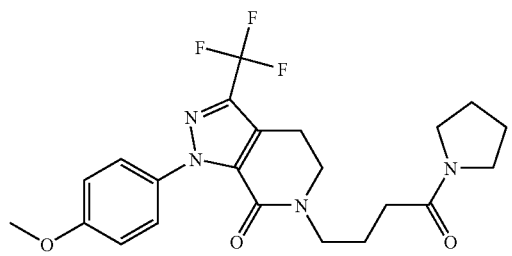

The title compound was prepared in a similar manner following the procedure outlined in Example 6 and 16. Mass Spec 451.3(M+H)+.

Example 25

5-[1-(4-Methoxy-phenyl)-7-oxo-3-trifluoromethyl-1,4,5,7-tetrahydro-pyrazolo[3,4-c]pyridin-6-yl]-pentanoic acid dimethylamide

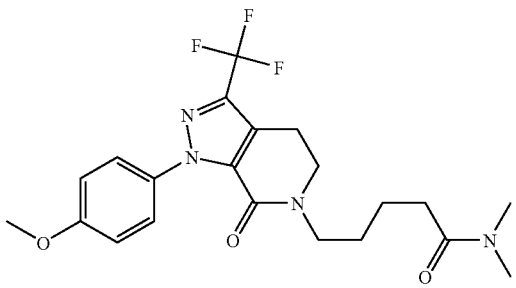

The title compound was prepared in a similar manner following the procedure outlined in Example 6 and 16. In this particular case 5-[1-(4-Methoxy-phenyl)-7-oxo-3-trifluoromethyl-1,4,5,7-tetrahydro-pyrazolo[3,4-c]pyridin-6-yl]-pentanoic acid methyl ester was used in the Weinreb reaction. Mass Spec 437.3(M–H)−.

Example 26

1-(4-Methoxy-phenyl)-6-(5-oxo-5-pyrrolidin-1-yl-pentyl)-3-trifluoromethyl-1,4,5,6-tetrahydro-pyrazolo[3,4-c]pyridin-7-one

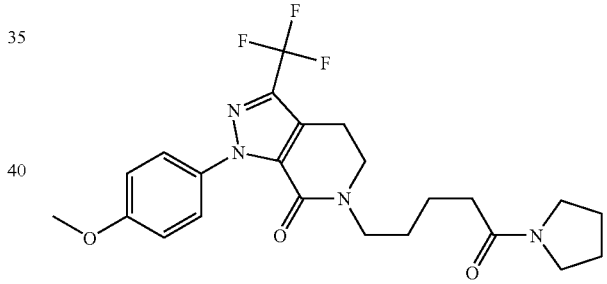

The title compound was prepared in a similar manner following the procedure outlined in Example 6, 16 and 26. Mass Spec (M–H)− 463.3.

Example 27

1-(4-Methoxy-phenyl)-6-(6-oxo-6-pyrrolidin-1-yl-hexyl)-3-trifluoromethyl-1,4,5,6-tetrahydro-pyrazolo[3,4-c]pyridin-7-one

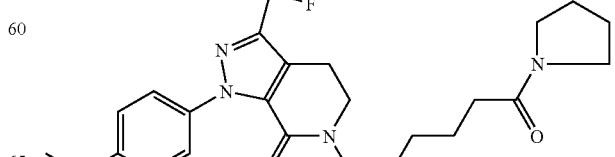

The title compound was prepared following the Weinreb methodology as outlined in Example 6. In this particular case 6-[1-(4-Methoxy-phenyl)-7-oxo-3-trifluoromethyl-1,4,5,7-tetrahydro-pyrazolo[3,4-c]pyridin-6-yl]-hexanoic acid methyl ester was used in the Weinreb reaction. Mass Spec (M–H)⁻ 477.4.

Example 28

6-[1-(4-Methoxy-phenyl)-7-oxo-3-trifluoromethyl-1,4,5,7-tetrahydro-pyrazolo[3,4-c]pyridin-6-yl]-hexanoic acid dimethylamide

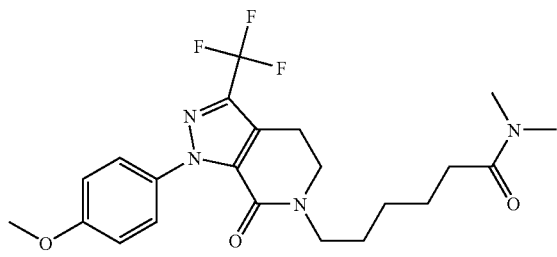

The title compound was prepared in a similar manner following the procedure outlined in Example 6, 16 and 27. Mass Spec (M+H)⁺ 451.3.

Example 29

6-(4-Hydroxy-4-methyl-pentyl)-1-(4-methoxy-phenyl)-3-trifluoromethyl-1,4,5,6-tetrahydro-pyrazolo[3,4-c]pyridin-7-one

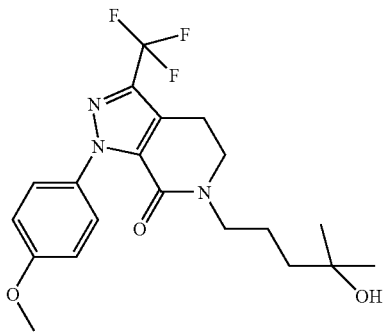

3M methylmagnesium bromide (0.682 g, 2.05 mmol) was added to 4-[1-(4-methoxy-phenyl)-7-oxo-3-trifluoromethyl-1,4,5,7-tetrahydro-pyrazolo[3,4-c]pyridin-6-yl]-butyric acid ethyl ester (0.348 g, 0.818 mmol) dissolved in tetrahydrofuran (10 mL). The reaction was stirred at rt overnight. The reaction was quenched with 1N hydrochloric acid (50 mL), extracted with ethyl acetate (3×50 mL), washed with brine (1×50 mL), dried over MgSO₄, concentrated, and purified by flash chromatography using 0–100% ethyl acetate/hexanes gradient as the eluent to afford 0.111 g (34%, based on recovered starting material): ¹H NMR (CDCl₃) δ 7.45 (d, j=9.2 Hz, 2H), 6.96 (d, j=8.7 Hz, 2H), 3.84 (s, 3H), 3.69 (t, j=6.8 Hz, 2H), 3.50(t, j=7.4 Hz, 2H), 3.00(t, j=6.8 Hz, 2H), 1.75–1.62 (m, 2H), 1.49–1.41 (m, 2H), 1.21 (s, 6H) ppm; Mass Spec (M+H)⁺ 412.3.

Example 30

6-(5-Hydroxy-5-methyl-hexyl)-1-(4-methoxy-phenyl)-3-trifluoromethyl-1,4,5,6-tetrahydro-pyrazolo[3,4-c]pyridin-7-one

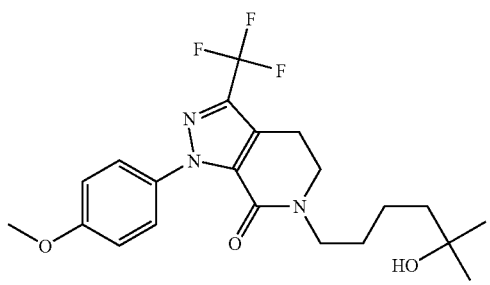

The title compound was prepared from 5-[1-(4-Methoxy-phenyl)-7-oxo-3-trifluoromethyl-1,4,5,7-tetrahydro-pyrazolo[3,4-c]pyridin-6-yl]-pentanoic acid methyl ester following the procedure outlined in Example 29. Mass Spec (M+H)⁺ 426.3.

Example 31

6-(6-Hydroxy-6-methyl-heptyl)-1-(4-methoxy-phenyl)-3-trifluoromethyl-1,4,5,6-tetrahydro-pyrazolo[3,4-c]pyridin-7-one

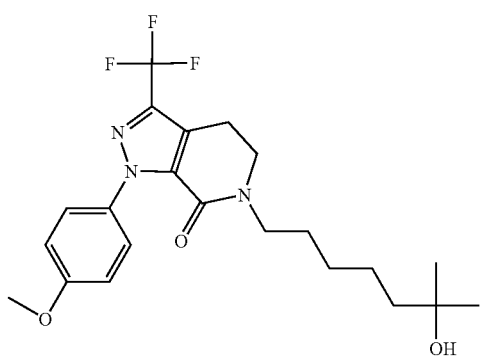

The title compound was prepared in a similar manner using 5-[1-(4-Methoxy-phenyl)-7-oxo-3-trifluoromethyl-1,4,5,7-tetrahydro-pyrazolo[3,4-c]pyridin-6-yl]-hexnoic acid methyl ester following the procedure outlined in Example 29. Mass Spec 440.3(M+H)⁺.

Example 32

[6-(2-Hydroxy-ethyl)-1-(4-methoxy-phenyl)-3-trifluoromethyl-1,4,5,6-tetrahydro-pyrazolo[3,4-c]pyridin-7-one

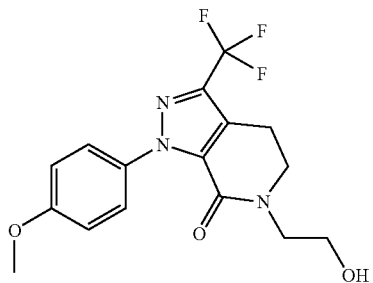

Part A: 1-(4-Methoxy-phenyl)-3-trifluoromethyl-1,4,5,6-tetrahydro-pyrazolo[3,4-c]pyridin-7-one (1.0 g, 3.213 mmol) was dissolved in N,N-dimethylformamide (20 mL) and cooled to 0° C. Sodium hydride (60%, 0.321 g, 8.032 mmol) was added followed by 2-bromoethyl acetate (0.709 mL, 6.425 mmol). The reaction was stirred at rt overnight. The reaction was quenched with 1N hydrochloric acid (100 mL), extracted with ethyl acetate (3×100 mL), washed with water (2×100 mL), washed with brine (1×100 mL), dried over MgSO$_4$, concentrated, and purified by flash chromatography using 0–100% ethyl acetate/hexanes gradient as the eluent to afford 1.26 g (99%): $^1$H NMR (CDCl$_3$) δ 7.45 (d, j=8.8 Hz, 2H), 6.96 (d, j=8.8 Hz, 2H), 4.26 (t, j=5.3 Hz, 2H), 3.85 (s, 3H), 3.83–3.71 (m, 4H), 3.02 (t, j=6.8 Hz, 2H), 2.06 (s, 3H) ppm.

Part B: Acetic acid 2-[1-(4-methoxy-phenyl)-7-oxo-3-trifluoromethyl-1,4,5,7-tetrahydro-pyrazolo[3,4-c]pyridin-6-yl]-ethyl ester (1.26 g, 3.17 mmol) was dissolved in methanol (100 mL) and water (5 mL). Potassium carbonate (1.31 g, 9.52 mmol) was added, and the reaction was stirred overnight at rt. The reaction was concentrated, quenched with water (250 mL), extracted with ethyl acetate (3×250 mL), washed with brine (1×100 mL), dried over MgSO$_4$, concentrated, and purified by flash chromatography with 0–100% ethyl acetate/hexanes gradient as eluent to afford the title compound (1.01 g, 90%): $^1$HNMR(CDCl$_3$) δ 7.45 (d, j=9.2 Hz, 2H), 6.96 (d, j=8.7 Hz, 2H), 3.84 (s, 3H), 3.82–3.77 (m, 4H), 3.66 (t, j=5.1 Hz, 2H), 3.03 (t, j=6.8 Hz, 2H) ppm; Mass Spec 356.3(M+H)$^+$.

Example 33

6-(4-Hydroxy-butyl)-1-(4-methoxy-phenyl)-7-oxo-4,5,6,7-tetrahydro-1H-pyrazolo[3,4-c]pyridine-3-carboxylic acid amide

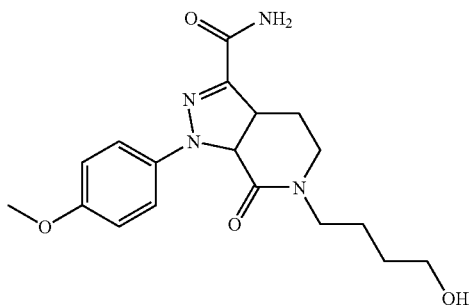

Condensation of ethylglyoxalate with 4-methoxyphenyl hydrazine and chlorination with NCS afforded (4-Methoxy-phenyl)-chlorohydrazono]-acetic acid ethyl ester. Separately d-valerolactam was dichlorinated with PCl$_5$ and treated with morpholine at reflux to afford 3-Morpholin-4-yl-5,6-dihydro-1H-pyridin-2-one. [3+2] cycloaddition of the chlorohydrazone with the morpholine dihydropyridinone obtained above in refluxing toluene and triethylamine afforded the key intermediate 1-(4-Methoxy-phenyl)-7-oxo-4,5,6,7-tetrahydro-1H-pyrazolo[3,4-c]pyridine-3-carboxylic acid ethyl ester. Alkylation (with 4-bromo-butyrylacetate) followed by deprotection of the acetate group as outlined outlined in Example 32, and amidation of the ester with ammonia afforded the desired compound. Mass Spec 357.3(M−H)$^-$.

Example 34

6-(2-Dimethylamino-ethyl)-1-(4-methoxy-phenyl)-3-trifluoromethyl-1,4,5,6-tetrahydro-pyrazolo[3,4-c]pyridin-7-one

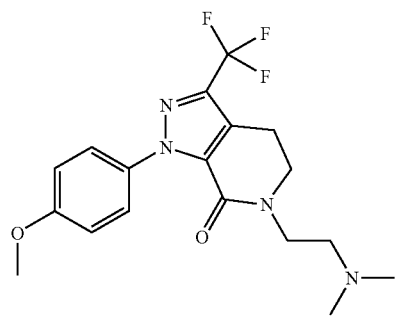

6-(2-Hydroxy-ethyl)-1-(4-methoxy-phenyl)-3-trifluoromethyl-1,4,5,6-tetrahydro-pyrazolo[3,4-c]pyridin-7-one (0.050 g, 0.141 mmol) and phosphorus tribromide (0.020 mL, 0.211 mmol) was dissolved in methylene chloride (4 mL) and stirred at rt for 2 hr. The reaction was quenched with water (25 mL), extracted with methylene chloride (3×25 mL), washed with saturated NaHCO$_3$ (1×25 mL), washed with brine (1×25 mL), dried over Na$_2$So$_4$, and concentrated. The bromide intermediate was redissolved in methylene chloride (6 mL), and 2M dimethylamine (0.493 mL, 0.985) was added. The reaction was stirred at rt overnight. The reaction was evaporated, and the crude material was redissolved in toluene (15 mL) and re-concentrated. Purification by reverse phase HPLC and freeze-drying afforded the title compound (0.024 g, 45%): $^1$H NMR (CDCl$_3$) δ 7.45 (d, j=9.1 Hz, 2H), 6.97 (d, j=9.2 Hz, 2H), 3.87 (s, 3H), 3.78 (t, j=6.8 Hz, 2H), 3.29 (t, j=6.8 Hz, 2H), 3.05 (t, 6.8 Hz, 2H) 2.89 (s, 6H) ppm; Mass Spec 384.4 (M+H)$^+$.

Example 35

1-(4-Methoxy-phenyl)-6-(2-pyrrolidin-1-yl-ethyl)-3-trifluoromethyl-1,4,5,6-tetrahydro-pyrazolo[3,4-c]pyridin-7-one

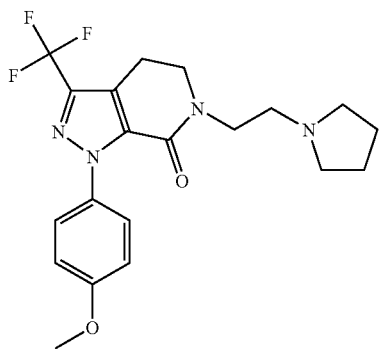

The title compound was prepared in a similar manner following the procedure outlined in Example 34. Mass Spec 409.4(M+H)$^{30}$.

Example 36

6-(4-Dimethylamino-butyl)-1-(4-methoxy-phenyl)-3-trifluoromethyl-1,4,5,6-tetrahydro-pyrazolo[3,4-c]pyridin-7-one

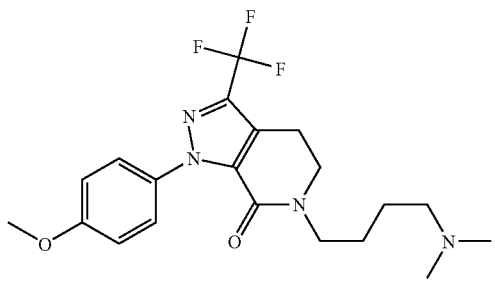

The title compound was prepared in a similar manner following the procedure outlined in Example 34. Mass Spec 411.4(M+H)$^{+}$.

Example 37

1-(4-Methoxy-phenyl)-6-(4-pyrrolidin-1-yl-butyl)-3-trifluoromethyl-1,4,5,6-tetrahydro-pyrazolo[3,4-c]pyridin-7-one

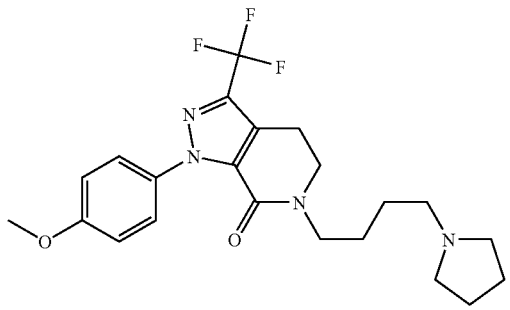

The title compound was prepared in a similar manner following the procedure outlined in Example 34. Mass Spec 437.4(M+H)$^{+}$.

Example 38

1-(4-Methoxy-phenyl)-6-[4-(2-oxo-piperidin-1-yl)-butyl]-3-trifluoromethyl-1,4,5,6-tetrahydro-pyrazolo[3,4-c]pyridin-7-one

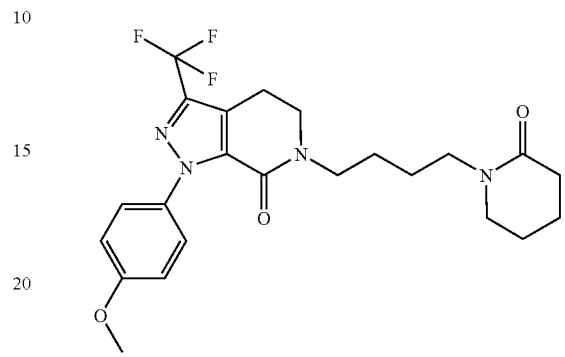

6-(4-Hydroxy-butyl)-1-(4-methoxy-phenyl)-3-trifluoromethyl-1,4,5,6-tetrahydro-pyrazolo[3,4-c]pyridin-7-one (0.100 g, 0.261 mmol) and phosphorus tribromide (0.037 mL, 0.391 mmol) was dissolved in methylene chloride (4 mL) and stirred at rt for 2 hr. The reaction was quenched with water (25 mL), extracted with methylene chloride (3×25 mL), washed with saturated NaHCO$_3$ (1×25 mL), washed with brine (1×25 mL), dried over Na$_2$So$_4$, and concentrated. 2-piperidone (0.052 g, 0.522 mmol) was dissolved in N,N-dimethylformamide (2 mL), and the reaction was cooled to 0° C. Sodium hydride (60%, 0.026 g, 0.652 mmol) was added, and the reaction was stirred at 0° C. for 30 min. The bromide intermediate dissolved in N,N-dimethylformamide (2 mL) was added, and the reaction was stirred at rt overnight. The reaction was quenched with water (50 mL), extracted with ethyl acetate (3×50 mL), washed with water (1×50 mL), washed with brine (1×50 mL), dried over MgSO$_4$, concentrated, and purified by flash chromatography using 0–100% ethyl acetate/hexanes gradient as the eluent. Further purification by reverse phase HPLC and freeze-drying afforded the title compound (0.079 g, 65%): $^1$H NMR (CDCl$_3$) δ 7.44 (d, j=8.7 Hz, 2H), 6.96 (d, j=9.1 Hz, 2H), 3.84 (s, 3H), 3.68 (t, j=6.8 Hz, 2H), 3.50(t, j=6.8 Hz, 2H), 3.3605 (t, 6.8 Hz, 2H), 323–3.19 (m, 2H), 2.98 (t, j=6.8 Hz, 2H), 2.37–2.32 (m, 2H), 1.80–1.53 (m, 8H) ppm.

Example 39

1-(4-Methoxy-phenyl)-6-[4-(2-oxo-2H-pyridin-1-yl)-butyl]-3-trifluoromethyl-1,4,5,6-tetrahydro-pyrazolo[3,4-c]pyridin-7-one

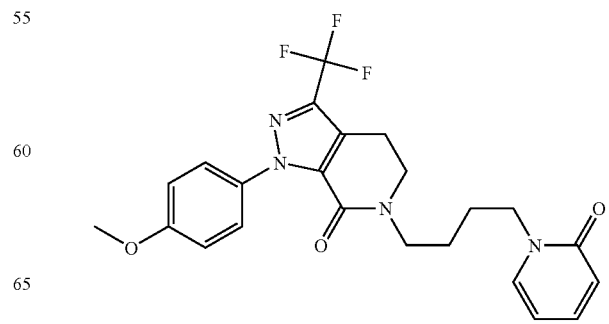

The title compound was prepared in a similar manner following the procedure outlined in Example 38. In this case the alkylation was carried out using 2-hydroxy pyridine. Mass Spec 461.2(M+H)+.

Example 40

6-(3-Dimethylamino-propyl)-1-(4-methoxy-phenyl)-3-trifluoromethyl-1,4,5,6-tetrahydro-pyrazolo[3,4-c]pyridin-7-one

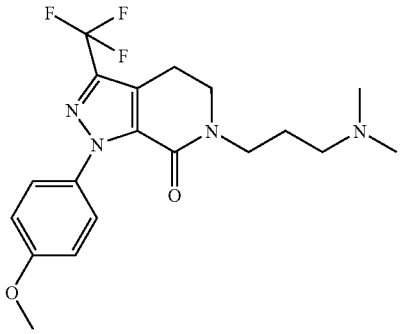

Part A: 1-(4-Methoxy-phenyl)-3-trifluoromethyl-1,4,5,6-tetrahydro-pyrazolo[3,4-c]pyridin-7-one (0.500 g, 1.606 mmol) was dissolved in N,N-dimethylformamide (20 mL) and cooled to 0° C. Sodium hydride (60%, 0.161 g, 4.016 mmol) was added followed by 3-bromopropoxy)-tert-butyldimethylsilane (0.744 mL, 3.213 mmol). The reaction was stirred at rt overnight. The reaction was quenched with 1N hydrochloric acid (100 mL), extracted with ethyl acetate (3×100 mL), washed with water (2×100 mL), washed with brine (1×100 mL), dried over MgSO₄, concentrated, and purified by flash chromatography using 0–100% ethyl acetate/hexanes gradient as the eluent to afford 1-(4-mMethoxy-phenyl)-3-trifluoromethyl-6-(3-trimethylsilanyloxy-propyl)-1,4,5,6-tetrahydro-pyrazolo[3,4-c]pyridin-7-one (0.377 g, 53%). This material (0.377 g, 0.854 mmol) was dissolved in tetrahydrofuran (20 mL) and 1M tetrabutylammonium fluoride (2.56 mL, 2.56 mmol) was added. The reaction was stirred overnight at rt, then quenched with water (100 mL), extracted with ethyl acetate (3×100 mL), washed with saturated potassium fluoride (1×100 mL), washed with brine (1×100 mL), dried over MgSO₄, concentrated, and purified by flash chromatography using 0–100% ethyl acetate/hexanes as the eluent to afford 0.296 g (94%): ¹H NMR (CDCl₃) δ 7.43 (d, j=9.2 Hz, 2H), 6.96 (d, j=8.8 Hz, 2H), 3.85 (s, 3H), 3.72–3.63 (m, 4H), 3.60–3.54 (m, 2H), 3.03 (t, j=6.8 Hz, 2H), 1.84–1.72 (m, 2H) ppm.

Part B: 6-(3-Hydroxy-propyl)-1-(4-methoxy-phenyl)-3-trifluoromethyl-1,4,5,6-tetrahydro-pyrazolo[3,4-c]pyridin-7-one (0.200 g, 0.542 mmol) and phosphorus tribromide (0.077 mL, 0.812 mmol) were dissolved in methylene chloride (20 mL) and stirred at rt for 2 hr. The reaction was quenched with water (100 mL), extracted with methylene chloride (3×100 mL), washed with saturated NaHCO₃ (1×100 mL), washed with brine (1×100 mL), dried over Na₂SO₄, and concentrated to afford 0.096 g (41%). The bromide intermediate (0.048 g, 0.111 mmol) was redissolved in methylene chloride (6 mL), and 2M dimethylamine (0.389 mL, 0.777) was added. The reaction was stirred at rt overnight. The reaction was evaporated, redissolved in toluene (15 mL), and re-concentrated. Purification was performed by reverse phase HPLC and freeze-dried to afford the title compound (0.014 g, 32%): ¹H NMR (CDCl₃) δ 7.43 (d, j=8.8 Hz, 2H), 6.96 (d, j=9.1 Hz, 2H), 3.85 (s, 3H), 3.71 (t, j=7.0 Hz, 2H), 3.56 (t, j=6.6 Hz, 2H), 3.08–2.98 (m, 4H), 2.80(s, 6H), 2.15–2.02 (m, 2H) ppm; Mass Spec 397.4(M+H)+.

Example 41

1-(4-Methoxy-phenyl)-6-(3-pyrrolidin-1-yl-propyl)-3-trifluoromethyl-1,4,5,6-tetrahydro-pyrazolo[3,4-c]pyridin-7-one

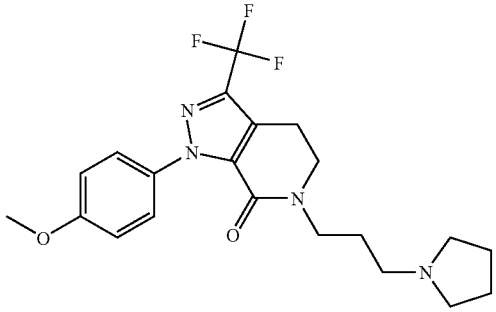

The title compound was prepared in a similar manner following the procedure outlined in Example 40. Mass Spec 423.4(M+H)+.

Example 42

6-(6-Dimethylamino-hexyl)-1-(4-methoxy-phenyl)-3-trifluoromethyl-1,4,5,6-tetrahydro-pyrazolo[3,4-c]pyridin-7-one

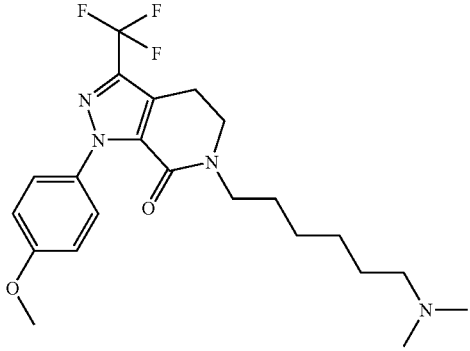

Part A: 1-(4-Methoxy-phenyl)-3-trifluoromethyl-1,4,5,6-tetrahydro-pyrazolo[3,4-c]pyridin-7-one (0.500 g, 1.606 mmol) was dissolved in N,N-dimethylformamide (20 mL) and cooled to 0° C. Sodium hydride (60%, 0.161 g, 4.016 mmol) was added followed by 5-bromopentyl acetate (0.535 mL, 3.213 mmol). The reaction was stirred at rt overnight, quenched with 1N hydrochloric acid (100 mL), extracted with ethyl acetate (3×100 mL), washed with water (2×100 mL), washed with brine (1×100 mL), dried over MgSO₄, concentrated, and purified by flash chromatography using 0–100% ethyl acetate/hexanes gradient as the eluent to afford 6-[1-(4-methoxy-phenyl)-7-oxo-3-trifluoromethyl-1,4,5,7-tetrahydro-pyrazolo[3,4-c]pyridin-6-yl]-hexanoic acid methyl ester (0.699 g, 99%). The ester (0.800 g, 1.82 mmol) was dissolved in tetrahydrofuran (40 mL), 1M lithium borohydride (3.64 mL, 3.64 mmol) was added, and the reaction was refluxed overnight. The reaction was quenched with water (150 mL), extracted with ethyl acetate (3×150 mL), washed with brine (1×150 mL), dried over MgSO₄, concentrated, and purified by flash chromatography using 0–100% ethyl acetate/hexanes as the eluent to afford 0.478 g (64%): $^1$H NMR (CDCl$_3$) δ 7.44 (d, j=8.8 Hz, 2H), 6.96 (d, j=9.2 Hz, 2H), 3.84 (s, 3H), 3.67 (t, j=6.8 Hz, 2H), 3.61 (t, j=6.4 Hz, 2H), 3.47 (t, j=7.5 Hz, 2H), 3.00(t, j=6.8 Hz, 2H), 1.65–1.50(m, 4H), 1.45–1.30(m, 4H) ppm.

Part B: 6-(6-Hydroxy-hexyl)-1-(4-methoxy-phenyl)-3-trifluoromethyl-1,4,5,6-tetrahydro-pyrazolo[3,4-c]pyridin-7-one (0.450 g, 1.093 mmol) and phosphorus tribromide (0.156 mL, 1.641 mmol) were dissolved in methylene chloride (20 mL) and stirred at rt for 2 hr. The reaction was quenched with water (100 mL), extracted with methylene chloride (3×100 mL), washed with saturated NaHCO$_3$ (1×100 mL), washed with brine (1×100 mL), dried over Na$_2$So$_4$, and concentrated to afford of a bromide intermediate (0.104 g, 20%). The bromide intermediate (0.052 g, 0.110 mmol) was redissolved in methylene chloride (6 mL), and 2M dimethylamine (0.384 mL, 0.767) was added. The reaction was stirred at rt overnight, evaporated, redissolved in toluene (15 mL), re-concentrated, purified by reverse phase HPLC and freeze-drying to afford the title compound (0.013 g, 28%): $^1$H NMR (CDCl$_3$) δ 7.43 (d, j=8.8 Hz, 2H), 6.95 (d, j=8.8 Hz, 2H), 3.84 (s, 3H), 3.68 (t, j=7.0 Hz, 2H), 3.46 (t, j=7.4 Hz, 2H), 3.05–2.98 (m, 4H), 2.83 (s, 3H), 2.82 (s, 3H), 1.75–1.68 (m, 2H), 1.62–1.56 (m, 2H), 1.38–1.34 (m, 4H) ppm; Mass Spec 439.4(M+H)$^+$.

Example 43

1-(4-Methoxy-phenyl)-6-(6-pyrrolidin-1-yl-hexyl)-3-trifluoromethyl-1,4,5,6-tetrahydro-pyrazolo[3,4-c]pyridin-7-one

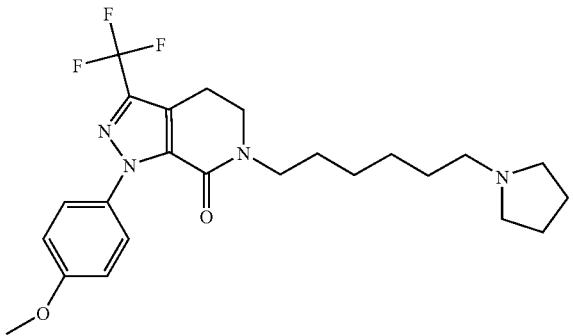

The title compound was prepared in a similar manner following the procedure outlined in Example 42. Mass Spec 465.4(M+H)$^+$.

Example 44

3-[1-(4-Methoxy-phenyl)-7-oxo-3-trifluoromethyl-1,4,5,7-tetrahydro-pyrazolo[3,4-c]pyridin-6-yl]-propionitrile

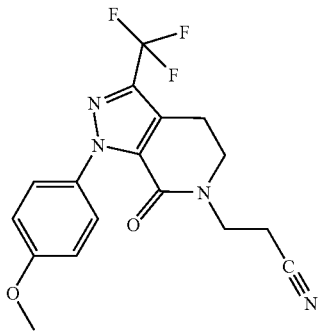

1-(4-Methoxy-phenyl)-3-trifluoromethyl-1,4,5,6-tetrahydro-pyrazolo[3,4-c]pyridin-7-one (1.00 g, 3.213 mmol) was dissolved in N,N-dimethylformamide (75 mL) and cooled to 0° C. Sodium hydride (60%, 0.321 g, 8.032 mmol) was added followed by 3-bromopropionitrile (0.533 mL, 6.425 mmol). The reaction was stirred at rt overnight, quenched with 1N hydrochloric acid (250 mL), extracted with ethyl acetate (3×200 mL), washed with water (2×200 mL), washed with brine (1×200 mL), dried over MgSO$_4$, concentrated, and purified by flash chromatography using 0–100% ethyl acetate/hexanes gradient as the eluent to afford the title compound (1.03 g, 88%): Mass Spec 382.4(M+H+H$_2$O)$^+$.

Example 45

5-[1-(4-Methoxy-phenyl)-7-oxo-3-trifluoromethyl-1,4,5,7-tetrahydro-pyrazolo[3,4-c]pyridin-6-yl]-pentanenitrile

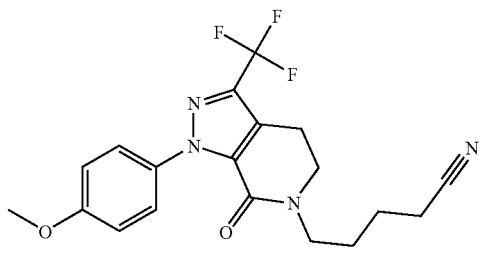

The title compound was prepared in a similar manner following the procedure outlined in Example 44. Mass Spec 393.3(M+H)$^+$.

Example 46

6-[1-(4-Methoxy-phenyl)-7-oxo-3-trifluoromethyl-1,4,5,7-tetrahydro-pyrazolo[3,4-c]pyridin-6-yl]-hexanenitrile

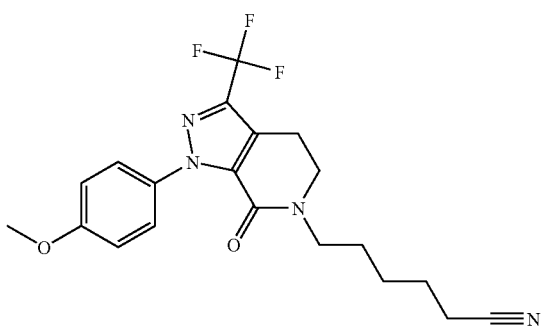

The title compound was prepared in a similar manner following the procedure outlined in Example 44. Mass Spec 407.3(M+H)$^+$.

Example 47

6-[1-(4-Methoxy-phenyl)-7-oxo-3-trifluoromethyl-1,4,5,7-tetrahydro-pyrazolo[3,4-c]pyridin-6-yl]-2,2-dimethyl-hexanenitrile

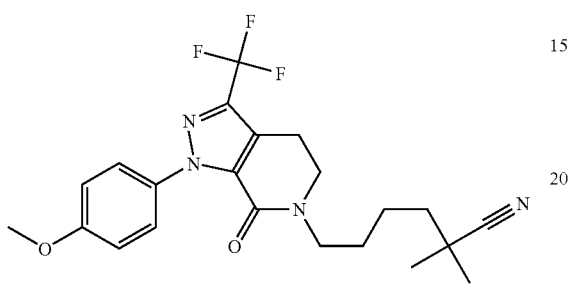

The title compound was prepared in a similar manner following the procedure outlined in Example 29. Mass Spec (M+H)+ 435.3.

Example 48

6-(3-Amino-propyl)-1-(4-methoxy-phenyl)-3-trifluoromethyl-1,4,5,6-tetrahydro-pyrazolo[3,4-c]pyridin-7-one

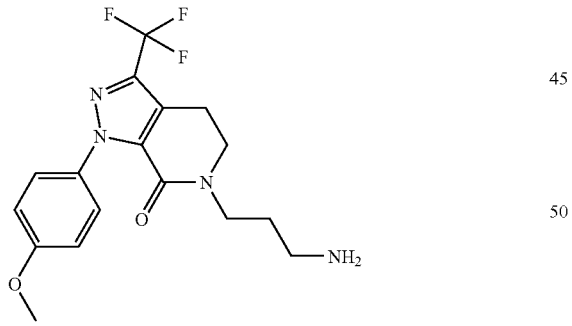

3-[1-(4-Methoxy-phenyl)-7-oxo-3-trifluoromethyl-1,4,5,7-tetrahydro-pyrazolo[3,4-c]pyridin-6-yl]-propionitrile (0.050 g, 0.137 mmol) was dissolved in methanol (20 mL) in a Parr bottle. Platinum oxide (0.005 g, 10%) and acetic acid (5 mL) were added and the reaction was hydrogenated under pressure overnight, filtered over Celite®, washed with methanol, concentrated, and purified with reverse phase HPLC and freeze-drying to afford the title compound (0.043 g, 85%): $^1$H NMR (CDCl$_3$) δ 8.22 (bs, 2H), 7.39 (d, j=8.8 Hz, 2H), 6.95 (d, j=8.8 Hz, 2H), 3.83 (s, 3H), 3.71 (t, j=6.8 Hz, 2H), 3.61–3.58 (m, 2H), 3.05 (t, j=6.8 Hz, 2H), 2.91 (bs, 2H), 1.99 (bs, 2H) ppm; Mass Spec 369.3(M+H)+.

Example 49

6-(5-Amino-pentyl)-1-(4-methoxyphenyl)-3-trifluoromethyl-1,4,5,6-tetrahydro-pyrazolo[3,4-c]pyridin-7-one

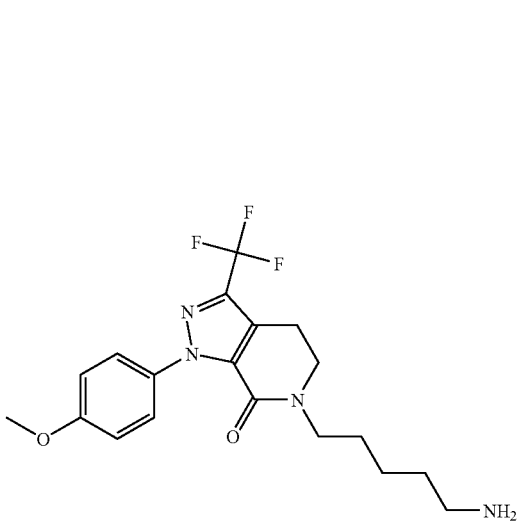

The title compound was prepared in a similar manner following the procedure outlined in Example 48. Mass Spec 397.3(M+H)+.

Example 50

6-(6-Amino-hexyl)-1-(4-methoxy-phenyl)-3-trifluoromethyl-1,4,5,6-tetrahydro-pyrazolo[3,4-c]pyridin-7-one

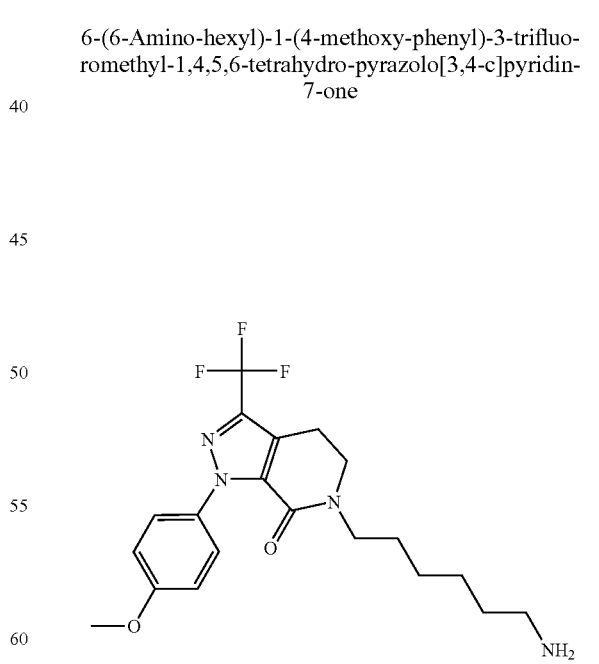

The title compound was prepared in a similar manner following the procedure outlined in Example 48. Mass Spec 411.3(M+H)+.

Example 51

6-(5-Dimethylamino-pentyl)-1-(4-methoxy-phenyl)-3-trifluoromethyl-1,4,5,6-tetrahydro-pyrazolo[3,4-c]pyridin-7-one

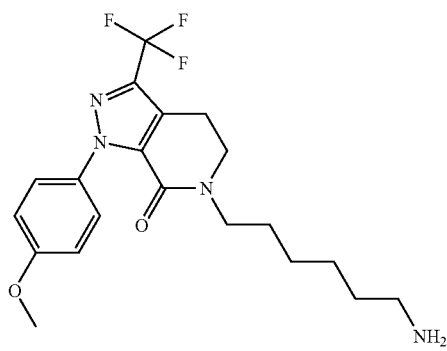

5-[1-(4-Methoxy-phenyl)-7-oxo-3-trifluoromethyl-1,4,5,7-tetrahydro-pyrazolo[3,4-c]pyridin-6-yl]-pentanenitrile (0.050 g, 0.127 mmol) was dissolved in methanol (20 mL) in a Parr bottle. Platinum oxide (0.005 g, 10%), formaldehyde (5 mL), and acetic acid (5 mL) were added. The reaction was hydrogenated under pressure overnight, filtered over Celite®, washed with methanol, concentrated, purified with reverse phase HPLC and freeze-dried to afford the title compound (0.040 g, 74%): $^1$H NMR (CDCl$_3$) δ 7.44 (d, j=9.1 Hz, 2H), 6.96 (d, j=9.2 Hz, 2H), 3.84 (s, 3H), 3.67 (t, j=6.8 Hz, 2H), 3.48 (t, j=6.8 Hz, 2H), 3.03–2.98 (m, 4H), 2.78 (s, 6H), 1.78 (bs, 2H), 1.66–1.58 (m, 4H), 1.42–1.30(m, 4H) ppm; Mass Spec 425.4(M+H)$^+$.

Example 52

6-(6-Dimethylamino-5,5-dimethyl-hexyl)-1-(4-methoxy-phenyl)-3-trifluoromethyl-1,4,5,6-tetrahydro-pyrazolo[3,4-c]pyridin-7-one

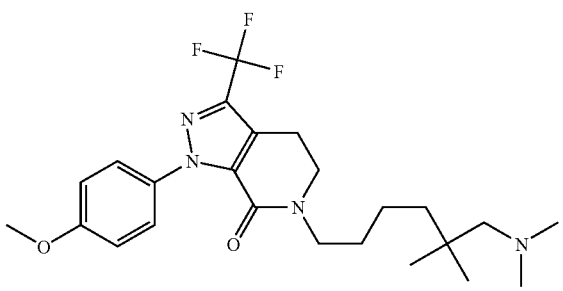

The title compound was prepared in a similar reductive manner (Pd/C in methanol acetic acid medium containing formaldehyde) from compound 47. The compound was purified by prep. HPLC. Mass Spec (M+H)$^+$ 467.4.

Example 53

5-[1-(4-Methoxy-phenyl)-7-oxo-3-trifluoromethyl-1,4,5,7-tetrahydro-pyrazolo[3,4-c]pyridin-6-yl]-N,N-dimethyl-pentanamidine

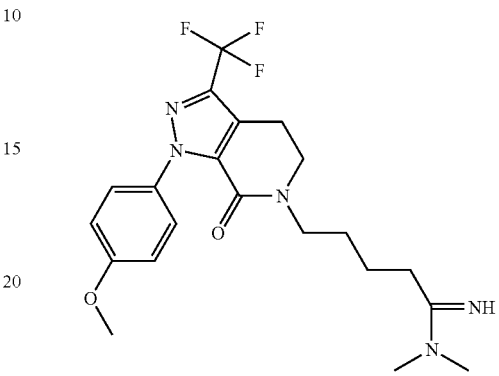

5-[1-(4-Methoxy-phenyl)-7-oxo-3-trifluoromethyl-1,4,5,7-tetrahydro-pyrazolo[3,4-c]pyridin-6-yl]-pentanenitrile (0.050 g, 0.127 mmol) was dissolved in 1:1 MeOH/CHCl$_3$ (15 mL). Hydrogen chloride gas was bubbled through the solution for 15 min. The reaction was tightly capped and sealed, stirred overnight at rt, and concentrated to dryness. The crude intermediate was dissolved in methanol (15 mL), and 2M dimethylamine (0.45 mL, 0.892 mmol) was added. The reaction was tightly capped and sealed and stirred overnight at rt, concentrated, and purified by reverse phase HPLC freeze-dried to afford the title compound (0.050 g, 89%): $^1$H NMR (CHCl$_3$) δ9.30 (bs, 0.5H), 8.76 (bs, 0.5H), 7.42 (d, j=9.1 Hz, 2H), 6.96 (d, j=8.8 Hz, 2H), 3.84 (s, 3H), 3.68 (t, j=6.8 Hz, 2H), 3.51 (t, j=6.3 Hz, 2H), 3.14 (s, 3H), 3.10(s, 3H), 3.01 (t, j=6.8 Hz, 2H), 2.66–2.62 (m, 2H), 1.72–1.60(m, 4H) ppm; Mass Spec 438.3(M+H)$^+$.

Example 54

6-(5-Imino-5-pyrrolidin-1-yl-pentyl)-1-(4-methoxy-phenyl)-3-trifluoromethyl-1,4,5,6-tetrahydro-pyrazolo[3,4-c]pyridin-7-one

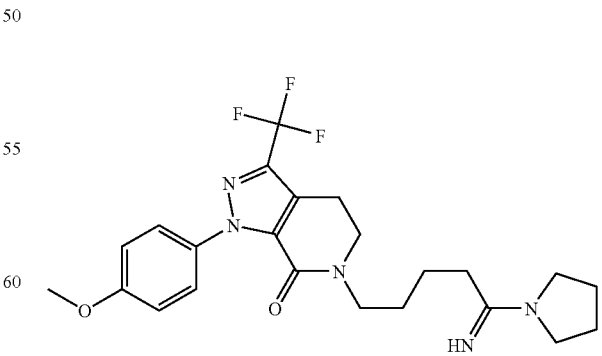

The title compound was prepared in a similar manner following the procedure outlined in Example 53. Mass Spec 464.3(M+H)$^+$.

Example 55

N-{1-Dimethylamino-5-[1-(4-methoxy-phenyl)-7-oxo-3-trifluoromethyl-1,4,5,7-tetrahydro-pyrazolo[3,4-c]pyridin-6-yl]-pentylidene}-methanesulfonamide

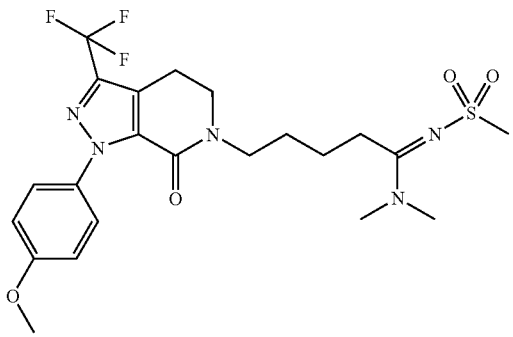

5-[1-(4-Methoxy-phenyl)-7-oxo-3-trifluoromethyl-1,4,5,7-tetrahydro-pyrazolo[3,4-c]pyridin-6-yl]-N,N-dimethyl-pentanamidine (0.050 g, 0.114 mmol) was dissolved in methylene chloride (10 mL). Methanesulfonyl chloride (0.1 mL, excess) and triethylamine (0.3, excess) were added to the reaction. The reaction was stirred at rt overnight, concentrated, and purified by flash chromatography using 0–100% ethyl acetate/hexanes as the eluent followed by a methanol flush. Further purification by reverse phase HPLC and freeze-drying afforded the title compound (0.120 g, 74%): $^1$H NMR (CHCl$_3$) δ 7.44 (d, j=8.7 Hz, 2H), 6.95 (d, j=8.8 Hz, 2H), 3.84 (s, 3H), 3.69 (t, j=7.0 Hz, 2H), 3.52 (t, j=6.3 Hz, 2H), 3.03 (s, 3H), 3.00(s, 3H), 2.99 (s, 3H), 3.14–2.98 (m, 2H), 2.89 (t, j=7.7 Hz, 2H), 1.75–1.62 (m, 2H) ppm; Mass Spec 516.3(M+H)$^+$.

Example 56

N-{5-[1-(4-Methoxy-phenyl)-7-oxo-3-trifluoromethyl-1,4,5,7-tetrahydro-pyrazolo[3,4-c]pyridin-6-yl]-1-pyrrolidin-1-yl-pentylidene}-methanesulfonamide

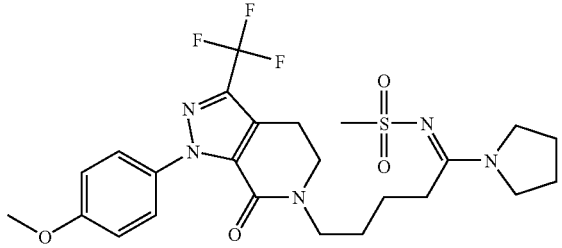

The title compound was prepared in a similar manner following the procedure outlined in Example 55. Mass Spec 542.3(M+H)$^+$.

Example 57

1-(4-Methoxy-phenyl)-6-[4-(1-methyl-4,5-dihydro-1H-imidazol-2-yl)-butyl]-3-trifluoromethyl-1,4,5,6-tetrahydro-pyrazolo[3,4-c]pyridin-7-one

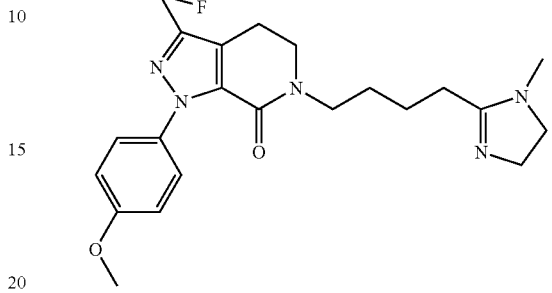

5-[1-(4-Methoxy-phenyl)-7-oxo-3-trifluoromethyl-1,4,5,7-tetrahydro-pyrazolo[3,4-c]pyridin-6-yl]-pentanenitrile (0.200 g, 0.510 mmol) was dissolved in 1:1 MeOH/CHCl$_3$ (25 mL). Hydrogen chloride gas was bubbled through the solution for 15 min. The reaction was tightly capped and sealed, stirred overnight at rt, and then concentrated to dryness. The crude intermediate was dissolved in methanol (15 mL). N-Methylethylenediamine (0.04 mL, 0.510 mmol) and triethylamine (0.36 mL, 2.55 mmol) were added. The reaction was tightly capped and sealed and stirred overnight at rt. The reaction was concentrated and purified by reverse phase HPLC and freeze-dried to yield the title compound (0.184 g, 80%): $^1$H NMR (CHCl$_3$) δ 7.43 (d, j=9.1 Hz, 2H), 6.95 (d, j=9.1 Hz, 2H), 3.95–3.83 (m, 2H), 3.85 (s, 3H), 3.71 (t, j=6.8 Hz, 2H), 3.58–3.50(m, 4H), 3.03 (t, j=7.9 Hz, 2H), 3.00(s, 2H), 2.68 (s, 4H), 1.73 (bs, 4H) ppm; Mass Spec 450.0(M+H)$^+$.

Example 58

N-Hydroxy-5-[1-(4-methoxy-phenyl)-7-oxo-3-trifluoromethyl-1,4,5,7-tetrahydro-pyrazolo[3,4-c]pyridin-6-yl]-pentanamidine

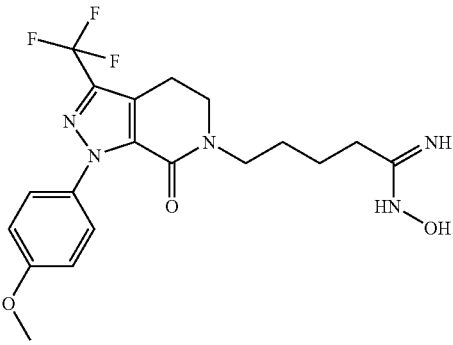

5-[1-(4-Methoxy-phenyl)-7-oxo-3-trifluoromethyl-1,4,5,7-tetrahydro-pyrazolo[3,4-c]pyridin-6-yl]-pentanenitrile (0.100 g, 0.255 mmol), hydroxylamine hydrochloride (0.027 g, 0.382 mmol), and triethylamine (0.071 mL, 0.510 mmol) were dissolved in ethanol (10 mL). The reaction was refluxed overnight, concentrated, and purified by reverse HPLC and freeze-drying to afford the title compound (0.45 g, 42%): $^1$H NMR (CHCl$_3$) δ 7.61 (bs, 0.5 H), 7.38 (d, j=8.5 Hz, 2H), 6.94 (d, j=8.8 Hz, 2H), 6.72 (bs, 0.5H), 3.82 (s, 3H), 3.68 (t, j=6.4 Hz, 2H), 3.48 (s, 2H), 3.01 (t, j=6.4 Hz, 2H), 3.35 (s, 3H), 1.56 (bs, 4H) ppm; Mass Spec 426.3(M+H)$^+$.

Example 59

N-Hydroxy-6-[1-(4-methoxy-phenyl)-7-oxo-3-trifluoromethyl-1,4,5,7-tetrahydro-pyrazolo[3,4-c]pyridin-6-yl]-2,2-dimethyl-hexanamidine

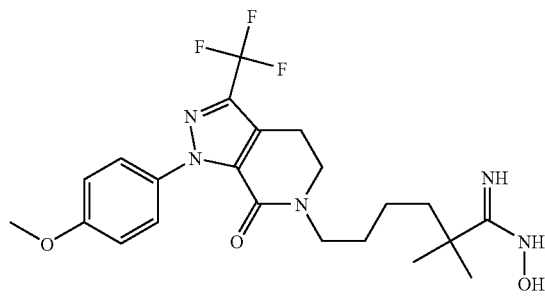

The titled compound was prepared from example 47 following the procedure outlined in example 59. Mass Spec 468.3(M+H)$^+$.

Example 60

1-(4-Methoxy-phenyl)-7-oxo-6-[4-(2-oxo-piperidin-1-yl)-butyl]-4,5,6,7-tetrahydro-1H-pyrazolo[3,4-c]pyridine-3-carboxylic acid amide

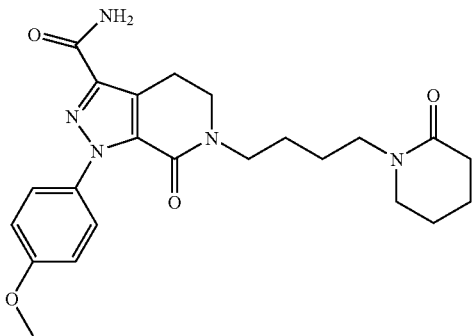

Part A: 1-(4-Methoxy-phenyl)-7-oxo-4,5,6,7-tetrahydro-1H-pyrazolo[3,4-c]pyridine-3-carboxylic acid ethyl ester (1.0 g, 3.17 mmol) was dissolved in N,N-dimethylformamide (40 mL) and cooled to 0° C. Sodium hydride (60%, 0.317 g, 7.93 mmol) was added followed by 4-bromobutyl acetate (0.918 mL, 6.34 mmol). The reaction was stirred at rt overnight, quenched with 1N hydrochloric acid (200 mL), extracted with ethyl acetate (3×250 mL), washed with water (2×200 mL), washed with brine (1×200 mL), dried over MgSO$_4$, concentrated, and purified by flash chromatography using 0–100% ethyl acetate/hexanes gradient as the eluent to afford 6-(4-acetoxy-butyl)-1-(4-methoxy-phenyl)-7-oxo-4,5,6,7-tetrahydro-1H-pyrazolo[3,4-c]pyridine-3-carboxylic acid ethyl ester (0.490 g, 36%). The ester (0.490 g, 0.114 mmol) was dissolved in 5% NH$_3$/ethylene glycol (6 mL) in a pressure tube, heated at 80° C. for 2 hr, cooled, quenched with water (100 mL), extracted with ethyl acetate (3×100 mL), washed with brine (1×100 mL), dried over MgSO$_4$, concentrated, and purified by flash chromatography using 0–100% ethyl acetate gradient and 0–100% methanol/ethyl acetate gradient as the eluents to afford 0.295 g (72%): $^1$H NMR (CHCl$_3$) δ 7.45 (d, j=8.8 Hz, 2H), 6.97 (d, j=9.1 Hz, 2H), 6.83 (s, 3H), 5.49 (s, 3H), 3.84 (s, 3H), 3.66 (t, j=6.2 Hz, 2H), 3.51 (t, j=7.3 Hz, 2H), 3.23 (t, j=6.8 Hz, 2H), 1.72–1.55 (m, 4H) ppm; Mass Spec 357.3(M−H)$^-$.

Part B. N,N-dimethylformamide (0.178 mL, 2.30 mmol) was added to acetonitrile (15 mL) and cooled to 0° C. Oxalyl chloride (0.167 mL, 1.92 mmol) was added to the reaction. Once gas evolution stopped, 6-(4-hydroxy-butyl)-1-(4-methoxy-phenyl)-7-oxo-4,5,6,7-tetrahydro-1H-pyrazolo[3,4-c]pyridine-3-carboxylic acid amide (0.275 g, 0.767 mmol) was dissolved in acetonitrile (5 mL), added to the reaction, and stirred at 0° C. for 20 min. Pyridine (0.310 mL, 3.84 mmol) was added to the reaction, and it was warmed to rt and stirred overnight. The reaction was quenched with 1N hydrochloric acid (100 mL), extracted with ethyl acetate (3×100 mL), washed with brine (1×50 mL), dried over MgSO$_4$, concentrated, and purified by flash chromatography using 0–100% ethyl acetate/hexanes gradient as eluent to afford 0.148 g (54%): $^1$H NMR (CHCl$_3$) δ 7.44 (d, j=9.2 Hz, 2H), 6.97 (d, j=9.2 Hz, 2H), 3.85 (s, 3H), 3.71 (t, j=7.0 Hz, 2H), 3.58–3.48 (m, 4H), 3.02 (t, j=6.8 Hz, 2H), 1.81–1.74 (m, 4H) ppm; Mass Spec 359.3(M+H)$^+$.

Part C: 6-(4-Chloro-butyl)-1-(4-methoxy-phenyl)-7-oxo-4,5,6,7-tetrahydro-1H-pyrazolo[3,4-c]pyridine-3-carbonitrile (0.148 g, 0.412 mmol) and potassium bromide (0.982 g, 8.24 mmol) were dissolved in acetone (25 mL) and refluxed overnight. The reaction was concentrated, quenched with water (100 mL), extracted with ethyl acetate (3×100 mL), washed with brine (1×100 mL), dried over MgSO$_4$, concentrated, and purified by flash chromatography using 0–100% ethyl acetate/hexanes gradient as eluent to afford 0.136 g (82%). 2-Piperidone (0.136 g, 0.340 mmol) was dissolved in N,N-dimethylformamide (7 mL) and the reaction was cooled to 0° C. Sodium hydride (60%, 0.040 g, 1.01 mmol) was added and the reaction was stirred at 0° C. for 30 min. The bromide intermediate (0.136 g, 0.34 mmol) dissolved in N,N-dimethylformamide (8 mL) was added, and the reaction was stirred at rt overnight. The reaction was quenched with 1N hydrochloric acid (100 mL), extracted with ethyl acetate (3×100 mL), washed with water (100 mL), washed with brine (1×100 mL), dried over MgSO$_4$, concentrated, and purified by flash chromatography using 0–100% ethyl acetate/hexanes gradient as the eluent. Further purification by reverse-phase HPLC and freeze-drying afforded 1-(4-methoxy-phenyl)-7-oxo-6-[4-(2-oxo-piperidin-1-yl)-butyl]-4,5,6,7-tetrahydro-1H-pyrazolo[3,4-c]pyridine-3-carbonitrile (0.060 g, 42%). The carbonitrile (0.060 g, 0.141 mmol), 1N sodium hydroxide (10 mL), hydrogen peroxide (30%, 10 mL), and catalytic tetrabutyl hydrogen sulfate were dissolved in methylene chloride (10 mL) and stirred overnight at rt. The reaction was quenched with 1N sodium hydroxide (20 mL), concentrated to about 10 mL of solution, water (100 mL) added, extracted with ethyl acetate (3×100 mL), washed with brine (1×100 mL), dried over MgSO$_4$, concentrated, and purified by reverse phase HPLC and freeze-dried to afford the title compound (0.034 g, 54%): $^1$H NMR (CHCl$_3$) δ 7.45 (d, j=8.8 Hz, 2H), 6.97 (d, j=8.8 Hz, 2H), 6.82 (s, 3H), 5.44 (s, 3H), 3.85 (s, 3H), 3.65 (t, j=7.0 Hz, 2H), 3.49 (t, j=7.0 Hz, 2H), 3.36 (t, j=6.8 Hz, 2H), 3.22 (t, j=7.0 Hz, 4H), 2.38–2.34 (m, 2H), 1.79–1.76 (m, 4H), 1.64–1.57 (m, 4H) ppm; Mass Spec 440.3(M+H)$^+$.

Example 61

1-(4-Methoxy-phenyl)-7-oxo-6-{2-[4-(2-oxo-2,3-dihydro-benzoimidazol-1-yl)-piperidin-1-yl]-ethyl}-4,5,6,7-tetrahydro-1H-pyrazolo[3,4-c]pyridine-3-carboxylic acid amide

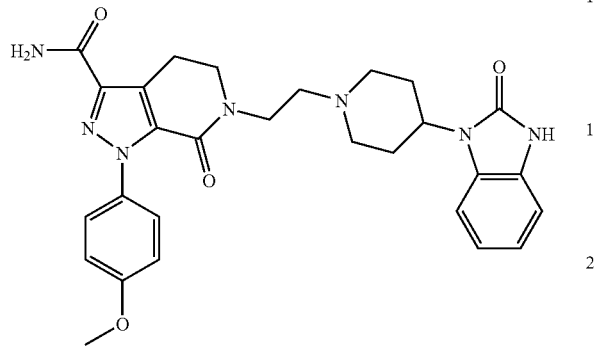

Part A. To 1-(4-methoxy-phenyl)-7-oxo-4,5,6,7-tetrahydro-1H-pyrazolo[3,4-c]pyridine-3-carbonitrile (0.53 g, 1.9 mmol) in DMF (5 mL) were added 2-bromoethylacetate (0.44 mL, 3.9 mmol) and sodium hydride (0.2 g, 4.9 mmol). The reaction was stirred 24 h, quenched with water, extracted with ethyl acetate, dried over MgSO$_4$, purified by chromatography on silica gel using 1:1 hexanes/ethyl acetate as eluent to afford the acetate (0.509 g, 72%); $^1$H NMR (CDCl$_3$) δ 7.46 (d, j=9.2 Hz, 2H), 6.98 (d, j=9.2 Hz, 2H), 4.27 (t, j=5.1 Hz, 2H), 3.85 (s, 3H), 3.81 (t, j=6.6 Hz, 2H), 3.75 (t, j=5.4 Hz, 2H), 3.05 (t, j=6.6 Hz, 2H), 2.06 (s, 3H) ppm.

Part B. The acetate from Part A (0.509 g, 1.4 mmol) was deprotected in a mixture of methanol (5 mL), water (5 mL) and K$_2$CO$_3$ (0.5 g) for 24 h. The solvent was stripped off. The residue partitioned in ethyl acetate/water, extracted, dried over MgSO$_4$, and purified by chromatography on silica gel using 1:1 hexanes/ethyl acetate as eluent to afford the amide (0.49 g, 95%); $^1$H NMR (CDCl$_3$) δ 8.3 (s, 1H), 7.47 (d, j=9.2 Hz, 2H), 6.97 (d, j=9.2 Hz, 2H), 3.84 (s, 3H), 3.81 (m, 2H), 3.77 (t, j=6.6 Hz, 2H), 3.75 (t, j=5.3 Hz, 2H), 3.13 (t, j=6.6 Hz, 2H) ppm.

Part C. To the amide from Part B (0.49 g, 1.5 mmol) in CHCl$_3$ (5 mL) was added phosphorous tribromide (0.186 mL, 1.9 mmol). The reaction was stirred 24 h, quenched with water, extracted with CHCl$_3$, and dried over Na$_2$SO$_4$ to afford 0.24 g (39%); Mass spec (M–H+H$_2$O) 409–411.1.

Part D. To the product from Part C (24 mg, 0.061 mmol) in THF (5 mL) were added 1-piperidin-4-yl-1,3-dihydro-benzoimidazol-2-one (26 mg, 0.122 mmol) and NaH (60%, 4.8 mg, 0.122 mmol). The reaction was stirred 24 h and purified by HPLC and freeze-drying to afford the title compound (27 mg, 69%); High Resolution Mass Spec for C$_{28}$H$_{32}$N$_7$O$_4$ is 530.2528.

Example 62

1-(4-Methoxy-phenyl)-6-{2-[4-(2-methoxy-phenyl)-piperazin-1-yl]-ethyl}-7-oxo-4,5,6,7-tetrahydro-1H-pyrazolo[3,4-c]pyridine-3-carboxylic acid amide

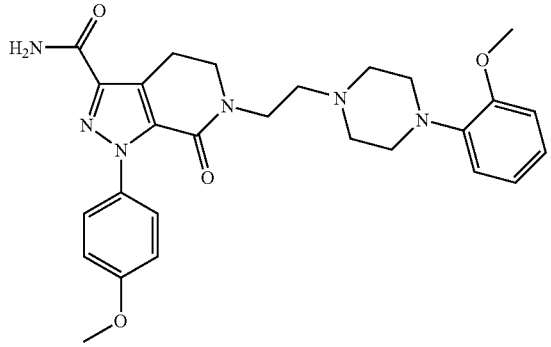

The title compound was prepared following the procedure outlined in Example 61. High Resolution Mass Spec for C$_{27}$H$_{33}$N$_6$O$_4$ is 505.2573.

Example 63

6-[2-(Benzyl-methyl-amino)-ethyl]-1-(4-methoxy-phenyl)-7-oxo-4,5,6,7-tetrahydro-1H-pyrazolo[3,4-c]pyridine-3-carboxylic acid amide

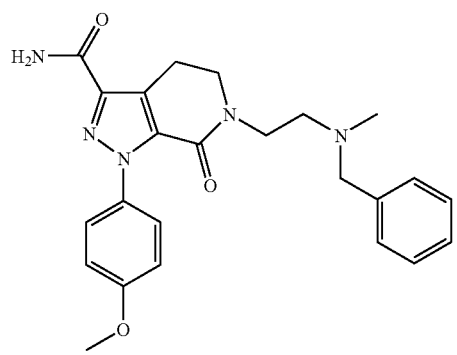

The title compound was prepared following the procedure outlined in Example 61. High Resolution Mass Spec for C$_{24}$H$_{28}$N$_6$O$_3$ is 434.2194.

Example 64

1-(4-Methoxy-phenyl)-6-[2-(methyl-phenyl-amino)-ethyl]-7-oxo-4,5,6,7-tetrahydro-1H-pyrazolo[3,4-c]pyridine-3-carboxylic acid amide

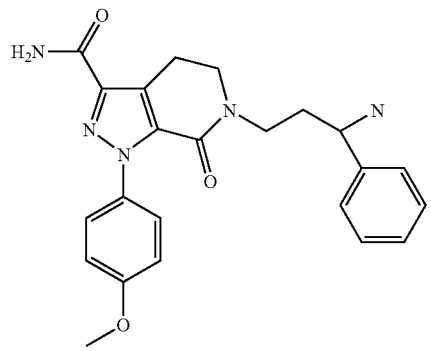

The title compound was prepared following the procedure outlined in Example 61. High Resolution Mass Spec for $C_{23}H_{26}N_6O_3$ is 420.2026.

Example 65

1-(4-Methoxy-phenyl)-6-[2-(3-methyl-piperidin-1-yl)-ethyl]-7-oxo-4,5,6,7-tetrahydro-1H-pyrazolo[3,4-c]pyridine-3-carboxylic acid amide

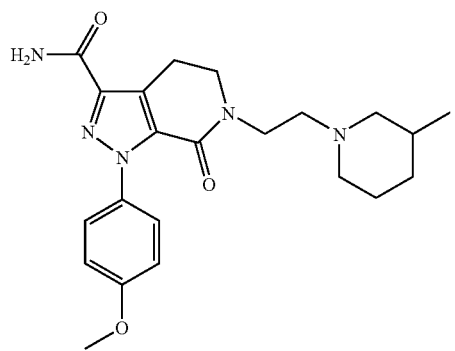

The title compound was prepared following the procedure outlined in Example 61. High Resolution Mass Spec for $C_{22}H_{30}N_6O_3$ is 412.2344.

Example 66

2-[1-(4-Methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-acetamide

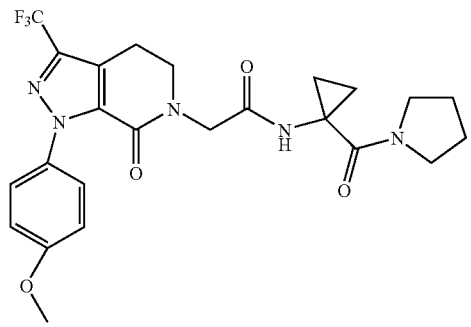

Part A: 1-(4-Methoxy-phenyl)-3-trifluoromethyl-1,4,5,6-tetrahydro-pyrazolo[3,4-c]pyridin-7-one (2.0 g, 6.43 mmol) was stirred in dry DMF (8 mL) at 0° C. NaH (60%, 0.35 g, 8.75 mmol, 1.4 eq) was added. Bromoacetic acid and t-butyl ester (1.0 mL, 6.77 mmol, 1.1 eq) were added dropwise. The mixture was stirred at 0° C. for 2 h and at rt overnight. The reaction was quenched with $H_2O$, extracted with EtOAc, washed with brine, concentrated, and purified by silica gel chromatography (1:1 EtOAc:hexanes) to give pure [1-(4-methoxy-phenyl)-7-oxo-3-trifluoromethyl-1,4,5,7-tetrahydro-pyrazolo[3,4-c]pyridin-6-yl]-acetic acid tert-butyl ester (2.73 g, yield: 99%).

Part B: The product from Part A (2.74 g, 6.44 mmol) was stirred in TFA (6 mL) and $CH_2Cl_2$ (6 mL) at rt for 1 h. The solvent was removed under vacuum to give [1-(4-methoxy-phenyl)-7-oxo-3-trifluoromethyl-1,4,5,7-tetrahydro-pyrazolo[3,4-c]pyridin-6-yl]-acetic acid (1.64 g, 69%).

Part C: The product from Part B (0.80 g, 2.17 mmol) was dissolved in $CH_2Cl_2$ (1 mL). $(COCl)_2$ (excess) was added dropwise followed by 2 drops of DMF. The mixture was stirred at rt for 2 h. The reaction was concentrated under vacuum to dryness. It was dissolved in $CH_2Cl_2$ (4 mL). 1-Amino-cyclopropylethyl ester (350 mg, 2.71 mmol, 1.25 eq) and DIEA (1.0 ml, 5.74 mmol, 2.65 eq) were added. The mixture was stirred at rt overnight. EtOAc was added. It was washed with $H_2O$, brine, dried over $MgSO_4$, filtered, concentrated to dryness, and purified by silica gel chromatography (EtOAc:hexanes) to give pure 1-{2-[1-(4-methoxy-phenyl)-7-oxo-3-trifluoromethyl-1,4,5,7-tetrahydro-pyrazolo[3,4-c]pyridin-6-yl]-acetylamino}-cyclopropanecarboxylic acid ethyl ester (130 mg, yield: 12%).

Part D: The product from Part C (130 mg, 0.27 mmol) was dissolved in MeOH (2 mL), and 1N NaOH (1 mL) was added. The reaction was stirred for 2 h at rt, concentrated, and partitioned between EtOAc and $H_2O$. The $H_2O$ layer was acidified with conc. HCl and extracted with EtOAc (2×). The organic layers were washed with $H_2O$, brine, dried over $MgSO_4$, filtered, and concentrated to dryness (110 mg, 89.8%). The residue (21 mg, 0.046 mmol) was dissolved in $CH_2Cl_2$ and DMF (0.5 mL), and treated with pyrrolidine (0.01 ml, 0.12 mmol, 2.6 eq), DIEA (0.08 mL, 0.46 mmol, 9.9 eq), and BOP (23 mg, 0.052 mmol, 1.1 eq). The reaction was stirred at rt for 12 h, quenched with 1N HCl, extracted with EtOAc, washed with 1N HCl, brine, dried over $MgSO_4$, filtered, concentrated, and purified with reverse phase HPLC to afford pure title compound (15 mg, yield: 65%). LC/MS ESI 506.6 (M+H).

Example 67

2-[1-(4-Methoxy-phenyl)-7-oxo-3-trifluoromethyl-1,4,5,7-tetrahydro-pyrazolo[3,4-c]pyridin-6-yl]-N-(1-pyrrolidin-1-ylmethyl-cyclopropyl)-acetamide

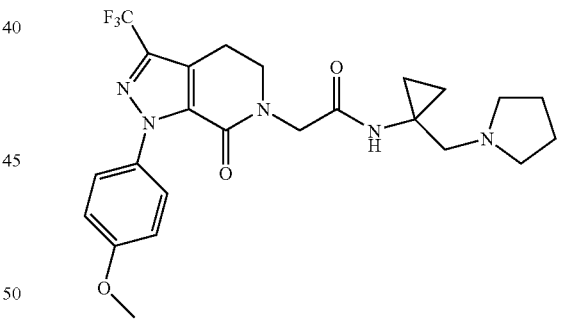

Part A: The acid from Part D of Example 65 (100 mg, 0.22 mmol) was dissolved in THF (0.5 mL) at 0° C. $Et_3N$ (0.05 mL, 0.36 mmol, 1.6 eq) was added followed by the dropwise addition of ClCOOEt (50 μL, 0.523 mmol, 2.3 eq). The mixture was stirred at 0° C. for 20 min. The reaction was filtered and diluted with THF and MeOH (total 3 mL). $NaBH_4$ (50 mg, 1.32 mmol, 6.0 eq) was added. The reaction was stirred at 0° C. for 45 min, quenched with sat'd $Na_2SO_4$, extracted with EtOAc, washed with $H_2O$, brine, dried over $Na_2SO_4$, filtered, and concentrated to dryness to give N-(1-hydroxymethyl-cyclopropyl)-2-[1-(4-methoxy-phenyl)-7-oxo-3-trifluoromethyl-1,4,5,7-tetrahydro-pyrazolo[3,4-c]pyridin-6-yl]-acetamide (75.6 mg, yield: 78%).

Part B: The product was stirred in $CH_2Cl_2$ (2 mL) at rt. NaOAc (85.9 mg, 1.05 mmol, 6.1 eq), 4 Å MS, and PCC (0.1108 g, 0.514 mmol, 3.0 eq) were added. The mixture was stirred at rt for 1.5 h. The reaction was diluted with CH₂Cl₂, filtered through Celite®, washed with H₂O (3×), dried over MgSO4, filtered, concentrated to give crude N-(1-formyl-cyclopropyl)-2-[1-(4-methoxy-phenyl)-7-oxo-3-trifluoromethyl-1,4,5,7-tetrahydro-pyrazolo[3,4-c]pyridin-6-yl]-acetamide (60 mg, 80%).

Part C: The product from Part B (60 mg, 0.14 mmol) was stirred in ClCH₂CH₂Cl (1 mL) at rt. Pyrrolidine (50 μL, 0.60 mmol, 4.4 eq), NaBH(OAc)₃ (0.175 g, 0.83 mmol, 6.0 eq), and HOAc (1 drop) were added. The mixture was stirred at rt overnight. The reaction was quenched with H₂O, extracted with EtOAc, washed with H₂O (2×), brine, dried over Na₂SO₄, filtered, and concentrated. The residue was purified by silica gel column chromatography (EtOAc, to 10% MeOH in CH₂Cl₂ with 0.5% Et₃N) to afford the pure product (10.9 mg, yield: 15%). LC/MS ESI492.6 (M+H).

Example 68

1-{2-[1-(4-Methoxy-phenyl)-7-oxo-3-trifluoromethyl-1,4,5,7-tetrahydro-pyrazolo[3,4-c]pyridin-6-yl]-acetylamino}-cyclopentanecarboxylic acid methyl ester methyl ester

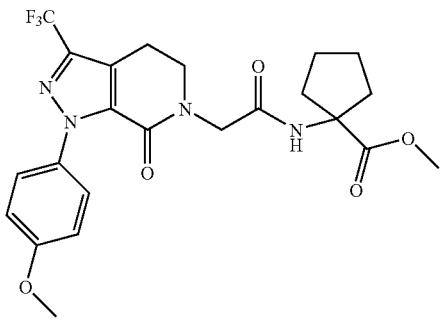

The title compound was prepared using similar processes as those in Example 66. LC/MS ESI 465.6 (M+H).

Example 69

1-{2-[1-(4-Methoxy-phenyl)-7-oxo-3-trifluoromethyl-1,4,5,7-tetrahydro-pyrazolo[3,4-c]pyridin-6-yl]-acetylamino}-cyclopentanecarboxylic acid dimethylamide

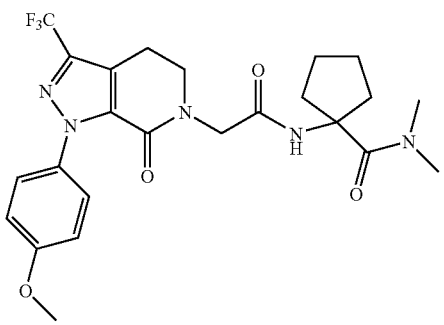

The title compound was prepared using similar processes as those in Example 66 and or 67. LC/MS ESI 508.6 (M+H).

Example 70

2-[1-(4-Methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopentyl]-acetamide

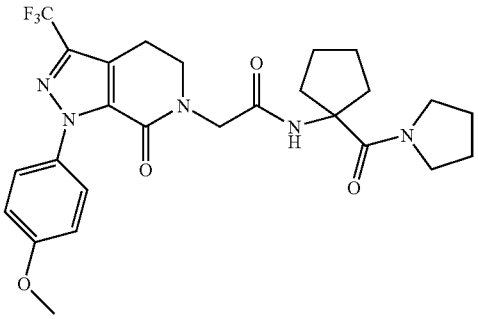

The title compound was prepared using similar processes as those in Example 66 and or 67. LC/MS ESI 534.6 (M+H).

Example 71

2-[1-(4-Methoxy-phenyl)-7-oxo-3-trifluoromethyl-1,4,5,7-tetrahydro-pyrazolo[3,4-c]pyridin-6-yl]-N-(1-pyrrolidin-1-ylmethyl-cyclopentyl)-acetamide

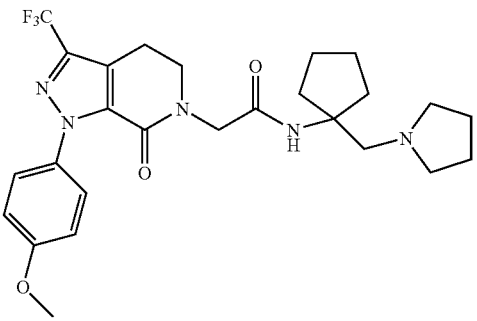

The title compound was prepared using similar processes as those in Example 66 and or 67. LC/MS (ESI) 520.6 (M+H).

Example 72

1-{3-[1-(4-Methoxy-phenyl)-7-oxo-3-trifluoromethyl-1,4,5,7-tetrahydro-pyrazolo[3,4-c]pyridin-6-yl]-propionylamino}-cyclopropanecarboxylic acid ethyl ester

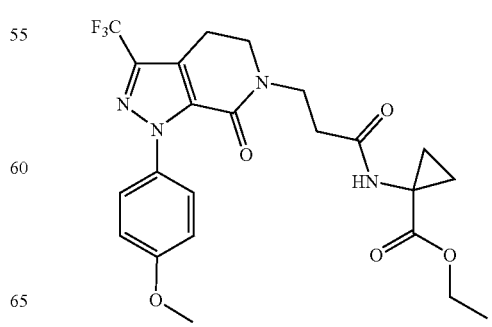

The title compound was prepared using similar processes as those in example 66. LC/MS ESI 495.6.

Example 73

1-{3-[1-(4-Methoxy-phenyl)-7-oxo-3-trifluoromethyl-1,4,5,7-tetrahydro-pyrazolo[3,4-c]pyridin-6-yl]-propionylamino}-cyclopentanecarboxylic acid methyl ester

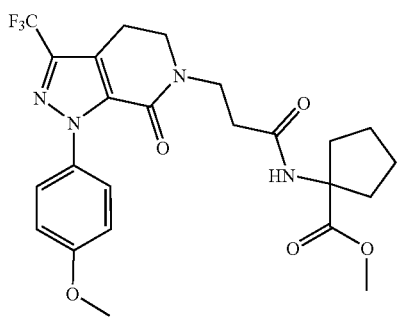

The title compound was prepared using similar processes as those in example 66. LC/MS ESI 509.6.

Example 74

1-{3-[1-(4-Methoxy-phenyl)-7-oxo-3-trifluoromethyl-1,4,5,7-tetrahydro-pyrazolo[3,4-c]pyridin-6-yl]-propionylamino}-cyclopentanecarboxylic acid dimethylamide

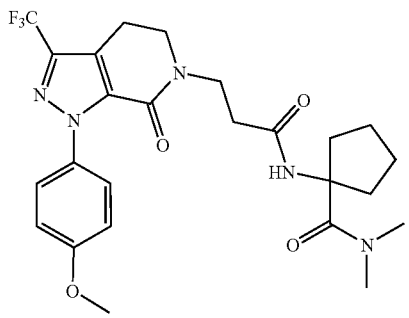

The title compound was prepared using similar processes as those in example 66 and or 67. LC/MS ESI 522.6

Example 75

3-[1-(4-Methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-propionamide

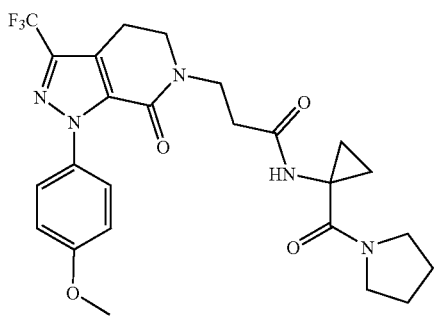

The title compound was prepared using similar processes as those in example 66 and or 67. LC/MS ESI 520.6

Example 76

1-{4-[1-(4-Methoxy-phenyl)-7-oxo-3-trifluoromethyl-1,4,5,7-tetrahydro-pyrazolo[3,4-c]pyridin-6-yl]-butyrylamino}-cyclopropanecarboxylic acid ethyl ester

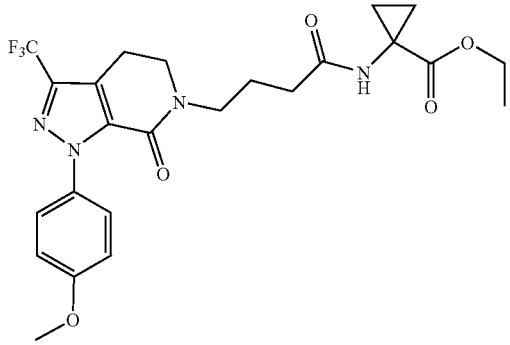

The title compound was prepared using similar processes as those in example 66. LC/MS ESI 509.6.

Example 77

1-{4-[1-(4-Methoxy-phenyl)-7-oxo-3-trifluoromethyl-1,4,5,7-tetrahydro-pyrazolo[3,4-c]pyridin-6-yl]-butyrylamino}-cyclopentanecarboxylic acid methyl ester

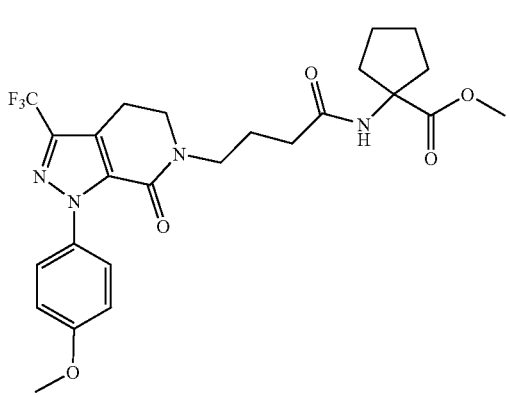

The title compound was prepared using similar processes as those in example 66. LC/MS ESI 523.6.

Example 78

1-{4-[1-(4-Methoxy-phenyl)-7-oxo-3-trifluoromethyl-1,4,5,7-tetrahydro-pyrazolo[3,4-c]pyridin-6-yl]-butyrylamino}-cyclopropanecarboxylic acid dimethylamide

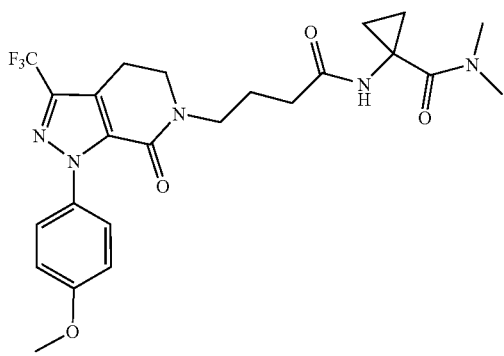

The title compound was prepared using similar processes as those in example 66 and or 67. LC/MS ESI 508.6.

Example 79

1-{4-[1-(4-Methoxy-phenyl)-7-oxo-3-trifluoromethyl-1,4,5,7-tetrahydro-pyrazolo[3,4-c]pyridin-6-yl]-butyrylamino}-cyclopropanecarboxylic acid dimethylamide

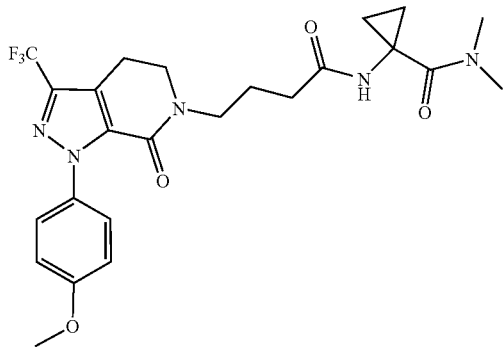

The title compound was prepared using similar processes as those in example 66 and or 67. LC/MS ESI 508.6.

Example 80

1-{4-[1-(4-Methoxy-phenyl)-7-oxo-3-trifluoromethyl-1,4,5,7-tetrahydro-pyrazolo[3,4-c]pyridin-6-yl]-butyrylamino}-cyclopentanecarboxylic acid dimethylamide

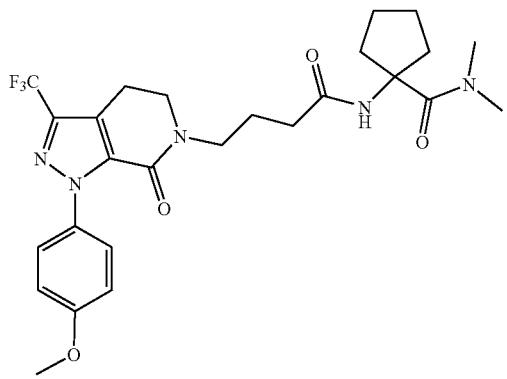

The title compound was prepared using similar processes as those in example 66 and or 67. LC/MS ESI 536.6 (M+H).

Example 81

4-[1-(4-Methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-butyramide

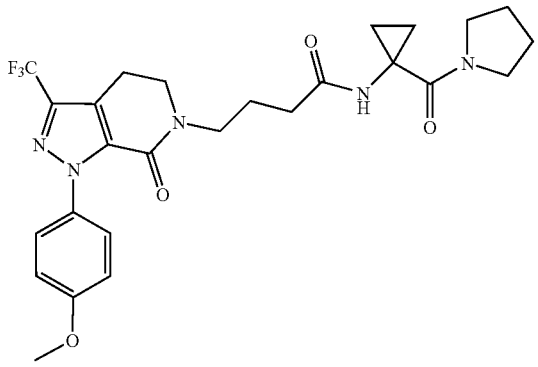

The title compound was prepared using similar processes as those in example 66 and or 67. LS/MS ESI 534.6.

Example 82

1-{5-[1-(4-Methoxy-phenyl)-7-oxo-3-trifluoromethyl-1,4,5,7-tetrahydro-pyrazolo[3,4-c]pyridin-6-yl]-pentanoylamino}-cyclopropanecarboxylic acid ethyl ester

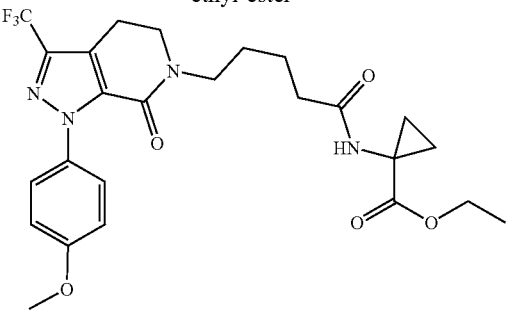

The title compound was prepared using similar processes as those in example 66. LC/MS ESI 523.6.

Example 83

1-{5-[1-(4-Methoxy-phenyl)-7-oxo-3-trifluoromethyl-1,4,5,7-tetrahydro-pyrazolo[3,4-c]pyridin-6-yl]-pentanoylamino}-cyclopentanecarboxylic acid methyl ester

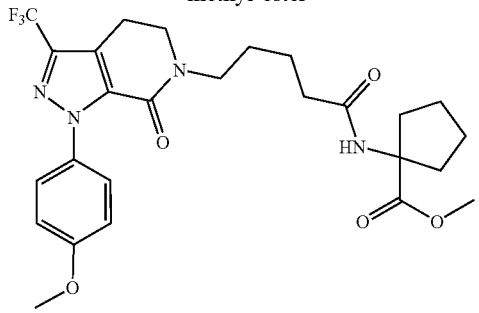

The title compound was prepared using similar processes as those in example 66. LC/MS ESI 537.6.

Example 84

1-{5-[1-(4-Methoxy-phenyl)-7-oxo-3-trifluoromethyl-1,4,5,7-tetrahydro-pyrazolo[3,4-c]pyridin-6-yl]-pentanoylamino}-cyclopropanecarboxylic acid dimethylamide

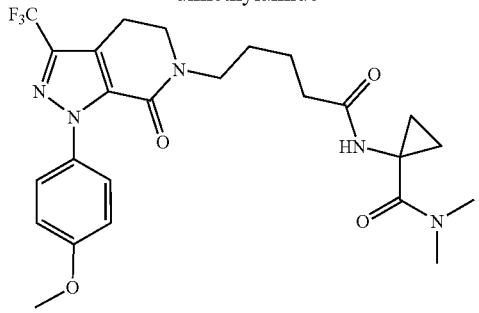

The title compound was prepared using similar processes as those in example 66 and or 67. LC/MS ESI 522.6

Example 85

5-[1-(4-Methoxy-phenyl)-7-oxo-3-trifluoromethyl-1,4,5,7-tetrahydro-pyrazolo[3,4-c]pyridin-6-yl]-pentanoic acid [1-(pyrrolidine-1-carbonyl)-cyclopropyl]-amide

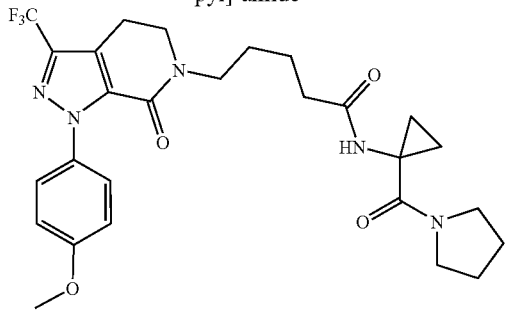

The title compound was prepared using similar processes as those in example 66 and or 67. LC/MS ESI 548.6.

Numerous modifications and variations of the present invention are possible in light of the above teachings. It is therefore to be understood that within the scope of the appended claims, the invention may be practiced otherwise that as specifically described herein.

What is claimed is:

1. A compound of formula I:

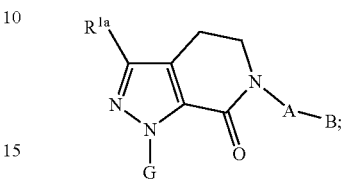

or a stereoisomer or pharmaceutically acceptable salt thereof, wherein;

G is a group of Formula IIa:

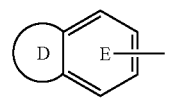

alternatively, ring D is absent and ring E is phenyl, and ring E is substituted with 1–3 R;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

A is 2–8 membered linear chain consisting of: carbon atoms, 0–2 carbonyl groups, and 0–3 heteroatoms selected from O, N, and $S(O)_p$, and A is substituted with 0–3 $R^{1a}$ and 0–2 $R^2$, and there are 0–2 double bonds and 0–1 triple bonds; provided that other than an S—S, S—O, or O—O bond is present in A;

B is selected from $OR^3$, $NR^3R^{3a}$, Y, $N(B^1)C(O)C(R^3R^{3g})_{1-4}NB^2B^3$,

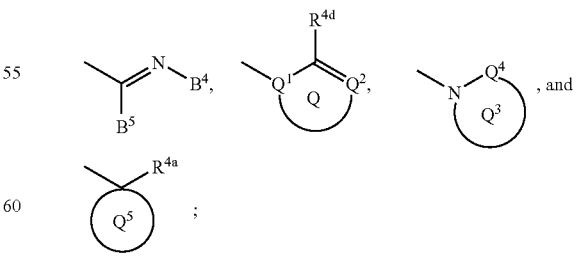

provided that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

$B^4$ is selected from H, $SO_2R^{3b}$, $C(O)R^{3b}$, $SO_2NR^3R^{3b}$, $C(O)NR^3R^{3b}$, $OR^2$, $SR^2$, —CN, and $NO_2$;

$B^5$ is $NR^2R^{2f}$ or $CR^3R^2R^{2f}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–8 membered ring consisting of, in addition to the $Q^1$-$CR^{4d}$=$Q^2$ group shown, carbon atoms and 0–2 heteroatoms selected from N, O, and $S(O)_p$, and the ring is substituted with an additional 0–2 $R^{4d}$;

ring $Q^3$ is a 4–7 membered monocyclic or tricyclic ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

$Q^4$ is selected from C=O and $SO_2$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and S(O)p, the carbocycle or heterocycle further comprises 0–2 double bonds and 0–2 carbonyl groups, and the carbocycle or heterocycle is substituted with 0–2 $R^4$;

Y is $CY^1Y^2R^{4a}$, and $Y^1$ and $Y^2$ are independently $C_{1-4}$ alkyl substituted with 0–2 $R^4$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—C(O)—$(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—C(=$NR^{1b}$)$NR^3R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5–10 membered saturated, partially saturated, or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or $C(O)-S(O)_p$ moiety;

$R^{2f}$, at each occurrence, is selected from H, $CF_3$, $C_{1-4}$ alkoxy substituted with 0–2 $R^{4b}$, $C_{1-6}$ alkyl substituted with 0–2 $R^{4b}$, $-(CH_2)_r-C_{3-10}$ carbocycle substituted with 0–2 $R^{4b}$, and $-(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $CR^2R^{2f}$ forms a 5–8 membered ring consisting of: carbon atoms and 0–2 heteroatoms selected from N, O, and $S(O)_p$, and this ring is substituted with 0–2 $R^{4b}$;

alternatively, $NR^2R^{2f}$ forms a 5–8 membered ring consisting of: carbon atoms and 0–2 additional heteroatoms selected from N, O, and $S(O)_p$, and this ring is substituted with 0–2 $R^{4b}$;

alternatively, when $B^4$ is $SO_2R^{3b}$ and $B^5$ is $NR^2R^{2f}$, $R^{3b}$ and $R^{2f}$ combine to form a 5–8 membered ring consisting of: carbon atoms and 0–2 additional heteroatoms selected from N, O, and $S(O)_p$, and this ring is substituted with 0–2 $R^{4b}$;

alternatively, when $B^4$ is $C(O)R^{3b}$ and $B^5$ is $NR^2R^{2f}$, $R^{3b}$ and $R^{2f}$ combine to form a 5–8 membered ring consisting of: carbon atoms and 0–2 additional heteroatoms selected from N, O, and $S(O)_p$, and this ring is substituted with 0–2 $R^{4b}$;

alternatively, when $B^5$ is $NR^2R^{2f}$, $B^4$ and $R^{2f}$ combine to form a 5–8 membered ring consisting of: carbon atoms and 0–2 additional heteroatoms selected from N, O, and $S(O)_p$, and this ring is substituted with 0–2 $R^{4b}$ and the $R^2$ group of $NR^2R^{2f}$, in addition to the groups recited below, is selected from $SO_2R^{3b}$, $C(O)R^{3b}$, and $-CN$;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $NR^3R^{3a}$ forms a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $-(CH_2)_r$-3–6 membered carbocycle, and $-(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_r$ $OR^2$, $(CR^3R^{3a})_rF$, $(CR^3R^{3a})_rCl$, $(CR^3R^{3a})_r$ Br, $(CR^3R^{3a})_rI$, $C_{1-4}$ alkyl, $(CR^3R^{3a})_rCN$, $(CR^3R^{3a})_r$ $NO_2$, $(CR^3R^{3a})_rNR^2R^{2a}$, $(CR^3R^{3a})_rC(O)R^{2c}$, $(CR^3R^{3a})_r$ $NR^2C(O)R^{2b}$, $(CR^3R^{3a})_rC(O)NR^2R^{2a}$, $(CR^3R^{3a})_r$ $NR^2C(O)NR^2R^{2a}$, $(CR^3R^{3a})_rC(=NR^2)$ $NR^2R^{2a}$, $(CR^3R^{3a})_rC(=NS(O)_2R^5)NR^2R^{2a}$, $(CR^3R^{3a})_r$ $NR^2C(=NR^2)NR^2R^{2a}$, $(CR^3R^{3a})_rC(O)$ $NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2-C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, $-(CR^3R^{3g})_r-C_{5-10}$ membered carbocycle substituted with 0–3 $R^{4c}$, $-(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_rCN$, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C$ $(R^{2e})(=NR^{2d})$, $(CR^3R^{3g})_rNR^{2d}R^{2d}$, $(CR^3R^{3g})_rN(\rightarrow O)$ $R^{2d}R^{2d}$, $(CR^3R^{3g})_rOR^{2d}$, $(CR^3R^{3g})_rNR^{2d}C(O)R^{2e}$, $(CR^3R^{3g})_rC(O)R^{2e}$, $(CR^3R^{3g})_rOC(O)R^{2e}$, $(CR^3R^{3g})_rC$ $(O)NR^{2d}R^{2d}$, $(CR^3R^{3g})_rC(O)OR^{2d}$, $(CR^3R^{3g})_rNR^{2d}C$ $(O)NR^{2d}R^{2d}$, $(CR^3R^{3g})_rOC(O)NR^{2d}R^{2d}$, $(CR^3R^{3g})_r$ $NR^{2d}C(O)OR^{2d}$, $(CR^3R^{3g})_rSO_2NR^{2d}R^{2d}$, $(CR^3R^{3g})_r$ $NR^{2d}SO_2NR^{2d}R^{2d}$, $(CR^3R^{3g})_rC(O)NR^{2d}SO_2R^{2d}$, $(CR^3R^{3g})_rNR^{2d}SO_2R^{2d}$, and $(CR^3R^{3g})_rS(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_r$ $OR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)$ $R^3$, $(CH_2)_rC(O)OR^{3c}$, $(CH_2)_rNR^3C(O)R^{3a}$, $(CH_2)_r$ $C(O)NR^3R^{3a}$, $(CH_2)_rNR^3C(O)NR^3R^{3a}$, $(CH_2)_rC (=NR³)NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣNR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, and (CH₂)ᵣ(CF₂)ᵣCF₃;

R⁴ᶜ, at each occurrence, is selected from =O, (CR³R³ᵃ)ᵣOR², (CR³R³ᵃ)ᵣF, (CR³R³ᵃ)ᵣBr, (CR³R³ᵃ)ᵣCl, (CR³R³ᵃ)ᵣCF₃, C₁₋₄ alkyl, C₂₋₆ alkenyl, C₂₋₆ alkynyl, (CR³R³ᵃ)ᵣCN, (CR³R³ᵃ)ᵣNO₂, (CR³R³ᵃ)ᵣNR²R²ᵃ, (CR³R³ᵃ)ᵣN(→O)R²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣN=CHOR³, (CR³R³ᵃ)ᵣC(O)NR²(CH₂)₂NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣNR²C(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣC(O)NR²SO₂—C₁₋₄ alkyl, (CR³R³ᵃ)ᵣNR²SO₂R⁵ᵃ, (CR³R³ᵃ)ᵣC(O)NR²SO₂R⁵ᵃ, (CR³R³ᵃ)ᵣS(O)ₚR⁵ᵃ, (CF₂)ᵣCF₃, (CR³R³ᵃ)ᵣC₃₋₁₀ carbocycle substituted with 0–2 R⁴ᵇ, and (CR³R³ᵃ)ᵣ4–10 membered heterocycle substituted with 0–2 R⁴ᵇ and consisting of carbon atoms and from 1–4 heteroatoms selected from the group consisting of N, O, and S(O)ₚ;

R⁴ᵈ, at each occurrence, is selected from H, (CR³R³ᵃ)ᵣOR², (CR³R³ᵃ)ᵣF, (CR³R³ᵃ)ᵣBr, (CR³R³ᵃ)ᵣCl, C₁₋₄ alkyl, (CR³R³ᵃ)ᵣCN, (CR³R³ᵃ)ᵣNO₂, (CR³R³ᵃ)ᵣNR²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣN=CHOR³, (CR³R³ᵃ)ᵣC(O)NH(CH₂)₂NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣNHC(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣNR²SO₂—C₁₋₄ alkyl, (CR³R³ᵃ)ᵣC(O)NHSO₂—C₁₋₄ alkyl, (CR³R³ᵃ)NR²SO₂R⁵, (CR³R³ᵃ)ᵣS(O)ₚR⁵ᵃ, (CR³R³ᵃ)ᵣ(CF₂)ᵣCF₃, (CR³R³ᵃ)ᵣ-5–6 membered carbocycle substituted with 0–1 R⁵, and a (CR³R³ᵃ)ᵣ-5–6 membered heterocycle consisting of: carbon atoms and 1–4 heteroatoms selected from the group consisting of N, O, and S(O)ₚ and substituted with 0–1 R⁵;

R⁵, at each occurrence, is selected from H, C₁₋₆ alkyl, =O, (CH₂)ᵣOR³, F, Cl, Br, I, —CN, NO₂, (CH₂)ᵣNR³R³ᵃ, (CH₂)ᵣC(O)R³, (CH₂)ᵣC(O)OR³ᶜ, (CH₂)ᵣNR³C(O)R³ᵃ, (CH₂)ᵣC(O)NR³R³ᵃ, (CH₂)ᵣNR³C(O)NR³R³ᵃ, (CH₂)ᵣCH(=NOR³ᵈ), (CH₂)ᵣC(=NR³)NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣNR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, (CF₂)ᵣCF₃, phenyl substituted with 0–2 R⁶, naphthyl substituted with 0–2 R⁶, and benzyl substituted with 0–2 R⁶;

R⁵ᵃ, at each occurrence, is selected from C₁₋₆ alkyl, (CH₂)ᵣOR³, (CH₂)ᵣNR³R³ᵃ, (CH₂)ᵣC(O)R³, (CH₂)ᵣC(O)OR³ᶜ, (CH₂)ᵣNR³C(O)R³ᵃ, (CH₂)ᵣC(O)NR³R³ᵃ, (CF₂)ᵣCF₃, phenyl substituted with 0–2 R⁶, naphthyl substituted with 0–2 R⁶, and benzyl substituted with 0–2 R⁶, provided that R⁵ᵃ does not form a S—N or S(O)ₚ—C(O) bond;

R⁶, at each occurrence, is selected from H, OH, (CH₂)ᵣOR², halo, C₁₋₄ alkyl, —CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl;

R⁷, at each occurrence, is selected from H, OH, C₁₋₆ alkyl, C₁₋₆ alkyl-C(O)—, C₁₋₆ alkyl-O—, (CH₂)ₙ-phenyl, C₁₋₄ alkyl-OC(O)—, C₆₋₁₀ aryl-O—, C₆₋₁₀ aryl-OC(O)—, C₆₋₁₀ aryl-CH₂C(O)—, C₁₋₄ alkyl-C(O)O—C₁₋₄ alkyl-OC(O)—, C₆₋₁₀ aryl-C(O)O—C₁₋₄ alkyl-OC(O)—, C₁₋₆ alkyl-NH₂—C(O)—, phenyl-NH₂—C(O)—, and phenyl-C₁₋₄ alkyl-C(O)—;

R⁸, at each occurrence, is selected from H, C₁₋₆ alkyl, and (CH₂)ₙ-phenyl;

alternatively, R⁷ and R⁸, when attached to the same nitrogen, combine to form a 5–10 membered heterocyclic ring consisting of carbon atoms and 0–2 additional heteroatoms selected from the group consisting of N, O, and S(O)ₚ;

R⁹, at each occurrence, is selected from H, C₁₋₆ alkyl, and (CH₂)ₙ-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

2. A compound according to claim 1, wherein

R is selected from H, C₁₋₄ alkyl, F, Cl, OH, OCH₃, OCH₂CH₃, OCH(CH₃)₂, —CN, C(=NH)NH₂, C(=NH)NHOH, C(=NH)NHOCH₃, NH₂, NH(C₁₋₃ alkyl), N(C₁₋₃ alkyl)₂, C(=NH)NH₂, CH₂NH₂, CH₂NH(C₁₋₃ alkyl), CH₂N(C₁₋₃ alkyl)₂, (CR⁸R⁹)ₜNR⁷R⁸, C(O)NR⁷R⁸, CH₂C(O)NR⁷R⁸, S(O)ₚNR⁷R⁸, CH₂S(O)ₚNR⁷R⁸, SO₂R³, and OCF₃;

A is 2–6 membered linear chain consisting of: carbon atoms, 0–2 carbonyl groups, and 0–3 heteroatoms selected from O, N, and S(O)ₚ, and A is substituted with 0–2 R¹ᵃ and 0–2 R², and there are 0–1 double bonds; provided that other than an S—S, S—O, or O—O bond is present in A;

B is selected from OR³, NR³R³ᵃ, Y, N(B¹)C(O)C(R³R³ᵍ)NB²B³, N(B¹)C(O)C(R³R³ᵍ)C(R³R³ᵍ)NB²B³,

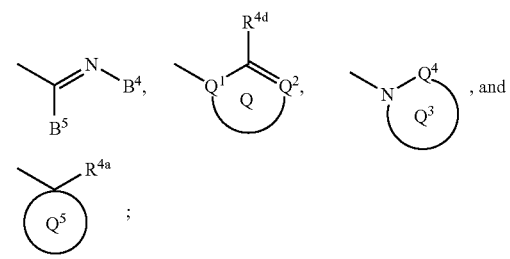

provided that the R⁴ᵈ shown is other than OH;

B¹ is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —(CH₂)₀₋₁—C₃₋₇ carbocycle substituted with 0–2 R⁴ᵇ, and —(CH₂)₀₋₁-5–6 membered heterocycle consisting of: carbon atoms and 1–4 heteroatoms selected from the group consisting of N, O, and S(O)ₚ and substituted with 0–2 R⁴ᵇ;

B² is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, NR²ᵈR²ᵈ, CH₂NR²ᵈR²ᵈ, CH₂CH₂NR²ᵈR²ᵈ, C(O)R²ᵉ, C(O)NR²ᵈR²ᵈ, SO₂NR²ᵈR²ᵈ, and S(O)ₚR⁵ᵃ;

B³ is selected from H, C₁₋₆ alkyl substituted with 0–1 R⁴ᶜ, —(CH₂)₀₋₁-3–6 membered carbocycle substituted with 0–1 R⁵, and a —(CH₂)₀₋₁-5–6 membered heterocycle consisting of: carbon atoms and 1–4 heteroatoms selected from the group consisting of N, O, and S(O)ₚ and substituted with 0–1 R⁵;

B⁴ is selected from H, SO₂R³ᵇ, C(O)R³ᵇ, SO₂NR³R³ᵇ, C(O)NR³R³ᵇ, OR², and —CN;

$B^5$ is $NR^2R^{2f}$ or $CR^3R^2R^{2f}$;

ring Q is a 5–6 membered ring consisting of, in addition to the $Q^1$-$CR^{4d}$=$Q^2$ group shown, carbon atoms and 0–2 heteroatoms selected from N, O, and $S(O)_p$, and the ring is substituted with an additional 0–2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

$Q^4$ is selected from C=O and $SO_2$;

ring $Q^3$ is a 4–7 membered monocyclic or tricyclic ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and S(O)p, the carbocycle or heterocycle further comprises 0–2 double bonds and 0–2 carbonyl groups, and the carbocycle or heterocycle is substituted with 0–2 $R^4$;

Y is $CY^1Y^2R^{4a}$, and $Y^1$ and $Y^2$ are independently $C_{1-3}$ alkyl substituted with 0–1 $R^4$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p R^{2b}$, $NR^2(CH_2)_r OR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_r OR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, a $CH_2$—$C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 hetero atoms selected from the group consisting of N, O, and $S(O)_p$, provided that $R^{2e}$ forms other than a C(O)-halo or C(O)—S(O)$_p$ moiety;

$R^{2f}$, at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

alternatively, $CR^2R^{2f}$ forms a 5–6 membered ring consisting of: carbon atoms and 0–2 heteroatoms selected from N, O, and $S(O)_p$, and this ring is substituted with 0–2 $R^{4b}$;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, when $B^5$ is $NR^2R^{2f}$, $B^4$ and $R^{2f}$ combine to form a 5–6 membered ring consisting of: carbon atoms and 0–2 additional heteroatoms selected from N, O, and $S(O)_p$, and this ring is substituted with 0–2 $R^{4b}$ and the $R^2$ group of $NR^2R^{2f}$, in addition to the groups recited below, is selected from $SO_2R^{3b}$ and $C(O)R^{3b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5–6 membered carbocycle substituted with 0–1 $R^{1a}$, and —$C_{0-1}$ alkyl)-5–6 membered heterocycle substituted with 0–1 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2NR^2R^{2a}$, $S(O)_pR^{5a}$, $NR^2SO_2$—$C_{1-4}$ alkyl, $NR^2SO_2R^5$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-3}$ alkenyl, $C_{2-3}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\to O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OR^2$, $CH_2OR^2$, $C_{1-4}$ alkyl, —CN, $CH_2CN$, $NO_2$, $CH_2NO_2$, $NR^2R^{2a}$, $CH_2NR^2R^{2a}$, $CH_2C(O)R^{2c}$, $C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2R^5$, $(CH_2)_rS(O)_pR^{5a}$, $CH_2CF_3$, $CF_3$, 5–6 membered carbocycle substituted with 0–1 $R^5$, $CH_2$-5–6 membered carbocycle substituted with 0–1 $R^5$, a 5–6 membered heterocycle consisting of: carbon atoms and 1–4 heteroatoms selected from the group consisting of N, O, and $S(O)_p$ and substituted with 0–1 $R^5$, and a $CH_2$-5–6 membered heterocycle consisting of: carbon atoms and 1–4 heteroatoms selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^{5a}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

3. A compound according to claim 2, wherein:

G is selected from the group: phenyl; 4-ethyl-phenyl; 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-aminosulfonyl-4-methoxy-phenyl; 2-aminosulfonyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4-chloro-phenyl; 3-aminomethyl-phenyl; 3-amino-phenyl; 3-chloro-4-fluoro-phenyl; 3-chloro-phenyl; 3-hydroxy-4-methoxy-phenyl; 4-chloro-3-fluoro-phenyl;

4-chloro-phenyl; 4-methoxy-2-methylsulfonyl-phenyl; 5-chloro-2-aminosulfonyl-phenyl; 5-chloro-2-methylsulfonyl-phenyl;

A is 2–6 membered linear chain consisting of: carbon atoms, 0–2 carbonyl groups, and 0–2 heteroatoms selected from O, N, and $S(O)_p$, and A is substituted with 0–2 $R^{1a}$ and 0–2 $R^2$, and there are 0–1 double bonds and 0–1 triple bonds; provided that other than an S—S, S—O, or O—O bond is present in A;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$ and $OR^2$;

$B^5$ is $NR^2R^{2f}$;

ring Q is a 5–6 membered ring consisting of, in addition to the N—$CR^{4d}$=N group shown, carbon atoms and 0–2 heteroatoms selected from N, O, and $S(O)_p$, and the ring is substituted with an additional 0–2 $R^{4d}$;

$Q^4$ is selected from C=O and $SO_2$;

ring $Q^3$ is a 5–7 membered ring consisting of, in addition to the N-$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^{4a}$;

alternatively, ring $Q^3$ is a 5–7 membered ring to which another ring is fused, wherein: the 5–7 membered ring consists of, in addition to the shown amide group, carbon atoms and 0–2 heteroatoms selected from $NR^{4c}$, O, S, S(O), and $S(O)_2$, and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 5–7 membered ring and the fusion ring, is substituted with 0–3 $R^{4a}$;

ring $Q^5$, is a $C_{3-6}$ monocyclic carbocycle or 5–6 membered monocyclic heterocycle, wherein the carobocycle or heterocycle consists of: carbon atoms and 0–2 heteroatoms selected from N, O, and S(O)p, the carbocycle or heterocycle further comprises 0–1 double bonds and 0–1 carbonyl groups, and the carbocycle or heterocycle is substituted with 0–2 $R^4$;

Y is $CY^1Y^2R^{4a}$, and $Y^1$ and $Y^2$ are independently $C_{1-2}$ alkyl substituted with 0–1 $R^4$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, OC(O) $R^2$, $CO_2R^{2a}$, $S(O)_pR^{2b}$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $CH_3$, $CH_2CH_3$, $CH_2CH_2CH_3$, $CH(CH_3)_2$, $OCH_3$, and benzyl;

alternatively, NR²R²f forms a 5–6 membered ring consisting of: carbon atoms and 0–2 additional heteroatoms selected from N, O, and S(O)$_p$, and this ring is substituted with 0–2 R$^{4b}$;

alternatively, B$^4$ and R$^{2f}$ combine to form a 5–6 membered ring consisting of: carbon atoms and 0–1 additional heteroatoms selected from N, O, and S(O)$_p$, and this ring is substituted with 0–2 R$^{4b}$ and the R$^2$ group of NR²R$^{2f}$, in addition to the groups recited below, can be SO$_2$R$^{3b}$;

R$^{3b}$, at each occurrence, is selected from H, CF$_3$, CH$_3$, CH$_2$CH$_3$, CH$_2$CH$_2$CH$_3$, and CH(CH$_3$)$_2$;

R$^4$, at each occurrence, is selected from H, =O, CH$_2$OR$^2$, (CH$_2$)$_2$OR$^2$, OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR²R$^{2a}$, CH$_2$NR²R$^{2a}$, (CH$_2$)$_2$NR²R$^{2a}$, C(O)R$^{2c}$, NR²C(O)R$^{2b}$, C(O)NR²R$^{2a}$, NR²C(O)NR²R$^{2a}$, SO$_2$NR²R$^{2a}$, CF$_3$, and CF$_2$CF$_3$;

R$^{4a}$ is selected from —(CR³R$^{3g}$)$_r$-5–6 membered carbocycle substituted with 0–3 R$^{4c}$, —(CR³R$^{3g}$)$_r$-5–6 membered heterocycle substituted with 0–3 R$^{4c}$ and consisting of: carbon atoms and 1–4 heteroatoms selected from the group consisting of N, O, and S(O)$_p$, (CR³R$^{3g}$)$_r$NR$^{2d}$R$^{2d}$, (CR³R$^{3g}$)$_r$N(→O)R$^{2d}$R$^{2d}$, (CR³R$^{3g}$)$_r$OR$^{2d}$, (CR³R$^{3g}$)$_r$NR$^{2d}$C(O)R$^{2e}$, (CR³R$^{3g}$)$_r$C(O)R$^{2e}$, (CR³R$^{3g}$)$_r$OC(O)R$^{2e}$, (CR³R$^{3g}$)$_r$C(O)NR$^{2d}$R$^{2d}$, (CR³R$^{3g}$)$_r$C(O)OR$^{2d}$, (CR³R$^{3g}$)$_r$NR$^{2d}$C(O)NR$^{2d}$R$^{2d}$, (CR³R$^{3g}$)$_r$NR$^{2d}$C(O)OR$^{2d}$, (CR³R$^{3g}$)$_r$SO$_2$NR$^{2d}$R$^{2d}$, (CR³R$^{3g}$)$_r$NR$^{2d}$SO$_2$R$^{2d}$, and (CR³R$^{3g}$)$_r$S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR³R$^{3a}$, CH$_2$NR³R$^{3a}$, C(O)R$^3$, CH$_2$C(O)R$^3$, C(O)OR$^{3c}$, CH$_2$C(O)OR$^{3c}$, NR³C(O)R$^{3a}$, CH$_2$NR³C(O)R$^{3a}$, C(O)NR³R$^{3a}$, CH$_2$C(O)NR³R$^{3a}$, SO$_2$NR³R$^{3a}$, CH$_2$SO$_2$NR³R$^{3a}$, NR₃SO$_2$—C$_{1-4}$ alkyl, CH$_2$NR³SO$_2$—C$_{1-4}$ alkyl, NR³SO$_2$-phenyl, CH$_2$NR³SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, and CF$_3$;

R$^{4c}$, at each occurrence, is selected from =O, OR$^2$, (CR³R$^{3a}$)OR$^2$, F, (CR³R$^{3a}$)F, Br, (CR³R$^{3a}$)Br, Cl, (CR³R$^{3a}$)Cl, CF$_3$, (CR³R$^{3a}$)CF$_3$, C$_{1-4}$ alkyl, C$_{2-3}$ alkenyl, C$_{2-3}$ alkynyl, —CN, (CR³R$^{3a}$)CN, NO$_2$, (CR³R$^{3a}$)NO$_2$, NR²R$^{2a}$, (CR³R$^{3a}$)NR²R$^{2a}$, N(→O)R²R$^{2a}$, (CR³R$^{3a}$)N(→O)R²R$^{2a}$, C(O)R$^{2c}$, (CR³R$^{3a}$)C(O)R$^{2c}$, NR²C(O)R$^{2b}$, (CR³R$^{3a}$)NR²C(O)R$^{2b}$, C(O)NR²R$^{2a}$, (CR³R$^{3a}$)C(O)NR²R$^{2a}$, NR²C(O)NR²R$^{2a}$, (CR³R$^{3a}$)NR²C(O)NR²R$^{2a}$, SO$_2$NR²R$^{2a}$, (CR³R$^{3a}$)SO$_2$NR²R$^{2a}$, NR²SO$_2$NR²R$^{2a}$, (CR³R$^{3a}$)NR²SO$_2$NR²R$^{2a}$, NR²SO$_2$R$^{5a}$, (CR³R$^{3a}$)NR²SO$_2$R$^{5a}$, S(O)$_p$R$^{5a}$, (CR³R$^{3a}$)S(O)$_p$R$^{5a}$, CF$_3$, CF$_2$CF$_3$, C$_{3-10}$ carbocycle substituted with 0–2 R$^{4b}$, (CR³R$^{3a}$)C$_{3-10}$ carbocycle substituted with 0–2 R$^{4b}$, 5–10 membered heterocycle consisting of carbon atoms and from 1–4 heteroatoms selected from the group consisting of N, O, and S(O)$_p$ and substituted with 0–2 R$^{4b}$, and (CR³R$^{3a}$)-5–10 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR²R$^{2a}$, CH$_2$NR²R$^{2a}$, C(O)R$^{2c}$, NR²C(O)R$^{2b}$, C(O)NR²R$^{2a}$, NR²C(O)NR²R$^{2a}$, NR²SO$_2$R$^5$, SO$_2$NR²R$^{2a}$, 6 membered carbocycle substituted with 0–1 R$^5$, and a 5–6 membered heterocycle consisting of: carbon atoms and 1–2 heteroatoms selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR³R$^{3a}$, CH$_2$NR³R$^{3a}$, C(O)R$^3$, CH$_2$C(O)R$^3$, C(O)OR$^{3c}$, CH$_2$C(O)OR$^{3c}$, NR³C(O)R$^{3a}$, C(O)NR³R$^{3a}$, SO$_2$NR³R$^{3a}$, NR³SO$_2$—C$_{1-4}$ alkyl, NR³SO$_2$CF$_3$, NR³SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR²R$^{2a}$, CH$_2$NR²R$^{2a}$, C(O)R$^{2b}$, CH$_2$C(O)R$^{2b}$, NR²C(O)R$^{2b}$, SO$_2$NR²R$^{2a}$, and NR²SO$_2$C$_{1-4}$ alkyl.

4. A compound according to claim 3, wherein:

G is selected from the group: 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-ammomethyl-5-methoxy-phenyl; 2-aminomethyl-6-fluoro-phenyl; 2-aminomethyl-phenyl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-4-chloro-phenyl; 4-methoxy-2-methylsulfonyl-phenyl; 4-methoxy-phenyl; 3-amidino-phenyl;

A is 2–6 membered linear chain consisting of: carbon atoms, 0–1 carbonyl groups, and 0–1 heteroatoms selected from O, N, and S(O)$_p$, and A is substituted with 0–1 R$^{1a}$ and 0–2 R$^2$, and there are 0–1 double bonds; provided that other than an S—S, S—O, or O—O bond is present in A;

B is selected from Y, N(B$^1$)C(O)C(R³R$^{3g}$)NB²B$^3$,

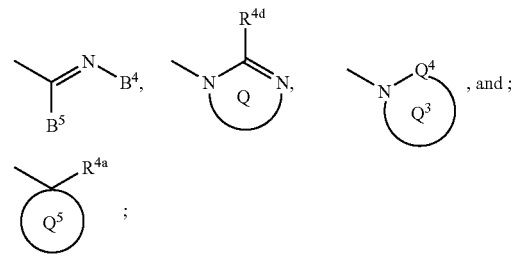

provided that the R$^{4d}$ shown is other than OH;

B$^1$ is selected from H, CH$_3$, CH$_2$CH$_3$, CH$_2$CH$_2$CH$_3$, and CH(CH$_3$)$_2$;

B$^2$ is selected from H, CH$_3$, CH$_2$CH$_3$, CH$_2$CH$_2$CH$_3$, and CH(CH$_3$)$_2$;

B$^3$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-5}$ alkyl substituted with 1 R$^{4c}$, —(CH$_2$)$_{0-1}$-3–6 membered carbocycle substituted with 0–1 R$^5$, and a —(CH$_2$)$_{0-1}$-5–6 membered heterocycle consisting of: carbon atoms and 1–4 heteroatoms selected from the group consisting of N, O, and S(O)$_p$ and substituted with 0–1 R$^5$;

$B^4$ is selected from H, $SO_2R^{3b}$ and $OR^2$;

$B^5$ is $NR^2R^{2f}$;

ring Q is a 5–6 membered ring consisting of, in addition to the $N—CR^{4d}$=N group shown, carbon atoms and 0–1 heteroatoms selected from N, O, and $S(O)_p$, and the ring is substituted with an additional 0–2 $R^{4d}$;

$Q^4$ is selected from C=O and $SO_2$;

ring $Q^3$ is a 6–7 membered ring consisting of, in addition to the $N-Q^4$ group shown, carbon atoms and 0–1 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 5–7 membered ring to which another ring is fused, wherein: the 5–7 membered ring consists of, in addition to the shown amide group, carbon atoms and 0–1 heteroatoms selected from $NR^{4c}$, O, S, S(O), and $S(O)_2$, and 0–1 double bonds are present within the ring; the fusion ring is phenyl;

ring $Q^3$, which includes the 5–7 membered ring and the fusion ring, is substituted with 0–2 $R^4$;

ring $Q^5$ is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and is substituted with 0–1 $R^4$;

Y is selected from $C(CH_3)_2R^{4a}$ and $C(CH_2CH_3)_2R^{4a}$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^{2b}$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated, or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$, and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—S(O)$_p$ moiety;

$R^{2f}$, at each occurrence, is selected from H, $CH_3$, $CH_2CH_3$, $OCH_3$, and benzyl;

alternatively, $NR^2R^{2f}$ forms a 5–6 membered ring consisting of: carbon atoms and 0–1 additional heteroatoms selected from N, O, and $S(O)_p$, and this ring is substituted with 0–1 $R^{4b}$;

alternatively, $B^4$ and $R^{2f}$ combine to form a 5 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H and $CH_3$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(→O)R^{2d}R^{2d}$, $(CR^3R^{3g})_rOR^{2d}$, $(CR^3R^{3g})_rNR^{2d}C(O)R^{2e}$, $(CR^3R^{3g})_rC(O)R^{2e}$, $(CR^3R^{3g})_rC(O)NR^{2d}R^{2d}$, $(CR^3R^{3g})_rNR^{2d}C(O)NR^{2d}R^{2d}$, $(CR^3R^{3g})_rNR^{2d}C(O)OR^{2d}$, $(CR^3R^{3g})_rNR^{2d}SO_2R^{2d}$, and $(CR^3R^{3g})_rS(O)_pR^{2d}$, provided that $S(O)_pR^{2d}$ forms other than $S(O)_2H$ or S(O)H;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-3}$ alkenyl, $C_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$_3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

5. A compound according to claim 4, wherein:

G is selected from: 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 3-amidino-phenyl;

A is 2–6 membered linear chain consisting of: carbon atoms, 0–1 carbonyl groups, and A is substituted with 0–1 R$^{1a}$ and 0–2 R$^2$, and there are 0–1 double bonds;

B is selected from Y, N(B$^1$)C(O)C(R$^3$R$^{3g}$)NB$^2$B$^3$,

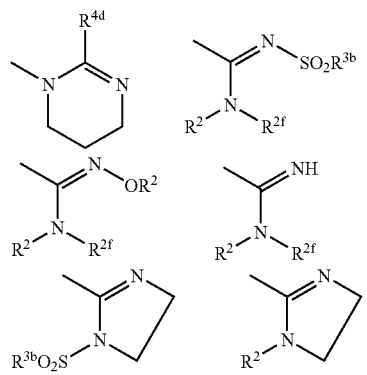

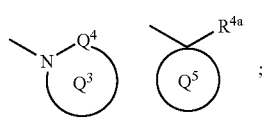

provided that the R$^{4d}$ shown is other than OH;

B$^1$ is selected from H, CH$_3$, CH$_2$CH$_3$, and CH$_2$CH$_2$CH$_3$;

B$^2$ is selected from H, CH$_3$, and CH$_2$CH$_3$;

B$^3$ is selected from CH$_3$, CH$_2$CH$_3$, CH$_2$CH$_2$CH$_3$, CH(CH$_3$)$_2$, CH$_2$CH$_2$CH$_2$CH$_3$, C(CH$_3$)$_3$, CH(CH$_3$)CH$_2$CH(CH$_3$)$_2$, CH$_2$CH$_2$OH, CH(CH$_3$)CH$_2$OH, CH(phenyl)CH$_2$CH$_3$, cyclopropyl, cyclobutyl, cyclopentyl, cyclohexyl, and CH$_2$-cyclopropyl;

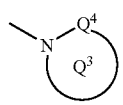

is attached to a different atom on A than M and is selected from the group:

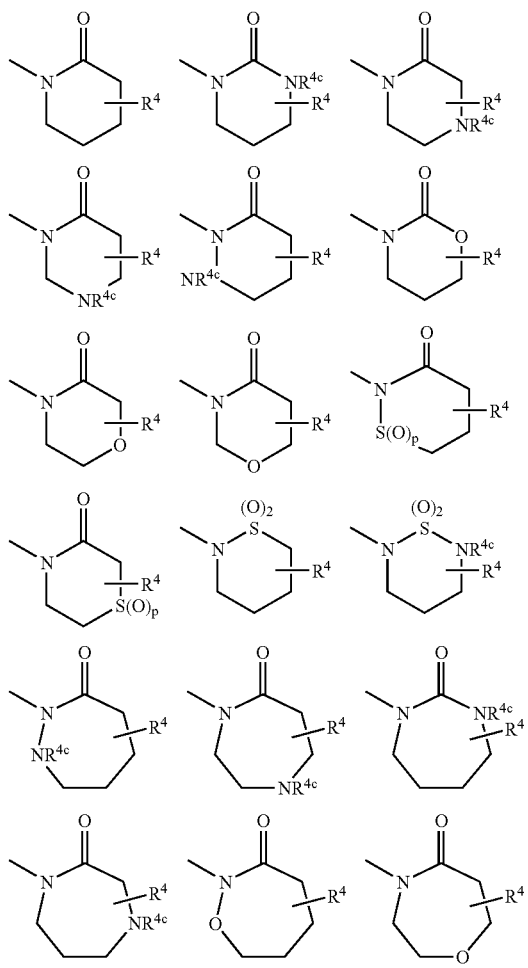

-continued

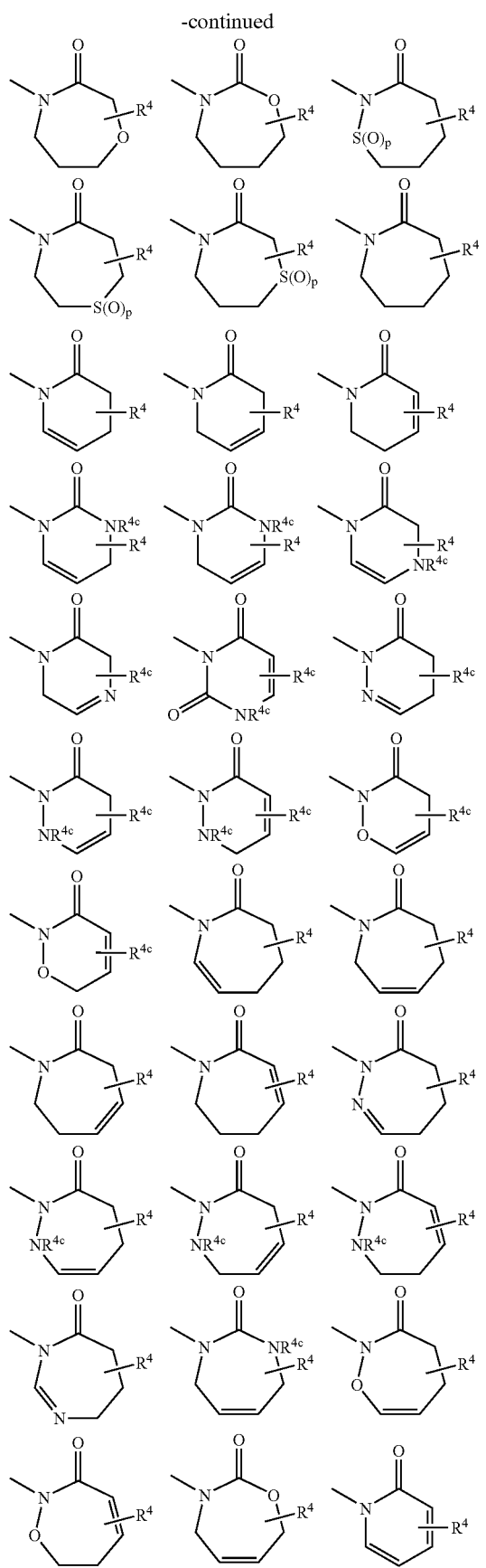

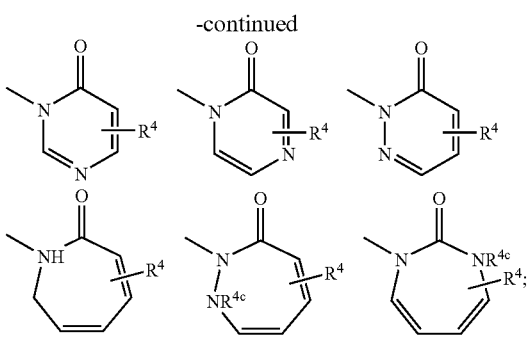

ring $Q^5$ is selected from cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$, at the 3-position), piperidinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

Y is selected from $C(CH_3)_2R^{4a}$ and $C(CH_2CH_3)_2R^{4a}$;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or $C(O)-S(O)_p$ moiety;

$R^{2f}$, at each occurrence, is selected from H, $CH_3$, $CH_2CH_3$, and $OCH_3$;

alternatively, $NR^2R^{2f}$ forms a ring selected from morpholine, piperazine, piperidine, and pyrrolidine;

$R^4$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from $-(CH_2)_r$-5–6 membered carbocycle substituted with 0–3 $R^{4c}$, $-(CH_2)_r$-5–6 membered heterocycle substituted with 0–3 $R^{4c}$ and consisting of: carbon atoms and 1–4 heteroatoms selected from the group consisting of N, O, and $S(O)_p$, $(CH_2)_rNR^{2d}R^{2d}$, $(CH_2)_rN(\rightarrow O)R^{2d}R^{2d}$, $(CH_2)_rOR^{2d}$, $(CH_2)_rC(O)NR^{2d}R^{2d}$, $(CH_2)_rNR^{2d}C(O)R^{2e}$, $(CH_2)_rC(O)R^{2e}$, $(CH_2)_r$ $NR^{2d}C(O)NR^{2d}R^{2d}$, $(CH_2)_rNR^{2d}C(O)OR^{2d}$, $(CH_2)_r$ $NR^{2d}SO_2R^{2d}$, and $(CH_2)_rS(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, $-CH_2$-cyclopropyl substituted with 0–1 $R^{4b}$, $-CH_2$-cyclobutyl substituted with 0–1 $R^{4b}$, $-CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)$ $R^{2b}$, $NR^2SO_2R^5$, phenyl, 2-oxo-pyrrolidinyl, and 2-oxo-piperidinyl;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2$-phenyl, $S(O)_2-CH_3$, $S(O)_2$-phenyl, $CF_3$, phenyl substituted with 0–2 $R^6$, naphthyl substituted with 0–2 $R^6$, and benzyl substituted with 0–2 $R^6$; and, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

6. A compound according to claim 5, wherein:

G is selected from:

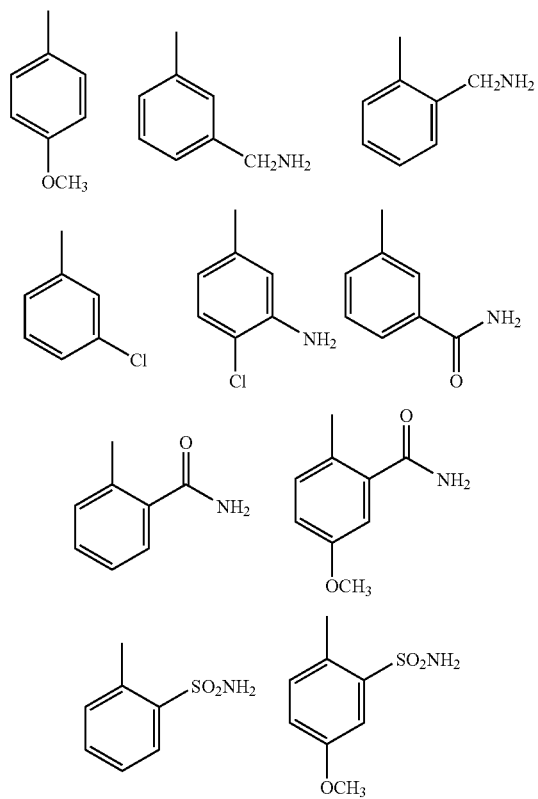

A is selected from:

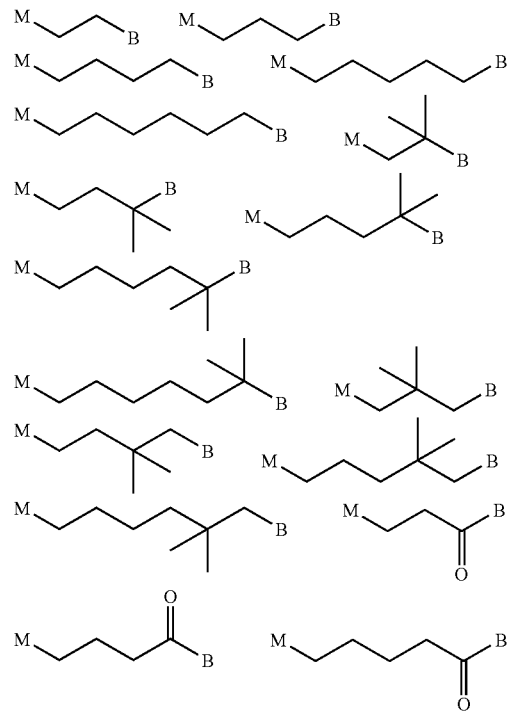

-continued
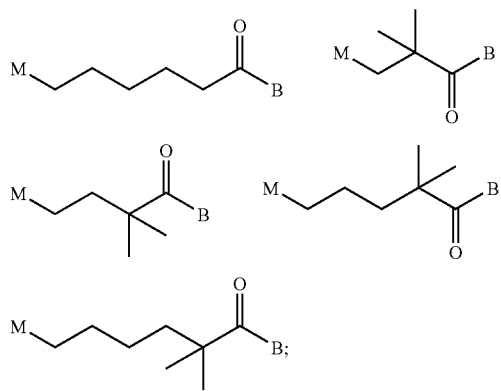
B is selected from:
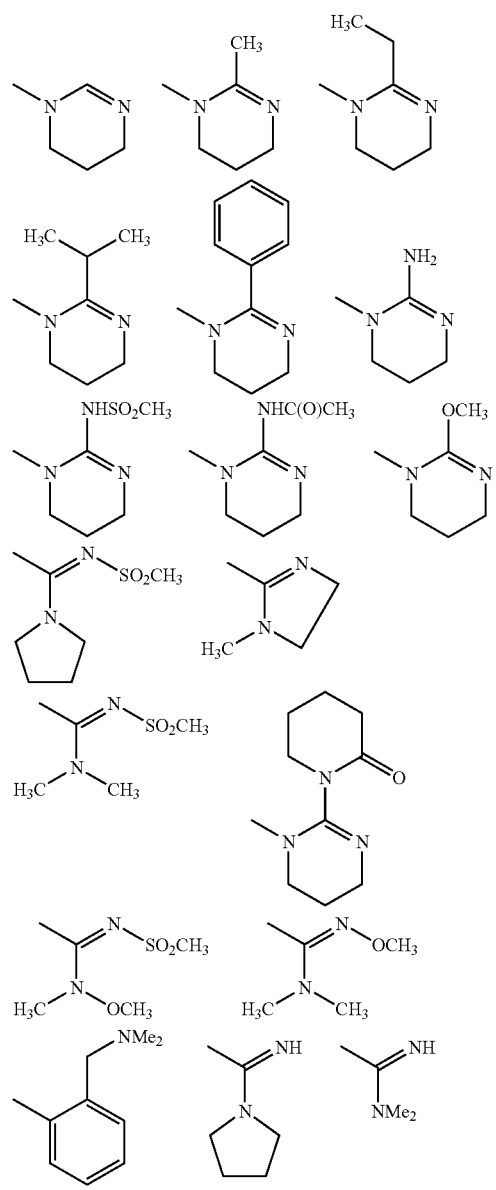
-continued
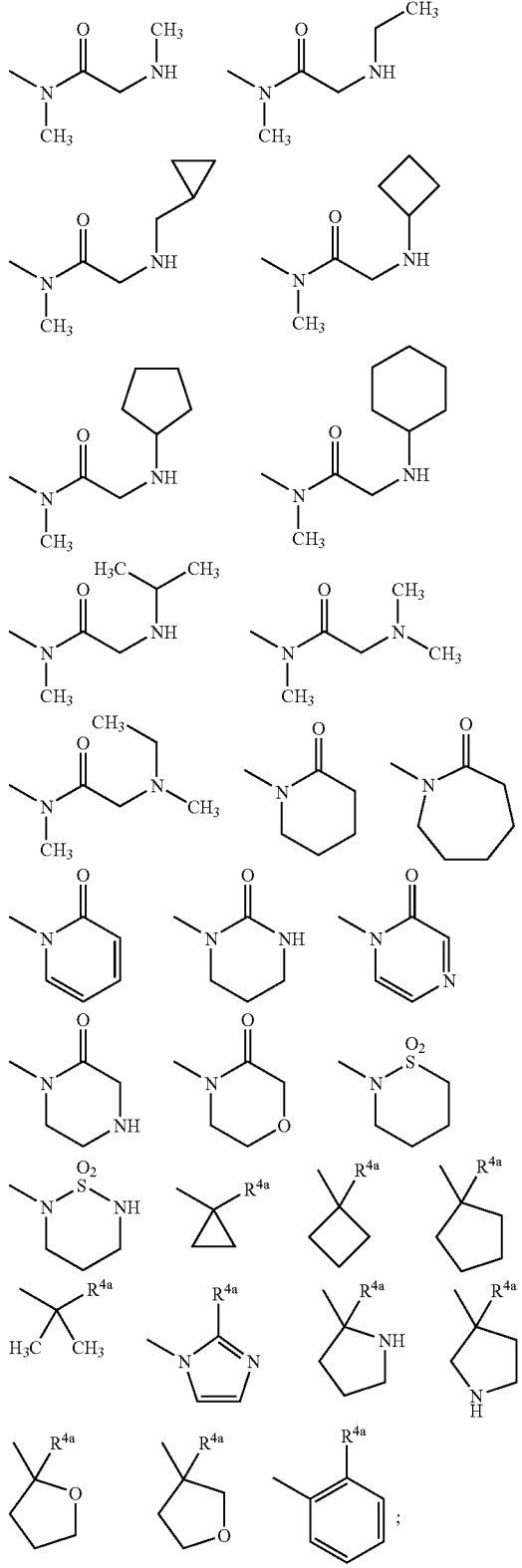
$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, C$_{1-4}$ alkyl substituted with 0–1 R$^{4c}$, C$_{3-6}$ cycloalkyl substituted with 0–2 R$^{4c}$, phenyl, substituted with 0–2 R$^{4c}$, and 5–6 membered aromatic heterocycle consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{4a}$ is selected from NR$^{2d}$R$^{2d}$, CH$_2$NR$^{2d}$R$^{2d}$, CH$_2$CH$_2$NR$^{2d}$R$^{2d}$, N(→O)R$^{2d}$R$^{2d}$, CH$_2$N(→O)R$^{2d}$R$^{2d}$, CH$_2$OR$^{2d}$, C(O)R$^{2e}$, C(O)NR$^{2d}$R$^{2d}$, CH$_2$C(O)NR$^{2d}$R$^{2d}$, NR$^{2d}$C(O)R$^{2e}$, CH$_2$NR$^{2d}$C(O)R$^{2e}$, NR$^{2d}$C(O)NR$^{2d}$R$^{2d}$, CH$_2$NR$^{2d}$C(O)NR$^{2d}$R$^{2d}$, NR$^{2d}$C(O)OR$^{2d}$, CH$_2$NR$^{2d}$C(O)OR$^{2d}$, NR$^{2d}$SO$_2$R$^{2d}$, CH$_2$NR$^{2d}$SO$_2$R$^{2d}$, S(O)$_p$R$^{2d}$, CH$_2$S(O)$_p$R$^{2d}$, 5–6 membered carbocycle substituted with 0–2 R$^{4c}$, —(CH$_2$)-5–6 membered carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CH$_2$)-5–6 membered heterocycle substituted with 0–2 R$^{4c}$ and consisting of: carbon atoms and 1–4 heteroatoms selected from the group consisting of N, O, and S(O)$_p$ provided that S(O)$_p$R$^{2d}$ forms other than S(O)$_2$H or S(O)H; and, R$^{4c}$ is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, CH=CH$_2$, CH≡CH, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, and CH$_2$S(O)$_p$R$^{5a}$.

7. A compound according to claim 6, wherein:

A is selected from:

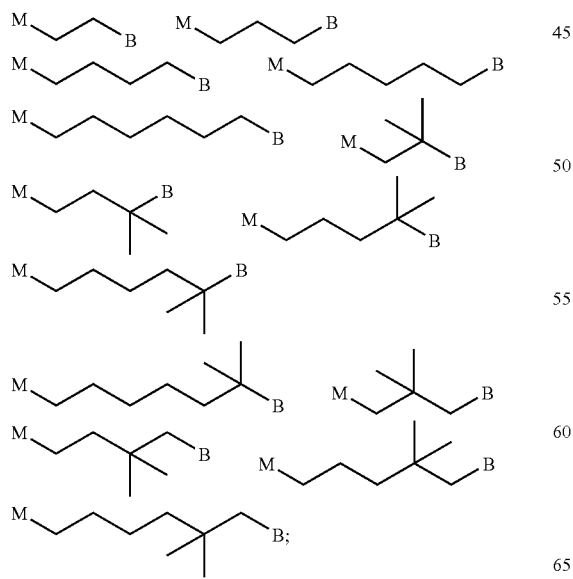

B is selected from:

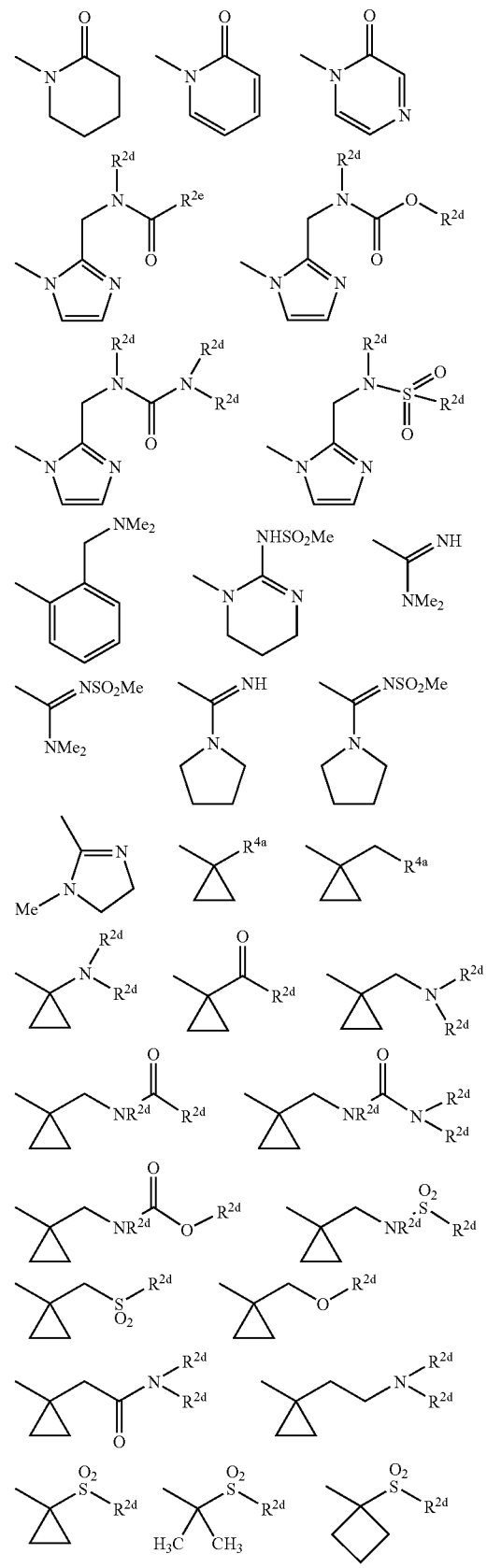

-continued

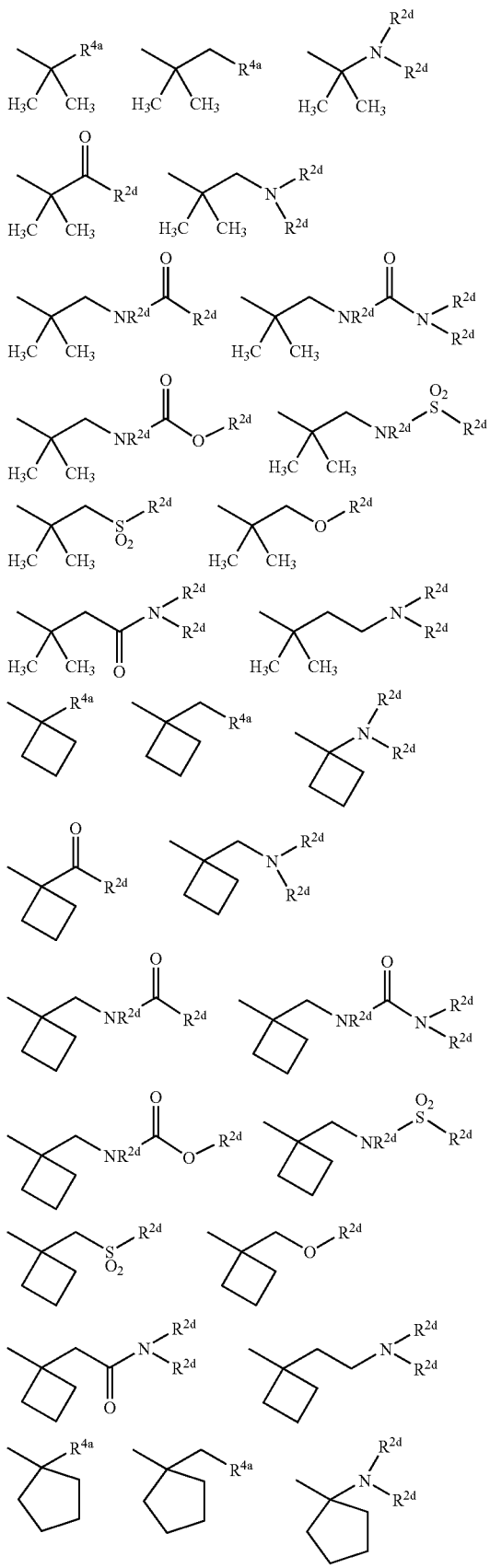
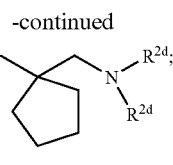

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2CCH$, $CH_2CH_2OH$, $CH_2C(O)NH_2$, cyclopropyl, $CH_2$-cyclopropyl, cyclobutyl, cyclopentyl, and thiazolyl;

$R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazolyl, imidazoline, imidazolidine, oxazoline, and thiazoline; and $R^{4c}$ is selected from =O, OH, $OCH_3$, and $CH_3$.

8. A compound according to claim 1, where the compound is selected from the group:

[1-(4-methoxy-phenyl)-7-oxo-3-trifluoromethyl-1,4,5,7-tetrahydro-pyrazolo[3,4-c]pyridin-6-yl]-acetic acid methyl ester;

4-[1-(4-methoxy-phenyl)-7-oxo-3-trifluoromethyl-1,4,5,7-tetrahydro-pyrazolo[3,4-c]pyridin-6-yl]-butyric acid ethyl ester;

5-[1-(4-methoxy-phenyl)-7-oxo-3-trifluoromethyl-1,4,5,7-tetrahydro-pyrazolo[3,4-c]pyridin-6-yl]-pentanoic acid methyl ester;

6-[1-(4-methoxy-phenyl)-7-oxo-3-trifluoromethyl-1,4,5,7-tetrahydro-pyrazolo[3,4-c]pyridin-6-yl]-hexanoic acid ethyl ester;

6-[1-(4-methoxy-phenyl)-7-oxo-3-trifluoromethyl-1,4,5,7-tetrahydro-pyrazolo[3,4-c]pyridin-6-yl]-2,2-dimethyl-hexanoic acid methyl ester;

1-(4-methoxy-phenyl)-6-(2-oxo-2-pyrrolidin-1-yl-ethyl)-3-trifluoromethyl-1,4,5,6-tetrahydro-pyrazolo[3,4-c]pyridin-7-one;

2-[1-(4-methoxy-phenyl)-7-oxo-3-trifluoromethyl-1,4,5,7-tetrahydro-pyrazolo[3,4-c]pyridin-6-yl]-N,N-dimethyl-acetamide;

N-ethyl-2-[1-(4-methoxy-phenyl)-7-oxo-3-trifluoromethyl-1,4,5,7-tetrahydro-pyrazolo[3,4-c]pyridin-6-yl]-N-methyl-acetamide;

1-(4-methoxy-phenyl)-6-(2-morpholin-4-yl-2-oxo-ethyl)-3-trifluoromethyl-1,4,5,6-tetrahydro-pyrazolo[3,4-c]pyridin-7-one;

N,N-diethyl-2-[1-(4-methoxy-phenyl)-7-oxo-3-trifluoromethyl-1,4,5,7-tetrahydro-pyrazolo[3,4-c]pyridin-6-yl]-acetamide;

1-(4-methoxy-phenyl)-6-(2-oxo-2-piperidin-1-yl-ethyl)-3-trifluoromethyl-1,4,5,6-tetrahydro-pyrazolo[3,4-c]pyridin-7-one;

1-(4-methoxy-phenyl)-6-[2-(4-methyl-piperazin-1-yl)-2-oxo-ethyl]-3-trifluoromethyl-1,4,5,6-tetrahydro-pyrazolo[3,4-c]pyridin-7-one;

6-[2-(1,3-dihydro-isoindol-2-yl)-2-oxo-ethyl]-1-(4-methoxy-phenyl)-3-trifluoromethyl-1,4,5,6-tetrahydro-pyrazolo[3,4-c]pyridin-7-one;

6-[2-(3,4-dihydro-1H-isoquinolin-2-yl)-2-oxo-ethyl]-1-(4-methoxy-phenyl)-3-trifluoromethyl-1,4,5,6-tetrahydro-pyrazolo[3,4-c]pyridin-7-one;

6-[2-(3,4-dihydro-2H-quinolin-1-yl)-2-oxo-ethyl]-1-(4-methoxy-phenyl)-3-trifluoromethyl-1,4,5,6-tetrahydro-pyrazolo[3,4-c]pyridin-7-one;
N,N-diethyl-3-[1-(4-methoxy-phenyl)-7-oxo-3-trifluoromethyl-1,4,5,7-tetrahydro-pyrazolo[3,4-c]pyridin-6-yl]-propionamide;
1-(4-methoxy-phenyl)-6-(3-morpholin-4-yl-3-oxo-propyl)-3-trifluoromethyl-1,4,5,6-tetrahydro-pyrazolo[3,4-c]pyridin-7-one;
1-(4-methoxy-phenyl)-6-(3-oxo-3-piperidin-1-yl-propyl)-3-trifluoromethyl-1,4,5,6-tetrahydro-pyrazolo[3,4-c]pyridin-7-one;
1-(4-methoxy-phenyl)-6-(3-oxo-3-pyrrolidin-1-yl-propyl)-3-trifluoromethyl-1,4,5,6-tetrahydro-pyrazolo[3,4-c]pyridin-7-one;
1-(4-methoxy-phenyl)-6-[3-(4-methyl-piperazin-1-yl)-3-oxo-propyl]-3-trifluoromethyl-1,4,5,6-tetrahydro-pyrazolo[3,4-c]pyridin-7-one;
N-ethyl-3-[1-(4-methoxy-phenyl)-7-oxo-3-trifluoromethyl-1,4,5,7-tetrahydro-pyrazolo[3,4-c]pyridin-6-yl]-N-methyl-propionamide;
N-benzyl-3-[1-(4-methoxy-phenyl)-7-oxo-3-trifluoromethyl-1,4,5,7-tetrahydro-pyrazolo[3,4-c]pyridin-6-yl]-N-methyl-propionamide;
4-[1-(4-methoxy-phenyl)-7-oxo-3-trifluoromethyl-1,4,5,7-tetrahydro-pyrazolo[3,4-c]pyridin-6-yl]-N,N-dimethyl-butyramide;
1-(4-methoxy-phenyl)-6-(4-oxo-4-pyrrolidin-1-yl-butyl)-3-trifluoromethyl-1,4,5,6-tetrahydro-pyrazolo[3,4-c]pyridin-7-one;
5-[1-(4-methoxy-phenyl)-7-oxo-3-trifluoromethyl-1,4,5,7-tetrahydro-pyrazolo[3,4-c]pyridin-6-yl]-pentanoic acid dimethylamide;
1-(4-methoxy-phenyl)-6-(5-oxo-5-pyrrolidin-1-yl-pentyl)-3-trifluoromethyl-1,4,5,6-tetrahydro-pyrazolo[3,4-c]pyridin-7-one;
1-(4-methoxy-phenyl)-6-(6-oxo-6-pyrrolidin-1-yl-hexyl)-3-trifluoromethyl-1,4,5,6-tetrahydro-pyrazolo[3,4-c]pyridin-7-one;
6-[1-(4-methoxy-phenyl)-7-oxo-3-trifluoromethyl-1,4,5,7-tetrahydro-pyrazolo[3,4-c]pyridin-6-yl]-hexanoic acid dimethylamide;
6-(4-hydroxy-4-methyl-pentyl)-1-(4-methoxy-phenyl)-3-trifluoromethyl-1,4,5,6-tetrahydro-pyrazolo[3,4-c]pyridin-7-one;
6-(5-hydroxy-5-methyl-hexyl)-1-(4-methoxy-phenyl)-3-trifluoromethyl-1,4,5,6-tetrahydro-pyrazolo[3,4-c]pyridin-7-one;
6-(6-hydroxy-6-methyl-heptyl)-1-(4-methoxy-phenyl)-3-trifluoromethyl-1,4,5,6-tetrahydro-pyrazolo[3,4-c]pyridin-7-one;
[6-(2-hydroxy-ethyl)-1-(4-methoxy-phenyl)-3-trifluoromethyl-1,4,5,6-tetrahydro-pyrazolo[3,4-c]pyridin-7-one;
6-(4-hydroxy-butyl)-1-(4-methoxy-phenyl)-7-oxo-4,5,6,7-tetrahydro-1H-pyrazolo[3,4-c]pyridine-3-carboxylic acid amide;
6-(2-dimethylamino-ethyl)-1-(4-methoxy-phenyl)-3-trifluoromethyl-1,4,5,6-tetrahydro-pyrazolo[3,4-c]pyridin-7-one;
1-(4-methoxy-phenyl)-6-(2-pyrrolidin-1-yl-ethyl)-3-trifluoromethyl-1,4,5,6-tetrahydro-pyrazolo[3,4-c]pyridin-7-one;
6-(4-dimethylamino-butyl)-1-(4-methoxy-phenyl)-3-trifluoromethyl-1,4,5,6-tetrahydro-pyrazolo[3,4-c]pyridin-7-one;
1-(4-methoxy-phenyl)-6-(4-pyrrolidin-1-yl-butyl)-3-trifluoromethyl-1,4,5,6-tetrahydro-pyrazolo[3,4-c]pyridin-7-one;
1-(4-methoxy-phenyl)-6-[4-(2-oxo-piperidin-1-yl)-butyl]-3-trifluoromethyl-1,4,5,6-tetrahydro-pyrazolo[3,4-c]pyridin-7-one;
1-(4-methoxy-phenyl)-6-[4-(2-oxo-2H-pyridin-1-yl)-butyl]-3-trifluoromethyl-1,4,5,6-tetrahydro-pyrazolo[3,4-c]pyridin-7-one;
6-(3-dimethylamino-propyl)-1-(4-methoxy-phenyl)-3-trifluoromethyl-1,4,5,6-tetrahydro-pyrazolo[3,4-c]pyridin-7-one;
1-(4-methoxy-phenyl)-6-(3-pyrrolidin-1-yl-propyl)-3-trifluoromethyl-1,4,5,6-tetrahydro-pyrazolo[3,4-c]pyridin-7-one;
6-(6-dimethylamino-hexyl)-1-(4-methoxy-phenyl)-3-trifluoromethyl-1,4,5,6-tetrahydro-pyrazolo[3,4-c]pyridin-7-one;
1-(4-methoxy-phenyl)-6-(6-pyrrolidin-1-yl-hexyl)-3-trifluoromethyl-1,4,5,6-tetrahydro-pyrazolo[3,4-c]pyridin-7-one;
6-(3-amino-propyl)-1-(4-methoxy-phenyl)-3-trifluoromethyl-1,4,5,6-tetrahydro-pyrazolo[3,4-c]pyridin-7-one;
6-(5-amino-pentyl)-1-(4-methoxy-phenyl)-3-trifluoromethyl-1,4,5,6-tetrahydro-pyrazolo[3,4-c]pyridin-7-one;
6-(6-amino-hexyl)-1-(4-methoxy-phenyl)-3-trifluoromethyl-1,4,5,6-tetrahydro-pyrazolo[3,4-c]pyridin-7-one;
6-(5-dimethylamino-pentyl)-1-(4-methoxy-phenyl)-3-trifluoromethyl-1,4,5,6-tetrahydro-pyrazolo[3,4-c]pyridin-7-one;
6-(6-dimethylamino-5,5-dimethyl-hexyl)-1-(4-methoxy-phenyl)-3-trifluoromethyl-1,4,5,6-tetrahydro-pyrazolo[3,4-c]pyridin-7-one;
5-[1-(4-methoxy-phenyl)-7-oxo-3-trifluoromethyl-1,4,5,7-tetrahydro-pyrazolo[3,4-c]pyridin-6-yl]-N,N-dimethyl-pentanamidine;
6-(5-imino-5-pyrrolidin-1-yl-pentyl)-1-(4-methoxy-phenyl)-3-trifluoromethyl-1,4,5,6-tetrahydro-pyrazolo[3,4-c]pyridin-7-one;
N-{1-dimethylamino-5-[1-(4-methoxy-phenyl)-7-oxo-3-trifluoromethyl-1,4,5,7-tetrahydro-pyrazolo[3,4-c]pyridin-6-yl]-pentylidene}-methanesulfonamide;
N-{5-[1-(4-methoxy-phenyl)-7-oxo-3-trifluoromethyl-1,4,5,7-tetrahydro-pyrazolo[3,4-c]pyridin-6-yl]-1-pyrrolidin-1-yl-pentylidene}-methanesulfonamide;
1-(4-methoxy-phenyl)-6-[4-(1-methyl-4,5-dihydro-1H-imidazol-2-yl)-butyl]-3-trifluoromethyl-1,4,5,6-tetrahydro-pyrazolo[3,4-c]pyridin-7-one;
N-hydroxy-5-[1-(4-methoxy-phenyl)-7-oxo-3-trifluoromethyl-1,4,5,7-tetrahydro-pyrazolo[3,4-c]pyridin-6-yl]-pentanamidine;
N-hydroxy-6-[1-(4-methoxy-phenyl)-7-oxo-3-trifluoromethyl-1,4,5,7-tetrahydro-pyrazolo[3,4-c]pyridin-6-yl]-2,2-dimethyl-hexanamidine;
1-(4-methoxy-phenyl)-7-oxo-6-[4-(2-oxo-piperidin-1-yl)-butyl]-4,5,6,7-tetrahydro-1H-pyrazolo[3,4-c]pyridine-3-carboxylic acid amide;
1-(4-methoxy-phenyl)-7-oxo-6-{2-[4-(2-oxo-2,3-dihydro-benzoimidazol-1-yl)-piperidin-1-yl]-ethyl}-4,5,6,7-tetrahydro-1H-pyrazolo[3,4-c]pyridine-3-carboxylic acid amide;
1-(4-methoxy-phenyl)-6-{2-[4-(2-methoxy-phenyl)-piperazin-1-yl]-ethyl}-7-oxo-4,5,6,7-tetrahydro-1H-pyrazolo[3,4-c]pyridine-3-carboxylic acid amide;
6-[2-(benzyl-methyl-amino)-ethyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-[2-(methyl-phenyl-amino)-ethyl]-7-oxo-4,5,6,7-tetrahydro-1H-pyrazolo[3,4-c]pyridine-3-carboxylic acid amide;

1-(4-methoxy-phenyl)-6-[2-(3-methyl-piperidin-1-yl)-ethyl]-7-oxo-4,5,6,7-tetrahydro-1H-pyrazolo[3,4-c]pyridine-3-carboxylic acid amide;

2-[1-(4-methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-acetamide;

2-[1-(4-methoxy-phenyl)-7-oxo-3-trifluoromethyl-1,4,5,7-tetrahydro-pyrazolo[3,4-c]pyridin-6-yl]-N-(1-pyrrolidin-1-ylmethyl-cyclopropyl)-acetamide;

1-{2-[1-(4-methoxy-phenyl)-7-oxo-3-trifluoromethyl-1,4,5,7-tetrahydro-pyrazolo[3,4-c]pyridin-6-yl]-acetylamino}-cyclopentanecarboxylic acid methyl ester methyl ester;

1-{2-[1-(4-methoxy-phenyl)-7-oxo-3-trifluoromethyl-1,4,5,7-tetrahydro-pyrazolo[3,4-c]pyridin-6-yl]-acetylamino}-cyclopentanecarboxylic acid dimethylamide;

2-[1-(4-methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopentyl]-acetamide;

2-[1-(4-methoxy-phenyl)-7-oxo-3-trifluoromethyl-1,4,5,7-tetrahydro-pyrazolo[3,4-c]pyridin-6-yl]-N-(1-pyrrolidin-1-ylmethyl-cyclopentyl)-acetamide;

1-{3-[1-(4-methoxy-phenyl)-7-oxo-3-trifluoromethyl-1,4,5,7-tetrahydro-pyrazolo[3,4-c]pyridin-6-yl]-propionylamino}-cyclopropanecarboxylic acid ethyl ester;

1-{3-[1-(4-methoxy-phenyl)-7-oxo-3-trifluoromethyl-1,4,5,7-tetrahydro-pyrazolo[3,4-c]pyridin-6-yl]-propionylamino}-cyclopentanecarboxylic acid methyl ester;

1-{3-[1-(4-methoxy-phenyl)-7-oxo-3-trifluoromethyl-1,4,5,7-tetrahydro-pyrazolo[3,4-c]pyridin-6-yl]-propionylamino}-cyclopentanecarboxylic acid dimethylamide;

3-[1-(4-methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-propionamide;

1-{4-[1-(4-methoxy-phenyl)-7-oxo-3-trifluoromethyl-1,4,5,7-tetrahydro-pyrazolo[3,4-c]pyridin-6-yl]-butyrylamino}-cyclopropanecarboxylic acid ethyl ester;

1-{4-[1-(4-methoxy-phenyl)-7-oxo-3-trifluoromethyl-1,4,5,7-tetrahydro-pyrazolo[3,4-c]pyridin-6-yl]-butyrylamino}-cyclopentanecarboxylic acid methyl ester;

1-{4-[1-(4-methoxy-phenyl)-7-oxo-3-trifluoromethyl-1,4,5,7-tetrahydro-pyrazolo[3,4-c]pyridin-6-yl]-butyrylamino}-cyclopropanecarboxylic acid dimethylamide;

1-{4-[1-(4-methoxy-phenyl)-7-oxo-3-trifluoromethyl-1,4,5,7-tetrahydro-pyrazolo[3,4-c]pyridin-6-yl]-butyrylamino}-cyclopropanecarboxylic acid dimethylamide;

1-{4-[1-(4-methoxy-phenyl)-7-oxo-3-trifluoromethyl-1,4,5,7-tetrahydro-pyrazolo[3,4-c]pyridin-6-yl]-butyrylamino}-cyclopentanecarboxylic acid dimethylamide;

4-[1-(4-methoxy-phenyl)-7-oxo-3-trifluoromethyl-1,4,5,7-tetrahydro-pyrazolo[3,4-c]pyridin-6-yl]-N-[1-(pyrrolidine-1-carbonyl)-cyclopropyl]-butyramide;

1-{5-[1-(4-methoxy-phenyl)-7-oxo-3-trifluoromethyl-1,4,5,7-tetrahydro-pyrazolo[3,4-c]pyridin-6-yl]-pentanoylamino}-cyclopropanecarboxylic acid ethyl ester;

1-{5-[1-(4-methoxy-phenyl)-7-oxo-3-trifluoromethyl-1,4,5,7-tetrahydro-pyrazolo[3,4-c]pyridin-6-yl]-pentanoylamino}-cyclopentanecarboxylic acid methyl ester;

1-{5-[1-(4-methoxy-phenyl)-7-oxo-3-trifluoromethyl-1,4,5,7-tetrahydro-pyrazolo[3,4-c]pyridin-6-yl]-pentanoylamino}-cyclopropanecarboxylic acid dimethylamide; and 5-[1-(4-methoxy-phenyl)-7-oxo-3-trifluoromethyl-1,4,5,7-tetrahydro-pyrazolo[3,4-c]pyridin-6-yl]-pentanoic acid [1-(pyrrolidine-1-carbonyl)-cyclopropyl]-amide;

or a pharmaceutically acceptable salt form thereof.

9. A pharmaceutical composition, comprising: a pharmaceutically acceptable carrier and a therapeutically effective amount of a compound of claim 1 or a pharmaceutically acceptable salt form thereof.

10. A method for treating a thromboembolic disorder, comprising: administering to a patient in need thereof a therapeutically effective amount of a compound of claim 1 or a pharmaceutically acceptable salt form thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart.

12. A method according to claim 10, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A pharmaceutical composition, comprising: a pharmaceutically acceptable carrier and a therapeutically effective amount of a compound of claim 8 or a pharmaceutically acceptable salt form thereof.

14. A method for treating a thromboembolic disorder, comprising: administering to a patient in need thereof a therapeutically effective amount of a compound of claim 8 or a pharmaceutically acceptable salt form thereof.

15. A method according to claim 14, wherein the thromboembolic disorder is selected from the group consisting of arterial cardiovascular thromboembolic disorders, venous cardiovascular thromboembolic disorders, and thromboembolic disorders in the chambers of the heart.

16. A method according to claim 14, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *